(12) United States Patent
Broddefalk et al.

(10) Patent No.: US 10,508,119 B2
(45) Date of Patent: *Dec. 17, 2019

(54) PYRAZOLE DERIVATIVES USEFUL AS 5-LIPDXYGENASE ACTIVATING PROTEIN (FLAP) INHIBITORS

(71) Applicant: ASTRAZENECA AB, Södertälje (SE)

(72) Inventors: Johan Olof Broddefalk, Mölndal (SE); Hans Fredrik Emtenâs, Mölndal (SE); Kenneth Lars Granberg, Mölndal (SE); Malin Anita Lemurell, Mölndal (SE); Daniel Tor Pettersen, Mölndal (SE); Alleyn Thomas Plowright, Mölndal (SE); Lars Johan Andreas Ulander, Mölndal (SE)

(73) Assignee: ASTRAZENECA AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/196,217

(22) Filed: Nov. 20, 2018

(65) Prior Publication Data

US 2019/0084991 A1 Mar. 21, 2019

Related U.S. Application Data

(63) Continuation of application No. 15/571,291, filed as application No. PCT/EP2016/059848 on May 3, 2016, now Pat. No. 10,183,947.

(60) Provisional application No. 62/156,424, filed on May 4, 2015.

(51) Int. Cl.
| | |
|---|---|
| *C07D 487/04* | (2006.01) |
| *C07D 231/40* | (2006.01) |
| *C07D 231/44* | (2006.01) |
| *C07D 231/50* | (2006.01) |
| *C07D 413/12* | (2006.01) |
| *C07D 417/12* | (2006.01) |
| *C07D 498/04* | (2006.01) |

(52) U.S. Cl.
CPC ......... *C07D 487/04* (2013.01); *C07D 231/40* (2013.01); *C07D 231/44* (2013.01); *C07D 231/50* (2013.01); *C07D 413/12* (2013.01); *C07D 417/12* (2013.01); *C07D 498/04* (2013.01)

(58) Field of Classification Search
CPC .. C07D 231/40; C07D 231/44; C07D 231/50; C07D 413/12; C07D 417/12; C07D 487/04; C07D 498/04
See application file for complete search history.

(56) References Cited

U.S. PATENT DOCUMENTS 10,183,947 B2 * 1/2019 Broddefalk .......... C07D 487/04

OTHER PUBLICATIONS

Hofmann, Bettina et al., 2010, "5-Lipoxygenase inhibitors: a review of recent patents (2010-2012)", Expert Opinion on Therapeutics Patent, 23(7):895-909.
Pergola, Carlo et al., 2010, "5-Lipoxygenase inhibitors: a review of recent developments and patents", Expert Opinion om Therapeutic Patents, 20(3):355-375.

* cited by examiner

*Primary Examiner* — Joseph R Kosack

(57) ABSTRACT

The present application relates to novel compounds of formula (I)

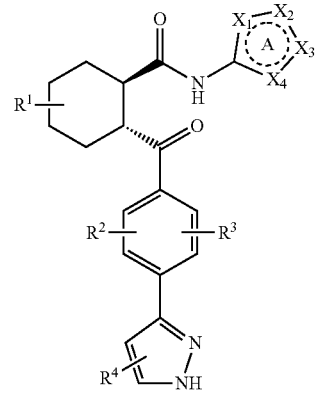

to their utility in treating and/or preventing clinical conditions including cardiovascular diseases (CVD), to methods for their therapeutic use, to pharmaceutical compositions containing them and to processes for preparing such compounds.

18 Claims, No Drawings

PYRAZOLE DERIVATIVES USEFUL AS 5-LIPDXYGENASE ACTIVATING PROTEIN (FLAP) INHIBITORS

CROSS-REFERENCE TO RELATED APPLICATIONS

This application is a continuation of U.S. application Ser. No. 15/571,291, filed Nov. 2, 2017, which is a National Stage Application of International Application No. PCT/EP2016/059848, filed on May 3, 2016, which claims benefit under 35 U.S.C. § 119(e) of the U.S. Provisional Application No. 62/156,424, filed May 4, 2015, each of which is incorporated by reference in its entirety.

FIELD

The present application relates to novel compounds that inhibit 5-lipoxygenase activating protein (FLAP) and therefore leukotriene production, to their utility in treating and/or preventing clinical conditions including cardiovascular diseases (CVD), such as atherosclerosis, coronary artery disease (CAD), coronary heart disease (CHD), heart failure (HF), high risk coronary artery disease (HRCAD), and abdominal aortic aneurysms (AAA), to methods for their therapeutic use, to pharmaceutical compositions containing to them and to processes for preparing such compounds.

BACKGROUND

FLAP, 5-lipoxygenase activating protein, plays a critical role in the production of leukotrienes by the 5-lipoxygenase (5-LO) pathway. In particular, FLAP mediates the transfer of the substrate, arachidonic acid, released from membrane phospholipids to the active site of 5-LO. Leukotrienes are lipid mediators released by leukocytes, in particular neutrophils, eosinophils, mast cells and monocyte/macrophages. They belong to the wider class of lipid mediators known as eicosanoids, formed from arachidonic acid released from cell membranes. Two distinct classes of leukotriene exist, $LTB_4$ and CysLTs ($LTC_4$, $LTD_4$ and $LTE_4$). Functions of $LTB_4$ include chemo-attraction and activation of leukocytes, inhibition of neutrophil apoptosis, and activation of adhesion molecule expression. Such effects are mediated through binding to one of two distinct G protein-coupled receptors (BLT1 and BLT2) which differ in their affinity and specificity for $LTB_4$. Cysteinyl leukotrienes have vaso-active properties and can affect blood flow and vasopermeability, actions that are mediated by two CysLT receptors, CysLT1 and CysLT2.

To initiate leukotriene biosynthesis, 5-LO translocates to intracellular membranes such as the nuclear membrane where it interacts with FLAP. Arachidonic acid released from membrane phospholipids by cytoplasmic PLA2 ($cPLA_2$) is transferred via FLAP to 5-LO which then stereospecifically incorporates oxygen at the fifth carbon position, with the formation of 5(S)-HpETE. This is subsequently converted by 5-LO to $LTA_4$, the common precursor for leukotriene $B_4$ ($LTB_4$) and the cysteinyl leukotrienes ($LTC_4$, $LTD_4$ and $LTE_4$). The conversion of $LTA_4$ to $LTB_4$ is mediated by $LTA_4$ Hydrolase ($LTA_4H$), a zinc-dependent epoxide hydrolase. Formation of cysteinyl leukotrienes involves conjugation of $LTA_4$ to glutathione, mediated by $LTC_4$ synthase in cell membranes in association with FLAP, and the resulting $LTC_4$ may be further processed to $LTD_4$ and $LTE_4$ via peptidase activities.

Compounds that inhibit the function of either 5-LO or FLAP can result in the inhibition of leukotriene production. FLAP inhibitors bind directly to FLAP in cell membranes and prevent leukotriene biosynthesis by preventing the membrane translocation of 5-LO and/or the supply of arachidonic acid substrate to its active site. In this way, inhibition of FLAP prevents the production of both $LTB_4$ and cysLTs by inhibiting production of the common precursor $LTA_4$. Distinct from 5-LO inhibitors, FLAP inhibitors do not directly suppress oxidation of arachidonic acid by 5-LO and do not inhibit leukotriene production in lysed cell extracts.

Despite the availability of drugs that deal with risk factors such as high cholesterol levels and elevated blood pressure, further treatment options are needed to reduce atherosclerotic cardiovascular disease and its sequellae. The role of lipid deposition in the formation of atherosclerotic plaques is well-established. However, another key factor in atherogenesis is inflammation, including both the recruitment of inflammatory cells to atherosclerotic lesions and their activation within plaques. Pharmacological approaches that target inflammation could therefore provide a novel approach to treating patients with atherosclerosis. Inhibition of leukotriene production by means of administering a FLAP inhibitor is one such approach.

Another risk factor associated with cardiovascular disease is microvascular dysfunction. By attenuating leukocyte activation and interaction with the microvasculature in addition to reducing the production of vasoactive cysteinyl leukotrienes, pharmacological inhibition of FLAP could improve microvascular function in cardiovascular disease patients.

A link between FLAP, 5-LO pathway activity, leukotriene production and cardiovascular disease is supported by the following lines of evidence: 1) expression and activity of the 5-LO pathway increases in association with atherosclerotic plaque progression and symptoms of plaque instability that could cause plaque rupture and thrombosis leading to myocardial infarction (MI) (Spanbroek et al (2003) PNAS 100, 1238; Cipollone et al (2005) ATVB 25, 1665); 2) leukotriene levels in blood and urine are elevated in the period following a recent acute coronary syndrome (ACS) event (Sanchez-Gala et al (2009) Cardiovascular Research 81, 216; Carry et al (1992) Circulation 85, 230); 3) genetic haplotypes in the FLAP (ALOX5AP) gene are significantly associated with the risk of myocardial infarction (Helgadottir et al (2004) Nature Genetics 36, 233).

Many companies over the course of the last few decades have pursued FLAP as a target, and patent filings associated with these efforts are summarized in various publications. See e.g., Pergola & Werz, *Expert Opin. Ther. Patents* (2010) 20(3); and Hofmann & Steinhilber *Expert Opin. Ther. Patents*, (2013) 23(7) and Whatling Bioorg. Med Chem. Lett. (2015) 25(2607). However, this application presents a new class of compounds distinct from these prior patent filings.

The instant application addresses the large unmet need by providing compounds, compositions and methods for the treatment or prevention of cardiovascular disease and related conditions.

BRIEF DESCRIPTION

In one aspect, there is provided a compound of formula (I):

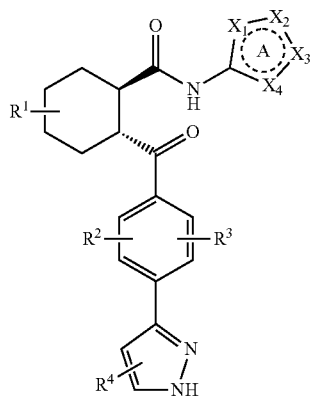

or a pharmaceutically acceptable salt thereof, wherein, $R^1$ is H, $C_1$-$C_3$ alkyl, halo, $C_1$-$C_3$ alkoxy, $C_1$-$C_3$ haloalkyl or $C_1$-$C_3$ haloalkoxy; each of $R^2$ and $R^3$ is independently H, $C_1$-$C_3$ alkyl, $C_1$-$C_3$ alkoxy, —CN or halo; $R^4$ is H, —$CH_3$, —$CH_2F$, —$CHF_2$, —$CF_3$ or halo; Ring A contains 2 double bonds; each $X_1$, $X_2$, $X_3$ and $X_4$ of Ring A is independently $CR^5$, CH, O, S, $NR^6$ or N; wherein at least one of $X_1$, $X_2$, $X_3$ and $X_4$ in Ring A is $NR^6$; each $R^5$ is optionally and independently $C_1$-$C_6$ alkyl, $C_1$-$C_6$ alkoxy, $C_1$-$C_3$ haloalkyl, $C_1$-$C_3$ haloalkoxy, —$S(O)_pR^7$, —CN, —CONR'R", or $C_3$-$C_6$ cycloalkyl; each p is independently 0, 1 or 2; or wherein when $X_4$ is $CR^5$ and $X_3$ is $NR^6$, then the $R^5$ and $R^6$ may be taken together to form a 5 to 6-membered heterocyclyl ring fused to Ring A, which heterocyclyl may optionally contain an additional heteroatom selected from N, O and S; said fused heterocyclyl may additionally contain a carbonyl or a —$S(O)_2$ directly adjacent to a heteroatom therein; and may be further substituted with one or two substituents selected from the group consisting of —$CH_3$ and halo; $R^6$ is H, —$CH_3$ or —$CH_2CH_3$; $R^7$ is —$CH_3$ or —NR'R"; and each R' and R" is independently —H or —$CH_3$; provided that the total number of substituents on Ring A is 0, 1 or 2; and further provided that when $R^5$ and $R^6$ are not combined to form a heterocyclyl ring fused to Ring A, that the total number of $R^5$ and $R^6$ substituents which is alkyl and/or haloalkyl is 0 or 1.

In a further aspect, there is provided pharmaceutical compositions comprising a therapeutically effective amount of the compound of formula (I), or a pharmaceutically acceptable salt thereof, and a pharmaceutically acceptable diluent, excipients and/or inert carrier.

In still a further aspect, there is provided the compound of formula (I) or a pharmaceutically acceptable salt thereof, for use in treatment or prophylaxis of diseases and conditions in which inhibition of FLAP is beneficial. In one embodiment, is a compound of formula (I) or a pharmaceutically acceptable salt thereof for use in the treatment of cardiovascular disease. In one embodiment, the cardiovascular disease is coronary artery disease, particularly high risk coronary artery disease.

In one aspect there is provided a method of treating diseases or conditions in which inhibition of FLAP is beneficial, comprising administering to a patient in need thereof an effective amount of a compound of formula (I) or a pharmaceutically acceptable salt thereof. In one embodiment, said disease or condition is coronary artery disease. In another embodiment, said disease or condition is high risk coronary artery disease.

In one aspect, is a compound according to formula (I), or a pharmaceutically acceptable salt thereof, for use as medicament.

In another aspect there is provided a process for the preparation of compounds of formula (I), and the intermediates used in the preparation thereof.

These and other aspects of the present application are described in greater detail herein below.

DETAILED DESCRIPTION

The object of the present application is to provide compounds that are inhibitors of 5-lipoxygenase activating protein (FLAP), their use as medicaments, pharmaceutical compositions containing them and synthetic routes to their production.

In one embodiment is a compound according to formula (I), or a pharmaceutically acceptable salt thereof, as described above.

In another embodiment is a compound according to formula (II):

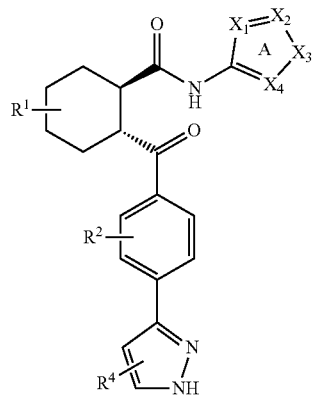

or a pharmaceutically acceptable salt thereof, wherein each $X_1$, $X_2$ and $X_4$ of Ring A is to independently $CR^5$, CH, or N; wherein at least one of $X_1$, $X_2$ and $X_4$ in Ring A is N; and $X_3$ is O, S or $NR^6$; or wherein when $X_4$ is $CR^5$ and $X_3$ is $NR^6$, then the $R^5$ and $R^6$ may be taken together to form a 5 to 6-membered heterocyclyl ring fused to Ring A, which heterocyclyl may optionally contain an additional heteroatom selected from N, O and S; said fused heterocyclyl may additionally contain a carbonyl or a —$S(O)_2$ directly adjacent to a heteroatom therein; and may be further substituted with one or two substituents selected from the group consisting of —$CH_3$ and halo; $R^1$, $R^2$, $R^4$, $R^5$ and $R^6$ are as hereinabove defined.

A further embodiment is a compound according to formula (III):

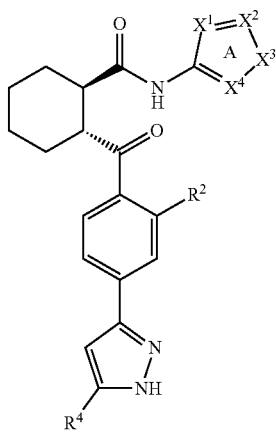

or a pharmaceutically acceptable salt thereof; wherein $X^1$ is CH or $CR^5$; $X^2$ is N; $X^3$ is O, S, or $NR^6$; $X^4$ is CH or $CR^5$; $R^2$ is —H or F; $R^5$ is —S(O)$_2$NR'R", —SO$_2$CH$_3$; —C(O)NR'R", —CN, C$_1$-C$_2$ alkoxy, C$_1$-C$_2$ haloalkoxy or C$_1$-C$_2$ haloalkyl; $R^6$ is H, —CH$_3$ or —CH$_2$CH$_3$; and each R' and R" is independently —H or —CH$_3$; or wherein when $X_4$ is $CR^5$ and $X_3$ is $NR^6$, then the $R^5$ and $R^6$ may be taken together to form a 5 to 6-membered heterocyclyl ring fused to Ring A, which heterocyclyl may optionally contain an additional heteroatom selected from N, O and S; said fused heterocyclyl may additionally contain a carbonyl or a —S(O)$_2$ directly adjacent to a heteroatom therein; and may be further substituted with one or two substituents selected from the group consisting of —CH$_3$ and halo; and $R^4$ is as hereinabove defined.

A further embodiment is a compound according to formula (III) or a pharmaceutically acceptable salt thereof; wherein $X^1$ is CH or $CR^5$; $X^2$ is N; $X^3$ is O, S, or $NR^6$; $X^4$ is CH or $CR^5$; $R^2$ is —H or F; $R^5$ is —S(O)$_2$NR'R", —SO$_2$CH$_3$; —C(O)NR'R", —CN, C$_1$-C$_2$ alkoxy, C$_1$-C$_2$ haloalkoxy or C$_1$-C$_2$ haloalkyl; $R^6$ is H, —CH$_3$ or —CH$_2$CH$_3$; and each R' and R" is independently —H or —CH$_3$; and $R^4$ is as hereinabove defined.

The compound according to formula (III), as defined hereinabove wherein one of $X^1$ is CH, $X^2$ is N and $X^3$ is $NR^6$; and $R^6$ is as hereinabove defined.

A further embodiment is a compound according to formula (III), as defined hereinabove, wherein $R^5$ is —S(O)$_2$CH$_3$, —CHF$_2$ or —OCHF$_2$.

A further embodiment is a compound according to formula (III), as defined hereinabove, wherein $R^5$ is —S(O)$_2$NH$_2$, —C(O)NH$_2$ or —CN; and $R^6$ is —H or —CH$_3$.

The compound according to formula (III), as defined hereinabove wherein one of $X^1$ is CH, $X^2$ is N and $X^3$ is $NR^6$; and $R^6$ is as hereinabove defined.

One embodiment is a compound according to formula (IV):

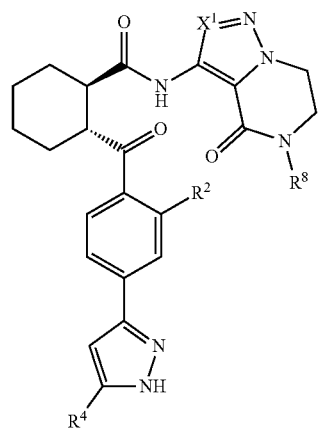

or a pharmaceutically acceptable salt thereof, wherein $X^1$ is CH or $CR^5$; $R^5$, if present, is —CH$_3$; $R^2$ is —H or —F; $R^4$ is —H or —CH$_3$; and $R^8$ is —H or CH$_3$.

Another embodiment is a compound according to formula (V):

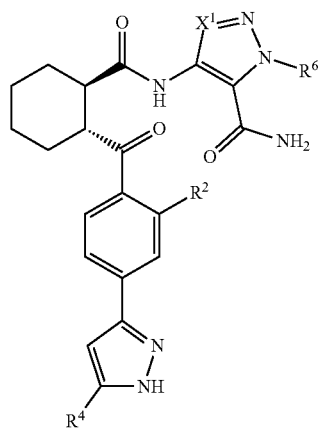

or a pharmaceutically acceptable salt thereof, wherein $X^1$ is CH or $CR^5$; $R^2$ is —H or —F; $R^4$ is —H or —CH$_3$; $R^5$, if present, is —CH$_3$; and $R^6$ is —H or —CH$_3$; provided that $R^5$ and $R^6$ are not both —CH$_3$ at the same time.

A further embodiment is a compound according to formula (VI):

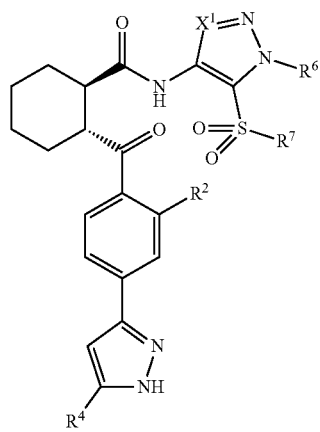

or a pharmaceutically acceptable salt, wherein $X^1$ is CH or $CR^5$; $R^2$ is —H or —F; $R^4$ is —H or —$CH_3$; $R^5$, if present, is —$CH_3$; and $R^6$ is —H or —$CH_3$; $R^7$ is —$CH_3$ or —NR'R''; and each R' and R'' is independently —H or —$CH_3$; provided that $R^5$ and $R^6$ are not both —$CH_3$ at the same time.

Another embodiment is a compound according to formula (VII):

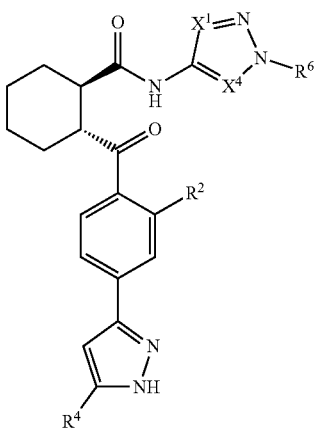

or a pharmaceutically acceptable salt, wherein one of $X^1$ and $X^4$ is CH, and the other is $CR^5$; $R^2$ is —H or —F; $R^4$ is —H or —$CH_3$; $R^5$ is —$CH_3$ or $C_1$-haloalkyl; and $R^6$ is —H or —$CH_3$; provided that the total number of $R^5$ and $R^6$ substituents in the A ring which is alkyl is 0 or 1.

In one aspect, for any one of formulae (I), (II), (III), (IV), (V), (VI) or (VII), or a pharmaceutically acceptable salt thereof, $R^1$ is —H.

In one aspect, for a compound of formula (I), or a pharmaceutically acceptable salt thereof, $R^2$ and $R^3$ are each independently —F or —H. In another aspect for any of formulae (I), (II), (III), (IV), (V), (VI) or (VII), or a pharmaceutically acceptable salt thereof, $R^2$ is —H or —F and $R^3$ is —H. In a further aspect, for any of formulae (I), (II), (III), (IV), (V), (VI) or (VII), or a pharmaceutically acceptable salt thereof, $R^2$ is —H and $R^3$ is —H.

In one aspect, for any one of formulae (I), (II), (III), (IV), (V), (VI) or (VII), or a pharmaceutically acceptable salt thereof, $R^4$ is —H. In another aspect for any one of to formulae (I), (II), (III), (IV), (V), (VI) or (VII), or a pharmaceutically acceptable salt thereof, $R^4$ is —$CH_3$.

In one aspect, for any one of formulae (I), (II), (III), (IV), (V), (VI) or (VII), or a pharmaceutically acceptable salt thereof, $R^1$ is —H; $R^2$ and $R^3$ are both —H; and $R^4$ is —H or —$CH_3$.

In one aspect for any one of formulae (II), (III) or (VII), or a pharmaceutically acceptable salt thereof, $X^1$ is CH or $CR^5$. In another aspect of this embodiment, $X^4$ is $CR^5$.

In one aspect, for any one of formulae (I), (II) or (III), or a pharmaceutically acceptable salt thereof, Ring A is optionally and independently substituted pyrazole, triazole, oxazole, thiazole, oxadiazole or thiadiazole.

In one aspect, for any of formulae (II) or (III), or a pharmaceutically acceptable salt thereof, one of $X^2$ is N and $X^3$ is $NR^6$.

In one aspect, for any of formulae (I), (II), (III), (V) or (VII), or a pharmaceutically acceptable salt thereof, $R^5$ is —$S(O)_2NH_2$, —$C(O)NH_2$ or —CN; and $R^6$ is —H or —$CH_3$. In one aspect, for any of formulae (I), (II), (III), (V) or (VII), or a pharmaceutically acceptable salt thereof, $R^5$ is —$S(O)_2CH_3$, —$CHF_2$ or —$OCHF_2$.

In one aspect, for any of formulae (I), (II) or (III), or a pharmaceutically acceptable salt thereof, $X^4$ is $CR^5$ and $X^3$ is $NR^6$ and together the $R^5$ and $R^6$ substituents form a 5 to 6 membered heterocyclyl ring fused to Ring A, selected from:

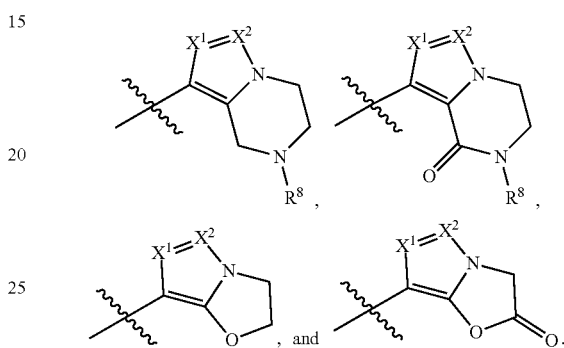

In another aspect $X^1$ is CH and $X^2$ is N in the bicyclic rings formed from ring A and the heterocyclic ring formed by $R^5$ and $R^6$ above.

In another aspect, for any of formulae (I), (II) or (III), or a pharmaceutically acceptable salt thereof, $X^4$ is $CR^5$ and $X^3$ is $NR^6$ and together the $R^5$ and $R^6$ substituents form a 5 to 6 membered heterocyclyl ring fused to Ring A, selected from:

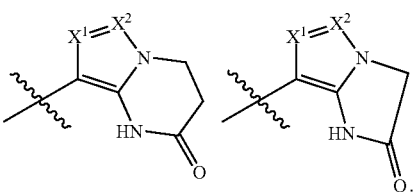

In another aspect $X^1$ is CH and $X^2$ is N in the bicyclic rings formed from ring A and the heterocyclic ring formed by $R^5$ and $R^6$ above.

Any embodiment described herein can be combined with any other suitable embodiment described herein to provide additional embodiments. For example, where one embodiment individually or collectively describes possible groups for $R^1$ and a separate embodiment describeds possible groups for $R^2$, it is understood that these embodiments can be combined to provide an additional embodiment utilizing the possible groups for $R^1$ with is the possible groups for $R^2$. Analogously, the application encompasses any embodiments called out individually for $R^1$, $R^2$, $R^3$, $R^4$, $R^5$, $R^6$, $R^7$, $R^8$, $X^1$, $X^2$, $X^3$, $X^4$, Ring A, R' and R'' in combination with any specific embodiments called out for each of the remaining variables.

Compounds of the application include the following:

| Example No. | Structure | Name |
|---|---|---|
| 1 | (+)-trans or (−)-trans | 1-Methyl-4-[({(1R,2R or 1S,2S)-2-[4-(1H-pyrazol-3-yl)benzoyl]-cyclohexyl}carbonyl)amino]-1H-pyrazole-3-carboxamide |
| 2 | 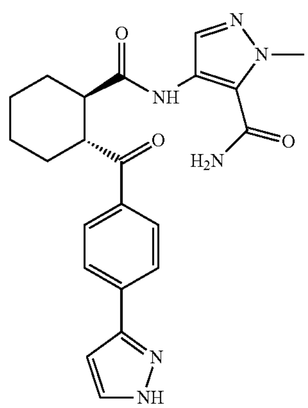 [SMILES: Cn1ncc(NC(=O)[C@@H]2CCCC[C@H]2C(=O)c2ccc(-c3cc[nH]n3)cc2)c1C(N)=O] | 1-Methyl-4-[({(1R,2R)-2-[4-(1H-pyrazol-3-yl)benzoyl]cyclohexyl}carbonyl)amino]-1H-pyrazole-5-carboxamide |
| 3 | 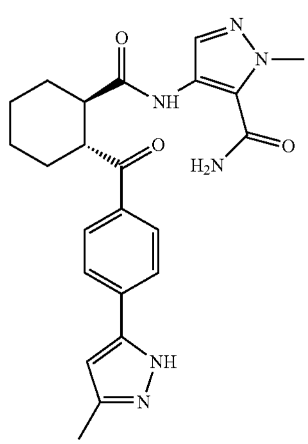 [SMILES: Cc1cc(-c2ccc(C(=O)[C@@H]3CCCC[C@H]3C(=O)Nc3cnn(C)c3C(N)=O)cc2)[nH]n1] | 1-Methyl-4-[({(1R,2R)-2-[4-(3-methyl-1H-pyrazol-5-yl)benzoyl]cyclohexyl}carbonyl)amino]-1H-pyrazole-5-carboxamide |

-continued

| Example No. | Structure | Name |
|---|---|---|
| 4 | 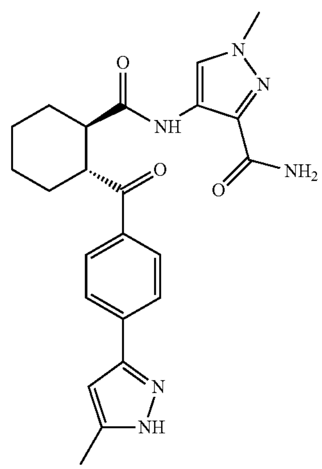 [SMILES: Cc1cc(-c2ccc(C(=O)[C@@H]3CCCC[C@H]3C(=O)Nc3cn(C)nc3C(N)=O)cc2)n[nH]1] | 1-Methyl-4-[({(1R,2R)-2-[4-(3-methyl-1H-pyrazol-5-yl)benzoyl]cyclohexyl}carbonyl)amino]-1H-pyrazole-3-carboxamide |
| 5a | (−)-trans | (1S,2S or 1R,2R)-N-(3-Cyano-1-methyl-1H-pyrazol-4-yl)-2-[4-(3-methyl-1H-pyrazol-5-yl)benzoyl]cyclohexanecarboxamide |
| 5b | (+)-trans | (1R,2R or 1S,2S)-N-(3-Cyano-1-methyl-1H-pyrazol-4-yl)-2-[4-(3-methyl-1H-pyrazol-5-yl)benzoyl]cyclohexanecarboxamide |

-continued
| Example No. | Structure | Name |
|---|---|---|
| 6 | 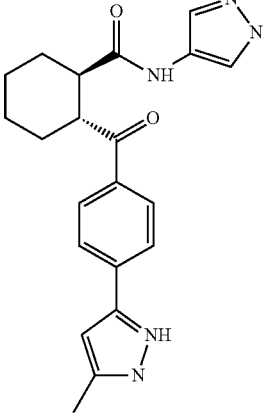 | (1R,2R)-2-[4-(3-Methyl-1H-pyrazol-5-yl)benzoyl]-N-(1H-pyrazol-4-yl)cyclohexanecarboxamide |
| 7 | 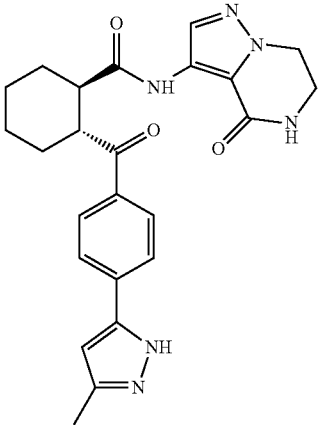 [SMILES: Cc1cc(-c2ccc(C(=O)[C@@H]3CCCC[C@H]3C(=O)Nc3cnn4c3C(=O)NCC4)cc2)[nH]n1] | (1R,2R)-2-[4-(3-Methyl-1H-pyrazol-5-yl)benzoyl]-N-(4-oxo-4,5,6,7-tetrahydropyrazolo[1,5-a]pyrazin-3-yl)cyclohexanecarboxamide |
| 8 | 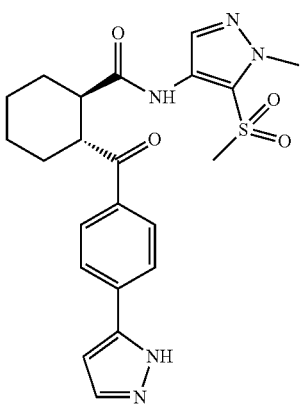 [SMILES: Cn1ncc(NC(=O)[C@@H]2CCCC[C@H]2C(=O)c2ccc(-c3ccn[nH]3)cc2)c1S(C)(=O)=O] | ((1R,2R)-N-[1-Methyl-5-(methylsulfonyl)-1H-pyrazol-4-yl]-2-[4-(1H-pyrazol-5-yl)benzoyl]cyclohexanecarboxamide |

-continued

| Example No. | Structure | Name |
|---|---|---|
| 9 | 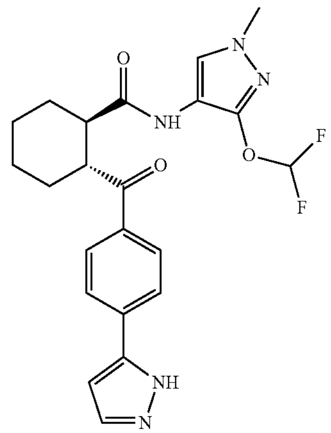 [SMILES: Cn1cc(NC(=O)[C@@H]2CCCC[C@H]2C(=O)c2ccc(-c3ccn[nH]3)cc2)c(OC(F)F)n1] | (1R,2R)-N-[3-(Difluoromethoxy)-1-methyl-1H-pyrazol-4-yl]-2-[4-(1H-pyrazol-5-yl)benzoyl]cyclohexanecarboxamide |
| 10 | 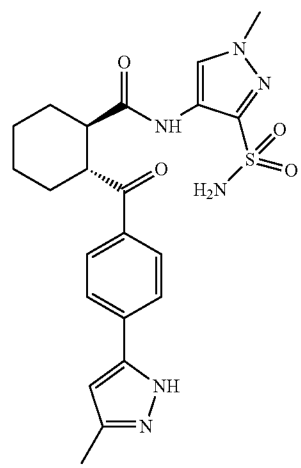 [SMILES: Cc1cc(-c2ccc(C(=O)[C@@H]3CCCC[C@H]3C(=O)Nc3cn(C)nc3S(N)(=O)=O)cc2)[nH]n1] | (1R,2R)-2-[4-(3-Methyl-1H-pyrazol-5-yl)benzoyl]-N-(1-methyl-3-sulfamoyl-1H-pyrazol-4-yl)cyclohexanecarboxamide |
| 11 | 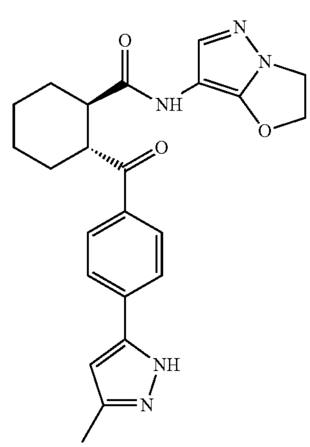 [SMILES: Cc1cc(-c2ccc(C(=O)[C@@H]3CCCC[C@H]3C(=O)Nc3cnn4c3OCC4)cc2)[nH]n1] | (1R,2R)-N-(2,3-Dihydropyrazolo[5,1-b][1,3]oxazol-7-yl)-2-[4-(3-methyl-1H-pyrazol-5-yl)benzoyl]cyclohexanecarboxamide |

-continued

| Example No. | Structure | Name |
|---|---|---|
| 12 | 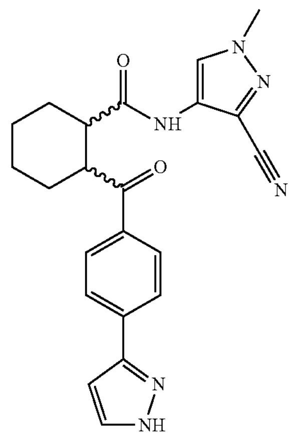 | (1R,2R or 1S,2S)-N-(3-Cyano-1-methyl-1H-pyrazol-4-yl)-2-[4-(1H-pyrazol-3-yl)benzoyl]cyclohexanecarboxamide<br><br>(−)-trans |
| 13 | 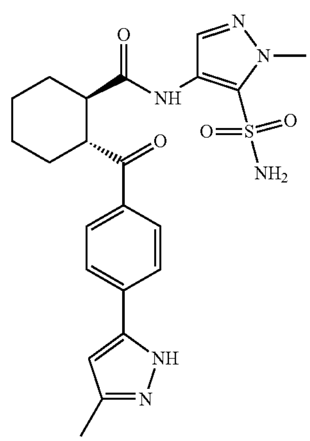 [SMILES: Cc1cc(-c2ccc(C(=O)[C@@H]3CCCC[C@H]3C(=O)Nc3cnn(C)c3S(N)(=O)=O)cc2)[nH]n1] | (1R,2R)-2-[4-(3-Methyl-1H-pyrazol-5-yl)benzoyl]-N-(1-methyl-5-sulfamoyl-1H-pyrazol-4-yl)cyclohexanecarboxamide |
| 14 | 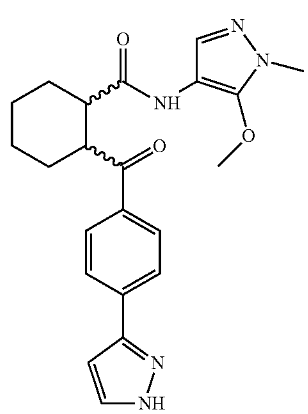 | (1R,2R and 1S,2S)-N-(5-Methoxy-1-methyl-1H-pyrazol-4-yl)-2-[4-(1H-pyrazol-3-yl)benzoyl]cyclohexanecarboxamide<br><br>(±)-trans |

-continued

| Example No. | Structure | Name |
|---|---|---|
| 15 | 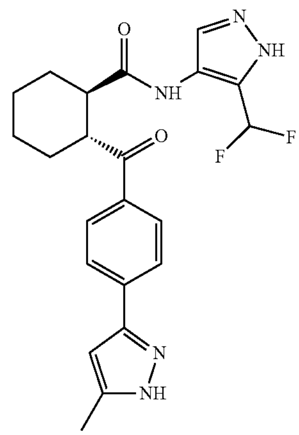 [SMILES: Cc1cc(-c2ccc(C(=O)[C@@H]3CCCC[C@H]3C(=O)Nc3cn[nH]c3C(F)F)cc2)n[nH]1] | (1R,2R)-N-[5-(Difluoromethyl)-1H-pyrazol-4-yl]-2-[4-(5-methyl-1H-pyrazol-3-yl)benzoyl]cyclohexanecarboxamide |
| 16 | 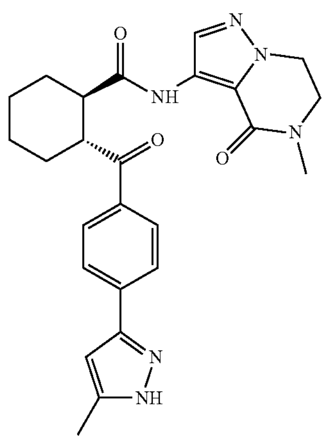 [SMILES: Cc1cc(-c2ccc(C(=O)[C@@H]3CCCC[C@H]3C(=O)Nc3cnn4c3C(=O)N(C)CC4)cc2)n[nH]1] | (1R,2R)-N-(5-Methyl-4-oxo-4,5,6,7-tetrahydropyrazolo[1,5-a]pyrazin-3-yl)-2-[4-(5-methyl-1H-pyrazol-3-yl)benzoyl]cyclohexanecarboxamide |
| 17 | 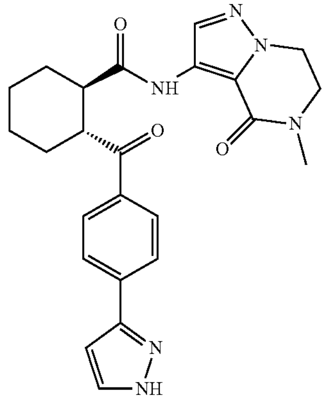 [SMILES: CN1CCn2ncc(NC(=O)[C@@H]3CCCC[C@H]3C(=O)c3ccc(-c4cc[nH]n4)cc3)c2C1=O] | (1R,2R)-N-(5-Methyl-4-oxo-4,5,6,7-tetrahydropyrazolo[1,5-a]pyrazin-3-yl)-2-[4-(1H-pyrazol-3-yl)benzoyl]cyclohexanecarboxamide |

-continued

| Example No. | Structure | Name |
| --- | --- | --- |
| 18a | 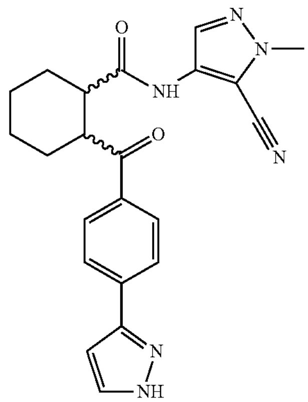 | (1R,2R or 1S,2S)-N-(5-Cyano-1-methyl-1H-pyrazol-4-yl)-2-[4-(1H-pyrazol-3-yl)benzoyl]cyclohexanecarboxamide<br><br>(−)-trans |
| 18b | 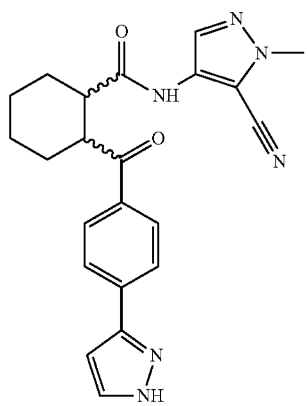 | (1S,2S or 1R,2R)-N-(5-Cyano-1-methyl-1H-pyrazol-4-yl)-2-[4-(1H-pyrazol-3-yl)benzoyl]cyclohexanecarboxamide<br><br>(+)-trans |
| 19 | 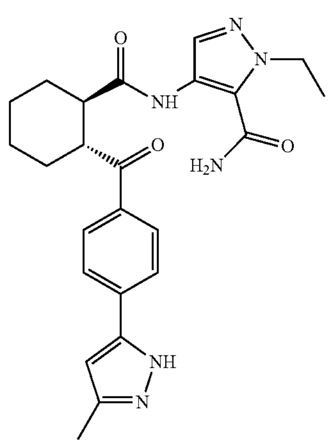 [SMILES: CCn1ncc(NC(=O)[C@@H]2CCCC[C@H]2C(=O)c2ccc(-c3cc(C)n[nH]3)cc2)c1C(N)=O] | 1-Ethyl-4-[({(1R,2R)-2-[4-(3-methyl-1H-pyrazol-5-yl)benzoyl]cyclohexyl}-carbonyl)amino]-1H-pyrazole-5-carboxamide |

| Example No. | Structure | Name |
|---|---|---|
| 20 | 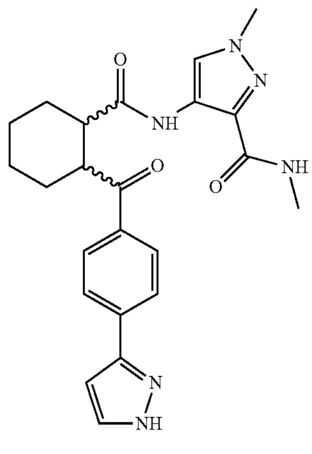 | N,1-Dimethyl-4-[({(1R,2R and 1S,2S)-2-[4-(1H-pyrazol-3-yl)benzoyl]cyclohexyl}-carbonyl)amino]-1H-pyraozle-3-carboxamide |
| | (±)-trans | |
| 21 | 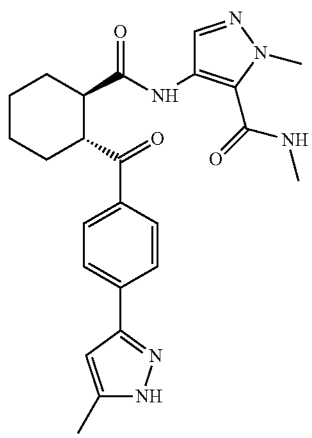 [SMILES: CNC(=O)c1c(NC(=O)[C@@H]2CCCC[C@H]2C(=O)c2ccc(-c3cc(C)[nH]n3)cc2)cnn1C] | N,1-Dimethyl-4-[({(1R,2R)-2-[4-(5-methyl-1H-pyrazol-3-yl)benzoyl]-cyclohexyl}carbonyl)amino]-1H-pyrazole-5-carboxamide |
| 22 | 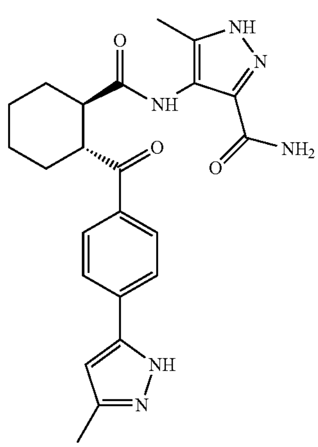 [SMILES: Cc1cc(-c2ccc(C(=O)[C@@H]3CCCC[C@H]3C(=O)Nc3c(C(N)=O)n[nH]c3C)cc2)[nH]n1] | 5-Methyl-4-[({(1R,2R)-2-[4-(3-methyl-1H-pyrazol-5-yl)benzoyl]-cyclohexyl}carbonyl)amino]-1H-pyrazole-3-carboxamide |

-continued

| Example No. | Structure | Name |
|---|---|---|
| 23 | 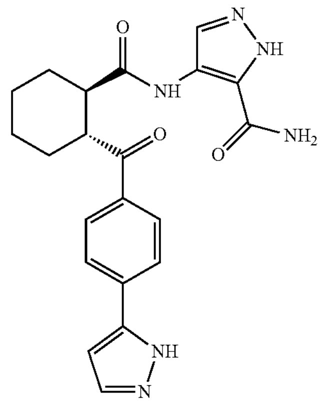 [SMILES: NC(=O)c1[nH]ncc1NC(=O)[C@@H]1CCCC[C@H]1C(=O)c1ccc(-c2ccn[nH]2)cc1] | 4-[({(1R,2R)-2-[4-(1H-Pyrazol-5-yl)benzoyl]cyclohexyl}carbonyl)amino]-1H-pyrazole-5-carboxamide |
| 24 | 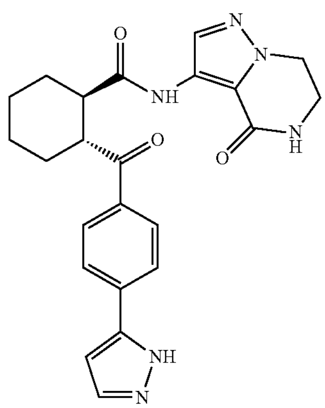 [SMILES: O=C1NCCn2ncc(NC(=O)[C@@H]3CCCC[C@H]3C(=O)c3ccc(-c4ccn[nH]4)cc3)c21] | (1R,2R)-N-(4-Oxo-4,5,6,7-tetrahydropyrazolo[1,5-a]pyrazin-3-yl)-2-[4-(1H-pyrazol-5-yl)benzoyl]cyclohexanecarboxamide |
| 25 | 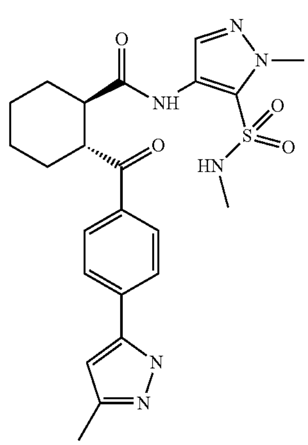 [SMILES: CNS(=O)(=O)c1c(NC(=O)[C@@H]2CCCC[C@H]2C(=O)c2ccc(-c3cc(C)n[nH]3)cc2)cnn1C] | (1R,2R)-N-[1-Methyl-5-(methylsulfamoyl)-1H-pyrazol-4-yl]-2-[4-(3-methyl-1H-pyrazol-5-yl)benzoyl]cyclohexanecarboxamide |

| Example No. | Structure | Name |
|---|---|---|
| 26 | 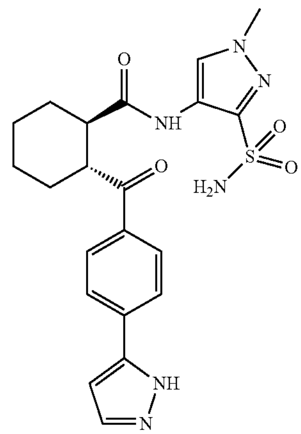 [SMILES: Cn1cc(NC(=O)[C@@H]2CCCC[C@H]2C(=O)c2ccc(-c3ccn[nH]3)cc2)c(S(N)(=O)=O)n1] | (1R,2R)-N-(1-Methyl-3-sulfamoyl-1H-pyrazol-4-yl)-2-[4-(1H-pyrazol-5-yl)benzoyl]cyclohexanecarboxamide |
| 27 | 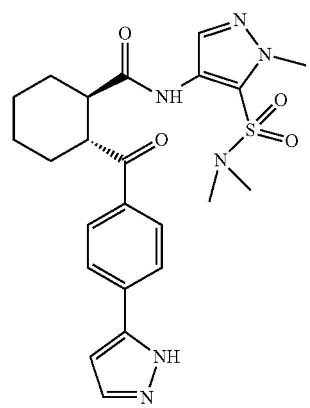 [SMILES: CN(C)S(=O)(=O)c1c(NC(=O)[C@@H]2CCCC[C@H]2C(=O)c2ccc(-c3ccn[nH]3)cc2)cnn1C] | (1R,2R)-N-[5-(Dimethylsulfamoyl)-1-methyl-1H-pyrazol-4-yl]-2-[4-(1H-pyrazol-5-yl)benzoyl]cyclohexanecarboxamide |
| 28 | 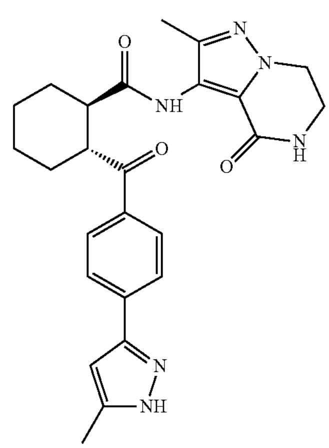 [SMILES: Cc1cc(-c2ccc(C(=O)[C@@H]3CCCC[C@H]3C(=O)Nc3c(C)nn4c3C(=O)NCC4)cc2)n[nH]1] | (1R,2R)-N-(2-Methyl-4-oxo-4,5,6,7-tetrahydropyrazolo[1,5-a]pyrazin-3-yl)-2-[4-(5-methyl-1H-pyrazol-3-yl)benzoyl]cyclohexanecarboxamide |

-continued

| Example No. | Structure | Name |
|---|---|---|
| 29 | 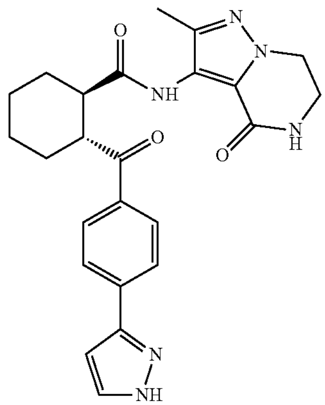 [SMILES: Cc1nn2c(c1NC(=O)[C@@H]1CCCC[C@H]1C(=O)c1ccc(-c3cc[nH]n3)cc1)C(=O)NCC2] | (1R,2R)-N-(2-Methyl-4-oxo-4,5,6,7-tetrahydropyrazolo[1,5-a]pyrazin-3-yl)-2-[4-(1H-pyrazol-5-yl)benzoyl]cyclohexanecarboxamide |
| 30 | 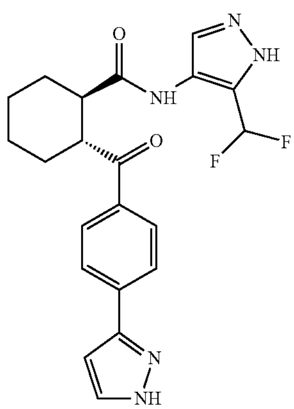 [SMILES: O=C(Nc1cn[nH]c1C(F)F)[C@@H]1CCCC[C@H]1C(=O)c1ccc(-c2cc[nH]n2)cc1] | (1R,2R)-N-[5-(Difluoromethyl)-1H-pyrazol-4-yl]-2-[4-(1H-pyrazol-3-yl)benzoyl]cyclohexanecarboxamide |
| 31 | 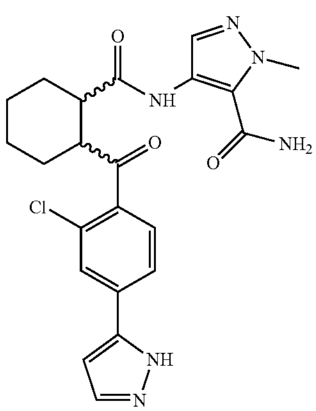 | 4-[({(1R,2R and 1S,2S)-2-[2-Chloro-4-(1H-pyrazol-5-yl)benzoyl]cyclohexyl}carbonyl)amino]-1-methyl-1H-pyrazole-5-carboxamide |

(±)-trans

-continued
| Example No. | Structure | Name |
|---|---|---|
| 32 | 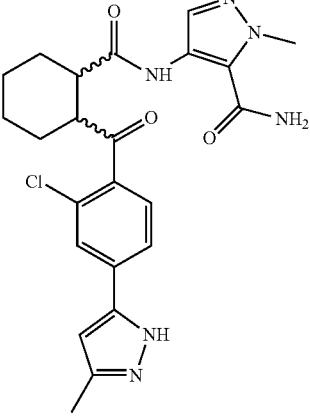 (±)-trans | 4-[({(1R,2R and 1S,2S)-2-[2-Chloro-4-(3-methyl-1H-pyrazol-5-yl)benzoyl]cyclohexyl}carbonyl)amino]-1-methyl-1H-pyrazole-5-carboxamide |
| 33 | 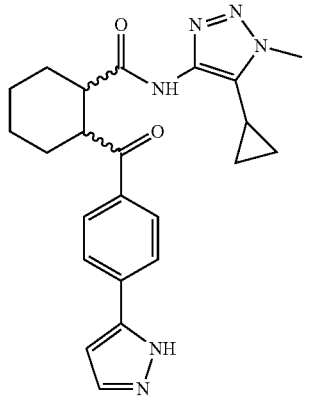 (±)-trans | (1R,2R and 1S,2S)-N-(5-Cyclopropyl-1-methyl-1H-1,2,3-triazol-4-yl)-2-[4-(1H-pyrazol-5-yl)benzoyl]cyclohexanecarboxamide |
| 34 | 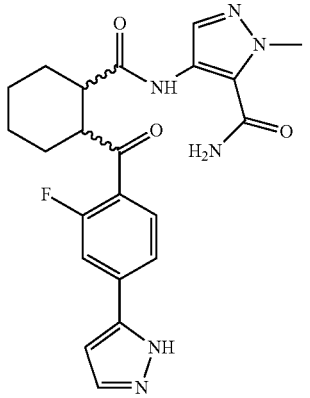 (−)-trans or (+)-trans | 4-[({(1R,2R or 1S,2S)-2-[2-Fluoro-4-(1H-pyrazol-5-yl)benzoyl]cyclohexyl}carbonyl)amino]-1-methyl-1H-pyrazole-5-carboxamide |

| Example No. | Structure | Name |
|---|---|---|
| 35 | 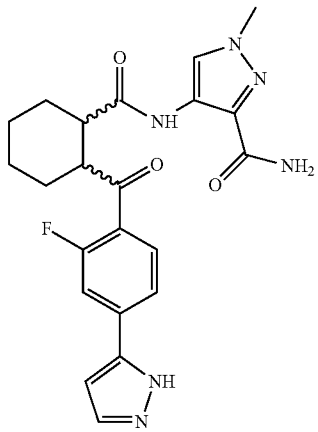 | 4-[({(1R,2R or 1S,2S)-2-[2-Fluoro-4-(1H-pyrazol-5-yl)benzoyl]cyclohexyl}carbonyl)amino]-1-methyl-1H-pyrazole-3-carboxamide<br><br>(−)-trans or (+)-trans |
| 36 | 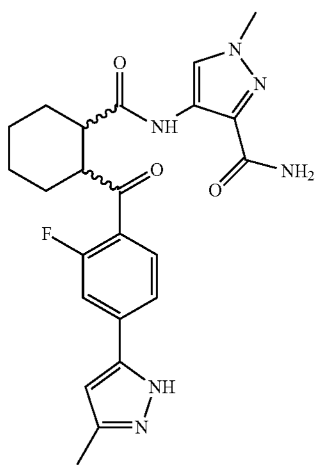 | 4-[({(1R,2R or 1S,2S)-2-[2-Fluoro-4-(3-methyl-1H-pyrazol-5-yl)benzoyl]cyclohexyl}carbonyl)amino]-1-methyl-1H-pyrazole-3-carboxamide<br><br>(−)-trans or (+)-trans |
| 37 | 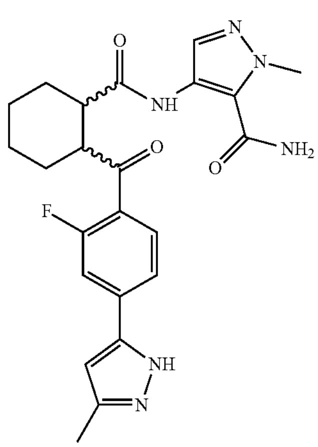 | 4-[({(1R,2R or 1S,2S)-2-[2-Fluoro-4-(3-methyl-1H-pyrazol-5-yl)benzoyl]cyclohexyl}carbonyl)amino]-1-methyl-1H-pyrazole-5-carboxamide<br><br>(+)-trans |

-continued

| Example No. | Structure | Name |
|---|---|---|
| 38 | 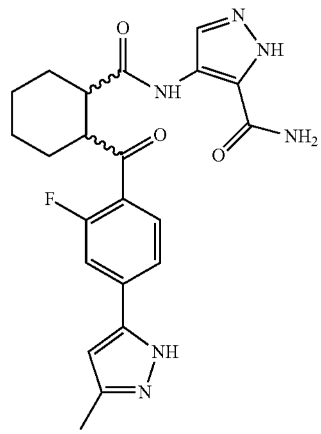 | 4-[({(1R,2R or 1S,2S)-2-[2-Fluoro-4-(3-methyl-1H-pyrazol-5-yl)benzoyl]cyclohexyl}carbonyl)amino]-1H-pyrazole-5-carboxamide<br><br>(−)-trans or (+)-trans |
| 39 | 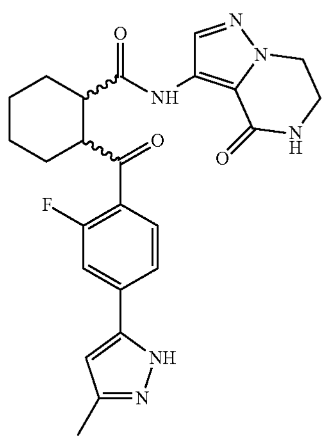 | (1R,2R or 1S,2S)-2-[2-Fluoro-4-(3-methyl-1H-pyrazol-5-yl)benzoyl]-N-(4-oxo-4,5,6,7-tetrahydropyrazolo[1,5-a]pyrazin-3-yl)cyclohexanecarboxamide<br><br>(−)-trans or (+)-trans |
| 40 | 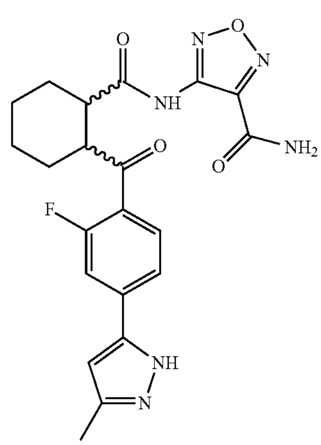 | 4-[({(1R,2R or 1S,2S)-2-[2-Fluoro-4-(3-methyl-1H-pyrazol-5-yl)benzoyl]cyclohexyl}carbonyl)amino]-1,2,5-oxadiazole-3-carboxamide<br><br>(−)-trans or (+)-trans |

-continued
| Example No. | Structure | Name |
|---|---|---|
| 41 | 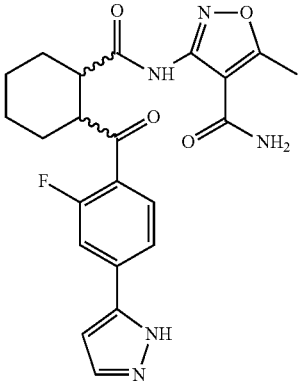 (−)-trans or (+)-trans | 3-[({(1R,2R or 1S,2S)-2-[2-Fluoro-4-(1H-pyrazol-5-yl)benzoyl]cyclohexyl}carbonyl)amino]-5-methyl-1,2-oxazole-4-carboxamide |
| 42 | 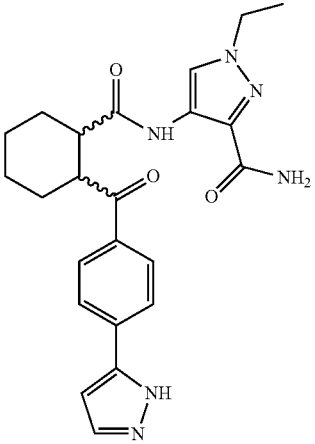 (±)-trans | 1-Ethyl-4-[({(1R,2R and 1S,2S)-2-[4-(1H-pyrazol-5-yl)benzoyl]cyclohexyl}carbonyl)amino]-1H-pyrazole-3-carboxamide |
| 43 | 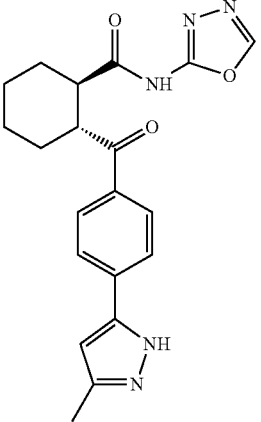 [SMILES: Cc1cc(-c2ccc(C(=O)[C@@H]3CCCC[C@H]3C(=O)Nc3nnco3)cc2)[nH]n1] | (1R,2R)-2-[4-(3-Methyl-1H-pyrazol-5-yl)benzoyl]-N-(1,3,4-oxadiazol-2-yl)cyclohexanecarboxamide |

-continued

| Example No. | Structure | Name |
| --- | --- | --- |
| 44 | (±)-trans | (1R,2R and 1S,2S)-N-(3-Methyl-1,2-oxazol-5-yl)-2-[4-(1H-pyrazol-5-yl)benzoyl]cyclohexanecarboxamide |
| 45 | (±)-trans | (1R,2R and 1S,2S)-N-(4-Methyl-1,3-oxazol-2-yl)-2-[4-(1H-pyrazol-5-yl)benzoyl]cyclohexanecarboxamide |
| 46 | (±)-trans | (1R,2R and 1S,2S)-N-(5-Cyano-1-methyl-1H-pyrazol-4-yl)-2-[4-(3-methyl-1H-pyrazol-5-yl)benzoyl]cyclohexanecarboxamide |

-continued

| Example No. | Structure | Name |
| --- | --- | --- |
| 47 | 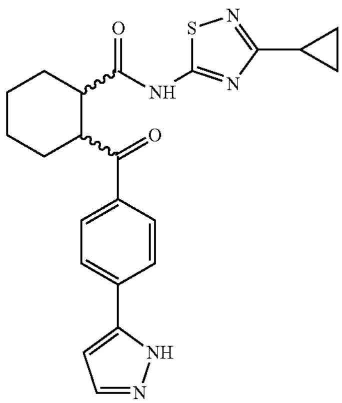 | (1R,2R and 1S,2S)-N-(3-Cyclopropyl-1,2,4-thiadiazol-5-yl)-2-[4-(1H-pyrazol-5-yl)benzoyl]cyclohexanecarboxamide<br>(±)-trans |
| 48 | 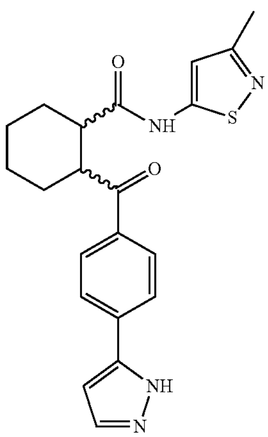 | (1R,2R and 1S,2S)-N-(3-Methyl-1,2-thiazol-5-yl)-2-[4-(1H-pyrazol-5-yl)benzoyl]cyclohexanecarboxamide<br>(±)-trans |
| 49 | 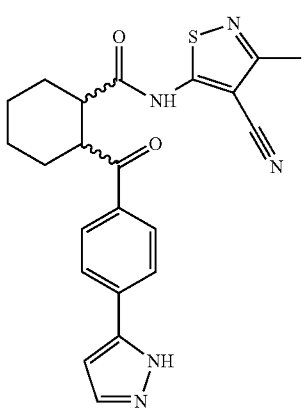 | (1R,2R and 1S,1S)-N-(4-Cyano-3-methyl-1,2-thiazol-5-yl)-2-[4-(1H-pyrazol-5-yl)benzoyl]cyclohexanecarboxamide<br>(±)-trans |

In one aspect, the compound of formula (I) is selected from the group of examples 1-49 shown above, or a pharmaceutically acceptable salt thereof. It shall be noted that any one of these specific compounds may be disclaimed from any of the herein mentioned embodiments.

Another aspect is a product obtainable by any of the processes or examples disclosed herein.

Listed below are definitions of various terms used in the specification and claims to describe some terms used herein.

For the avoidance of doubt it is to be understood that where in this specification a group is qualified by "defined above" the said group encompasses the first occurring and broadest definition as well as each and all of the other definitions for that group.

For the avoidance of doubt it is to be understood that in this specification "$C_1$-$C_6$" means a carbon group having 1, 2, 3, 4, 5 or 6 carbon atoms, "$C_1$-$C_4$" means a carbon is group having 1, 2, 3 or 4 carbon atoms, "$C_1$-$C_3$" means a carbon group having 1, 2 or 3 carbon atoms, and "$C_1$-$C_2$" means a carbon group having 1 or 2 carbon atoms.

In this specification, unless stated otherwise, the term "alkyl" includes both straight and branched chain alkyl groups and may be, but is not limited to, methyl, ethyl, n-propyl, i-propyl, n-butyl, i-butyl, s-butyl, t-butyl, n-pentyl, i-pentyl, t-pentyl, neo-pentyl, n-hexyl, i-hexyl or t-hexyl.

In this specification, unless stated otherwise, the term "haloalkyl" means an alkyl group containing one or more halogen atoms, and includes, but is not limited to, monofluoromethyl, difluoromethyl, trifluoromethyl, 1-fluoroethyl, 2-fluoroethyl, 2,2-difluoroethyl, 2,2,2-trifluoroethyl, 3-fluoropropyl, 3,3-difluoropropyl or 3,3,3-trifluoroethyl.

In this specification, unless otherwise stated, the term "alkoxy" includes both straight and branched chain alkyl group containing an oxygen atom, which an attachment point of said group being through the oxygen atom. Examples include, but are not limited to, methoxy, ethoxy, propoxy, i-propoxy, butoxy, i-butoxy, s-butoxy, t-butoxy, and the like.

In this specification, unless otherwise stated, the term "haloalkoxy" means an alkoxy group, as described above, wherein one more of the hydrogen atoms on the alkyl portion is substituted with a halogen atom. Examples of this include, but are not limited to, monofluoromethoxy, difluoromethoxy, trifluoromethoxy, 2-fluoroethoxy, 2,2-difluoroethoxy, 2,2,2-trifluoroethoxy, 3-monofluoropropoxy, 3,3-difluoropropoxy and 3,3,3-trifluoropropoxy.

In this specification, unless stated otherwise, the term "halo" refers to fluoro, chloro or bromo.

In this specification, unless stated otherwise, the term "$C_3$-$C_6$ cycloalkyl" means a saturated cyclic alkyl group of 3-6 carbon atoms, and includes, but is not limited to, cyclopropyl, cyclobutyl, cyclopentyl, and cyclohexyl.

In this specification, unless stated otherwise, the term "5 to 6 membered heterocyclyl" refers to a saturated or partially saturated, non-aromatic monocyclic ring containing 5 to 6 ring atoms, of which at least one ring atom is selected from nitrogen, sulfur, and oxygen, and of which a —$CH_2$— group may be optionally replaced by a —C(O)— group. Ring nitrogen atoms may be optionally oxidized to form an N-oxide. Ring sulfur atoms may be optionally oxidized to form S-oxides or sulphones. Said heterocyclyl ring may optionally be substituted with one or two substituents selected from the group consisting of methyl and halo. Examples of a a 5-6 membered heterocyclyl ring includes, but are not limited to pyrrolidinyl, imidazolidinyl, oxazolidine, 4-oxooxazolidinyl, thiazolidinyl, piperidinyl, piperazinyl, 2-oxopiperazinyl, isoxazolidinyl, isothiazolidinyl, pyrazolidinyl, hexahydropyridazinyl, hexahydropyrimidinyl, morpholinyl, thiomorpholinyl, oxazinanyl, 2-oxopyrrolidinyl, 1,3-thiazinanyl and oxo-1,3-thiazolidinyl. In the context of this application, a 5-6 membered heterocyclyl may be fused to Ring A when $X^3$ is $NR^6$ and $X^4$ is $CR^5$ and the $R^5$ and $R^6$ substituents are taken together to form the heterocyclyl. The ring systems described in this paragraph describe only half of the bicyclic ring system, and include the nitrogen atom and carbon atom from Ring A, with $X^1$ and $X^2$ as defined for Formula (I).

For the avoidance of doubt by 'said fused heterocyclyl may additionally contain a carbonyl or a —$S(O)_2$ directly adjacent to a heteroatom therein' in the definition of $R^5$ and $R^6$, it is meant that the ring atom adjacent to a ring heteroatom in the fused heterocycle may be a ring carbon substituted by an oxo or a ring sulphur atom oxidised to an $S(O)_2$ respectively.

In this specification, unless otherwise state, the term "high risk coronary artery disease" as used herein refers to recent acute coronary syndrome (ACS) or by biomarkers to of microvascular and cardiac function. Such biomarkers may include inflammatory biomarkers such as leukotrienes and interleukins, leukocyte counts and/or markers for cardiac and vascular function such as CFR, NT-Pro-BNP and/or TnT.

In this specification, unless otherwise stated, the term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In this specification, unless otherwise stated, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

Compounds of Formulae (I), (II), (III), (IV), (V), (VI) or (VII) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with to amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic is physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Compounds of Formulae (I), (II), (III), (IV), (V), (VI) or (VII) have one or more chiral centers, and it is to be understood that the application encompasses all such stereoisomers, including enantiomers and diastereoisomers. Thus, it is to be understood that, insofar as certain of the compounds of Formulae (I), (II), (III), (IV), (V), (VI) or (VII) may exist in optically active or racemic forms by virtue of one or more asymmetric carbon atoms, the application includes in its definition any such optically active or racemic form which possesses the above-mentioned activity. The present application encompasses all such stereoisomers having activity as herein defined.

The synthesis of optically active forms may be carried out by standard techniques of organic chemistry well known in the art, for example by synthesis from optically active starting materials or by resolution of a racemic form. Racemates may be separated into individual enantiomers using known procedures (see, for example, Advanced Organic Chemistry: 3rd Edition: author J. March, p 104-107). A suitable procedure involves formation of diastereomeric derivatives by reaction of the racemic material with a chiral auxiliary, followed by separation, for example by chromatography, of the diastereomers and then cleavage of the auxiliary species. Similarly, the above-mentioned activity may be evaluated using the standard laboratory techniques referred to hereinafter.

Thus, throughout the specification, where reference is made to the compound of Formulae (I), (II), (III), (IV), (V), (VI) or (VII), it is to be understood that the term compound includes isomers, mixtures of isomers, and stereoisomers that are FLAP inhibitors.

Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different is physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent.

When a specific stereoisomer is provided (whether provided by separation, by chiral synthesis, or by other methods) it is favorably provided substantially isolated from other stereoisomers of the same compound. In one aspect, a mixture containing a particular stereoisomer of a compound of Formulae (I), (II), (III), (IV), (V), (VI) or (VII), may contain less than 30%, particularly less than 20%, and more particularly less than 10% by weight of other stereoisomers of the same compound. In another aspect, a mixture containing a particular stereoisomer of a compound of Formulae (I), (II), (III), (IV), (V), (VI) or (VII), may contain less than 6%, particularly less than 3%, and more particularly less than 2% by weight of other stereoisomers of the compound. In another aspect, a mixture containing a particular stereoisomer of a compound of Formulae (I), (II), (III), (IV), (V), (VI) or (VII), may contain less than 1%, particularly less than 0.5%, and more particularly less than 0.3%, and still more particularly less 0.1% by weight of other stereoisomers of the compound.

It is to be understood that, insofar as certain of the compounds of Formulae (I), (II), (III), (IV), (V), (VI) or (VII), defined above may exist in tautomeric forms, the application includes in its definition any such tautomeric form which possesses the above-mentioned activity. Thus, the disclosure relates to all tautomeric forms of the compounds of Formulae (I), (II), (III), (IV), (V), (VI) or (VII), whether explicitly detailed in the specification or not.

It is also to be understood that certain compounds of Formulae (I), (II), (III), (IV), (V), (VI) or (VII), and pharmaceutically salts thereof, can exist in solvated as well as unsolvated forms such as, for example, hydrated and anhydrous forms. It is to be to understood that the compounds herein encompass all such solvated forms. For the sake of clarity, this includes both solvated (e.g., hydrated) forms of the free form of the compound, as well as solvated (e.g., hydrated) forms of the salt of the compound.

For the sake of clarity, it should be understood that the atoms of the compounds of Formulae (I), (II), (III), (IV), (V), (VI) or (VII), and of any of the examples or embodiments disclosed herein, are intended to encompass all isotopes of the atoms. For example, H (or hydrogen) includes any isotopic form of hydrogen including $^{1}H$, $^{2}H$ (D), and $^{3}H$ (T); C includes any isotopic form of carbon including $^{12}C$, $^{13}C$, and $^{14}C$; O includes any isotopic form of oxygen including $^{16}O$, $^{17}O$ and $^{18}O$; N includes any isotopic form of nitrogen including $^{13}N$, $^{14}N$ and $^{15}N$; P includes any isotopic form of phosphorous including $^{31}P$ and $^{32}P$; S includes any isotopic form of sulfur including $^{32}S$ and $^{35}S$; F includes any isotopic form of fluorine including $^{19}F$ and $^{18}F$; Cl includes any isotopic form of chlorine including $^{35}Cl$, $^{37}Cl$ and $^{36}Cl$; and the like. In one aspect, the compounds of Formulae (I), (Ia), (II), (III), (IV) or (V) include isotopes of the atoms covered therein in amounts corresponding to their naturally occurring abundance. However, in certain instances, it may be desirable to enrich one or more atom in a particular isotope which would normally be present in a lower abundance. For example, $^{1}H$ would normally be present in greater than 99.98% abundance; however, in one aspect, a compound of any formula presented herein may be enriched in $^{2}H$ or $^{3}H$ at one or more positions where H is present. In another aspect, when a compound of any formula presented herein is enriched in a radioactive isotope, for example $^{3}H$ and $^{14}C$, the compound may be useful in drug and/or substrate tissue distribution assays. It is to be understood that the present application encompasses all such isotopic forms.

The present application further provides a process for the preparation of a compound of formula (I) as defined above which comprises reaction Schemes 1-10.

Method of Preparation

Reactions in Schemes 1-10 illustrate synthetic routes to certain molecules of formula (I), wherein $R^1$, $R^2$, $R^3$, $R^4$, and Ring A are as defined in formula (I), $R^9$ is an alkyl group e.g. methyl or ethyl, $L_1$, $L_2$, $L_3$, and $L_4$ are a leaving groups, e.g., Br, I, OTf, and $PG_1$ is a protective group e.g. 2-methyltetrahydro-2H-pyryl.

Scheme 1

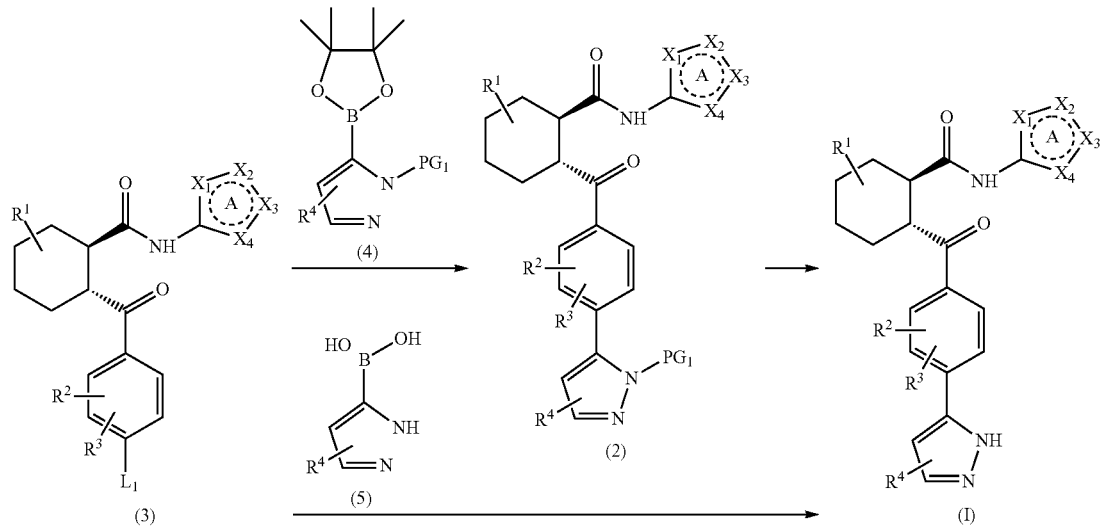

Reactions in Scheme 1 illustrate two synthetic routes to certain molecules of formula (I).

A compound of formula (3) may be reacted with a compound of formula (4) to give a compound of formula (2), or a compound of formula (3) may be reacted with a compound of formula (5) to give a compound of formula (I). Either reaction may be is performed in the presence of a base, e.g. $K_2CO_3$ or $Na_2CO_3$, and may be performed in the temperature interval from rt to reflux in an organic solvent, such as dioxane or DMF, which may be mixed with $H_2O$. The reaction may be catalysed by a palladium reagent, such as $Pd(dtbpf)Cl_2$ or $Pd(dppf)Cl_2$. A compound of formula (2), may be treated with acid e.g. HCl in an organic solvent e.g. MeOH or dioxane optionally in the presence of water, in a temperature interval from 0° C.-10° C., to deliver a compound of formula (I).

Reactions in Scheme 2 illustrate two synthetic routes to certain molecules of formula (I).

A compound of formula (6), may be formed by reacting a compound of formula (7), with an ammonia synthetic equivalent, e.g. $NH_4Cl$, and may be performed in the temperature interval from rt to reflux in an inert organic solvent, such as DMF, EtOAc, dichloroethane or NMP, and in the presence of a base e.g. $Et_3N$, DIPEA or DMAP. The reaction may be facilitated by a coupling reagent, such as HATU, TBTU or T3P. Then, a to compound of formula (6), may be reacted with a compound of formula (8). The reaction may be performed in the presence of a base, e.g. $Cs_2CO_3$ or NaOt-Bu, and may be performed in the temperature interval from rt to reflux in an organic solvent, such as dioxane. The reaction may be catalyzed by a suitable Pd reagent, such as or $Pd(dppf)Cl_2$ or $Pd(OAc)_2$ using a suitable ligand e.g. XantPhos, to deliver a compound of formula (I).

Scheme 2

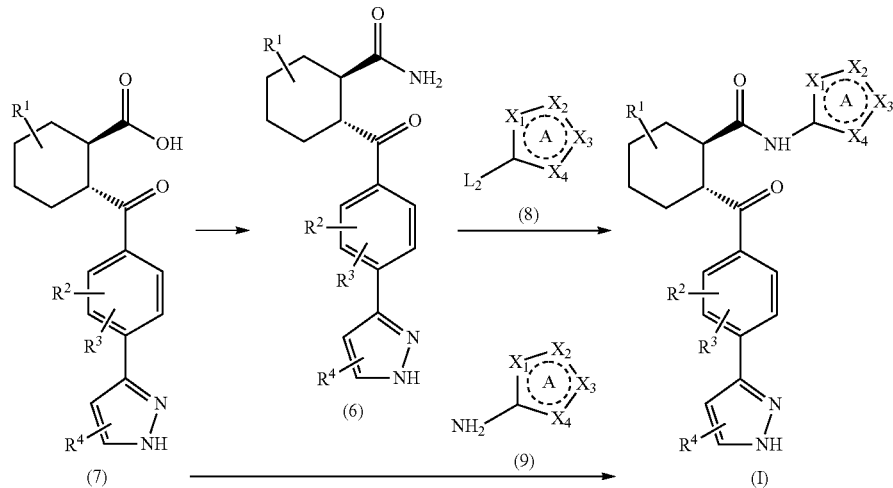

Alternatively, a compound of formula (7), may be reacted with a compound of formula (9), which reaction may be performed in the temperature interval from rt to reflux in an inert organic solvent, such as DMF, EtOAc, dichloroethane or NMP, and in the presence of a base e.g. Et$_3$N, DIPEA or DMAP. The reaction may be facilitated by a coupling reagent, such as HATU, TBTU or T3P to deliver a compound of formula (I).

Scheme 3

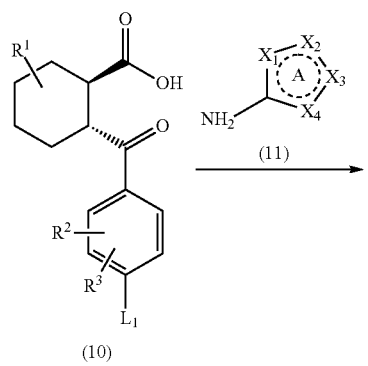

(10)    (11)

-continued

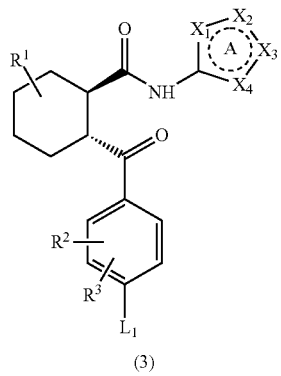

(3)

Reaction in Scheme 3 illustrates a synthetic route to certain molecules of formula (3).

A compound of formula (10), may be reacted with a compound of formula (11), and may be performed in the temperature interval from rt to reflux in an inert organic solvent, such as DMF, EtOAc, dichloroethane or NMP, and in the presence of a base e.g. Et$_3$N, DIPEA or DMAP. The reaction may be facilitated by a coupling reagent, such as HATU, TBTU or T3P to deliver a compound of formula (3).

Scheme 4

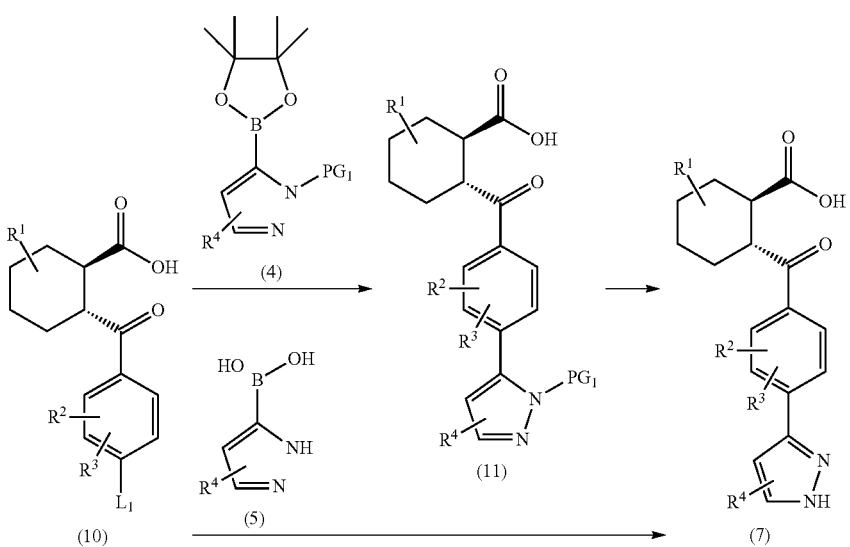

Reactions in Scheme 4 illustrate two synthetic routes to certain molecules of formula (7).

A compound of formula (10) may be reacted with a compound of formula (4) or formula (5). The reaction may be performed under conditions described for the analogous is reactions described in Scheme 1.

Scheme 5

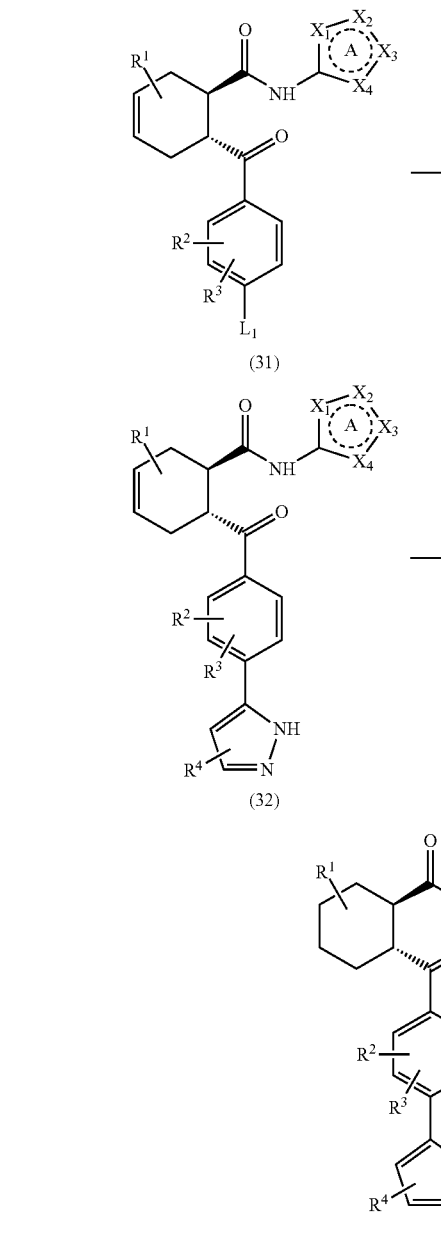

Reactions in Scheme 5 illustrate a synthetic route to certain molecules of formula (I).

A compound of formula (31), may be formed by reacting a compound of formula (13), with a compound of formula (8), (9) or (11), described in Schemes 2 and 3, using the same or similar conditions as described for the reactions of compounds (7) or (10) in Scheme 2 and Scheme 3.

A compound of formula (32), may be formed by reacting a compound of formula (31) with a compound of formula (4) or (5), described in Scheme 1, using the same or to similar conditions as described for the reactions of compound (3) in Scheme 1.

A compound of formula (I) may be formed by reacting either a compound of formula (31) or a compound of formula (32) using the same or similar conditions as described for the reactions transforming a compound of formula (13) to a compound of formula (10) in Scheme 5.

Scheme 6

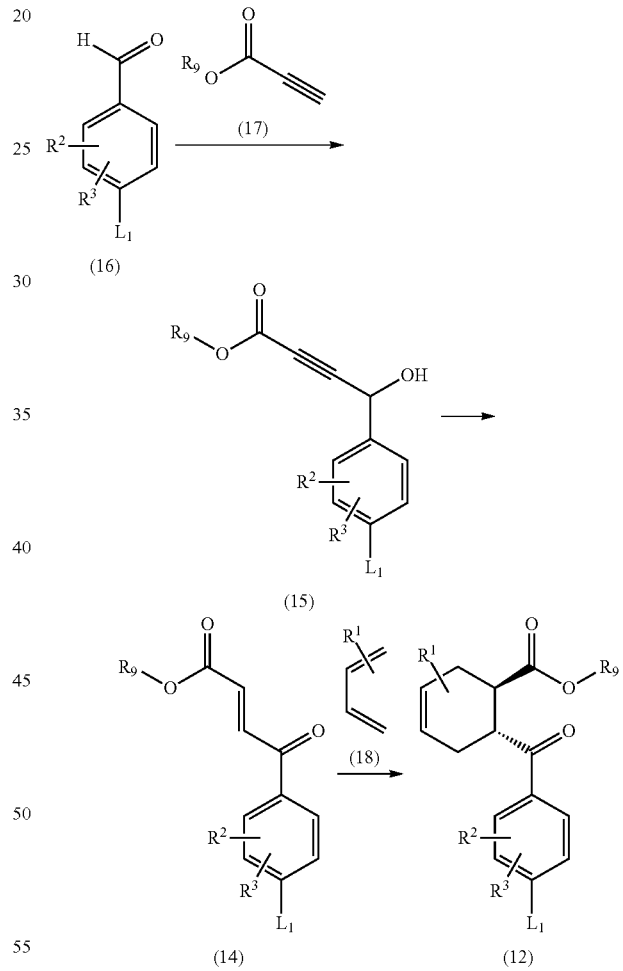

Reactions in Scheme 6 illustrate a synthetic route to certain molecules of formula (12).

A compound of formula (15), may be formed by reacting a compound of formula (16), with a preformed metallo anion e.g. a lithium anion, of a compound of formula (17).

The reaction may be performed in an organic solvent such as e.g. THF, and may be performed at a suitable temperature such as below −70° C. It may also be formed using synthetic procedures described in the literature e.g. *Synlett* 12 (2004) 2165-2166 or *Tetrahedron* 67 (2011) 3881-3886.

A compound of formula (14) may be formed by treating a compound of formula (15) with a base, e.g. Et₃N, and may be performed in an organic solvent e.g. dioxan. The reaction may be performed at elevated temperatures e.g. 60° C. A compound of formula (14) may be obtained commercially or may be formed in analogy to synthetic procedures analogous to those described in the literature e.g. *Synlett* 12 (2004) 2165-2166 or *J. Org. Chem.* 71 (2006) 6254-6257.

A compound of formula (12) may be formed by reacting a compound of formula (14), with a compound of formula (18). The reaction may be performed in an inert organic solvent e.g. toluene and may be performed in a temperature interval of rt to 220° C. and may optionally be performed in the presence of a stabilizer e.g. hydroquinon or may be performed in a temperature interval of −30° C. to rt, optionally in the presence of a catalyst, e.g. a Lewis is acid such as $AlCl_3$.

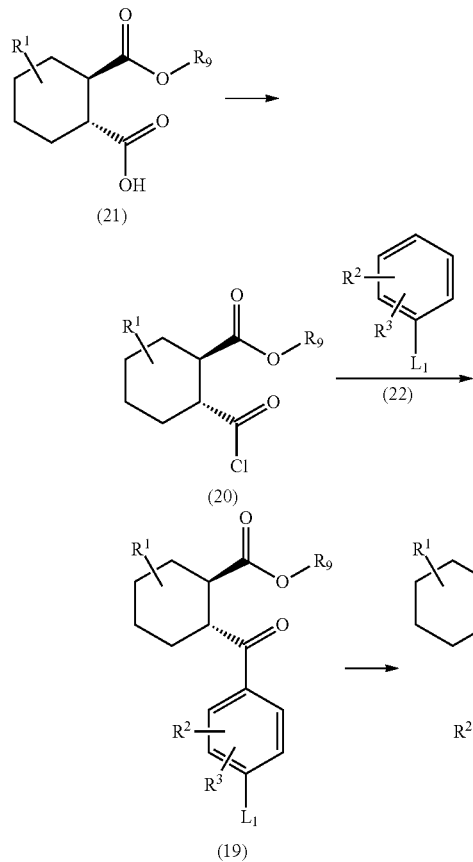

Reactions in Scheme 7 illustrate a synthetic route to certain molecules of formula (10).

A compound of formula (20) may be formed by reacting a compound of formula (21) with a chlorinating agent e.g. $SOCl_2$ in an organic solvent e.g. DCM and in a temperature interval from −20° C. to reflux, and optionally in the presence of a catalyst e.g. DMF, or by using other methods described in the literature and known to person skilled in the art.

A compound of formula (19) could be formed by reacting a compound of formula (20), with a compound of formula (22). The reaction may be performed in the presence of a catalyst e.g. a Lewis acid catalyst e.g. $AlCl_3$ and optionally it may be performed in the presence of an inert organic solvent e.g. DCM and it may be performed in a temperature interval of 0° C. to 100° C.

A compound of formula (10) could be formed by reacting a compound of formula (19) with a base, e.g. NaOH or LiOH in an organic solvent e.g. THF or MeOH, or mixtures thereof, and optionally in the presence of water. The reaction may be performed in a temperature interval from 0° C. to reflux.

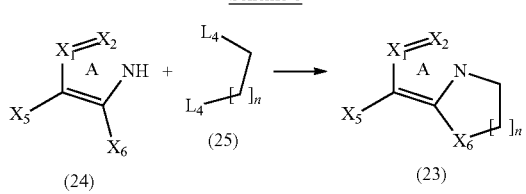

The reaction in Scheme 8 illustrates a synthetic route to certain molecules of formula (23), wherein $X_1$ and $X_2$ are as described in formula (II), $X_5$ is optionally and independently to selected from e.g. H, $NO_2$ or $NHPG_2$; wherein $PG_2$ is a protective group, e.g. tert-butylcarbamate, $X_6$ is independently selected from an heteroatom, e.g. N, O or S, and n is 1 or 2.

A compound of formula (23) may be formed by reacting a compound of formula (24), with a compound of formula (25), wherein $L_4$ is a leaving group, e.g. an halide or a is sulfonyl ester e.g. OTf, in the presence of a base, e.g. $K_2CO_3$, and in the presence of an organic solvent, e.g. MeCN or DMF, and the reaction may be performed in a temperature interval from 0° C. to reflux.

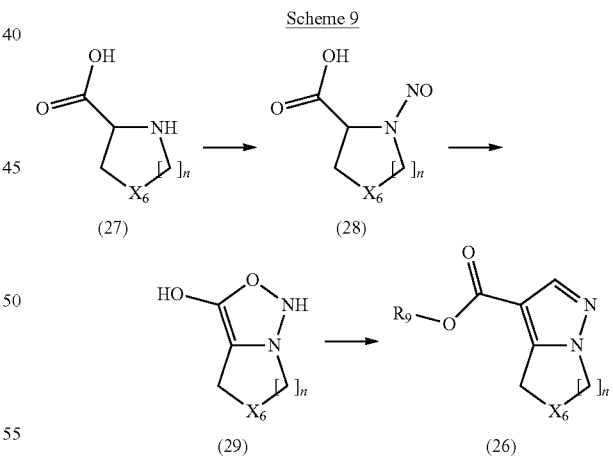

Reactions in Scheme 9 illustrate a synthetic route to certain molecules of formula (26), wherein $X_6$ and n are defined in Scheme 8.

A compound of formula (28), may be formed by reacting a compound of formula (27), with a nitrite source e.g. a nitrite salt e.g. $NaNO_2$, in a solvent e.g. water, and in the presence of an acid e.g. HCl or $CH_3CO_2H$. The reaction may be performed in a temperature interval from −5° C. to rt. A compound of formula (29), may be formed by reacting a compound of formula (28), with an acid anhydride e.g.

trifluoroacetic anhydride, in an organic solvent, e.g. THF, and in a temperature interval from −5° C. to rt. A compound of formula (26), may be formed by reacting a compound of formula (29), with an alkynyl ester e.g. an ethyl propynoate or a methyl propynoate, in an organic solvent e.g. xylene or o-xylene. The reaction may be performed at elevated temperatures e.g. from rt to reflux.

Scheme 10

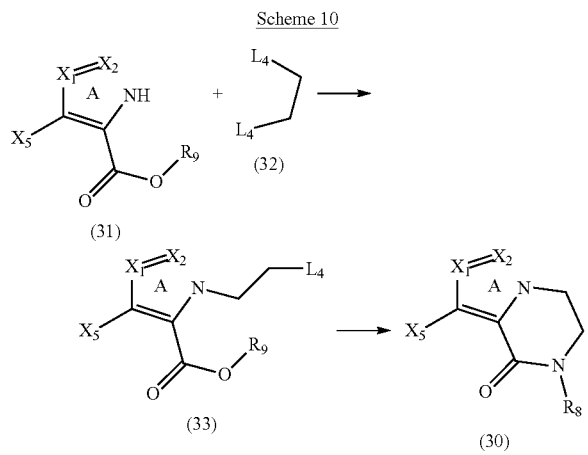

Reactions in Scheme 10 illustrates a synthetic route to certain molecules of formula (30), wherein $R^8$ is optionally selected from H or an alkyl group, e.g. methyl, and $X_5$ is independently selected from e.g. H, $NO_2$ or $NHPG_2$.

A compound of formula (33), wherein $L_4$ is as defined in scheme 8, may be formed by reacting a compound of formula (31), with a compound of formula (32) in the presence of a base, e.g. $K_2CO_3$, and in the presence of an organic solvent, e.g. MeCN or DMF, and the reaction may be performed in a temperature interval from 0° C. to reflux.

A compound of formula (30), may be formed by reacting a compound of formula (33), with a primary amine, e.g. ammonia, or an alkylamine, e.g. ammonia, ammonia hydrate or methylamine, in an organic solvent, e.g. MeCN or THF, and the reaction may be performed in a temperature interval from 0° C. to reflux.

Various permutations of Ring A can be purchased or synthesized using standard reaction conditions.

It is understood that organic reactions described herein are performed according to laboratory practice known to person skilled in the art. It is understood that some of the reactions described herein may optionally be performed in different orders than laid out herein. It is understood that chiral isomers of compounds described herein can be resolved at any stage in the synthetic process using chiral resolving agents described in the literature and known to person skilled in the art or using chiral chromatography methods described in the literature and known to person skilled in the art or as described further in the Examples.

It is understood that additional protective groups may optionally be needed in some of the steps described above, and it is further understood that a deprotection step therefore optionally may be performed, using methods described in the literature and well known to person skilled in the art. The protection and deprotection of functional groups is described in 'Protective Groups in Organic Synthesis' $2^{nd}$ Ed, E. W. Greene and P. G. M. Wuts, Wiley-Interscience (1991) and 'Protecting Groups', P. J. Kocienski, Georg Thieme Verlag (1994), which publication is incorporated herein by reference.

Medical and Pharmaceutical Use

The compounds of Formulae (I), (II), (III), (IV), (V), (VI) and (VII) may be useful in the prevention or treatment of cardiovascular disease in a mammal, particularly a human. Cardiovascular disease includes, but is not limited to, conditions associated with cardiac dysfunction and/or microvascular dysfunction and/or macrovascular pathology, such as atherosclerosis, arteriosclerosis, coronary artery disease including stable and high risk coronary artery disease (defined as recent acute coronary syndrome (ACS) or by biomarkers of microvascular and cardiac dysfunction), myocardial infarction, restenosis following revascularization procedures, heart failure, abdominal aortic aneurysm (AAA), peripheral artery disease (PAD) including erectile dysfunction due to vascular disease, stroke, transient ischemic attack (TIA) and reversible ischemic neurologic disease (RIND), multi-infarct dementia and renal arterial disease.

The compounds of Formulae (I), (II), (III), (IV), (V), (VI) and (VII) may be useful in the prevention or treatment of patients with remaining risk for a cardiovascular event despite standard of care (SoC) treatment, such as, but not limited to, lipid lowering statins, anti-platelets, ACS inhibitors and beta blockers.

The compounds of Formulae (I), (II), (III), (IV), (V), (VI) and (VII) may be useful in the prevention or treatment of chronic kidney disease.

The compounds of Formulae (I), (II), (III), (IV), (V), (VI) and (VII) may be useful in the prevention or treatment of type II diabetes mellitus and complications of type II diabetes mellitus in a mammal, particularly a human. This includes and is not restricted to, diabetic micro and macrovascular pathology, neuropathy and nephropathy.

The compounds of Formulae (I), (II), (III), (IV), (V), (VI) and (VII) may be useful in the prevention or treatment of respiratory inflammatory disease and complications associated with respiratory inflammatory disease in a mammal, particularly a human. Respiratory inflammatory disease includes, but is not limited to asthma, chronic obstructive pulmonary disease, emphysema and rhinitis.

The compounds of Formulae (I), (II), (III), (IV), (V), (VI) and (VII) may be useful in the prevention or treatment of renal inflammatory and vascular diseases and complications associated with renal disease in a mammal, particularly a human. Renal inflammatory and vascular disease includes, but is not limited to chronic kidney disease, drug and toxin induced nephrotoxicity, glomerulonephritis, nephrotic syndrome, IgA nephritis, reflux nephropathy, focal segmental glomerulosclerosis, Henoch-Schonleins purpura, and diabetic nephropathy.

The compounds of Formulae (I), (II), (III), (IV), (V), (VI) and (VII) may be useful in the prevention or treatment of non-alcoholic fatty liver disease (NAFLD) and non-alcoholic steatohepatitis (NASH).

Treatment with the compounds of Formulae (I), (II), (III), (IV), (V), (VI) and (VII) is may lower the cardiovascular and/or cerebrovascular and/or renal and/or peripheral arterial disease morbidity and mortality associated with cardiac dysfunction and/or microvascular dysfunction and/or macrovascular pathology due to their anti-inflammatory properties and influence on vasoactive mechanisms.

The compounds of Formulae (I), (II), (III), (IV), (V), (VI) and (VII) may serve to prevent or reduce the risk of developing cardiac dysfunction and/or microvascular dysfunction and/or macrovascular pathology, as well as for halting or slowing the progression and/or promoting the regression of atherosclerotic cardiovascular disease once it has become clinically evident, comprising the administration of a prophylactically or therapeutically effective amount, as appropriate, of a compound of formula (I) to a mammal, including a human, who is at risk of developing atherosclerosis or who already has atherosclerotic cardiovascular disease.

Compounds of Formulae (I), (II), (III), (IV), (V), (VI) and (VII) may be useful in preventing or reducing the incidence or severity of acute events related to atherosclerotic plaque rupture or erosion, including, but not limited to, myocardial infarction, unstable angina and stroke.

Compounds of Formulae (I), (II), (III), (IV), (V), (VI) and (VII) may be useful in preventing or reducing the incidence or severity of acute events by improving microvascular function, macrovascular pathology and/or cardiac function.

Compounds of Formulae (I), (II), (III), (IV), (V), (VI) and (VII) may be useful in preventing or reducing the progression of abdominal aortic aneurysms (AAA) and incidence of rupture.

For the avoidance of doubt, as used herein, the term "treatment" includes therapeutic and/or prophylactic treatment. "Treatment" also includes administration of a compound of Formulae (I), (II), (III), (IV), (V), (VI) or (VII) in order to alleviate symptoms of cardiovascular disease (including coronary artery disease and high risk coronary artery disease) and/or to lessen the severity of, or progression of, the same.

The compounds disclosed herein may be thus indicated both in the therapeutic and/or prophylactic treatment of these conditions.

The compounds disclosed herein may have the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds known in the prior art.

Combination Therapy

The compounds of any one of Formulae (I), (II), (III), (IV), (V), (VI) or (VII), or a pharmaceutically acceptable salt thereof, may also be administered in conjunction with other compounds used for the treatment of the above conditions.

In another embodiment, there is a combination therapy wherein a compound of any one of Formulae (I), (II), (III), (IV), (V), (VI) or (VII), or a pharmaceutically acceptable salt thereof, and a second active ingredient are administered concurrently, sequentially or in admixture, for the treatment of one or more of the conditions listed above. Such a combination may be used in combination with one or more further active ingredients.

Compounds described herein may be of use in treating cardiovascular, metabolic and renal disease in combination with agents that are
 cardiac therapies,
 anti-hypertensives,
 diuretics,
 peripheral vasodilators,
 lipid modifying agents,
 anti-diabetic,
 anti-inflammatory
 anti-coagulant
 anti-platelet Examples of the above include, but are not restricted to, *digitalis* glycosides, anti-arrhythmics, calcium channel antagonists, ACE inhibitors, angiotensin receptor blockers (e.g. candesartan), endothelin receptor blockers, β-blockers, thiazide diuretics, loop diuretics, cholesterol synthesis inhibitors such as statins (e.g. Rosuvastatin), cholesterol absorption inhibitors, cholesterylester transfer protein (CETP) inhibitors, anti-diabetic drugs such as insulin and analogues, GLP-1 analogues, sulphonamides, dipeptidyl peptidase 4 inhibitors, thiazolidinediones, SGLT-2 inhibitors, and anti-inflammatory drugs such as NSAID's and CCR2 antagonists, anti-coagulants such as heparins, thrombin is inhibitors and inhibitors of factor Xa, platelet aggregation inhibitors (e.g., P2Y12 antagonists or ticagrelor) and neprilysin inhibitors (e.g. Sacubitril).

When used in a combination therapy, it is contemplated that the compounds of any one of Formulae (I), (II), (III), (IV), (V), (VI) or (VII), or a pharmaceutically acceptable salt thereof, and the other active ingredients may be administered in a single composition, completely separate compositions, or a combination thereof. It also is contemplated that the active ingredients may be administered concurrently, simultaneously, sequentially, or separately. The particular composition(s) and dosing frequency(ies) of the combination therapy will depend on a variety of factors, including, for example, the route of administration, the condition being treated, the species of the patient, any potential interactions between the active ingredients when combined into a single composition, any interactions between the active ingredients when they are administered to the animal patient, and various other factors known to physicians, and others skilled in the art.

Administration

There is provided a method of treatment of a condition where inhibition of FLAP is required, which method comprises administration of a therapeutically effective amount of a compound of Formulae (I), (II), (III), (IV), (V), (VI) or (VII), or a pharmaceutically acceptable salt thereof, to a person suffering from, or susceptible to, such a condition.

The compounds of Formulae (I), (II), (III), (IV), (V), (VI) or (VII), or a pharmaceutically acceptable salt thereof, will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated and the route of administration, the compositions may be administered at varying doses. Suitable daily doses of the compounds of Formulae (I), (II), (III), (IV), (V), (VI) or (VII), or a pharmaceutically acceptable salt thereof, in therapeutic treatment of humans are about 0.0001-100 mg/kg body weight, preferably 0.01-30 mg/kg body weight.

Oral formulations are preferred particularly tablets or capsules which may be formulated by methods known to those skilled in the art to provide doses of the active is compound in the range of 0.1 mg to 1000 mg for example 1 mg, 3 mg, 5 mg, 10 mg, 25 mg, 50 mg, 100 mg, 250 mg and 500 mg.

According to a further aspect there is thus provided a pharmaceutical composition including any of the compounds of Formulae (I), (II), (III), (IV), (V), (VI) or (VII), or a pharmaceutically acceptable salt thereof, in admixture with pharmaceutically acceptable adjuvants, diluents and/or carriers.

Biological Tests

The following test procedures may be employed:

FLAP Binding Assay (Test A)

Compounds were tested in a competition binding assay using $^3$H-MK591 as tracer. (Preparation of MK-591 is described in *Bioorg. Med. Chem. Lett.* 1999, 9, 2391). A 100,000×g pellet from COS-7 cells stably transfected with a plasmid expressing human ALOX5AP was the source of FLAP. Membrane pellets were resuspended in buffer (100 mM Tris-HCl, 0.05% Tween-20, 140 mM NaCl, 2 mM EDTA, 0.5 mM DTT, 5% Glycerol, pH 7.5) to give a final protein concentration of 12 mg/mL (2 μg/well). To perform assays, 1.4 μL compounds were dispensed into 96-well plates in 3-fold dilution series in triplicate. 84 μL radioligand (25000 CPM, 2 nM final concentration in assay) was then added followed by 84 μL membrane suspension and incubation at rt for 60 min. Following filtration, filter plates were dried 12 h at RT (or 50° C. for 1 hour). 50 μL scintillant was then added, the filterplates were sealed and radioactivity was measured in a microbeta counter. Specific binding was defined as total binding minus non-specific binding. Total binding was defined as $^3$H-MK591 bound to membranes in the absence of competitor, non-specific binding was defined as $^3$H-MK591 in the presence of 0.1 mM MK-591. $IC_{50}$ values were determined by plotting % inhibition versus log compound concentration and using a one site dose response model. Data for each compound tested is shown in Table 1.

TABLE 1

| Example | $IC_{50}$ nM |
|---|---|
| 1 | 73 |
| 2 | 34 |
| 3 | 37 |
| 4 | 36 |
| 5a | 2500 |
| 5b | 22 |
| 6 | 57 |
| 7 | 6.3 |
| 8 | 45 |
| 9 | 30 |
| 10 | 270 |
| 11 | 82 |
| 12 | 41 |
| 13 | 33 |
| 14 | 400 |
| 15 | 8.6 |
| 16 | 22 |
| 17 | 20 |
| 18a | 3700 |
| 18b | 28 |
| 19 | 29 |
| 20 | 180 |
| 21 | 230 |
| 22 | 24 |
| 23 | 35 |
| 24 | 8.1 |
| 25 | 25 |
| 26 | 290 |
| 27 | 65 |
| 28 | 3.9 |
| 29 | 4.8 |
| 30 | 12 |
| 31 | 190 |
| 32 | 170 |
| 33 | 54 |
| 34 | 41 |
| 35 | 83 |
| 36 | 90 |
| 37 | 27 |
| 38 | 20 |
| 39 | 9 |
| 40 | 70 |
| 41 | 160 |
| 42 | 200 |
| 43 | 140 |
| 44 | 46 |
| 45 | 210 |
| 46 | 86 |
| 47 | 53 |

TABLE 1-continued

| Example | $IC_{50}$ nM |
|---|---|
| 48 | 23 |
| 49 | 44 |

FLAP Whole Blood Assay (Test B)

Compounds were tested for the inhibition of $LTB_4$ production in fresh human whole blood obtained by venapuncture using heparin to prevent clotting. 1.5 μL compounds or DMSO carrier were dispensed into the wells of a 96-well deep-well plate in 3-fold dilution series. 500 μL hepamised whole blood was then added followed by incubation at 37° C. for 30 min (method A) or 4 h (method B). 100 μL blood was subsequently transferred in triplicate to pre-dispensed 0.5 μL 2 mM calcium ionophore (calcimycin; A23187) in a second 96-well plate. Following incubation at 37° C. for 20 min, to the assays were stopped by adding 10 μL of stop solution (100 mM EGTA, pH 7.4) and the plate was transferred to ice. The plate was centrifuged at 3000 rpm at 4° C. for 10 min and μL plasma was transferred to a fresh 96 well plate containing 90 μL pre-dispensed EIA assay buffer (0.1 M phosphate buffer+0.1% BSA). $LTB_4$ was then measured using reagents from a commercial EIA (Cayman Chemicals). $LTB_4$ production was defined as is the $LTB_4$ level in the presence of a given concentration of test compound minus the $LTB_4$ level in the presence of 50 nM 5-[[4-[(2S, 4R)-4-hydroxy-2-methyl-tetrahydropyran-4-yl]-2-thienyl] sulfanyl]-1-methyl-indolin-2-one. (Preparation of 5-[[4-[(2S,4R)-4-hydroxy-2-methyl-tetrahydropyran-4-yl]-2-thienyl]sulfanyl]-1-methyl-indolin-2-one was described in *Org. Process Res. Dev.*, 2005, 9, 555-569 or EP623614 B1). Inhibition of $LTB_4$ production was defined as the $LTB_4$ level in the presence of a given concentration of test compound expressed as a % of the $LTB_4$ level in the presence of DMSO. $IC_{50}$ values were determined by plotting % inhibition versus log compound concentration and using a one site dose response model. Data for each example tested is shown in Table 2.

TABLE 2

| Example | $IC_{50}$ nM (method A or B) |
|---|---|
| 1 | 112 (A) |
| 2 | 60 (B) |
| 3 | 70 (B) |
| 4 | 290 (B) |
| 5a | ND |
| 5b | 95 (B) |
| 6 | 380 (B) |
| 7 | 40 (B) |
| 8 | 35 (B) |
| 9 | 110 (B) |
| 10 | 340 (B) |
| 11 | 140 (B) |
| 12 | 100 (B) |
| 13 | 260 (B) |
| 14 | 654 (A) |
| 15 | 28 (B) |
| 16 | 41 (B) |
| 17 | 18 (B) |
| 18a | ND |
| 18b | 114 (B) |
| 19 | 80 (B) |
| 20 | 281 (A) |
| 21 | 360 (A) |
| 22 | 740 (B) |
| 23 | 130 (B) |

TABLE 2-continued

| Example | IC$_{50}$ nM (method A or B) |
|---|---|
| 24 | 18 (B) |
| 25 | 210 (B) |
| 26 | 250 (B) |
| 27 | 55 (B) |
| 28 | 380 (B) |
| 29 | 330 (B) |
| 30 | 50 (B) |
| 31 | 390 (B) |
| 32 | 915 (B) |
| 33 | 117 (B) |
| 34 | 41 (B) |
| 35 | 79 (B) |
| 36 | 148 (B) |
| 37 | 40 (B) |
| 38 | 69 (B) |
| 39 | 34 (B) |
| 40 | 208 (A) |
| 41 | 272 (B) |
| 42 | 149 (A) |
| 43 | 904 (B) |
| 44 | 197 (A) |
| 45 | ND |
| 46 | 170 (A) |
| 47 | 260 (A) |
| 48 | 270 (A) |
| 49 | 640 (A) |

ND = not determined

EXAMPLES

The compounds of the application will now be further explained by reference to the following non limiting examples.

In the examples, high resolution mass spectra were recorded on a Micromass LCT mass spectrometer equipped with an electrospray interface (LC-HRMS). $^1$H NMR measurements were performed on Varian UNITY plus 400, 500 and 600 spectrometers or Varian INOVA 400, 500 and 600 spectrometers or Bruker Avance 400, 500 and 600 spectrometers, operating at $^1$H frequencies of 400, 500 and 600 MHz, respectively. The to experiments were typically recorded at 25° C. Chemical shifts are given in ppm with the solvent as internal standard. Flash chromatography was performed using straight phase flash chromatography on a SP1™ Purification system from Biotage™ using normal phase silica FLASH+™ (40M, 25M or 12 M) or SNAP™ KP-Sil Cartridges (340, 100, 50 or 10) unless otherwise stated. In general, all solvents used were commercially available and of analytical grade. Anhydrous solvents were routinely used for reactions. Phase Separators used in the examples are ISOLUTE® Phase Separator columns. The Intermediates and Examples named below were named using ACD/Name 12.01 from Advanced Chemistry Development, Inc. (ACD/Labs).

The following abbreviations are used
AcOH acetic acid
aq aqueous
Boc20 di-tert-butyl dicarbonate
DCE dichloroethane
DCM dichloromethane
DEA diethylamine
DIPEA N,N-diisopropylethylamine
DMAP dimethylaminopyridine
DME dimethoxyethane
DMF N,N-dimethylformamide
DMSO dimethylsulfoxide
DPPA diphenyl phosphorazidate
dppf 1,1'-bis(diphenylphosphino)ferrocene
dtbpf 1,1'-bis(ditertbutylphosphino)ferrocene
EtOAc ethylacetate
EtOH ethanol
h hour(s)
HATU (dimethylamino)-N,N-dimethyl(3-oxido-1H-[1,2,3]triazolo[4,5-b]pyridinyl)methaniminium hexafluorophosphate
MeCN acetonitrile
MeOH methanol
min minute(s)
MS mass spectrometer
NMP N-methyl-2-pyrrolidone
NMR nuclear magnetic resonanse
Pd(dppf)Cl$_2$*DCM 1,1'-bis(di-tert-butylphosphino)ferrocene palladium dichloride
rt room temperature
sat saturated
SFC supercricica fluid chromatography
T3P 2,4,6-tripropyl-1,3,5,2,4,6-trioxatriphosphinane 2,4,6-trioxide
TBTU 2-(1H-benzo[d][1,2,3]triazol-1-yl)-1,1,3,3-tetramethylisouronium tetrafluoroborate
THF tetrahydrofuran
TLC thin layer chromatography
Xantphos 4,5-bis(diphenylphosphino)-9,9-dimethylxanthene Synthesis of Starting Materials and Intermediates Intermediate 1: (1R,2R and 1S,2S)-2-[4-(1H-Pyrazol-3-yl)benzoyl]-cyclohexanecarboxylic acid

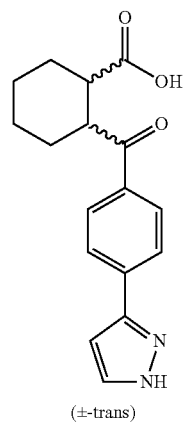 [SMILES: O=C(O)C1CCCCC1C(=O)c1ccc(-c2cc[nH]n2)cc1]

(±-trans)

A mixture of (1R,2R and 1S,2S)-2-(4-bromobenzoyl)cyclohexanecarboxylic acid (200 mg, 0.64 mmol), 1H-pyrazol-3-ylboronic acid (129 mg, 1.16 mmol) and Pd(dppf)Cl$_2$*DCM (46.5 mg, 0.06 mmol) and K$_2$CO$_3$ (266 mg, 1.93 mmol) in dioxane (4 mL)/water (4 mL) was heated at reflux for 90 min. The mixture was diluted with EtOAc and water. The phases were separated and the water phase was washed with EtOAc. The combined water layers were acidified with HCl (6 M) until pH was approximately 4-5 and the product was extracted into EtOAc. The organic layer was dried over Na$_2$SO$_4$, filtered and evaporated to give the title compound (240 mg) as a brown solid.

MS m/z 299 (M+H)$^+$

Intermediate 2: 4-({[(1R,2R)-2-(4-Bromobenzoyl)cyclohexyl]carbonyl}amino)-1-methyl-1H-pyrazole-5-carboxamide

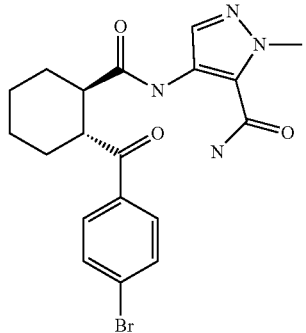 [SMILES: Cn1ncc(NC(=O)[C@@H]2CCCC[C@H]2C(=O)c2ccc(Br)cc2)c1C(N)=O]

T3P, (50% in EtOAc, 800 µl, 1.34 mmol) was added to a solution of (1R,2R)-2-(4-bromobenzoyl)cyclohexanecarboxylic acid (200 mg, 0.64 mmol), 4-amino-1-methyl-1H-pyrazole-5-carboxamide (180 mg, 1.28 mmol) and Et$_3$N (356 µl, 2.57 mmol) in dry EtOAc (3 mL) and the reaction mixture was heated at 80° C. for 4 h in a microwave reactor. The mixture was diluted with EtOAc and washed twice with NaHCO$_3$ (sat, aq) and brine. The organic phase was dried using a phase separator and the solvent evaporated. The compound was purified by preparative HPLC on a XBridge C18 column (10 µm 250×19 ID mm) using a gradient of 30-85% MeCN in H$_2$O/MeCN/NH$_3$ (95/5/0.2) buffer system at pH10 as mobile phase. The desired fractions were collected and the solvent evaporated to give the title compound (130 mg, 47%).

$^1$H NMR (400 MHz, CDCl3) δ 1.2-1.54 (m, 3H), 1.70 (ddd, 1H), 1.81-1.98 (m, 2H), 2.02-2.17 (m, 2H), 2.78-2.94 (m, 1H), 3.56-3.73 (m, 1H), 4-4.1 (m, 3H), 6.11 (d, 2H), 7.55-7.65 (m, 3H), 7.81 (d, 2H), 8.00 (s, 1H) MS m/z 433.1 [M+H]$^+$ Intermediate 3: 3-Methyl-1-(tetrahydro-2H-pyran-2-yl)-5-(4,4,5,5-tetramethyl-1,3,2-dioxaborolan-2-yl)-1H-pyrazole

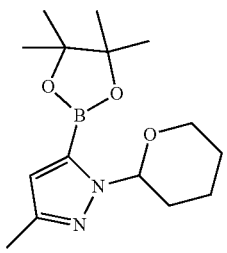 [SMILES: Cc1cc(B2OC(C)(C)C(C)(C)O2)n(C2CCCCO2)n1]

Step 1—3-Methyl-1-(tetrahydro-2H-pyran-2-yl)-1H-pyrazole

3-Methyl-1H-pyrazole (2 mL, 24.8 mmol) was dissolved in 3,4-dihydro-2H-pyran (6.8 mL, 74.5 mmol). Trifluoroacetic acid (0.134 mL, 1.74 mmol) was added and the clear solution was warmed to 75° C. for 18 h. The reaction mixture was diluted with Et$_2$O and the organic phase was washed with NaHCO$_3$ (sat, aq), water and brine, filtered using a phase separator and concentrated in vacuo. The residue was purified by flash chromatography (10%→20% of EtOAc in heptane) to give the subtitle compound. (2.4 g, 58%, 70% correct isomer)

$^1$H NMR (500 MHz, CDCl$_3$) δ 7.44 (d, 1H), 7.40 (s, 0.3H), 6.04 (d, 1H), 6.00 (s, 0.3H), 5.21-5.28 (m), 3.94-4.09 (m), 3.57-3.68 (m), 2.47 (s, OH), 2.31 (s, 1H), 2.26 (s, 3H), 1.9-2.16 (m), 1.59-1.75 (m).

Step 2—3-Methyl-1-(tetrahydro-2H-pyran-2-yl)-5-(4,4,5,5-tetramethyl-1,3,2-dioxaborolan-2-yl)-1H-pyrazole n-Butyllithium (6.1 mL, 15.2 mmol, 2.5M in THF) was added during 10 min to a solution of 3-methyl-1-(tetrahydro-2H-pyran-2-yl)-1H-pyrazole (2.4 g, 14.4 mmol) in THF (20 mL) at −78° C. During a period of 15 min tripropan-2-yl borate (3.7 mL, 15.9 mmol) was added dropwise at −78° C. and the reaction mixture was stirred for 15 min, where after it was allowed to reach rt. 2,3-Dimethylbutane-2,3-diol (1.88 g, 15.9 mmol) was added followed by AcOH (1.65 mL, 28.9 mmol) and the reaction mixture was stirred at rt over night. The reaction mixture was diluted with heptane and the organic phase was washed with NH$_4$Cl (aq), NaHCO$_3$ (aq) and brine, filtered using a phase separator and concentrated. The residue was diluted with heptane and concentrated to give the title compound (3.86, 91%). MS m/z 293.2 [M+H]$^+$ Intermediate 4: 1-Methyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-5-carboxamide

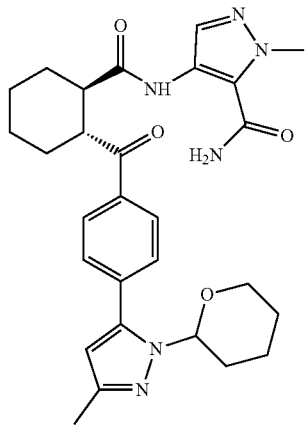 [SMILES: Cc1cc(-c2ccc(C(=O)[C@@H]3CCCC[C@H]3C(=O)Nc3cnn(C)c3C(N)=O)cc2)n(C2CCCCO2)n1]

Step 1—4-({[(1R,2R)-2-(4-bromobenzoyl)cyclohexyl]carbonyl}amino)-1-methyl-1H-pyrazole-5-carboxamide Et$_3$N (5.5 mL, 39.7 mmol) and T3P (50% in EtOAc, 12 mL, 20.2 mmol) was added to a solution of (1R,2R)-2-(4-bromobenzoyl)cyclohexanecarboxylic acid (3 g, 9.6 mmol), 4-amino-1-methyl-1H-pyrazole-5-carboxamide (2.7 g, 19.3 mmol) and Et$_3$N (5.5 mL, 39.7 mmol) in EtOAc (45 mL) and the reaction mixture was heated at 75-80° C. for 2 h. The to mixture was diluted with EtOAc (100 mL) and washed four times with NaHCO$_3$ (sat, aq) and twice with NH$_4$Cl (sat, aq)

and water. The organic phase was dried using a phase-separator and the solvent was removed under vacuum. The residue was dissolved in EtOAc and the organic phase was washed twice with NaHCO₃ (sat, aq) and twice with NH₄Cl (sat, aq) and finally water. The organic phase was dried using a phase separator, and the solvent is was removed under vacuum to give the crude subtitle compound (3.55 g) as a cream-colored residue.

¹H NMR (500 MHz, CDCl₃) δ 1.31-1.56 (m, 3H), 1.70 (qd, 1H), 1.81-1.97 (m, 3H), 2.07-2.15 (m, 1H), 2.81-2.93 (m, 1H), 3.61-3.71 (m, 1H), 4.04 (s, 3H), 6.29 (s, 2H), 7.51-7.69 (m, 3H), 7.81 (d, 2H), 8.08 (s, 1H) MS m/z 433 [M+H]⁺

Step 2—1-Methyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-5-carboxamide 3-Methyl-1-(tetrahydro-2H-pyran-2-yl)-5-(4,4,5,5-tetramethyl-1,3,2-dioxaborolan-2-yl)-1H-pyrazole (Intermediate 3, 4.2 g, 14.37 mmol) and a solution of K₂CO₃ (3.19 g, 23.08 mmol) in water (35 mL) was added to a solution of 4-({[(1R,2R)-2-(4-bromobenzoyl)cyclohexyl]-carbonyl}amino)-1-methyl-1H-pyrazole-5-carboxamide (Intermediate 2, 2.5 g, 5.77 mmol) in dioxane (35 mL) under an atmosphere of nitrogen. Pd(dtbpf)Cl₂ (0.371 g, 0.58 mmol) was added and the resulting mixture was heated at 70-80° C. for 20 min and then at 80° C. for 30 min. The reaction mixture was diluted with EtOAc (200 mL) and washed with brine (sat). The aqueous phase was extracted twice with EtOAc and the combined organic phase was dried using a phase separator and concentrated. The residue was purified by flash chromatography (50→100% EtOAc in heptane, then 100% EtOAc) to give the title compound (2.15 g, 72%).

¹H NMR (500 MHz, CDCl₃) δ 1.29-1.46 (m, 2H), 1.75 (dq, 3H), 1.85-1.98 (m, 2H), 2.02 (s, 1H), 2.04 (s, 3H), 2.14 (d, 2H), 2.32 (s, 3H), 2.62-2.45 (m, 1H), 2.93 (t, 1H), 3.59 (td, 1H), 3.7-3.85 (m, 1H), 4.02-4.1 (m, 3H), 5.10 (t, 1H), 6.16 (s, 1H), 6.22-6.45 (bs, 2H), 7.60 (dd, 3H), 8.04 (dd, 2H), 8.13-8.33 (bs, 1H). MS m/z 519.4 [M+H]⁺

Intermediate 5: Methyl 4-({[(1R,2R)-2-(4-bromobenzoyl)cyclohexyl]carbonyl}amino)-1-methyl-1H-pyrazole-3-carboxylate

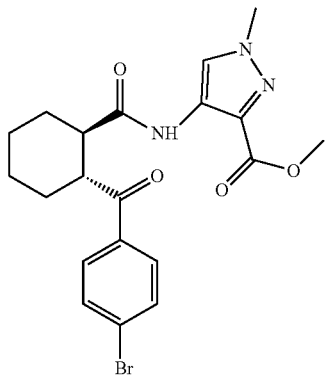 [SMILES: COC(=O)c1nn(C)cc1NC(=O)[C@@H]1CCCC[C@H]1C(=O)c1ccc(Br)cc1]

T3P (50% in EtOAc, 1.9 mL, 3.2 mmol) was added to a solution of (1R,2R)-2-(4-bromobenzoyl)cyclohexanecarboxylic acid (674 mg, 2.17 mmol), methyl 4-amino-1-methyl-1H-pyrazole-3-carboxylate hydrochloride (457 mg, 2.38 mmol) and Et₃N (0.63 mL, 4.5 mmol) in EtOAc (9 mL) and the reaction mixture was heated at 80° C. for 2 h and then at rt for 2 days. The reaction mixture was washed with NaHCO₃ (sat, aq), NH₄Cl (sat. aq) and brine. The organic phase was dried using a phase separator and the solvent was removed under vacuum. The residue was purified by flash chromatography (50% of EtOAc) to give the title compound (640 mg 66%).

¹H NMR (500 MHz, CDCl₃) δ 1.26-1.35 (m, 1H), 1.35-1.49 (d, 2H), 1.57-1.7 (m, 1H), 1.88 (dd, 2H), 1.98-2.04 (m,), 2.09-2.18 (m, 1H), 2.87-2.99 (m, 1H), 3.6-3.69 (m, 1H), 3.85 (s, 3H), 3.96 (s, 3H), 7.57 (d, 2H), 7.84 (d, 2H), 8.04 (s, 1H), 9.09 (s, 1H). MS m/z 448 [M+H]⁺

Intermediate 6: 4-({[(1R,2R)-2-(4-Bromobenzoyl)cyclohexyl]carbonyl}amino)-1-methyl-1H-pyrazole-3-carboxamide

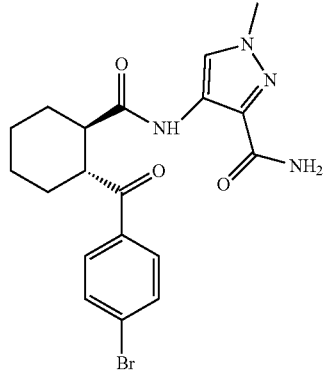 [SMILES: Cn1cc(NC(=O)[C@@H]2CCCC[C@H]2C(=O)c2ccc(Br)cc2)c(C(N)=O)n1]

Step 1—4-({[(1R,2R)-2-(4-bromobenzoyl)cyclohexyl]carbonyl}amino)-1-methyl-1H-pyrazole-3-carboxylic acid LiOH (1 M aq) (3 mL, 3.00 mmol) was added to a solution of methyl 4-({[(1R,2R)-2-(4-bromobenzoyl)cyclohexyl]carbonyl}amino)-1-methyl-1H-pyrazole-3-carboxylate (Intermediate 5, 640 mg, 1.43 mmol) in THF (3 mL) and MeOH (3 mL) and the reaction mixture was stirred at rt for 2 h. The reaction mixture was concentrated and HCl (3.8 M, aq) (1 mL) was added followed by water (20 mL). The water phase was extracted twice with EtOAc and the combined organic phase was filtered using a phase separator and concentrated to give the subtitle compound (640 mg, 103%). MS m/z 432 [M–H]⁻

Step 2—4-({[(1R,2R)-2-(4-bromobenzoyl)cyclohexyl]carbonyl}amino)-1-methyl-1H-pyrazole-3-carboxamide DIPEA (0.68 mL, 3.9 mmol), TBTU (749 mg, 2.33 mmol) and ammonium chloride (139 mg, 2.59 mmol) was added to a solution of 4-({[(1R,2R)-2-(4-bromobenzoyl)cyclohexyl]carbonyl}amino)-1-methyl-1H-pyrazole-3-carboxylic acid (563 mg, 1.30 mmol) in DMF (5 mL) and the reaction mixture was stirred at rt overnight. The reaction mixture was diluted with DMSO and purified by preparative HPLC on a XBridge C18 column (10 m 250×50 ID mm) using a gradient of 5-75% MeCN in H₂O/MeCN/NH₃ (95/5/0.2) buffer system as mobile phase. The desired fractions were collected, concentrated and extracted with EtOAc. The organic phase was filtered using a phase separator and concentrated to give the title compound (280 mg, 50%).

$^1$H NMR (500 MHz, DMSO-d$_6$) δ 1.16 (dd, 1H), 1.33-1.55 (m, 3H), 1.67-1.85 (m, 2H), 1.90 (d, 1H), 2.02 (d, 1H), 2.81-2.92 (m, 1H), 3.63-3.71 (m, 1H), 3.79 (s, 3H), 7.46 (s, 1H), 7.64 (s, 1H), 7.73 (d, 2H), 7.93 (d, 2H), 8.04 (s, 1H), 9.75 (s, 1H).

Intermediate 7: (1R,2R and 1S,2S)-2-(4-bromobenzoyl)-N-(3-cyano-1-methyl-1H-pyrazol-4-yl)cyclohexanecarboxamide

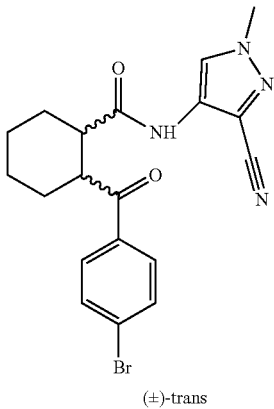 [SMILES: Cn1cc(NC(=O)C2CCCCC2C(=O)c2ccc(Br)cc2)c(C#N)n1]

(±)-trans

T$_3$P (50% in EtOAc, 1.6 g, 4.9 mol) was added to a mixture of (1R,2R and 1S,2S)-2-(4-bromobenzoyl)cyclohexanecarboxylic acid (1.3 g, 4.1 mol), 4-amino-1-methyl-1H-pyrazole-3-carbonitrile (0.5 g, 4.1 mol) and DMAP (1.0 g, 8.2 mol) in DCE (10 mL) and the reaction mixture was heated in a microwave reactor at 100° C. for 1 h. The mixture was cooled to rt and diluted with DCM. The organic phase was washed with brine, dried and concentrated and the residue was purified by flash chromatography (petroleum ether:EtOAc, 3:1) to give the title compound (0.4 g, 24%) as a white solid.

$^1$H NMR (400 MHz, CDCl$_3$) δ 1.49-1.39 (m, 3H), 1.76-1.69 (m, 1H), 1.95-1.86 (m, 2H), 2.12-2.03 (m, 2H), 2.91-2.84 (m, 1H), 3.69-3.62 (m, 1H), 3.85 (s, 3H), 7.59 (d, 2H), 7.64 (s, 1H), 7.83 (d, 2H), δ 7.99 (s, 1H)

Intermediate 8: (1R,2R)-2-{4-[3-Methyl-1-(tetrahydro-2H-pyran-2-yl)-1H-pyrazol-5-yl]benzoyl}cyclohexanecarboxylic acid

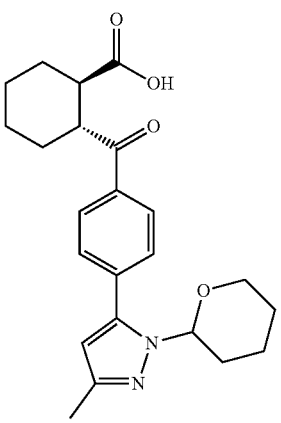 [SMILES: Cc1cc(-c2ccc(C(=O)[C@@H]3CCCC[C@H]3C(=O)O)cc2)n(C2CCCCO2)n1]

K$_2$CO$_3$ (4.02 g, 29.05 mmol) and Pd(dtbpf)Cl$_2$ (0.28 g, 0.36 mmol) were added to a solution of (1R,2R)-2-(4-bromobenzoyl)cyclohexanecarboxylic acid (2.26 g, 7.26 mmol) and 3-methyl-1-(tetrahydro-2H-pyran-2-yl)-5-(4,4,5,5-tetramethyl-1,3,2-dioxaborolan-2-yl)-1H-pyrazole (Intermediate 3, 3.18 g, 10.89 mmol) dissolved in 1,4-dioxane (40 mL) and water (20 mL). The mixture was evacuated and purged with nitrogen three times and then heated at 80° C. for 1 h. The mixture was cooled to rt and diluted with EtOAc. NaHCO$_3$ (sat, aq) was added and the mixture was acidified with KHSO$_4$ (1 M, aq). The phases were separated and the aqueous phase was extracted twice with EtOAc. The combined organic phase was dried using a phase separator and the solvent was removed under vacuum. The crude residue was purified by preparative HPLC on a Kromasil C8 column (10 μm 250×50 ID mm) using a gradient of 30%-90% MeCN in H$_2$O/MeCN/AcOH (95/5/0.2) buffer system as mobile phase. The selected fractions were combined and concentrated under vacuum and the aqueous residue was extracted twice with DCM. The combined organic phase was dried using a phase separator and the solvent was removed under vacuum to give the title compound (2.79 g, 97%) as a light brown solid.

$^1$H NMR (500 MHz, CDCl$_3$) δ 1.21-1.64 (m, 6H), 1.71-1.94 (m, 4H), 2.02-2.12 (m, 2H), 2.23-2.31 (m, 1H), 2.34 (s, 3H), 2.52-2.64 (m, 1H), 2.93-3.02 (m, 1H), 3.53-3.66 (m, 2H), 4.11-4.19 (m, 1H), 5.13 (dd, 1H), 6.18 (s, 1H), 7.56-7.63 (m, 2H), 8.01-8.07 (m, 2H) MS m/z 395.3 [M−H]$^-$

Intermediate 9: Methyl 4-[(tert-butoxycarbonyl)amino]-1H-pyrazole-5-carboxylate

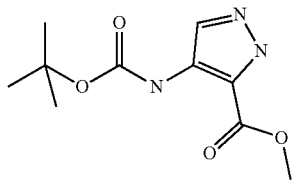 [SMILES: COC(=O)c1[nH]ncc1NC(=O)OC(C)(C)C]

Di-tert-Butyl dicarbonate (159 mL, 0.68 mol) was added to methyl 4-amino-1H-pyrazole-3-carboxylate (87.6 g, 0.62 mol) and pyridine (100 mL, 1.24 mol) in MeOH (1 L) at 10° C. over a period of 15 min. The reaction mixture was stirred at rt for 5 h. The solvent was removed under vacuum. The crude product was purified by crystallization from MeOH (700 mL) to give the title compound (80 g, 53%) as a purple solid.

MS m/z 228 [M+H]$^+$ $^1$H NMR (400 MHz, DMSO-d$_6$) δ 1.47 (s, 9H), 3.83 (s, 3H), 7.70-8.20 (m, 2H), 13.45 (s, 1H)

Intermediate 10: Methyl 1-(2-bromoethyl)-4-[(tert-butoxycarbonyl)amino]-1H-pyrazole-5-carboxylate

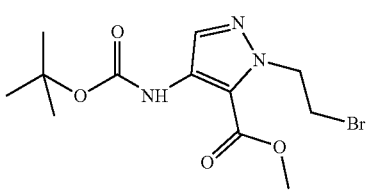 [SMILES: COC(=O)c1c(NC(=O)OC(C)(C)C)cnn1CCBr]

1,2-dibromoethane (1.97 mL, 22.8 mmol) was added to a solution of methyl 4-[(tert-butoxycarbonyl)amino]-1H-pyrazole-5-carboxylate (Intermediate 9, 5.0 g, 20.7 mmol) and $K_2CO_3$ (4.3 g, 31.1 mmol) in DMF (50 mL) at 0° C. over a period of 10 min and the reaction mixture was stirred at rt for 5 h. Water was added to the reaction mixture and the aqueous phase was extracted with EtOAc. The organic layer was dried over $MgSO_4$, filtered and evaporated and the crude product was purified by flash chromatography (5%→20% 2-methylpentane in EtOAc). Pure fractions were evaporated to dryness to give the title compound (2.5 g, 35%) as a colorless oil.

$^1$H NMR (300 MHz, DMSO-$d_6$) δ 1.47 (s, 9H), 3.80 (t, 2H), 3.87 (s, 3H), 4.79 (t, 2H), 7.86 (s, 1H), 8.24 (s, 1H) MS m/z 348 [M+H]$^+$

Intermediate 11: tert-Butyl (4-oxo-4,5,6,7-tetrahydropyrazolo[1,5-a]pyrazin-3-yl)carbamate

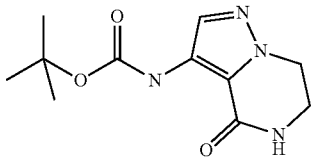 [SMILES: CC(C)(C)OC(=O)Nc1cnn2c1C(=O)NCC2]

Ammonia hydrate (10 g, 287.2 mmol) was added to a solution of methyl 1-(2-bromoethyl)-4-[(tert-butoxycarbonyl)amino]-1H-pyrazole-5-carboxylate (Intermediate 10, 10.0 g, 28.7 mmol) in MeCN (100 mL) and the reaction vessel was sealed and heated at 90° C. for 20 h. The solvent was removed under vacuum and the crude product was purified by flash chromatography, elution gradient (1%→10% DCM in MeOH). Pure fractions were evaporated to dryness to give the title compound (6.0 g, 83%) as a white solid.

$^1$H NMR (400 MHz, DMSO-$d_6$) δ 1.47 (s, 9H), 3.60 (t, 2H), 4.22 (t, 2H), 7.76 (s, 1H), 7.95 (s, 1H), 8.30 (s, 1H) MS m/z 253 [M+H]$^+$

Intermediate 12: 3-Amino-6,7-dihydropyrazolo[1,5-a]pyrazin-4(5H)-one hydrochloride

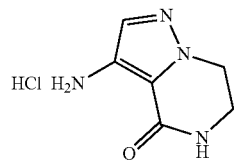 [SMILES: Cl ; Nc1cnn2c1C(=O)NCC2]

HCl (g) was added to a solution of tert-butyl (4-oxo-4,5,6,7-tetrahydropyrazolo[1,5-a]pyrazin-3-yl)carbamate (Intermediate 11, 9 g, 35.68 mmol) in MeOH (50 mL) and the reaction mixture was stirred at rt for 2 h. The precipitate was collected by filtration, washed with EtOAc and dried under vacuum to give the title compound (6.00 g, 89%) as a white solid. MS m/z 153 [M+H]$^+$ Intermediate 13: (1R,2R)-2-(4-Bromobenzoyl)-N-(4-oxo-4,5,6,7-tetrahydropyrazolo[1,5-a]pyrazin-3-yl)cyclohexanecarboxamide

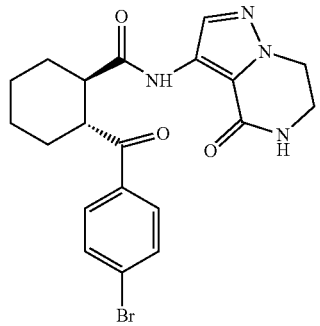 [SMILES: O=C1NCCn2ncc(NC(=O)[C@@H]3CCCC[C@H]3C(=O)c3ccc(Br)cc3)c21]

A mixture of 3-amino-6,7-dihydropyrazolo[1,5-a]pyrazin-4(5H)-one hydrochloride (Intermediate 12, 1.0 g, 5.30 mmol) and $Et_3N$ (2.96 mL, 21.21 mmol) in DMF (10 mL) was added to a stirred solution of (1R,2R)-2-(4-bromobenzoyl)cyclohexanecarboxylic acid (1.82 g, 5.83 mmol) and HATU (4.03 g, 10.60 mmol) in DMF (10 mL), over a period of 5 min. The reaction mixture was stirred at 50° C. for 15 h. The reaction mixture was diluted to with EtOAc, and washed sequentially with $NaHCO_3$ (sat, aq), brine (sat.), and water. The organic layer was dried over $MgSO_4$, filtered and evaporated and the crude product was purified by flash chromatography (1%→10% DCM in MeOH). Pure fractions were evaporated to dryness to give the title compound (1.2 g, 51%) as a white solid.

MS m/z 445 [M+H]$^+$

Intermediate 14: (1R,2R)-2-{4-[3-Methyl-1-(tetrahydro-2H-pyran-2-yl)-1H-pyrazol-5-yl]benzoyl}-N-(4-oxo-4,5,6,7-tetrahydropyrazolo[1,5-a]pyrazin-3-yl)cyclohexanecarboxamide

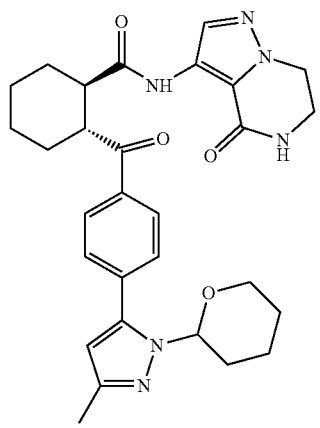 [SMILES: Cc1cc(-c2ccc(C(=O)[C@@H]3CCCC[C@H]3C(=O)Nc3cnn4c3C(=O)NCC4)cc2)n(C2CCCCO2)n1]

Pd(dppf)$Cl_2$*DCM (0.092 g, 0.11 mmol) was added to a solution of (1R,2R)-2-(4-bromobenzoyl)-N-(4-oxo-4,5,6,7-tetrahydropyrazolo[1,5-a]pyrazin-3-yl)cyclohexanecarboxamide (Intermediate 13, 1.0 g, 2.25 mmol), 3-methyl-1-

(tetrahydro-2H-pyran-2-yl)-5-(4,4,5,5-tetramethyl-1,3,2-dioxaborolan-2-yl)-1H-pyrazole (Intermediate 3, 0.984 g, 3.37 mmol) and Na$_2$CO$_3$ (0.952 g, 8.98 mmol) in dioxane (20 mL) and water (5 mL) over a period of 10 min under nitrogen atmosphere. The reaction mixture was stirred at 90° C. for 3 h. The solvent was removed under vacuum and the residue was diluted with EtOAc. The organic phase was washed sequentially with NaHCO$_3$ (sat, aq), a solution of brine (sat.), and water. The organic layer was dried over Na$_2$SO$_4$, filtered and evaporated. The crude product was purified by flash chromatography (10%→50% 2-methylpentane in EtOAc) to give the title compound (1.0 g, 84%) as a yellow solid.

MS m/z 531 [M+H]$^+$

Intermediate 15: tert-Butyl [1-methyl-5-(methylsulfanyl)-1H-pyrazol-4-yl]carbamate

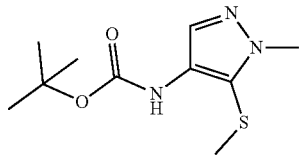 [SMILES: CSc1c(NC(=O)OC(C)(C)C)cnn1C]

Et$_3$N (873 mg, 8.63 mmol) and DPPA (1.19 g, 4.32 mmol) was added to a solution of 1-methyl-5-(methylsulfanyl)-1H-pyrazole-4-carboxylic acid (400 mg, 2.32 mmol) in tert-butanol (15 mL) under inert atmosphere and the reaction mixture was stirred at 20° C. for 2 h and then heated to reflux for an additional 13 h. The resulting mixture was concentrated in vacuo and the residue was dissolved in EtOAc. The organic phase was washed with water and brine, dried over Na$_2$SO$_4$, filtered and concentrated under vacuum. The residue is was purified by silica gel column chromatography (9% EtOAc in petroleum ether) to give the title compound (330 mg, 58%) as a white solid.

MS m/z 244 [M+H]$^+$

Intermediate 16: 1-Methyl-5-(methylsulfanyl)-1H-pyrazol-4-amine hydrochloride

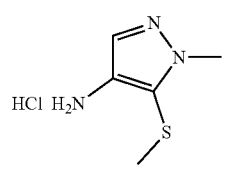

HCl (g) was bubbled into a solution of tert-butyl [1-methyl-5-(methylsulfanyl)-1H-pyrazol-4-yl]carbamate (Intermediate 15, 1.6 g, 6.58 mmol) in MeOH (30 mL) at 20° C. with stirring for 1 h. The reaction mixture was concentrated under vacuum to give the title compound (1.56 g, crude) as a light yellow solid.

MS m/z 144 [M+H]$^+$

Intermediate 17: (1R,2R)-2-(4-Bromobenzoyl)-N-[1-methyl-5-(methylsulfanyl)-1H-pyrazol-4-yl]cyclohexanecarboxamide

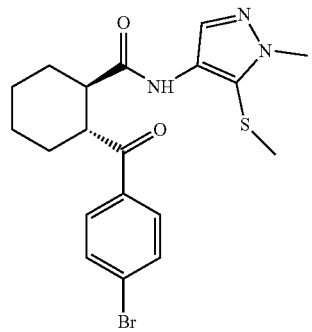 [SMILES: CSc1c(NC(=O)[C@@H]2CCCC[C@H]2C(=O)c2ccc(Br)cc2)cnn1C]

HATU (3.8 g, 9.99 mmol) was added to a stirred solution of (1R,2R)-2-[(4-bromophenyl)carbonyl]cyclohexane-1-carboxylic acid (2.3 g, 7.39 mmol) in DMF (20 mL) at 0° C. A solution of 1-methyl-5-(methylsulfanyl)-1H-pyrazol-4-amine hydrochloride (Intermediate 16, 1.5 g, 8.35 mmol) in DMF (10 mL) and DIPEA (3.24 g, 25.07 mmol) was added dropwise to the reaction mixture at 0° C. and the reaction mixture was stirred at rt for 2 h. The reaction mixture was concentrated under vacuum and the residue was dissolved in EtOAc. The organic phase was washed with NaHCO$_3$ (sat, aq) and brine, dried over Na$_2$SO$_4$ and concentrated in vacuo. The residue was purified by silica gel to column (28% EtOAc in petroleum ether) to give the title compound (2.1 g 65%) as a yellow solid.

$^1$H NMR (300 MHz, DMSO-d$_6$) δ 1.19-1.09 (m, 1H), 1.43-1.31 (m, 3H), 1.93-1.73 (m, 3H), 2.11-2.08 (m, 1H), 2.24 (s, 3H), 3.04-2.95 (m, 1H), 3.72-3.64 (t, 1H), 3.81 (s, 3H), 7.57 (s, 1H), 7.75-7.72 (d, 2H), 7.94-7.91 (d, 2H), 9.42 (s, 1H) MS m/z 436 [M+H]$^+$

Intermediate 18: (1R,2R)-2-(4-Bromobenzoyl)-N-[1-methyl-5-(methylsulfonyl)-1H-pyrazol-4-yl]cyclohexanecarboxamide

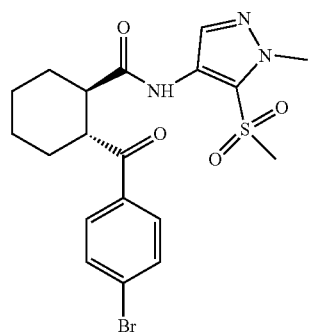 [SMILES: Cn1ncc(NC(=O)[C@@H]2CCCC[C@H]2C(=O)c2ccc(Br)cc2)c1S(C)(=O)=O]

3-Chloroperoxybenzoic acid (356 mg, 2.06 mmol) was added in portions at 0° C. to a solution of (1R,2R)-2-(4-bromobenzoyl)-N-[1-methyl-5-(methylsulfanyl)-1H-pyrazol-4-yl]cyclohexanecarboxamide (Intermediate 17, 600 mg, 1.4 mmol) in DCM (10 mL). The reaction mixture was stirred 0° C. for 40 min. 3-Chloroperoxybenzoic acid (356 mg, 2.06 mmol) was added in portions at 0° C. to the reaction mixture after which the mixture was stirred at rt for 60 min. The reaction mixture was diluted with DCM and the organic phase was washed with water and brine, dried over Na₂SO₄, filtered and concentrated under vacuum. The residue was purified by silica gel chromatography (96% DCM in MeOH) to give the title compound (630 mg, 98%) as a white solid.

MS m/z 468 [M+H]⁺

Intermediate 19: tert-Butyl [3-(difluoromethoxy)-1-methyl-1H-pyrazol-4-yl]carbamate

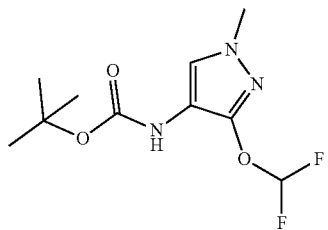 [SMILES: Cn1cc(NC(=O)OC(C)(C)C)c(OC(F)F)n1]

DIPEA (580 mg, 4.49 mmol) was added in portions to a solution of 3-(difluoromethoxy)-1-methyl-1H-pyrazole-4-carboxylic acid (575 mg, 2.99 mmol) in tert-BuOH (20 mL) under an atmosphere of nitrogen. DPPA (1.0 g, 3.63 mmol) was added dropwise with stirring to the reaction mixture and after which it was stirred at 80° C. for 12 h. The reaction mixture was concentrated under vacuum and the residue was purified by silica gel column chromatography (5%→20% EtOAc in petroleum) to give the title compound (630 mg, 80%) as light yellow oil.

MS m/z 264 [M+H]⁺

Intermediate 20:
3-(Difluoromethoxy)-1-methyl-1H-pyrazol-4-amine hydrochloride

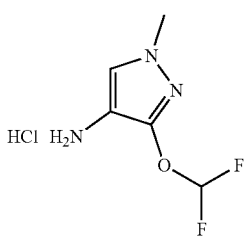

HCl(g) was bubbled into a solution of tert-butyl [3-(difluoromethoxy)-1-methyl-1H-pyrazol-4-yl]carbamate (Intermediate 19, 500 mg, 1.90 mmol) in EtOAc (20 mL) and the reaction mixture was stirred at rt for 2 h. The reaction mixture was concentrated under vacuum and the residue was washed with a solution of EtOAc/Petroleum ether (5 mL, 1:1) to give the title compound (320 mg, 84%) as a white solid.

¹H NMR (300 MHz, CDCl₃) δ 3.77 (s, 3H), 7.32 (t, 1H), 7.95 (s, 1H), 10.37 (bs, 2H)

Intermediate 21: (1R,2R)-2-(4-Bromobenzoyl)-N-[3-(difluoromethoxy)-1-methyl-1H-pyrazol-4-yl]cyclohexanecarboxamide

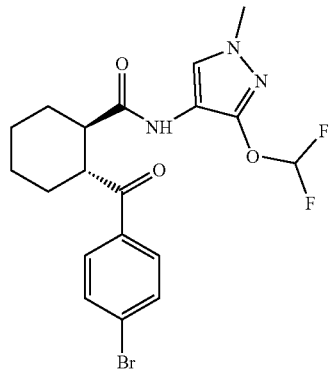 [SMILES: Cn1cc(NC(=O)[C@@H]2CCCC[C@H]2C(=O)c2ccc(Br)cc2)c(OC(F)F)n1]

DIPEA (778 mg, 6.02 mmol) and T3P (50% in EtOAc, 1.92 g, 6.03 mmol) was added to a solution of (1R,2R)-2-(4-bromobenzoyl)cyclohexanecarboxylic acid (514 mg, 1.65 mmol) and 3-(difluoromethoxy)-1-methyl-1H-pyrazol-4-amine hydrochloride (Intermediate 20, 300 mg, 1.50 mmol) in EtOAc (10 mL) and the reaction mixture was stirred at 75° C. for 2 h. The reaction mixture was concentrated under vacuum and the residue was purified by silica gel column chromatography (5%→20% EtOAc in petroleum) to give the title compound (360 mg, 52%) as light yellow solid.

MS m/z 456 [M+H]⁺

Intermediate 22:
1-Methyl-4-nitro-1H-pyrazole-3-sulfonyl chloride

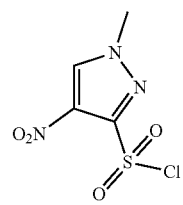

Step 1

CuCl₂*2H₂O (4.1 g, 24 mmol) was added to a solution of SO₂ (g) in AcOH (32%, aq) (246 g, 3.84 mol) and the reaction mixture was stirred at −10° C. for 1 h in an ice/salt bath with SO₂ gas being bubbled into the reaction mixture.

Step 2

NaNO₂ (6.9 g, 100 mmol) in water (50 mL) was added dropwise during 1 h to a solution of 1-methyl-4-nitro-1H-pyrazol-3-amine (13.5 g, 95 mmol) in AcOH/HCO₂H (5:1, 180 mL) and HCl (12 M, aq) (16 mL) at −10° C. under an atmosphere of nitrogen. The formed yellow solution was added in portions into the preformed solution from Step 1 during 1 h resulting in immediate evolution of nitrogen. The reaction mixture was stirred for 1 h and concentrated under vacuum. The residue was diluted with EtOAc and the organic phase was washed twice with water and twice with brine. The organic layer was dried and concentrated under vacuum to give the title compound (15 g, 70%) as a yellow semi-solid.

MS m/z 227 [M+H]⁺

Intermediate 23: 1-Methyl-4-nitro-1H-pyrazole-3-sulfonamide

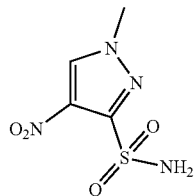

A solution of 1-methyl-4-nitro-1H-pyrazole-3-sulfonyl chloride (Intermediate 22, 5.1 g, 22.6 mmol) in THF (50 mL) was added dropwise during 1 h to a saturated solution of ammonia in THF (200 mL) at rt and the reaction mixture was stirred at rt for 5 h. The solids formed were collected by filtration and washed with DCM (100 mL), water (50 mL) and MeOH (50 mL) to give the title compound (2.4 g, 51%) as a white solid.
MS m/z 207 [M+H]$^+$

Intermediate 24: 4-Amino-1-methyl-1H-pyrazole-3-sulfonamide

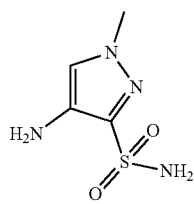

A solution of 1-methyl-4-nitro-1H-pyrazole-3-sulfonamide (Intermediate 23, 3.1 g, 15.0 mmol) in MeOH (200 mL). Pd/C (10%, 400 mg) was added and the reaction mixture was stirred at rt for 6 h under an atmosphere of H$_2$ (g). The solids were filtered out and the reaction mixture was concentrated under vacuum. The resulting solids were washed with MeOH (50 mL) to give the title compound (2.1 g, 79%) as a light pink solid.
$^1$H NMR (300 MHz, DMSO-d$_6$) δ 3.75 (s, 3H), 4.33 (s, 2H), 7.15 (s, 1H), 7.26 (s, 2H) MS m/z 177 [M+H]$^+$

Intermediate 25: (1R,2R)-2-(4-Bromobenzoyl)-N-(1-methyl-3-sulfamoyl-1H-pyrazol-4-yl)cyclohexanecarboxamide

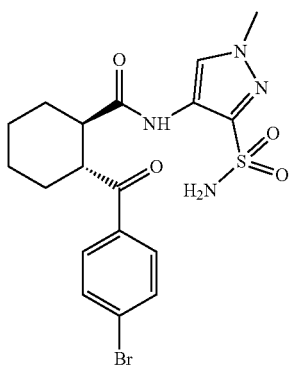 [SMILES: Cn1cc(NC(=O)[C@@H]2CCCC[C@H]2C(=O)c2ccc(Br)cc2)c(S(N)(=O)=O)n1]

T$_3$P (50% in EtOAc, 3.61 g, 5.68 mmol), Et$_3$N (861 mg, 8.51 mmol) and (1R,2R)-2-(4-bromobenzoyl)cyclohexanecarboxylic acid (500 mg, 1.61 mmol) was added to a solution of 4-amino-1-methyl-1H-pyrazole-3-sulfonamide (Intermediate 24, 884 mg, 5.02 mmol) in EtOAc (50 mL) and the reaction mixture was stirred at 80° C. for 5 h. The reaction mixture was washed with NaHCO$_3$ (sat, aq), twice with water and finally twice with brine.

The organic layer was dried over Na$_2$SO$_4$, filtered and concentrated under vacuum to give the title compound (720 mg, 31%) as a white solid.
MS m/z 469 [M+H]$^+$

Intermediate 26: 2,3-Dihydropyrazolo[5,1-b][1,3]oxazole

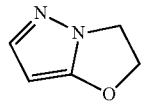

1,2-Dibromoethane (73.7 g, 392.5 mmol) was added to a solution of 1H-pyrazol-3-ol (11 g, 130.83 mmol) and K$_2$CO$_3$ (48.3 g, 349.3 mmol) in MeCN (200 mL) at rt and the reaction mixture was heated at 80° C. for 6 h. The reaction mixture was filtered and the filtrate was to concentrated under vacuum and purified by flash chromatography (1%→2.5% MeOH in DCM) to give the title compound (4.0 g, 28%) as a yellow solid.
$^1$H NMR (300 MHz, CDCl$_3$) δ 4.30 (t, 2H), 5.06 (t, 2H), 5.34 (s, 1H), 7.36 (s, 1H) MS m/z 111 [M+H]$^+$

Intermediate 27: 7-Nitro-2,3-dihydropyrazolo[5,1-b][1,3]oxazole

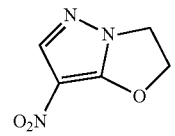

HNO$_3$ (36.1 mL, 802.3 mmol) and H$_2$SO$_4$ (36.1 mL, 676.8 mmol) were added over a period of 1 h to a solution of 2,3-dihydropyrazolo[5,1-b][1,3]oxazole (Intermediate 26, 15.89 g, 144.3 mmol) in H$_2$SO$_4$ (72 mL) at 0° C. under an atmosphere of nitrogen and then the reaction mixture was stirred at rt for 16 h. The reaction mixture was added to ice water and the aqueous layer was extracted two times with DCM. The combined organic layer was dried over Na$_2$SO$_4$, filtered and evaporated. The crude product was purified by flash chromatography (0%→100% EtOAc in petroleum ether) to give the title compound (12.5 g, 56%) as an off-white solid.
$^1$H NMR (400 MHz, CDCl$_3$) δ 4.44 (t, 2H), 5.35 (t, 2H), 7.90 (s, 1H) MS m/z 156 [M+H]$^+$

Intermediate 28: tert-Butyl 2,3-dihydropyrazolo[5,1-b][1,3]oxazol-7-ylcarbamate

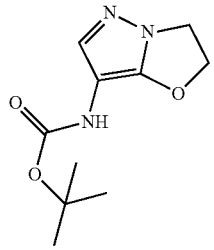 [SMILES: CC(C)(C)OC(=O)Nc1cnn2c1OCC2]

Di-tert-butyl dicarbonate (21.1 g, 96.7 mmol) and Pd-C (2.1 g, 19.7 mmol) were added to a solution of 7-nitro-2,3-dihydropyrazolo[5,1-b][1,3]oxazole (Intermediate 27, 5 g, 32.23 mmol) in MeOH (100 mL) and the reaction mixture was stirred at rt under an atmosphere of $H_2$ (1 atm) for 35 h. The reaction mixture was filtered, the filtrate was concentrated under vacuum and the crude product was purified by flash chromatography (0%→90% EtOAc in petroleum ether) to give the title compound (2.55 g, 35%) as a pale yellow solid.

MS m/z 226 $[M+H]^+$

Intermediate 29: 2,3-Dihydropyrazolo[5,1-b][1,3]oxazol-7-amine hydrochloride

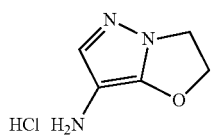

HCl (g) was bubbled for 1 h at rt into a solution of tert-butyl 2,3-dihydropyrazolo[5,1-b][1,3]oxazol-7-ylcarbamate (Intermediate 28, 500 mg, 2.22 mmol) in EtOAc (20 mL).

The reaction mixture was concentrated under vacuum to give the title compound (350 mg, 98%) as an off-white solid.

$^1$H NMR (300 MHz, DMSO-$d_6$) δ 4.32 (t, 2H), 5.17 (t, 2H), 7.41 (s, 1H) MS m/z 126 $[M+H]^+$

Intermediate 30: (1R,2R)-2-(4-Bromobenzoyl)-N-(2,3-dihydropyrazolo[5,1-b][1,3]oxazol-7-yl)cyclohexanecarboxamide

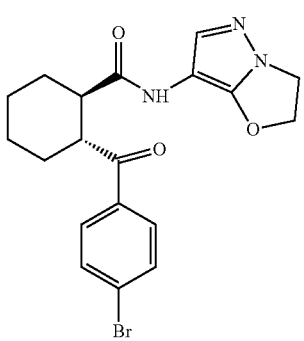 [SMILES: O=C(Nc1cnn2c1OCC2)[C@@H]1CCCC[C@H]1C(=O)c1ccc(Br)cc1]

(1R,2R)-2-(4-Bromobenzoyl)cyclohexanecarboxylic acid (402 mg, 1.29 mmol) was added to a solution of 2,3-dihydropyrazolo[5,1-b][1,3]oxazol-7-amine hydrochloride (Intermediate 29, 209 mg, 1.29 mmol), HATU (738 mg, 1.94 mmol) and DIPEA (0.90 mL, 5.17 mmol) in DMF (6 mL) at rt and the reaction mixture was stirred at for 16 h. The reaction mixture was concentrated in vacuo and diluted with EtOAc. The organic phase was washed twice with brine, dried over $Na_2SO_4$, filtered and evaporated. The crude product was purified by preparative TLC (9% MeOH in DCM) to give the title compound (200 mg, 37%).

MS m/z 418 $[M+H]^+$

Intermediate 31: (5-Methyl-1H-pyrazol-3-yl)boronic acid hydrochloride

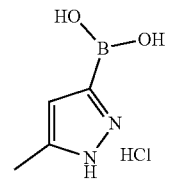

A solution of 3-methyl-1-(tetrahydro-2H-pyran-2-yl)-5-(4,4,5,5-tetramethyl-1,3,2-dioxaborolan-2-yl)-1H-pyrazole (Intermediate 3, 2.95 g, 10.10 mmol) in MeOH (10 mL) was added dropwise at 0° C. to HCl (3M in MeOH, 50 mL) and the reaction mixture was stirred at rt overnight. The reaction mixture was concentrated under vacuum and the residue was washed with hexane (2×20 mL) to give the title compound (1.3 g) as a light brown solid.

MS m/z 127 $[M+H]^+$

Intermediate 32: Ethyl 5-(benzylsulfanyl)-1-methyl-1H-pyrazole-4-carboxylate

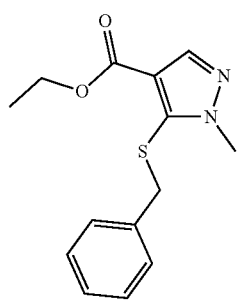 [SMILES: CCOC(=O)c1cnn(C)c1SCc1ccccc1]

Dibenzyl disulfide (101.9 g, 413.57 mmol) was added in portions to a solution of ethyl 5-amino-1-methyl-1H-pyrazole-4-carboxylate (10 g, 59.11 mmol) in MeCN (400 mL) in an atmosphere of nitrogen and at rt. CuCl (293 mg, 7.14 mmol) was added in portions at rt to the reaction mixture and it was stirred at rt for 30 min. 3-Methyl-1-nitrobutane (41.5 g, 354.26 mmol) was added to the reaction mixture and the resulting solution was stirred at rt for 30 min and then at 60° C. for 1 h. The reaction mixture was allowed to reach rt and the solids were filtered off. The filtrate was concentrated under vacuum and the residue was purified by silica gel column chromatography (EtOAc/petroleum ether, 1:8) to give the title compound (11.6 g, 71%) as yellow oil.

MS m/z 277 $[M+H]^+$

Intermediate 33: 5-(Benzylsulfanyl)-1-methyl-1H-pyrazole-4-carboxylic acid

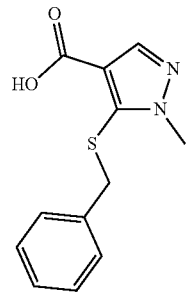 [SMILES: Cn1ncc(C(=O)O)c1SCc1ccccc1]

Sodium hydroxide (5.04 g, 126.01 mmol) in water (30 mL) was added dropwise at 0° C. to a solution of ethyl 5-(benzylsulfanyl)-1-methyl-1H-pyrazole-4-carboxylate (Intermediate 32, 11.6 g, 41.98 mmol) in MeOH (150 mL) and the reaction mixture was stirred at rt for 15 h. The reaction mixture was concentrated under vacuum, the residue was dissolved in water and the aqueous phase was washed EtOAc. The pH of the aqueous layer was adjusted to 5-6 with HCl (12 M, aq) and the solids formed were collected by filtration and dried under vacuum to give the title compound (8.8 g, 84%) as a light yellow solid.

MS m/z 249 [M+H]$^+$=249

Intermediate 34: tert-Butyl [5-(benzylsulfanyl)-1-methyl-1H-pyrazol-4-yl]carbamate

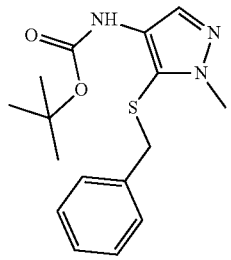 [SMILES: Cn1ncc(NC(=O)OC(C)(C)C)c1SCc1ccccc1]

Boc$_2$O (30 g, 137.61 mmol) and Et$_3$N (10.7 g, 105.74 mmol) was added under an atmosphere of nitrogen to a solution of 5-(benzylsulfanyl)-1-methyl-1H-pyrazole-4-carboxylic acid (Intermediate 33, 8.8 g, 35.44 mmol) in tert-butanol (200 mL). Diphenyl is phosphoryl azide (19.5 g, 70.86 mmol) was added dropwise to the reaction mixture and it was stirred at rt for 4 h and then at 88° C. for 15 h. The reaction mixture was concentrated under vacuum. The residue was dissolved in EtOAc and the organic phase was washed with NaHCO$_3$ (sat, aq) and brine, dried over Na$_2$SO$_4$, filtered and concentrated under vacuum. The residue was purified by silica gel column chromatography (EtOAc/petroleum ether, 1:6) to give the title compound (9.8 g, 87%) as yellow oil.

MS m/z 320 [M+H]$^+$

Intermediate 35: 5-(Benzylsulfanyl)-1-methyl-1H-pyrazol-4-amine hydrochloride

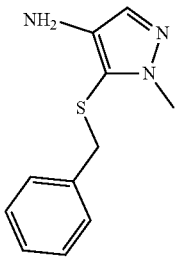

HCl (g) was bubbled into a solution of tert-butyl [5-(benzylsulfanyl)-1-methyl-1H-pyrazol-4-yl]carbamate (Intermediate 34, 9.8 g, 30.68 mmol) in MeOH (150 mL) at rt for 6 h. The reaction mixture was concentrated under vacuum to give the title compound (7.5 g, 96%) as a light yellow solid.

MS m/z 220 [M+H]$^+$

Intermediate 36: (1R,2R)—N-[5-(Benzylsulfanyl)-1-methyl-1H-pyrazol-4-yl]-2-(4-bromobenzoyl)cyclohexanecarboxamide

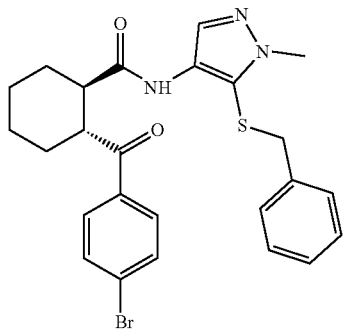 [SMILES: Cn1ncc(NC(=O)[C@@H]2CCCC[C@H]2C(=O)c2ccc(Br)cc2)c1SCc1ccccc1]

HATU (223 mg, 0.59 mmol) and 5-(benzylsulfanyl)-1-methyl-1H-pyrazol-4-amine to hydrochloride (Intermediate 35, 100 mg, 0.39 mmol) was added to a solution of (1R,2R)-2-[(4-bromophenyl)carbonyl]cyclohexane-1-carboxylic acid (122 mg, 0.39 mmol) in DMF (10 mL). DIPEA (152 mg, 1.18 mmol) was added dropwise to the reaction mixture and it was stirred at 20° C. for 15 h. Water was added to the reaction mixture and the aqueous phase was extracted with EtOAc. The organic layer was washed with NaHCO$_3$ (sat, aq) is and brine, dried over Na$_2$SO$_4$, filtered and concentrated under vacuum. The residue was purified by preparative TLC (EtOAc/Petroleum Ether, 1:5) and the crude product was purified by preparative HPLC on a Sunfire C18 column (150 mm) using a gradient of 55-100% MeCN in a H$_2$O/HCO$_2$H (99.5/0.5) buffer system as mobile phase to give the title compound (111 mg, 55%) as a white solid.

$^1$H NMR (300 MHz, DMSO-d$_6$) δ 1.23-1.12 (m, 1H), 1.52-1.37 (m, 3H), 1.94-1.74 (m, 3H), 2.11-2.07 (m, 1H), 3.06-2.98 (t, 1H), 3.26 (s, 3H), 3.74-3.66 (t, 1H), 3.89 (s,

2H), 7.06-7.03 (m, 2H), 7.25-7.21 (m, 3H), 7.57 (s, 1H), 7.74-7.71 (d, 2H), 7.95-7.92 (d, 2H), 9.36 (s, 1H) MS m/z 512 [M+H]$^+$

Intermediate 37: (1R,2R)-2-(4-Bromobenzoyl)-N-(1-methyl-5-sulfamoyl-1H-pyrazol-4-yl)cyclohexanecarboxamide

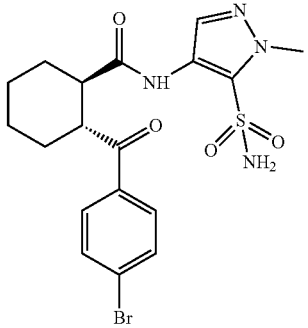 [SMILES: Cn1ncc(NC(=O)[C@@H]2CCCC[C@H]2C(=O)c2ccc(Br)cc2)c1S(N)(=O)=O]

Step 1—4-({[(1R,2R)-2-(4-Bromobenzoyl)cyclohexyl]carbonyl}amino)-1-methyl-1H-pyrazole-5-sulfonyl chloride A mixture of (1R,2R)—N-[5-(benzylsulfanyl)-1-methyl-1H-pyrazol-4-yl]-2-(4-bromobenzoyl)cyclohexanecarboxamide (Intermediate 36, 7 g, 13.66 mmol) in AcOH (60 mL) was diluted with water and cooled to −10° C. 1,3-Dichloro-5,5-dimethylimidazolidine-2,4-dione (4.05 g, 20.56 mmol) was added in one portion at −10° C. and the reaction mixture was stirred at −5° C. for 30 min. 1,3-Dichloro-5,5-dimethylimidazolidine-2,4-dione (1.35 g, 6.85 mmol) was added at 0° C. and the reaction mixture was stirred for 30 min. 1,3-Dichloro-5,5-dimethylimidazolidine-2,4-dione (1.35 g, 6.85 mmol) was added at about −5° C. and the reaction mixture was stirred for 30 min. 1,3-Dichloro-5,5-dimethylimidazolidine-2,4-dione (1.35 g, 6.85 mmol) was added at about −5° C. and the reaction mixture was stirred below 5° C. for 60 min. The reaction mixture was diluted with water and the aqueous phase was extracted with DCM. The organic layer was washed with NaHCO$_3$ (8%, aq) until pH of the aqueous layer was about 6~7. The organic phase was concentrated under vacuum to give the sub-title compound (12 g, crude).
MS 488 m/z [M+H]$^+$=/490

Step 2—(1R,2R)-2-(4-Bromobenzoyl)-N-(1-methyl-5-sulfamoyl-1H-pyrazol-4-yl)cyclohexanecarboxamide NH$_3$ (g) was bubbled into THF (300 mL) at −5° C. until the solvent was near saturation. A solution of 4-({[(1R,2R)-2-(4-bromobenzoyl)cyclohexyl]carbonyl}amino)-1-methyl-1H-pyrazole-5-sulfonyl chloride (19 g, 38.87 mmol) in THF (500 mL) was added dropwise with stirring at −5° C. and the reaction mixture was stirred at rt for 30 min. The reaction mixture was concentrated under vacuum and the residue was purified by silica gel column chromatography (EtOAc/petroleum ether, 1:1) and then by silica gel medium pressure column chromatography using a gradient of 20%→45% of MeCN in H$_2$O/HCO$_2$H (99.9/0.1) buffer system as mobile phase to give the title compound (12.0 g, 66%) as an off-white solid.

$^1$H NMR (400 MHz, DMSO-d$_6$) δ 1.21-1.10 (m, 1H), 1.52-1.32 (m, 3H), 1.83-1.72 (m, 2H), 2.08-1.90 (m, 2H), 2.90-2.83 (t, 1H), 3.71-3.65 (t, 1H), 3.95 (s, 3H), 7.76-7.74 (d, 2H), 7.79 (s, 1H), 7.95-7.93 (d, 2H), 8.03 (s, 2H), 8.82 (s, 1H) MS 469 m/z [M+H]$^+$

Intermediate 38: 3-(Difluoromethyl)-1-(tetrahydro-2H-pyran-2-yl)-1H-pyrazol-4-amine

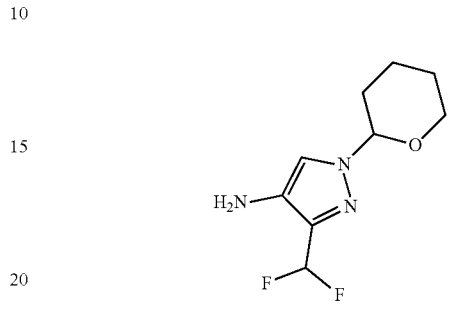

Step 1—Ethyl 3-(difluoromethyl)-1-(tetrahydro-2H-pyran-2-yl)-1H-pyrazole-4-carboxylate 3,4-Dihydro-2H-pyran (1.3 g, 15.45 mmol) and 4-methylbenzenesulfonic acid (400 mg, 2.33 mmol) was added to a solution of ethyl 3-(difluoromethyl)-1H-pyrazole-4-carboxylate (2.3 g, 12.10 mmol) in THF (50 mL) and the reaction mixture was stirred overnight at rt.

The reaction mixture was concentrated under vacuum and the residue was diluted with NaHCO$_3$ (aq, 50 mL) and then extracted with EtOAc. The organic phase was washed with brine, dried over Na$_2$SO$_4$ and concentrated under vacuum. The residue was purified by is silica gel column chromatography (1.5→5% EtOAc in petroleum ether) to give the subtitle compound (5 g, crude) as a brown oil.

Step 2—3-(Difluoromethyl)-1-(tetrahydro-2H-pyran-2-yl)-1H-pyrazole-4-carboxylic acid A solution of sodium hydroxide (220 mg, 5.50 mmol) in water (2 mL) was added to a solution of ethyl 3-(difluoromethyl)-1-(tetrahydro-2H-pyran-2-yl)-1H-pyrazole-4-carboxylate (300 mg, 1.09 mmol) in EtOH (5 mL) and the reaction mixture was stirred at 60° C. for 5 h. The reaction mixture was concentrated under vacuum and the residue was diluted with water (3 mL) and the pH value of the solution was adjusted to ~3-4 with HCl (2M. aq). The precipitate was collected by filtration and the solid was dried in an oven under vacuum to give the subtitle compound (0.15 g, 56%) as a white solid.

Step 3—Benzyl [3-(difluoromethyl)-1-(tetrahydro-2H-pyran-2-yl)-1H-pyrazol-4-yl]carbamate DPPA (5.4 g, 19.62 mmol) and Et$_3$N (3.2 g, 31.62 mmol) was added to 3-(difluoromethyl)-1-(tetrahydro-2H-pyran-2-yl)-1H-pyrazole-4-carboxylic acid (4 g, 16.25 mmol) dissolved in a mixture of benzyl alcohol and toluene (60 mL, 5:1) under a nitrogen atmosphere and the reaction mixture was heated to reflux for 2 h. The reaction mixture was extracted with EtOAc and the combined organic layer was washed with brine, dried over Na$_2$SO$_4$, and concentrated under vacuum. The residue was purified by silica gel column chromatography (5→33% EtOAc in petroleum ether) to give the subtitle compound (6 g, crude) as a yellow oil.

Step 4—3-(Difluoromethyl)-1-(tetrahydro-2H-pyran-2-yl)-1H-pyrazol-4-amine

Pd/C (1 g) was added to a solution of benzyl [3-(difluoromethyl)-1-(tetrahydro-2H-pyran-2-yl)-1H-pyrazol-4-yl]carbamate (4.2 g, 11.95 mmol) in EtOH (50 mL) and the reaction mixture was stirred at rt overnight under an atmosphere of H$_2$ (g). The solids were filtered to off and the filtrate was concentrated under vacuum. The residue was purified by silica gel column chromatography (3→50% EtOAc in petroleum ether) to give the title compound (2.4 g, 92%) as a red oil.

$^1$H-NMR (300 MHz, DMSO-d$_6$) δ 1.40-1.75 (m, 3H), 1.75-2.05 (m, 3H), 3.50-3.70 (m, 1H), 4.30 (bs, 2H), 5.25 (d, 1H), 6.90 (t, 1H), 7.25 (s, 1H). MS m/z 218 [M+H]$^+$

Intermediate 39: (1R,2R)-2-(4-Bromobenzoyl)-N-[5-(difluoromethyl)-1-(tetrahydro-2H-pyran-2-yl)-1H-pyrazol-4-yl]cyclohexanecarboxamide

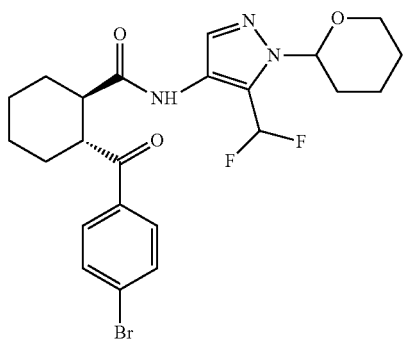 [SMILES: O=C(Nc1cnn(C2CCCCO2)c1C(F)F)[C@@H]1CCCC[C@H]1C(=O)c1ccc(Br)cc1]

HATU (2 g, 7.9 mmol) and DIPEA (2.2 g, 17 mmol) was added to a solution of (1R,2R)-2-(4-bromobenzoyl)cyclohexanecarboxylic acid (2 g, 6.45 mmol) in DMF (40 mL) and the reaction mixture was stirred at rt for 20 min. 3-(Difluoromethyl)-1-(tetrahydro-2H-pyran-2-yl)-1H-pyrazol-4-amine (Intermediate 38, 1.68 g, 7.74 mmol) was added and the reaction mixture was stirred at rt for 2 h. Ice-water (100 mL) was added to the reaction mixture and the precipitate was filtered and washed with water. The crude solid was dissolved in DCM (200 mL), dried over Na$_2$SO$_4$ and concentrated under vacuum to give the title compound (1.5 g, 45%) as a white solid.

MS m/z 532 [M+Na]$^+$

Intermediate 40: tert-Butyl (5-methyl-4-oxo-4,5,6,7-tetrahydropyrazolo[1,5-a]pyrazin-3-yl)carbamate

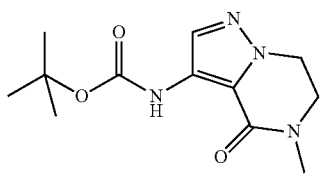 [SMILES: CN1CCn2ncc(NC(=O)OC(C)(C)C)c2C1=O]

Methyl 1-(2-bromoethyl)-4-[(tert-butoxycarbonyl)amino]-1H-pyrazole-5-carboxylate (Intermediate 10, 5 g, 14.36 mmol) was added to a solution of methylamine (30 mL, 60.00 mmol) in THF (30 mL) at 25° C. and the reaction mixture was stirred at 70° C. for 15 h. The reaction mixture was filtered through a pad of Celite and the filtrate was concentrated in vacuum. The crude product was purified by flash chromatography (0%→1% MeOH in DCM) to give the title compound (3.20 g, 84%) as a white solid.

$^1$H NMR (400 MHz, DMSO-d$_6$) δ 1.46 (s, 9H), 2.98 (s, 3H), 3.75 (t, 2H), 4.30 (t, 2H), 7.75 (s, 1H), 8.01 (s, 1H) MS m/z 267 [M+H]$^+$

Intermediate 41: 3-Amino-5-methyl-6,7-dihydropyrazolo[1,5-a]pyrazin-4(5H)-one hydrochloride

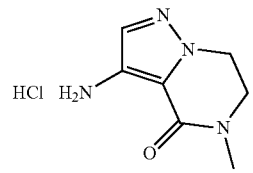

HCl gas was bubbled into a solution of tert-butyl (5-methyl-4-oxo-4,5,6,7-tetrahydropyrazolo[1,5-a]pyrazin-3-yl)carbamate (Intermediate 40, 3.1 g, 11.64 mmol) in EtOAc (100 mL) and the reaction mixture was stirred at rt for 2 h. The precipitate was collected by filtration, washed with EtOAc (50 mL) and dried under vacuum to give the title compound (2.2 g, 93%) as a white solid.

MS m/z 167 [M+H]$^+$

Intermediate 42: (1R,2R)-2-(4-Bromobenzoyl)-N-(5-methyl-4-oxo-4,5,6,7-tetrahydropyrazolo[1,5-a]pyrazin-3-yl)cyclohexanecarboxamide

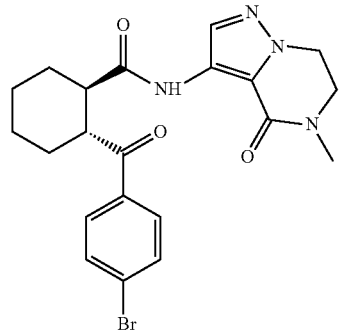 [SMILES: CN1CCn2ncc(NC(=O)[C@@H]3CCCC[C@H]3C(=O)c3ccc(Br)cc3)c2C1=O]

T3P (50% in EtOAc, 14.58 g, 22.92 mmol) was added to a mixture of (1R,2R)-2-(4-bromobenzoyl)cyclohexanecarboxylic acid (1.78 g, 5.73 mmol), 3-amino-5-methyl-6,7-dihydropyrazolo[1,5-a]pyrazin-4(5H)-one hydrochloride (Intermediate 41, 1 g, 6.02 mmol) and Et$_3$N (3.20 mL, 22.92 mmol) in butyl acetate (1 mL) at 25° C. and the reaction mixture was stirred at 60° C. for 15 h. The solvent was removed under vacuum and the crude product was purified by flash chromatography (0%→5% MeOH in DCM) to give the title compound (0.69 g, 26%) as a white solid.

$^1$H NMR (400 MHz, DMSO-d$_6$) δ 1.55-1.10 (m, 4H), 1.83-1.70 (m, 2H), 2.10-1.88 (m, 2H), 2.98 (t, 1H), 3.01 (s, 3H), 3.70 (t, 1H), 3.78 (t, 2H), 4.30 (t, 2H), 7.75 (d, 2H), 7.81 (s, 1H), 7.92 (d, 2H), 9.20 (s, 1H) MS m/z 459 [M+H]$^+$

Intermediate 43: (1R,2R and 1S,2S)-2-(4-Bromobenzoyl)-N-(5-cyano-1-methyl-1H-pyrazol-4-yl)cyclohexanecarboxamide

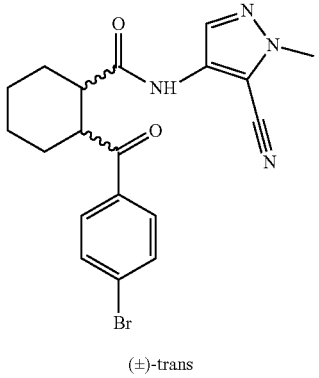 [SMILES: Cn1ncc(NC(=O)C2CCCCC2C(=O)c2ccc(Br)cc2)c1C#N]

(±)-trans (1R,2R and 1S,2S)-2-(4-Bromobenzoyl)cyclohexanecarboxylic acid (2.0 g, 6.4 mol) was added to a mixture of 4-amino-1-methyl-1H-pyrazole-5-carbonitrile (2.0 g, 6.4 mol), T3P (50% in EtOAc, 2.0 g, 9.4 mol) and DMAP (1.8 g, 1.5 mol) in DCE (10 mL) and the reaction mixture was stirred in a microwave reactor at 100° C. for 1 h. The reaction mixture was diluted with DCM and the organic layer was washed with brine, dried and concentrated in vacuum. The residue was purified by silica gel chromatography (17% EtOAc in petroleum ether) give the title compound (0.4 g, 17%) as a white solid.

$^1$H NMR (400 MHz, CDCl$_3$) δ 1.39-1.49 (m, 3H), 1.69-1.76 (m, 1H), 1.85-1.94 (m, 2H), 2.04-2.10 (m, 2H), 2.83-2.90 (m, 1H), 3.64-3.71 (m, 1H), 3.95 (s, 3H), 7.56 (s, 1H), 7.59 (d, J=8.4 Hz, 2H), 7.83 (d, J=8.4 Hz, 2H), 7.89 (s, 2H) MS m/z 415.1 [M+H]$^+$

Intermediate 44: 1-Ethyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-5-carboxamide

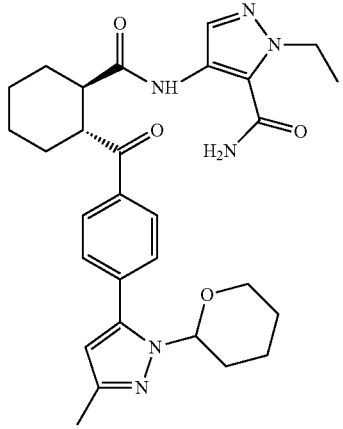 [SMILES: CCn1ncc(NC(=O)[C@@H]2CCCC[C@H]2C(=O)c2ccc(-c3cc(C)nn3C3CCCCO3)cc2)c1C(N)=O]

T3P (50% in EtOAc, 293 μL, 0.98 mmol) and Et$_3$N (422 μL, 3.03 mmol) were added to a solution of (1R,2R)-2-{4-[3-methyl-1-(tetrahydro-2H-pyran-2-yl)-1H-pyrazol-5-yl]benzoyl}cyclohexanecarboxylic acid (Intermediate 8, 300 mg, 0.76 mmol) and 4-amino-1-ethyl-1H-pyrazole-5-carboxamide (152 mg, 0.98 mmol) in EtOAc (2.3 mL) and the reaction mixture was heated in a sealed vessel at 80° C. for 1.5 h. 4-Amino-1-ethyl-1H-pyrazole-5-carboxamide (152 mg, 0.98 mmol), Et$_3$N (422 μL, 3.03 mmol) and T3P (50% in EtOAc, 293 μL, 0.98 mmol) were added to the reaction mixture and it was heated at 80° C. for 1 h and then stirred at rt over night. The reaction mixture was purified by flash chromatography using EtOAc as mobile phase to give the title compound (150 mg, 37%).

MS m/z 531.3 [M−H]$^-$

Intermediate 45: Methyl 4-({[(1R,2R)-2-(4-bromobenzoyl)cyclohexyl]carbonyl}-amino)-1-methyl-1H-pyrazole-5-carboxylate

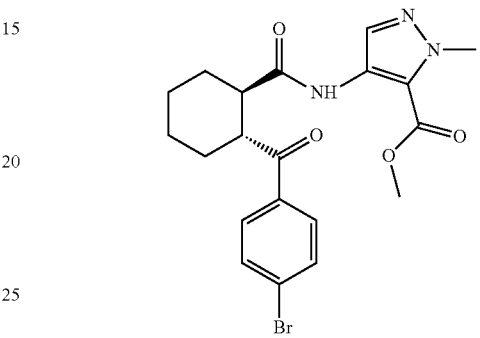

Et$_3$N (1.8 mL, 12.99 mmol) and T3P (50% in EtOAc, 4 mL, 6.72 mmol) were added to a solution of (1R,2R)-2-(4-bromobenzoyl)cyclohexanecarboxylic acid (1 g, 3.21 mmol) and methyl 4-amino-1-methyl-1H-pyrazole-5-carboxylate (1 g, 6.45 mmol) in EtOAc (15 mL) and the reaction mixture was stirred at rt for 1 h and then heated at 73-77° C. for 2 h. The reaction mixture was diluted with EtOAc (100 mL) and the organic phase was washed with NaHCO$_3$ (sat, aq), dried using a phase separator and concentrated in vacuum. The residue was purified by flash chromatography (30%→100% EtOAc in heptane) to give the title compound (1.22 g, 85%) as a white solid.

$^1$H NMR (500 MHz, CDCl$_3$) δ 1.25-1.40 (m, 1H), 1.43 (dqt, 2H), 1.71 (qd, 1H), 1.84-1.95 (m, 2H), 1.99-2.08 (m, 1H), 2.11 (dd, 1H), 2.92 (ddd, 1H), 3.67 (ddd, 1H), 4.03 (s, 3H), 4.07 (s, 3H), 7.56-7.63 (m, 2H), 7.8-7.87 (m, 2H), 8.12 (s, 1H), 8.88 (s, 1H). MS m/z 448 [M+H]$^+$

Intermediate 46: Methyl 1-methyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-5-carboxylate

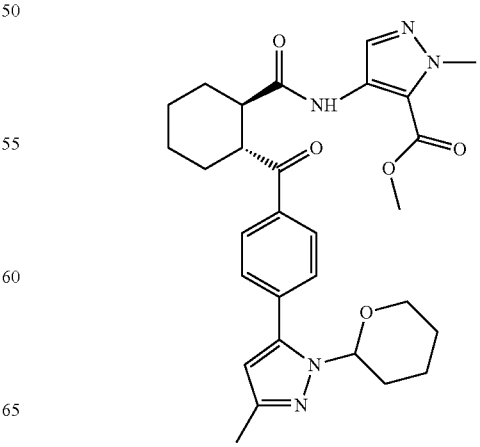

A solution of K₂CO₃ (1.44 g, 10.44 mmol) in water (15 mL) followed by Pd(dtbpf)Cl₂ (168 mg, 0.26 mmol) was added to a solution of methyl 4-({[(1R,2R)-2-(4-bromobenzoyl)cyclohexyl]carbonyl}amino)-1-methyl-1H-pyrazole-5-carboxylate (Intermediate 45, 1.17 g, 2.61 mmol) and 3-methyl-1-(tetrahydro-2H-pyran-2-yl)-5-(4,4,5,5-tetramethyl-1,3,2-dioxaborolan-2-yl)-1H-pyrazole (Intermediate 3, 1.91 g, 6.52 mmol) in dioxane (15 mL) under an atmosphere of nitrogen and the reaction mixture was heated to 80° C. for 1 h. The reaction mixture was diluted with EtOAc (200 mL) and the organic phase was washed with brine (sat.), dried using a phase separator and concentrated in vacuum. The residue was purified by flash chromatography (20%→100% of EtOAc in is heptane) to give the title compound (0.85 g, 61%).

¹H NMR (500 MHz, CDCl₃) δ 1.23-1.6 (m, 6H), 1.69 (tdd, 3H), 1.8-1.93 (m, 2H), 2.08 (dd, 2H), 2.39 (d, 1H), 2.52 (tdt, 1H), 2.87-3.01 (m, 1H), 3.55 (qd, 1H), 3.72 (ddd, 1H), 3.98 (s, 3H), 3.99-4.04 (m, 3H), 5.06 (dt, 1H), 6.12 (s, 1H), 7.54 (d, 2H), 8.02 (d, 2H), 8.09 (d, 1H), 8.88 (s, 1H).

MS m/z 534.2 [M+H]⁺

Intermediate 47: N,1-Dimethyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-5-carboxamide

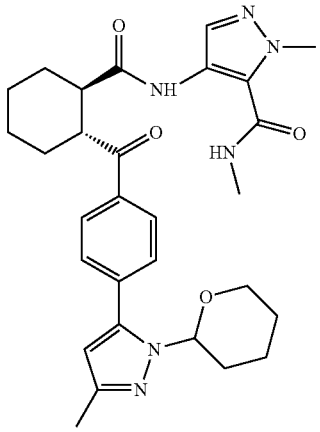 [SMILES: CNC(=O)c1c(NC(=O)[C@@H]2CCCC[C@H]2C(=O)c2ccc(-c3cc(C)nn3C3CCCCO3)cc2)cnn1C]

Step 1—1-Methyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-5-carboxylic acid LiOH (1M in H₂O, 3 mL, 3.00 mmol) was added dropwise over 10 min to a solution of methyl 1-methyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-5-carboxylate (Intermediate 46, 0.78 g, 1.46 mmol) in THF (3 mL) and MeOH (3 mL) and the reaction mixture was stirred at rt for 50 min. The reaction mixture was diluted with EtOAc and stirred at rt for 5 min and then concentrated in vacuum to give the title compound (0.75 g, 99%).

MS m/z 519.0 [M+H]⁺

Step 2—N,1-Dimethyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-5-carboxamide T3P (50% in EtOAc, 344 µL, 0.58 mmol), methylamine hydrochloride (22 µL, 0.38 mmol) and DIPEA (134 µL, 0.77 mmol) were added to a suspension of 1-methyl-4-({[(1R,2R)-2-{4-[3-methyl-1-(tetrahydro-2H-pyran-2-yl)-1H-pyrazol-5-yl]benzoyl}cyclohexyl]-carbonyl}-amino)-1H-pyrazole-5-carboxylic acid (0.1 g, 0.19 mmol) in EtOAc (0.8 mL) and the reaction mixture was stirred at rt for 1 h and then heated in a microwave reactor at 60° C. for 1 h. Methylamine hydrochloride (22 µL, 0.38 mmol) and DIPEA (134 µL, 0.77 mmol) was added to the reaction mixture and it was heated in a microwave reactor at 60° C. for 1 h. The reaction mixture was diluted with EtOAc and NaHCO₃ (sat., aq) and the organic phase was dried using a phase separator and concentrated in vacuum. The crude product was purified by flash chromatography (100% EtOAc) to give the title compound (0.067 g, 65%).

MS m/z 531.4 [M−H]⁻

Intermediate 48: 5-Methyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-3-carboxamide

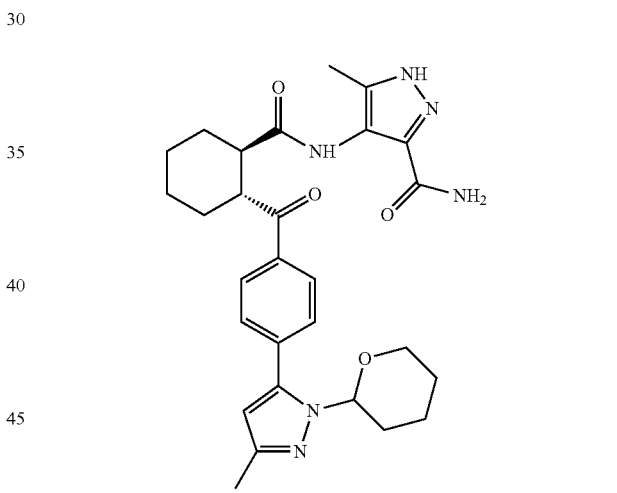

DIPEA (352 µL, 2.02 mmol) and HATU (230 mg, 0.61 mmol) were added to a solution of (1R,2R)-2-{4-[3-methyl-1-(tetrahydro-2H-pyran-2-yl)-1H-pyrazol-5-yl]benzoyl}-cyclohexanecarboxylic acid (Intermediate 8, 200 mg, 0.50 mmol) in DMF (4 mL) and the reaction mixture was stirred at rt for 5 min. 4-Amino-5-methyl-1H-pyrazole-3-carboxamide (106 mg, 0.76 mmol) was added to the reaction mixture and it was stirred at rt for 15 h. The reaction mixture was diluted with EtOAc and the organic phase was washed with NaHCO₃ (sat., aq), NH₄Cl (sat., aq) and brine. The organic phase was dried using a phase separator and concentrated under vacuum. The residue was purified by flash chromatography (0%→10% of EtOH in EtOAc), the compound containing fractions were collected, concentrated in vacuum, and the residue was dissolved in DCM and concentrated in vacuum to give the title compound (190 mg, 73%) as a beige solid.

MS m/z 417.1 [M−H]⁻

Intermediate 49: 1 4-({[(1R,2R)-2-{4-[1-(Tetrahydro-2H-pyran-2-yl)-1H-pyrazol-5-yl]benzoyl}cyclohexyl]carbonyl}amino)-1H-pyrazole-5-carboxamide

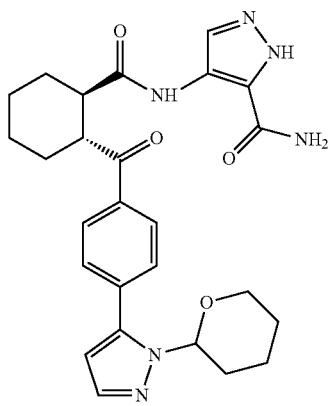 [SMILES: NC(=O)c1[nH]ncc1NC(=O)[C@@H]1CCCC[C@H]1C(=O)c1ccc(-c2ccnn2C2CCCCO2)cc1]

A solution of (1R,2R)-2-{4-[1-(tetrahydro-2H-pyran-2-yl)-1H-pyrazol-5 yl]benzoyl}cyclohexanecarboxylic acid (Intermediate 69, 300 mg, 0.78 mmol) in DMF (3.0 mL) was added to a solution of 4-amino-1H-pyrazole-5-carboxamide hydrochloride (255 mg, 1.57 mmol) and Et$_3$N (381 µL, 2.75 mmol) in EtOAc (3 mL). T3P (50% in EtOAc, 0.70 mL, 1.18 mmol) was added and the reaction mixture was heated at 80° C. for 1 h and then stirred at rt over night. The reaction mixture was diluted with NaHCO$_3$ (8%, aq) and EtOAc. The aqueous layer was extracted with EtOac and the combined organic layer was dried using a phase separator and concentrated under vacuum. The residue was purified by preparative HPLC on an XBridge C18 column (10 µm 250×19 ID mm) using a gradient of 10-80% MeCN in a H$_2$O/MeCN/NH$_3$ (95/5/0.2) buffer system, to give the title compound (97 mg 25%).
MS m/z 489.3 [M−H]$^-$ Intermediate 50: (1R,2R)—N-(4-Oxo-4,5,6,7-tetrahydropyrazolo[1,5-a]pyrazin-3-yl)-2-{4-[1-(tetrahydro-2H-pyran-2-yl)-1H-pyrazol-5-yl]benzoyl}cyclohexanecarboxamide

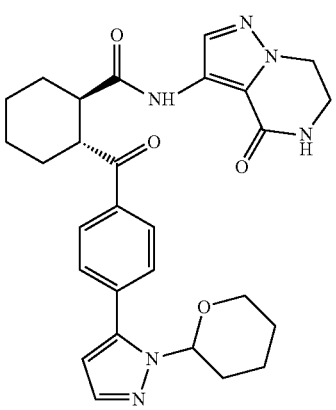 [SMILES: O=C1NCCn2ncc(NC(=O)[C@@H]3CCCC[C@H]3C(=O)c3ccc(-c4ccnn4C4CCCCO4)cc3)c21]

A solution of 1-(tetrahydro-2H-pyran-2-yl)-5-(4,4,5,5-tetramethyl-1,3,2-dioxaborolan-2-yl)-1H-pyrazole (0.511 g, 1.84 mmol) in dioxane (5 mL) was added to (1R,2R)-2-(4-bromobenzoyl)-N-(4-oxo-4,5,6,7-tetrahydropyrazolo[1,5-a]pyrazin-3-yl)cyclohexanecarboxamide (Intermediate 13, 0,545 g, 1.22 mmol). A solution of K$_2$CO$_3$ (0.677 g, 4.90 mmol) in water (5 mL) was added to the reaction mixture and it was evacuated and purged with nitrogen three times. The reaction mixture was heated to 50° C. and Pd(dtbpf)Cl$_2$ (0.040 g, 0.06 mmol) was added and the reaction mixture was heated at is 50° C. for 10 min. The reaction mixture was diluted with EtOAc (5 ml) and the organic phase was washed with water. The aqueous phase was extracted with EtOAc and then the combined organic phase was washed with brine, dried using a phase separator and concentrated in vacuum. The residue was purified by flash chromatography (EtOAc) to give the title compound (0.460 g, 72.8%) as an oil.
$^1$H NMR (400 MHz, CDCl$_3$) δ 1.31-1.53 (m, 3H), 1.63-1.99 (m, 6H), 2.06-2.25 (m, 3H), 2.47-2.71 (m, 1H), 2.93-3.08 (m, 1H), 3.63 (q, 1H), 3.80 (d, 3H), 4.13 (q, 2H), 4.31 (t, 2H), 5.21 (d, 1H), 5.91 (s, 1H), 6.33-6.46 (m, 1H), 7.62 (dd, 3H), 8.10 (d, 2H), 8.16 (s, 1H), 8.84 (s, 1H).
MS m/z 515.6 [M−H]$^-$ Intermediate 51: Ethyl 1-methyl-5-(methylsulfamoyl)-1H-pyrazole-4-carboxylate

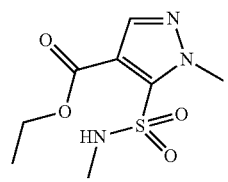 [SMILES: CCOC(=O)c1cnn(C)c1S(=O)(=O)NC]

A solution of ethyl 5-(chlorosulfonyl)-1-methyl-1H-pyrazole-4-carboxylate (10.0 g, 39.6 mmol) in THF (20 mL) was added dropwise with stirring at 0-2° C. during 20 min to a mixture of methylamine (33% aq, 20.4 g, 217 mmol) and K$_2$CO$_3$ (5.4 g, 38.79 mmol). The reaction mixture was stirred at 0-2° C. in a water/ice bath for 40 min. The reaction mixture was concentrated under vacuum. The residue was extracted with tert-butyl methyl ether and the organic layer was dried over Na$_2$SO$_4$ and concentrated in vacuum to give the title compound (9.5 g, 97%) as a yellow oil.
$^1$H NMR (300 MHz, CDCl$_3$) δ 1.35 (t, 3H), 2.67 (d, 3H), 4.20 (s, 3H), 4.32 (q, 2H), 6.85-6.74 (m, 1H), 7.92 (s, 1H)

Intermediate 52: 1-Methyl-5-(methylsulfamoyl)-1H-pyrazole-4-carboxylic acid

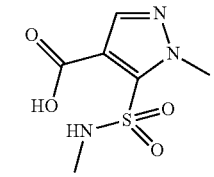

A solution of NaOH (3.9 g, 97.5 mmol) in water (20 mL) was added to a solution of ethyl 1-methyl-5-(methylsulfamoyl)-1H-pyrazole-4-carboxylate (Intermediate 51, 9.5 g, 38.4 is mmol) in MeOH (10 mL) and the reaction mixture was stirred at 40° C. for 1 h. The reaction mixture was concentrated under vacuum and the resulting mixture was washed twice with tert-butyl methyl ether. The pH value of the solution was adjusted to 2-3 with HCl (6 M, aq). The solids were collected by filtration to give the title compound (5.7 g, 68%) as an off-white solid.

¹H NMR (300 MHz, DMSO-d₆) δ 2.53 (s, 3H), 4.08 (s, 3H), 7.50 (s, 1H), 7.94 (s, 1H), 13.20 (s, 1H).

Intermediate 53: 2,7-Dimethyl-4,7-dihydropyrazolo[4,3-e][1,2,4]thiadiazin-3(2H)-one 1,1-dioxide

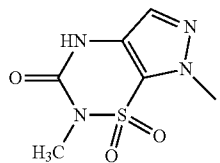

DIPEA (3.67 g, 28.40 mmol) was added to a solution of 1-methyl-5-(methylsulfamoyl)-1H-pyrazole-4-carboxylic acid (Intermediate 52, 4.8 g, 21.90 mmol) in toluene (25 mL). DPPA (7.83 g, 28.45 mmol) was added dropwise to the reaction mixture with stirring at 80-85° C. in 20 min and the reaction mixture was stirred at 85° C. for 3 h. The reaction mixture was concentrated under vacuum and the residue was purified by silica gel column chromatography (50% EtOAc in Petroleum ether) to give the title compound (3.2 g, 68%) as an off-white solid.

¹H NMR (400 MHz, CDCl₃) δ 3.40 (s, 3H), 4.12 (s, 3H), 7.34 (s, 1H), 9.28 (s, 1H).

Intermediate 54: 4-Amino-N,1-dimethyl-1H-pyrazole-5-sulfonamide hydrochloride

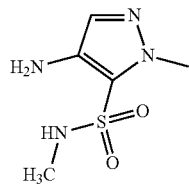

HCl (6M, aq, 43 mL) was added to a solution of 2,7-dimethyl-4,7-dihydropyrazolo[4,3-e][1,2,4]thiadiazin-3(2H)-one 1,1-dioxide (Intermediate 53, 3.5 g, 16.19 mmol) in 1,4-dioxane (2 mL) and the reaction mixture was stirred at 95° C. for 3 days. The reaction mixture was allowed to reach rt and the pH value of the solution was adjusted to 9-10 with K₂CO₃ is (sat., aq). The resulting solution was extracted with EtOAc and the organic layer was dried over Na₂SO₄ and concentrated under vacuum. The residue was purified by silica gel column chromatography (50% EtOAc in Petroleum ether) to give the title compound (2.8 g, 91%) as a light yellow solid.

¹H NMR (400 MHz, DMSO-d₆) δ 2.43 (s, 3H), 3.81 (s, 3H), 4.66 (s, 2H), 7.05 (s, 1H), 7.67 (s, 1H) MS m/z 191 [M+H]⁺

Intermediate 55: (1R,2R)-2-(4-Bromobenzoyl)-N-[1-methyl-5-(methylsulfamoyl)-1H-pyrazol-4-yl]cyclohexanecarboxamide

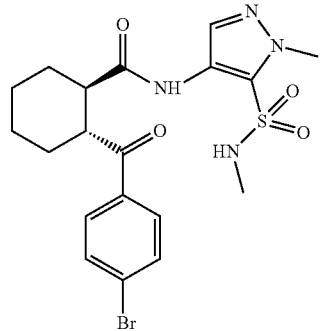 [SMILES: CNS(=O)(=O)c1c(NC(=O)[C@@H]2CCCC[C@H]2C(=O)c2ccc(Br)cc2)cnn1C]

T3P (50% in EtOAc, 2.73 g, 8.58 mmol) and Et₃N (870 mg, 8.60 mmol) were added to a solution of (1R,2R)-2-[(4-bromophenyl)carbonyl]cyclohexane-1-carboxylic acid (533 mg, 1.71 mmol) and 4-amino-N,1-dimethyl-1H-pyrazole-5-sulfonamide hydrochloride (Intermediate 54, 327 mg, 1.72 mmol) in EtOAc (10 mL) and the reaction mixture was stirred at 70° C. for 4 h. The reaction mixture was extracted with EtOAc and the combined organic layer was washed with sodium hydroxide (2N, aq), brine, dried over Na₂SO₄ and concentrated under vacuum. The residue was purified by silica gel column chromatography (17%→33% EtOAc in Petroleum ether) to give the title compound (350 mg, 42%) as a white solid.

MS m/z 483 [M+H]⁺

Intermediate 56: (1R,2R)—N-[1-Methyl-5-(methylsulfamoyl)-1H-pyrazol-4-yl]-2-{4-[3-methyl-1-(tetrahydro-2H-pyran-2-yl)-1H-pyrazol-5-yl]benzoyl}cyclohexane-carboxamide

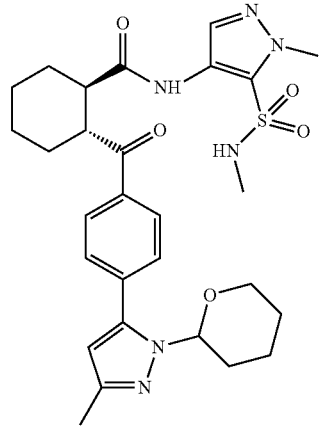 [SMILES: CNS(=O)(=O)c1c(NC(=O)[C@@H]2CCCC[C@H]2C(=O)c2ccc(-c3cc(C)nn3C3CCCCO3)cc2)cnn1C]

Pd(dppf)Cl₂*DCM (33.8 mg, 0.05 mmol) and K₂CO₃ (171 mg, 1.24 mmol) was added to a mixture of (1R,2R)-2-(4-bromobenzoyl)-N-[1-methyl-5-(methylsulfamoyl)-1H-pyrazol-4-yl]cyclohexanecarboxamide (Intermediate 55, 200 mg, 0.41 mmol) and 3-methyl-1-(tetrahydro-2H-pyran- 2-yl)-5-(4,4,5,5-tetramethyl-1,3-dioxolan-2-yl)-1H-pyrazole (Intermediate 3, 218 mg, 1.04 mmol) in dioxane/H$_2$O (1:1, 5 mL) and the reaction mixture was stirred at 50° C. for 30 min. The reaction mixture was extracted with EtOAc and the combined organic layer was washed with brine, dried over Na$_2$SO$_4$ and concentrated under vacuum. The residue was purified by silica gel column chromatography (11%→50% EtOAc in Petroleum ether) to give the title compound (240 mg, 97%) as a red solid.

MS m/z 569 [M+H]$^+$

Intermediate 57: Ethyl 5-(dimethylsulfamoyl)-1-methyl-1H-pyrazole-4-carboxylate

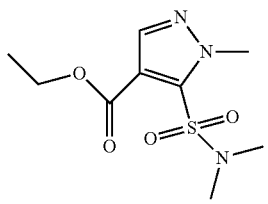 [SMILES: CCOC(=O)c1cnn(C)c1S(=O)(=O)N(C)C]

Ethyl 5-(chlorosulfonyl)-1-methyl-1H-pyrazole-4-carboxylate (10 g, 39.58 mmol) was added to a solution of dimethylamine (2 M in THF, 45 mL, 89.45 mmol) in THF (30 mL) and the reaction mixture was stirred at rt for 10 min. The reaction mixture was diluted with EtOAc (100 mL) and the organic phase was washed with water, brine and concentrated in vacuum to give the title compound (8 g, 77%) as red oil.

MS m/z 262 [M+H]$^+$

Intermediate 58: 5-(Dimethylsulfamoyl)-1-methyl-1H-pyrazole-4-carboxylic acid

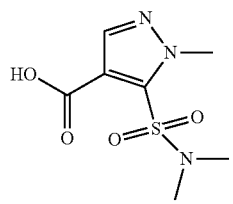

A solution of NaOH (3.8 g, 95.01 mmol) in water (50 mL) was added to a solution of ethyl 5-(dimethylsulfamoyl)-1-methyl-1H-pyrazole-4-carboxylate (Intermediate 57, 5 g, 19.14 mmol) in MeOH (100 mL) and the reaction mixture was stirred at 40° C. for 2 h. The solvent was removed in vacuo and the pH value of the solution was adjusted to 2-3 with HCl (1M, aq). The solid was collected by filtration and the filtrate was extracted with of EtOAc (2×20 mL). The organic layer was concentrated and the solids were combined and is dried in vacuum to give the title compound (3.8 g, 85%) as a red solid.

MS m/z 234 [M+H]$^+$

Intermediate 59: tert-Butyl [5-(dimethylsulfamoyl)-1-methyl-1H-pyrazol-4-yl]carbamate

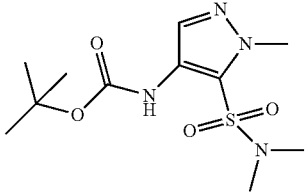 [SMILES: CN(C)S(=O)(=O)c1c(NC(=O)OC(C)(C)C)cnn1C]

DPPA (6.1 g, 22.3 mmol) and DIPEA (3.8 g, 29.40 mmol) was added to a solution of 5-(dimethylsulfamoyl)-1-methyl-1H-pyrazole-4-carboxylic acid (Intermediate 58, 3.7 g, 15.86 mmol) in tert-BuOH (50 mL) and the reaction mixture was stirred at 85° C. for 15 h.

The solvent was removed under vacuum and the residue was dissolved in EtOAc. The organic phase was washed with water, concentrated in vacuum and the residue was purified by silica gel column chromatography (33% EtOAc in Petroleum ether) to give the title compound (2.5 g, 52%) as a yellow solid.

MS m/z 305 [M+H]$^+$

Intermediate 60: 4-Amino-N,N,1-trimethyl-1H-pyrazole-5-sulfonamide hydrochloride

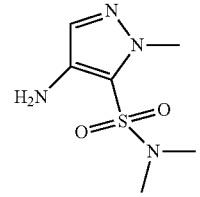

A solution of tert-butyl [5-(dimethylsulfamoyl)-1-methyl-1H-pyrazol-4-yl]carbamate (Intermediate 59, 500 mg, 1.64 mmol) in EtOAc (20 mL), was treated with HCl (g) and the reaction mixture was stirred at rt for 1 h. The solvent was removed under vacuum to give the title compound (390 mg, 99%) as a pink solid.

MS m/z 205 [M+H]$^+$

Intermediate 61: (1R,2R)-2-(4-Bromobenzoyl)-N-[5-(dimethylsulfamoyl)-1-methyl-1H-pyrazol-4-yl]cyclohexanecarboxamide

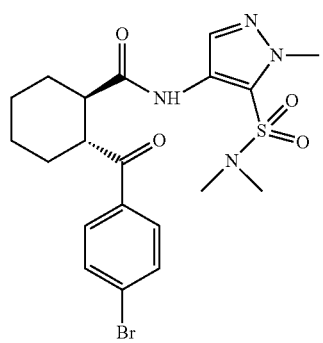 [SMILES: CN(C)S(=O)(=O)c1c(NC(=O)[C@@H]2CCCC[C@H]2C(=O)c2ccc(Br)cc2)cnn1C]

HATU (844 mg, 2.22 mmol) and DIPEA (573 mg, 4.43 mmol) was added to a solution of (1R,2R)-2-[(4-bromophenyl)carbonyl]cyclohexane-1-carboxylic acid (358 mg, 1.15 mmol) and 4-amino-N,N,1-trimethyl-1H-pyrazole-5-sulfonamide hydrochloride (Intermediate 60, 280 mg, 1.16 mmol) in DMF (8 mL) the reaction mixture was stirred at rt for 4 h. The is solvent was removed under vacuum and the residue was purified by preparative TLC (4.7% MeOH in DCM) to give the title compound (130 mg, 23%) as a yellow solid.

MS m/z 497 [M+H]$^+$

Intermediate 62: Ethyl 4-amino-3-methyl-1H-pyrazole-5-carboxylate

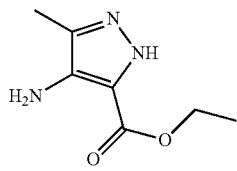

Pd-C (500 mg, 4.70 mmol) was added to a solution of ethyl 3-methyl-4-nitro-1H-pyrazole-5-carboxylate (4.75 g, 23.85 mmol) in MeOH (50 mL) and the reaction mixture was stirred under an atmosphere of hydrogen at rt for 20 h. The solid was filtered off and the filtrate was concentrated under vacuum to give the title compound (3.8 g, 94%).

MS m/z 170 [M+H]$^+$

Intermediate 63: Ethyl 4-[(tert-butoxycarbonyl)amino]-3-methyl-1H-pyrazole-5-carboxylate

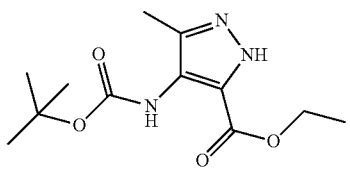 [SMILES: CCOC(=O)c1[nH]nc(C)c1NC(=O)OC(C)(C)C]

Boc$_2$O (2.13 mL, 9.16 mmol) was added to a solution of ethyl 4-amino-3-methyl-1H-pyrazole-5-carboxylate (Intermediate 62, 1.5 g, 8.87 mmol) and pyridine (1.42 mL, 17.57 mmol) in MeOH (40 mL) and the reaction mixture was stirred at rt for 4 h. The reaction mixture was concentrated under vacuum to give the title compound (2.1 g, 88%)

MS m/z 270 [M+H]$^+$

Intermediate 64: Ethyl 1-(2-bromoethyl)-4-[(tert-butoxycarbonyl)amino]-3-methyl-1H-pyrazole-5-carboxylate

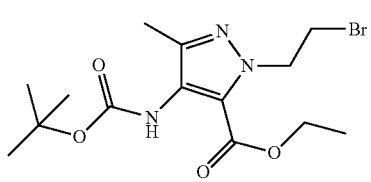 [SMILES: CCOC(=O)c1c(NC(=O)OC(C)(C)C)c(C)nn1CCBr]

1,2-Dibromoethane (1.6 g, 8.52 mmol) was added to a solution of ethyl 4-[(tert-butoxycarbonyl)amino]-3-methyl-1H-pyrazole-5-carboxylate (Intermediate 63, 2.1 g, 7.80 is mmol) and K$_2$CO$_3$ (2.1 g, 15.19 mmol) in DMF (80 mL) and the reaction mixture was stirred at rt for 3 h. The solids were filtered off and the filtrate was concentrated under vacuum. The residue was purified by silica gel column chromatography (20% EtOAc in Petroleum ether) to give the title compound (1 g, 34%).

$^1$H NMR (400 MHz, DMSO-d$_6$) δ 1.30 (t, 3H), 1.43 (s, 9H), 2.08 (s, 3H), 3.78 (t, 2H), 4.25 (q, 2H), 4.73 (t, 2H) MS m/z 376 [M+H]$^+$

Intermediate 65: tert-Butyl (2-methyl-4-oxo-4,5,6,7-tetrahydropyrazolo[1,5-a]pyrazin-3-yl)carbamate

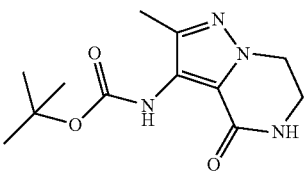 [SMILES: Cc1nn2c(c1NC(=O)OC(C)(C)C)C(=O)NCC2]

Ethyl 1-(2-bromoethyl)-4-[(tert-butoxycarbonyl)amino]-3-methyl-1H-pyrazole-5-carboxylate (Intermediate 64, 1 g, 2.66 mmol) was suspended in MeCN (9 mL) and ammonia (25%, aq, 3 mL, 77.04 mmol) in a pressure reactor and the reactor was heated in an oil bath at 60° C. for 16 h. The reaction mixture was concentrated under vacuum and the resulting mixture was washed with a mixture of EtOAc/Petroleum ether (1:2). The solids were collected by filtration and dried under vacuum to give the title compound (650 mg, 92%) as an off-white solid.

MS m/z 267 [M+H]$^+$

Intermediate 66: 3-Amino-2-methyl-6,7-dihydropyrazolo[1,5-a]pyrazin-4(5H)-one hydrochloride

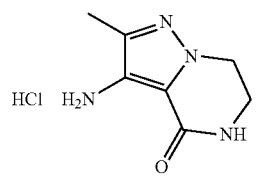

HCl (gas) was bubbled into a solution of tert-butyl (2-methyl-4-oxo-4,5,6,7-tetrahydropyrazolo[1,5-a]pyrazin-3-yl)carbamate (Intermediate 65, 650 mg, 2.44 mmol) in MeOH (15 mL) at rt for 20 min. The resulting mixture was concentrated under vacuum to give the title compound (460 mg, 93%) as a white solid.

$^1$H NMR (300 MHz DMSO-d$_6$) δ 2.23 (s, 3H), 3.63-3.58 (m, 2H), 4.23-4.19 (t, 2H), 7.49-7.15 (m, 2H), 8.46 (s, 1H), 9.78-8.78 (br, 1H) MS m/z 167 [M+H]$^+$

Intermediate 67: (1R,2R)-2-(4-Bromobenzoyl)-N-(2-methyl-4-oxo-4,5,6,7-tetrahydropyrazolo[1,5-a]pyrazin-3-yl)cyclohexanecarboxamide

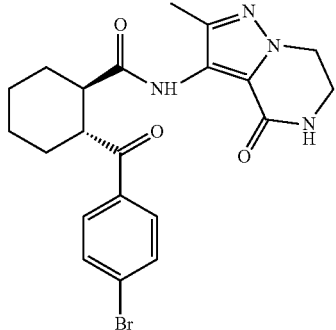 [SMILES: Cc1nn2c(c1NC(=O)[C@@H]1CCCC[C@H]1C(=O)c1ccc(Br)cc1)C(=O)NCC2]

3-Amino-2-methyl-6,7-dihydropyrazolo[1,5-a]pyrazin-4(5H)-one hydrochloride (Intermediate 66, 460 mg, 2.27 mmol) and DIPEA (1.18 g, 9.13 mmol) were added to a mixture of (1R,2R)-2-(4-bromobenzoyl)cyclohexanecarboxylic acid (708 mg, 2.28 mmol) and HATU (1.73 g, 4.55 mmol) in DMF (20 mL) and the reaction mixture was heated at 50° C. for 16 h. The reaction mixture was concentrated under vacuum and the residue was dissolved in EtOAc. The reaction mixture was diluted with EtOAc and the organic phase was washed with NaHCO$_3$ (aq) and brine, dried over Na$_2$SO$_4$, filtered and concentrated in vacuum. The residue was purified by silica gel column chromatography (4.7% MeOH in DCM) to give the title compound (630 mg, 60%) as a light yellow solid.
MS m/z 441 [M+H]$^+$

Intermediate 68: (1R,2R)—N-[5-(Difluoromethyl)-1-(tetrahydro-2H-pyran-2-yl)-1H-pyrazol-4-yl]-2-[4-(1H-pyrazol-3-yl)benzoyl]cyclohexanecarboxamide

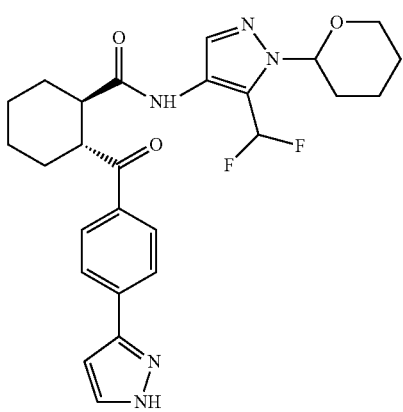 [SMILES: O=C(Nc1cnn(C2CCCCO2)c1C(F)F)[C@@H]1CCCC[C@H]1C(=O)c1ccc(-c2cc[nH]n2)cc1]

1H-Pyrazol-3-ylboronic acid (169 mg, 1.51 mmol), K$_2$CO$_3$ (568 mg, 4.11 mmol) and Pd(dppf)Cl$_2$*DCM (112 mg, 0.14 mmol) were added to a solution of (1R,2R)-2-(4-bromobenzoyl)-N-[5-(difluoromethyl)-1-(tetrahydro-2H-pyran-2-yl)-1H-pyrazol-4-yl]cyclohexanecarboxamide (Intermediate 39, 700 mg, 1.37 mmol) in a mixture of dioxane and water (4:1, 15 mL) under an atmosphere of nitrogen and the reaction mixture was stirred at 50° C. for 2 h. The reaction mixture was diluted with EtOAc and the organic phase was washed with water, brine (sat.), dried over Na$_2$SO$_4$ and concentrated under is vacuum. The residue was purified by silica gel column chromatography (33% EtOAc in Petroleum ether) to give the title compound (520 mg, 76%) as brown oil.
MS m/z 498 [M+H]$^+$

Intermediate 69: (1R,2R)-2-{4-[1-(Tetrahydro-2H-pyran-2-yl)-1H-pyrazol-5 yl]benzoyl}cyclohexanecarboxylic acid

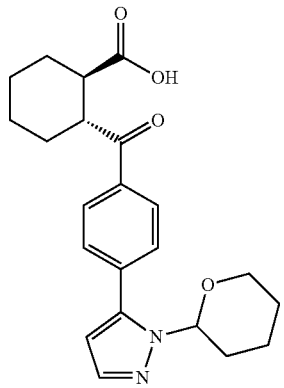 [SMILES: O=C(O)[C@@H]1CCCC[C@H]1C(=O)c1ccc(-c2ccnn2C2CCCCO2)cc1]

K$_2$CO$_3$ (3.94 g, 28.5 mmol) and Pd(dtbpf)Cl$_2$ (232 mg, 0.36 mmol) were added to a solution of (1R,2R)-2-(4-bromobenzoyl)cyclohexanecarboxylic acid (2.22 g, 7.12 mmol) and 1-(tetrahydro-2H-pyran-2-yl)-5-(4,4,5,5-tetramethyl-1,3,2-dioxaborolan-2-yl)-1H-pyrazole (2.97 g, 10.68 mmol) in 1,4-dioxane (40 mL) and water (20 mL). The reaction mixture was evacuated and purged with nitrogen three times and then heated at 80° C. for 1 h. The reaction mixture was diluted with EtOAc washed with KHSO$_4$ (1M, aq). The aqueous phase was extracted with EtOAc (×2) and the combined organic phase was dried using phase separator and concentrated under reduced pressure. The crude product was purified by preparative HPLC on a Kromasil C8 column (10 μm 250×50 ID mm) using a gradient of 30-90% MeCN in H$_2$O/MeCN/AcOH (95/5/0.2) buffer system to give the title product (2.72 g, 100%) as a brown solid.
$^1$H NMR (500 MHz, CDCl$_3$) δ 1.23-1.34 (m, 1H), 1.36-1.47 (m, 2H), 1.47-1.66 (m, 3H), 1.71-1.83 (m, 1H), 1.83-1.94 (m, 3H), 2.05-2.12 (m, 2H), 2.24-2.31 (m, 1H), 2.54-2.65 (m, 1H), 2.95-3.02 (m, 1H), 3.54-3.68 (m, 2H), 4.12-4.18 (m, 1H), 5.22 (dd, 1H), 6.38-6.41 (m, 1H), 7.61-7.67 (m, 3H), 8.03-8.09 (m, 2H). MS m/z 381.3 [M–H]$^-$

Intermediate 70: Ethyl 4-(4-bromo-2-chlorophenyl)-4-hydroxybut-2-ynoate

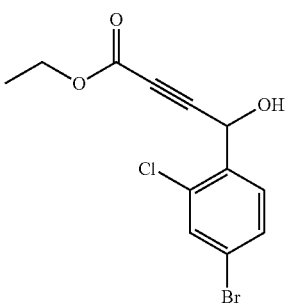 [SMILES: CCOC(=O)C#CC(O)c1ccc(Br)cc1Cl]

n-Butyllithium (1.6M in hexane, 44 mL, 70.4 mmol) was added to a solution of DIPEA (10 mL, 69.2 mmol) in THF (100 mL) under an atmosphere of nitrogen at −78° C. for 30 min. Ethyl prop-2-ynoate (6.5 mL, 64.3 mmol) was added dropwise to the reaction mixture followed by the addition of a solution of 4-bromo-2-chlorobenzaldehyde (14.11 g, 64.3 mmol) in THF (25 mL) and the reaction mixture was stirred at −78° C. over night. AcOH (12 mL) in THF (50 mL) was added to the reaction mixture and it was then poured into water (800 mL). The reaction mixture was extracted four times with DCM. The combined organic phase was dried over MgSO$_4$, filtered and concentrated in vacuo. The crude product was purified by flash chromatography (20%→50% EtOAc in heptane) to give the title compound (11.0 g, 54%).

$^1$H NMR (400 MHz, CDCl$_3$) δ 1.31 (t, 3H), 2.70 (d, 1H), 4.24 (q, 2H), 5.86 (d, 1H), 7.47 (dd, 1H), 7.55-7.61 (m, 2H) MS m/z 316.9 [M−H]$^−$

Intermediate 71: Ethyl (2E)-4-(4-bromo-2-chlorophenyl)-4-oxobut-2-enoate

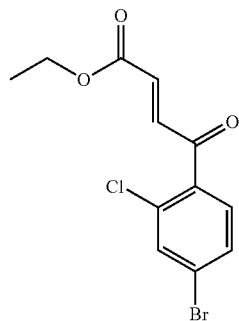 [SMILES: CCOC(=O)/C=C/C(=O)c1ccc(Br)cc1Cl]

Et$_3$N (5 mL, 36.07 mmol) was added to a solution of ethyl 4-(4-bromo-2-chlorophenyl)-4-hydroxybut-2-ynoate (Intermediate 70, 11 g, 34.6 mmol) in 1,4-dioxane (50 mL) and the reaction mixture was stirred at 60° C. for 4 h. The reaction mixture was concentrated in vacuo, the residue was redissolved in EtOAc and the organic phase was washed with HCl (1M, aq). The crude product was purified by flash chromatography (0%→25% EtOAc in heptane) to give the title compound (7.8 g, 71%).

$^1$H NMR (400 MHz, CDCl$_3$) δ 1.33 (t, 3H), 4.28 (q, 2H), 6.66 (d, 1H), 7.38 (d, 1H), 7.46-7.54 (m, 2H), 7.64 (d, 1H).

Intermediate 72: Ethyl (1R,6R and 1S,6S)-6-(4-bromo-2-chlorobenzoyl)cyclohex-3-ene-1-carboxylate

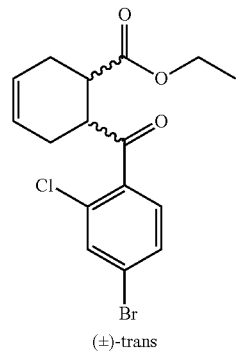 [SMILES: CCOC(=O)C1CC=CCC1C(=O)c1ccc(Br)cc1Cl]
(±)-trans

Buta-1,3-diene (14 mL, 165.65 mmol), condensed at −78° C., was added to a mixture of ethyl (2E)-4-(4-bromo-2-chlorophenyl)-4-oxobut-2-enoate (Intermediate 71, 4.04 g, 12.72 mmol) and hydroquinone (0.011 g, 0.10 mmol) in toluene (15 mL) at −78° C. and the reaction vessel was sealed and stirred at rt for 1 h and then heated at 210° C. for 15 h. The crude product was purified by flash chromatography (5%→25% EtOAc in heptane) to give the title compound (4.47 g, 95%).

$^1$H NMR (400 MHz, CDCl$_3$) δ 1.24 (t, 3H), 2.08 (dddd, 1H), 2.21 (dddd, 1H), 2.26-2.39 (m, 1H), 2.52 (dd, 1H), 3.02 (td, 1H), 3.63 (td, 1H), 4.12 (qd, 2H), 5.63-5.77 (m, 2H), 7.47 (dd, 1H), 7.56 (d, 1H), 7.60 (d, 1H).

Intermediate 73: 4-({[(1R,6R and 1S,6S)-6-(4-Bromo-2-chlorobenzoyl)cyclohex-3-en-1-yl]carbonyl}amino)-1-methyl-1H-pyrazole-5-carboxamide

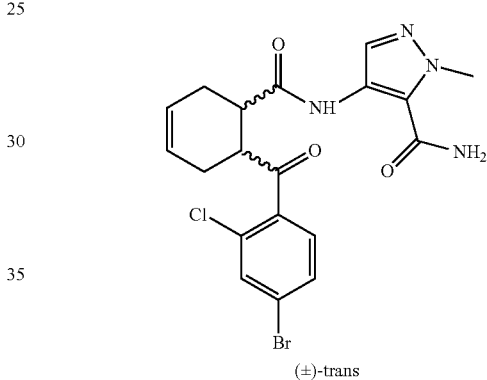
(±)-trans

Step 1 (1R,6R and 1S,6S)-6-(4-Bromo-2-chlorobenzoyl)cyclohex-3-ene-1-carboxylic acid Water (20 mL) and LiOH (1.0 g, 41.76 mmol) was added to a solution of ethyl (1R,6R and 1S,6S)-6-(4-bromo-2-chlorobenzoyl)cyclohex-3-ene-1-carboxylate (Intermediate 72, 4.43 g, 11.92 mmol) in THF (40 mL) and MeOH (40 mL) and the reaction mixture was stirred at 60° C. for 2 h. The reaction mixture was concentrated in vacuo and the residue was acidified by the addition of HCl (2M, aq). The water phase was extracted three times with diethyl ether and the combined organic phase was dried over MgSO$_4$, filtered and concentrated in vacuo to give the subtitle compound (3.69 g, 90%).

Step 2: 4-({[(1R,6R and 1S,6S)-6-(4-Bromo-2-chlorobenzoyl)cyclohex-3-en-1-yl]carbonyl}amino)-1-methyl-1H-pyrazole-5-carboxamide T3P (50% in EtOAc, 640 mg, 2.01 mmol) and DMAP (300 mg, 2.46 mmol) were added to a solution of (1R,6R and 1S,6S)-6-(4-bromo-2-chlorobenzoyl)cyclohex-3-ene-1-carboxylic acid (Intermediate 73 Step 1, 571 mg, 1.16 mmol) and 4-amino-1-methyl-1H-pyrazole-5-carboxamide (280 mg, 2.0 mmol) in THF (12 mL) and DCM (1 mL) and the reaction mixture was stirred at rt for 15 h. Water (5 mL) was added and the reaction mixture was concentrated under reduced pressure. The residue was diluted with water and the water phase was extracted with EtOAc. The organic phase was washed with brine and concentrated under reduced pressure. The residue was dissolved in DCM, dried using a phase separator and the crude product was purified by flash chromatography (20% acetone in EtOAc) to give the title compound (470 mg, 87%).

¹H NMR (400 MHz, CDCl₃) δ 2.04-2.15 (m, 1H), 2.31-2.56 (m, 3H), 2.98 (td, 1H), 3.74 (td, 1H), 4.09 (s, 3H), 5.76 (d, 2H), 6.17 (s, 2H), 7.44-7.49 (m, 1H), 7.54 (d, 1H), 7.61 (d, 1H), 7.70 (s, 1H), 8.09 (s, 1H).

MS m/z 465.1 [M−H]⁻

Intermediate 74: 4-[({(1R,6R and 1S,6S)-6-[2-Chloro-4-(1H-pyrazol-5-yl)benzoyl]-cyclohex-3-en-1-yl}carbonyl)amino]-1-methyl-1H-pyrazole-5-carboxamide

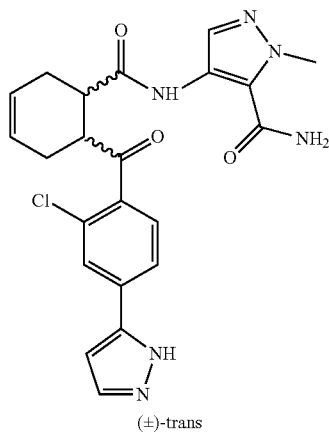 [SMILES: Cn1ncc(NC(=O)C2CC=CCC2C(=O)c2ccc(-c3ccn[nH]3)cc2Cl)c1C(N)=O]

(±)-trans 4-({[(1R,6R and 1S, 6S)-6-(4-Bromo-2-chlorobenzoyl) cyclohex-3-en-1-yl]carbonyl}amino)-1-methyl-1H-pyrazole-5-carboxamide (Intermediate 73, 230 mg, 0.49 mmol), 1H-pyrazol-5-ylboronic acid (112 mg, 1 mmol), K₂CO₃ (140 mg, 1.01 mmol) and Pd(dtbpf)Cl₂ (20 mg, 0.03 mmol) were suspended in a mixture of dioxane (8 ml) and water (2 mL). The reaction vessel was evacuated and purged with nitrogen (g) and then heated at 90° C. for 1.5 h. The reaction mixture was concentrated in vacuo and the residue was diluted with EtOH (50 mL). NaHCO₃ (sat., aq) was added until pH 8 and the reaction is mixture was concentrated to dryness under reduced pressure. The crude product was purified by preparative HPLC on a XBridge C18 column (10 m, 250×19 ID mm) using a gradient of 5-95% MeCN in a H₂O/MeCN/NH₃ (95/5/0.2) buffer system as mobile phase to give the title compound (28 mg, 13%).

MS m/z 451.1 [M−H]⁻

Intermediate 75: 4-[({(1R,6R and 1S,2S)-6-[2-Chloro-4-(3-methyl-1H-pyrazol-5-yl)benzoyl]cyclohex-3-en-1-yl}carbonyl)amino]-1-methyl-1H-pyrazole-5-carboxamide

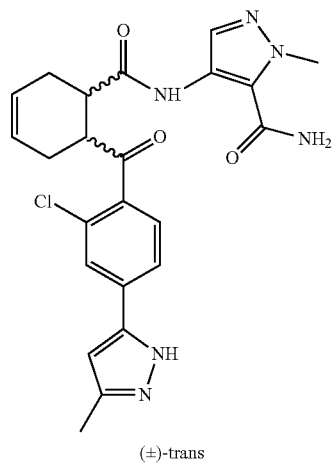 [SMILES: Cc1cc(-c2ccc(C(=O)C3CC=CCC3C(=O)Nc3cnn(C)c3C(N)=O)c(Cl)c2)[nH]n1]

(±)-trans

Step 1: 4-({[(1R,6R and 1S,6S)-6-{2-Chloro-4-[3-methyl-1-(tetrahydro-2H-pyran-2-yl)-1H-pyrazol-5-yl]benzoyl}cyclohex-3-en-1-yl]carbonyl}amino)-1-methyl-1H-pyrazole-5-carboxamide 4-({[(1R,6R and 1S, 6S)-6-(4-Bromo-2-chlorobenzoyl) cyclohex-3-en-1-yl]carbonyl}-amino)-1-methyl-1H-pyrazole-5-carboxamide (Intermediate 73, 230 mg, 0.49 mmol), 3-methyl-1-(tetrahydro-2H-pyran-2-yl)-5-(4,4,5,5-tetramethyl-1,3,2-dioxaborolan-2-yl)-1H-pyrazole (Intermediate 3, 300 mg, 1.03 mmol), K₂CO₃ (150 mg, 1.09 mmol) and Pd(dtbpf)Cl₂ (20 mg, 0.03 mmol) were suspended in a mixture of dioxane (8 mL) and water (2 mL). The reaction vessel was evacuated and purged with nitrogen (g) and heated to at 90° C. for 30 min. The reaction mixture was used directly after cooling in the next step.

Step 2: 4-[({(1R,6R and 1S,2S)-6-[2-Chloro-4-(3-methyl-1H-pyrazol-5-yl)benzoyl]-cyclohex-3-en-1-yl}carbonyl)amino]-1-methyl-1H-pyrazole-5-carboxamide HCl (4 M in dioxane, 0.5 mL, 2.00 mmol) was added to the reaction mixture from Intermediate 75 Step 1 and the reaction mixture was stirred at rt for 10 min. The reaction is mixture were concentrated at reduced pressure, NaHCO₃ (sat., aq) was added to the residue until pH 8 and the water phase was extracted twice with DCM. The combined organic phase was dried using a phase separator and concentrated to dryness at reduced pressure. The crude product was purified by flash chromatography (EtOAc) and then by preparative HPLC on a XBridge C18 column (10 μm 250×19 ID mm) using a gradient of 5-95% MeCN in a H₂O/MeCN/NH₃ (95/5/0.2) buffer system as mobile phase to give the title compound (100 mg, 59%).

MS m/z 465.2 [M−H]⁻

Intermediate 76: Methyl 4-(4-bromo-2-fluorophenyl)-4-hydroxybut-2-ynoate

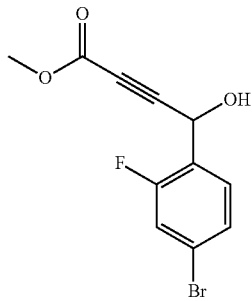 [SMILES: COC(=O)C#CC(O)c1ccc(Br)cc1F]

n-Butyllithium (1.6 M in Hexane, 45 mL, 72.0 mmol) was added to a solution of DIPEA (10 mL, 69.2 mmol) in THF (100 mL) under an atmosphere of nitrogen at −78° C. and the reaction mixture was stirred at −78° C. for 30 min. Methyl prop-2-ynoate (5.7 mL, 64.5 mmol) was added dropwise, then a solution of 4-bromo-2-fluorobenzaldehyde (13.1 g, 64.5 mmol) in THF (20 mL) was added and the reaction mixture was stirred at −78° C. over night. AcOH (10 mL) was added to the reaction mixture and it was poured into water. The reaction mixture was extracted with DCM and the combined organic phase was dried over $MgSO_4$, filtered and concentrated in vacuo. The crude product was purified flash chromatography (20%→50% EtOAc in heptane) to give the title compound (12.9 g, 70%).

$^1$H NMR (400 MHz, $CDCl_3$) δ 2.62 (s, 1H), 3.79 (s, 3H), 5.78 (s, 1H), 7.29 (dd, 1H), 7.35 (dd, 1H), 7.49 (t, 1H).

MS m/z 285.0 [M−H]$^-$

Intermediate 77: Methyl (2E)-4-(4-bromo-2-fluorophenyl)-4-oxobut-2-enoate

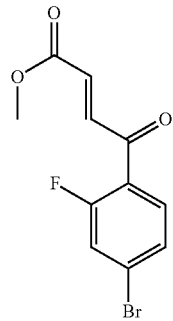

$Et_3N$ (12.5 mL, 90.2 mmol) was added to a solution of methyl 4-(4-bromo-2-fluorophenyl)-4-hydroxybut-2-ynoate (Intermediate 76, 12.9 g, 44.9 mmol) in 1,4-dioxane (40 mL) and the reaction mixture was stirred at rt over night and then heated at 60° C. for 30 min. The reaction mixture was concentrated in vacuo and the crude product was purified by flash chromatography (0%→25% EtOAc in heptane) to give the title is compound (9.7 g, 75%).

$^1$H NMR (400 MHz, $CDCl_3$) δ 3.84 (s, 3H), 6.85 (dd, 1H), 7.31-7.49 (m, 2H), 7.65-7.8 (m, 2H).

Intermediate 78: Methyl (1R,6R and 1S,6S)-6-(4-bromo-2-fluorobenzoyl)cyclohex-3-ene-1-carboxylate

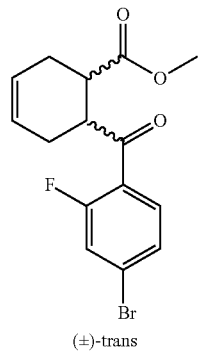 [SMILES: COC(=O)C1CC=CCC1C(=O)c1ccc(Br)cc1F]
(±)-trans

Buta-1,3-diene (20 mL, 236.6 mmol), condensed at −78° C., was added to a mixture of methyl (2E)-4-(4-bromo-2-fluorophenyl)-4-oxobut-2-enoate (Intermediate 77, 5.5 g, 19.2 mmol) and hydroquinone (0.020 g, 0.18 mmol) in toluene (15 mL) at −78° C. and the reaction vessel was sealed and heated at 210° C. for 14 h. The crude product was purified by flash chromatography (5%→30% EtOAc in heptane) to give the title compound (5.69 g, 87%).

$^1$H NMR (400 MHz, $CDCl_3$) δ 1.95-2.14 (m, 1H), 2.14-2.27 (m, 1H), 2.49 (ddd, 2H), 3.07 (tdd, 1H), 3.56-3.77 (m, 4H), 5.73 (s, 2H), 7.29-7.46 (m, 2H), 7.72 (t, 1H).

Intermediate 79: (1R,6R and 1S,6S)-6-(4-Bromo-2-fluorobenzoyl)cyclohex-3-ene-1-carboxylic acid

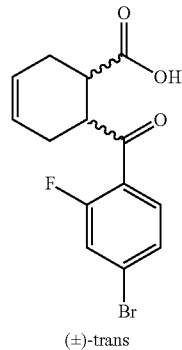 [SMILES: O=C(O)C1CC=CCC1C(=O)c1ccc(Br)cc1F]
(±)-trans

A solution of LiOH (0.40 g, 16.7 mmol) in water (50 mL) was added to a solution of methyl (1R,6R and 1S,6S)-6-(4-bromo-2-fluorobenzoyl)cyclohex-3-ene-1-carboxylate to (Intermediate 78, 5.6 g, 16.41 mmol) in THF (50 mL) and the reaction mixture was stirred at rt over night. LiOH (0.33 g, 13.8 mmol) was added to the reaction mixture and it was stirred at rt for 4 h. The reaction mixture was filtered and the filtrate was concentrated under reduced pressure. The crude residue was acidified using HCl (2M, aq) and the water phase was extracted three times with EtOAc. The combined organic phase was dried over is $MgSO_4$, filtered, and concentrated slightly in vacuo. Heptane was added and the solids formed were filtered off and dried to give the title compound (4.19 g, 78%).

$^1$H NMR (400 MHz, $CDCl_3$) δ 1.92-2.08 (m, 1H), 2.12-2.36 (m, 1H), 2.33-2.6 (m, 2H), 3.06 (td, 1H), 3.64 (td, 1H), 5.72 (s, 2H), 7.3-7.47 (m, 2H), 7.70 (t, 1H).

Intermediate 80: (1R,6R or 1S,6S)-6-(4-Bromo-2-fluorobenzoyl)cyclohex-3-ene-1-carboxylic acid

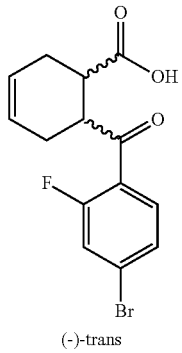

(−)-trans

The enantiomers of (1R,6R and 1S,6S)-6-(4-bromo-2-fluorobenzoyl)cyclohex-3-ene-1-carboxylic acid (Intermediate 79, 8.0 g, 24.5 mmol) were separated by chiral SFC chromatography on a Lux $C_2$ column (5 µm, 250×30 mm). 500 mg (200 mg/mL in MeOH) was injected and eluted with 20% MeOH in $CO_2$ (g) (175 bar) at a flow rate of 100 mL/min and detected at 265 nm. The first eluted compound was collected and evaporated to give the title compound (3.95 g, 49%, 99.9% ee).

$^1$H NMR (400 MHz, CDCl$_3$) δ 1.92-2.06 (m, 1H), 2.19-2.31 (m, 1H), 2.39-2.6 (m, 2H), 2.96-3.12 (m, 1H), 3.64 (td, 1H), 5.72 (s, 2H), 7.29-7.44 (m, 2H), 7.71 (t, 1H). Optical rotation: −29.9° (1 g/100 mL in MeCN, 589 nm, 20° C.).

Intermediate 81: 4-({[(1R,6R or 1S,6S)-6-(4-Bromo-2-fluorobenzoyl)cyclohex-3-en-1-yl]carbonyl}amino)-1-methyl-1H-pyrazole-5-carboxamide

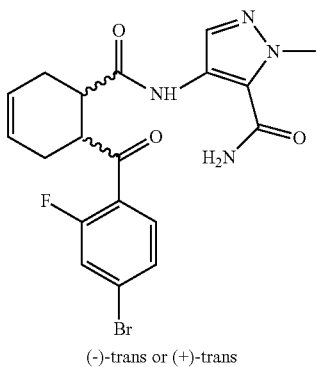 [SMILES: Cn1ncc(NC(=O)C2CC=CCC2C(=O)c2ccc(Br)cc2F)c1C(N)=O]

(−)-trans or (+)-trans

T3P (50% in EtOAc, 1 ml, 1.68 mmol) was added to a solution of (1R,6R or 1S,6S)-6-(4-bromo-2-fluorobenzoyl)cyclohex-3-ene-1-carboxylic acid (Intermediate 80, 250 mg, 0.76 is mmol), 4-amino-1-methyl-1H-pyrazole-5-carboxamide (215 mg, 1.53 mmol) and Et$_3$N (411 µl, 2.96 mmol) in EtOAc (3.5 mL) and the reaction mixture was heated in a microwave reactor at 80° C. for 60 min and then stirred at rt over night. The reaction mixture was diluted with EtOAc and washed twice with NaHCO$_3$ (sat. aq) and brine. The organic phase was dried using a phase separator and concentrated in vacuo. The crude product was purified by preparative HPLC on a XBridge C18 column (10 µm, 250×19 ID mm) using a gradient of 30-85% MeCN in a H$_2$O/MeCN/NH$_3$ (95/5/0.2) buffer system as mobile phase to give the title compound (140 mg, 41%).

MS m/z 451 [M+2]$^+$

Intermediate 82: 4-[({(1R,6R or 1S,6S)-6-[2-Fluoro-4-(1H-pyrazol-5-yl)benzoyl]-cyclohex-3-en-1-yl}carbonyl)amino]-1-methyl-1H-pyrazole-5-carboxamide

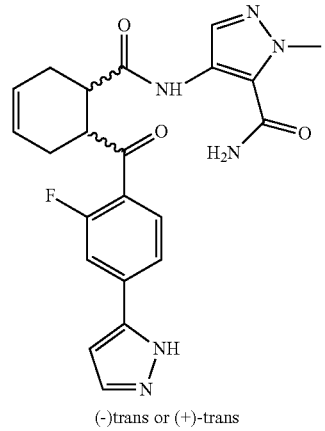 [SMILES: Cn1ncc(NC(=O)C2CC=CCC2C(=O)c2ccc(-c3ccn[nH]3)cc2F)c1C(N)=O]

(−)trans or (+)-trans

Pd(dtbpf)Cl$_2$ (20 mg, 0.03 mmol) was added to a mixture of 4-({[(1R,6R or 1S,6S)-6-(4-bromo-2-fluorobenzoyl)cyclohex-3-en-1-yl]carbonyl}amino)-1-methyl-1H-pyrazole-5-carboxamide (Intermediate 81, 140 mg, 0.31 mmol), 1H-pyrazol-5-ylboronic acid (70 mg, 0.63 mmol), K$_2$CO$_3$ (170 mg, 1.23 mmol) in dioxane (2.5 mL) and water (1.2 mL). The reaction mixture was purged with nitrogen (g) and then heated in a microwave reactor at 80° C. for 45 min. NaHCO$_3$ (sat., aq) was added to the reaction mixture and the mixture was to extracted with EtOAc. The organic phase was dried using a phase separator, concentrated in vacuo and the crude product was purified by preparative HPLC on a XBridge C18 column (10 µm, 250×19 ID mm) using a gradient of 20-65% MeCN in a H$_2$O/MeCN/NH$_3$ (95/5/0.2) buffer system as mobile phase to give the title compound (52 mg, 38%).

MS m/z 435.2 [M−H]$^-$

Intermediate 83: (1R,2R or 1S,2S)-2-(4-Bromo-2-fluorobenzoyl)cyclohexane-carboxylic acid

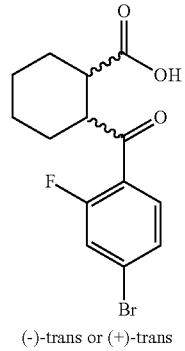 [SMILES: O=C(O)C1CCCCC1C(=O)c1ccc(Br)cc1F]

(−)-trans or (+)-trans

Rhodium catalyst (5% Rh/C, 628 mg, 0.31 mmol) was added to a solution of (1R,6R or 1S,6S)-6-(4-bromo-2-fluorobenzoyl)cyclohex-3-ene-1-carboxylic acid (Intermediate 80, 10 g, 30.57 mmol) in THF (100 mL) and the reaction mixture was stirred under an atmosphere of hydrogen (2 bar) at rt for 16 h. The crude product was filtered through a pad of celite and the solids were rinsed with THF. The filtrate was concentrated in vacuo to afford an oil which solidified upon standing. The solid product was dissolved and precipitated from methyl tert-butylether and heptane, and dried in vacuo to give the title compound (9.16 g, 91%).

$^1$H NMR (500 MHz, CDCl$_3$, 23° C.) δ 0.98-1.09 (m), 1.13-1.38 (m, 3H), 1.67-1.79 (m, 2H), 1.94 (d, 1H), 2.04-2.13 (m, 1H), 2.73 (t, 1H), 3.19-3.29 (m, 1H), 7.18-7.3 (m, 2H), 7.60 (t, 1H).

Intermediate 84: 4-({[(1R,2R or 1S,2S)-2-(4-Bromo-2-fluorobenzoyl)cyclohexyl]-carbonyl}amino)-1-methyl-1H-pyrazole-3-carboxamide

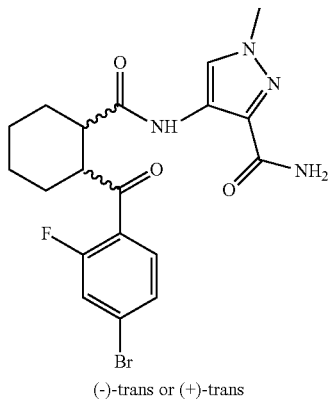 [SMILES: Cn1cc(NC(=O)C2CCCCC2C(=O)c2ccc(Br)cc2F)c(C(N)=O)n1]

(−)-trans or (+)-trans

4-Amino-1-methyl-1H-pyrazole-3-carboxamide (358 mg, 2.55 mmol) was added to a to solution of (1R,2R or 1S,2S)-2-(4-bromo-2-fluorobenzoyl)cyclohexanecarboxylic acid (Intermediate 83, 560 mg, 1.70 mmol), HATU (647 mg, 1.70 mmol) and DIPEA (593 µL, 3.40 mmol) in DMF (3 mL) and the reaction mixture was stirred at rt for 3 h. The crude product was purified by preparative HPLC on a XBridge C18 column (10 µm, 250×19 ID mm) using a gradient of 5-80% MeCN in a H$_2$O/MeCN/NH$_3$ (95/5/0.2) buffer system as is mobile phase to give the title compound (640 mg, 83%).

$^1$H NMR (500 MHz, CDCl$_3$) δ 1.24 (qd, 1H), 1.41 (q, 2H), 1.59 (qd, 1H), 1.84-1.92 (m, 2H), 2.07-2.2 (m, 2H), 2.81-2.99 (m, 1H), 3.47-3.62 (m, 1H), 3.82 (s, 3H), 5.43 (s, 1H), 6.64 (s, 1H), 7.3-7.42 (m, 2H), 7.74 (t, 1H), 8.03 (s, 1H), 9.53 (s, 1H).

Intermediate 85: 4-({[(1R,2R or 1S,2S)-2-{2-Fluoro-4-[1-(tetrahydro-2H-pyran-2-yl)-1H-pyrazol-5-yl]benzoyl}cyclohexyl]carbonyl}amino)-1-methyl-1H-pyrazole-3-carboxamide

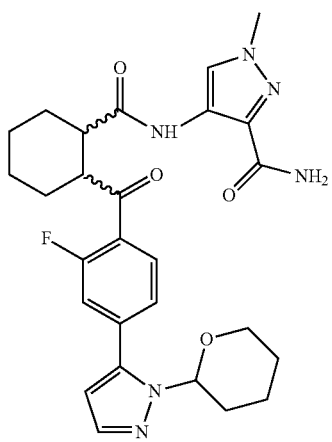 [SMILES: Cn1cc(NC(=O)C2CCCCC2C(=O)c2ccc(-c3ccnn3C3CCCCO3)cc2F)c(C(N)=O)n1]

K$_2$CO$_3$ (262 mg, 1.90 mmol) and Pd(dtbpf)Cl$_2$ (27 mg, 0.04 mmol) were added to a solution of 4-({[(1R,2R or 1S,2S)-2-(4-bromo-2-fluorobenzoyl)cyclohexyl]carbonyl}-amino)-1-methyl-1H-pyrazole-3-carboxamide (Intermediate 84, 214 mg, 0.47 mmol) and 1-(tetrahydro-2H-pyran-2-yl)-5-(4,4,5,5-tetramethyl-1,3,2-dioxaborolan-2-yl)-1H-pyrazole (198 mg, 0.71 mmol) in dioxane (1.5 mL) and water (1.5 mL). The reaction mixture was evacuated and purged with nitrogen (g) three times, and then heated in a microwave reactor at 80° C. for 60 min. The reaction mixture was diluted with EtOAc and the organic phase was washed with NaCl (sat., aq). The aqueous phase was extracted with EtOAc. The combined organic phase was dried using a phase separator and concentrated under reduced pressure. The crude product was purified by flash chromatography (75%→100% EtOAc in heptane) to give the title compound (273 mg).

MS m/z 521.4 [M−H]$^−$

Intermediate 86: 4-({[(1R,2R or 1S,2S)-2-{2-Fluoro-4-[3-methyl-1-(tetrahydro-2H-pyran-2-yl)-1H-pyrazol-5-yl]benzoyl}cyclohexyl]carbonyl}amino)-1-methyl-1H-pyrazole-3-carboxamide

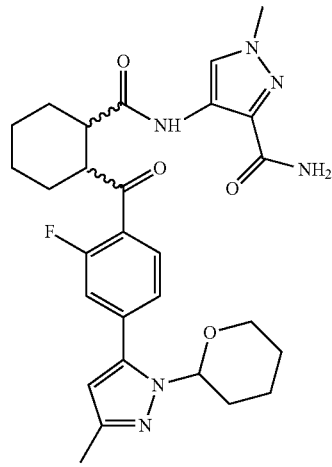 [SMILES: Cc1cc(-c2ccc(C(=O)C3CCCCC3C(=O)Nc3cn(C)nc3C(N)=O)c(F)c2)n(C2CCCCO2)n1]

K$_2$CO$_3$ (213 mg, 1.54 mmol) and Pd(dtbpf)Cl$_2$ (22 mg, 0.03 mmol) were added to a solution of 4-({[(1R,2R or 1S,2S)-2-(4-bromo-2-fluorobenzoyl)cyclohexyl]carbonyl}-amino)-1-methyl-1H-pyrazole-3-carboxamide (Intermediate 84, 174 mg, 0.39 mmol) and 3-methyl-1-(tetrahydro-2H-pyran-2-yl)-5-(4,4,5,5-tetramethyl-1,3,2-dioxaborolan-2-yl)-1H-pyrazole (Intermediate 3, 169 mg, 0.58 mmol) in dioxane (1.5 mL) and water (1.5 mL). The reaction mixture was evacuated and purged with nitrogen (g) three times, and then heated in a microwave reactor at 80° C. for 60 min. The reaction mixture was diluted with EtOAc and the organic phase was washed with NaCl (sat., aq). The aqueous phase was extracted with EtOAc and the combined organic phase was dried using a phase separator and concentrated under reduced pressure. The crude product was purified by flash chromatography (75%→100% EtOAc in heptane) to give the title compound (216 mg, 100%).

MS m/z 535.5 [M−H]$^−$

Intermediate 87: Ethyl 4-(4-bromo-2-fluorophenyl)-4-hydroxybut-2-ynoate

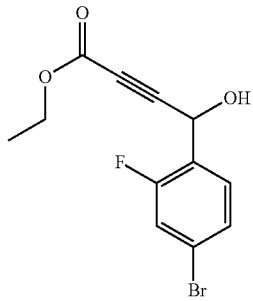 [SMILES: CCOC(=O)C#CC(O)c1ccc(Br)cc1F]

n-Butyllithium (1.6 M in hexane, 44 mL, 70.4 mmol) was added to a solution of DIPEA (10 mL, 69.2 mmol) in THF (100 mL) under an atmosphere of nitrogen and the reaction mixture was stirred at −78° C. for 30 min. Ethylprop-2-ynoate (6.5 mL, 64.3 mmol) was added dropwise to the reaction mixture followed by the addition of a solution of 4-bromo-2-fluorobenzaldehyde (13.1 g, 64.5 mmol) in THF (20 mL). The reaction mixture was stirred at −78° C. over night. The reaction mixture was warmed to 0° C., AcOH (15 mL) dissolved in THF (50 mL) was added, followed by water (800 mL). The reaction mixture to was extracted three times with DCM and the combined organic phase was dried over MgSO$_4$, filtered and concentrated in vacuo. The crude product was purified by flash chromatography (20%→50% EtOAc in heptane) to give the title compound (14.7 g, 76%).

$^1$H NMR (400 MHz, CDCl$_3$) δ 1.31 (t, 3H), 2.57 (bs, 1H), 4.25 (q, 2H), 5.78 (s, 1H), 7.29 (dd, 1H), 7.35 (d, 1H), 7.50 (t, 1H).

Intermediate 88: Ethyl (2E)-4-(4-bromo-2-fluorophenyl)-4-oxobut-2-enoate

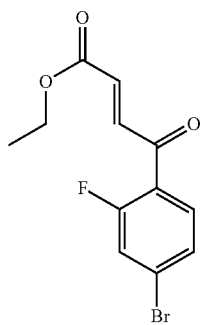 [SMILES: CCOC(=O)/C=C/C(=O)c1ccc(Br)cc1F]

Et$_3$N (14 mL, 101 mmol) was added to a solution of ethyl 4-(4-bromo-2-fluorophenyl)-4-hydroxybut-2-ynoate (Intermediate 87, 14.6 g, 48.5 mmol) in 1,4-dioxane (40 mL) and the reaction mixture was stirred at 60° C. for 6 h and then concentrated in vacuo. The residue was dissolved in EtOAc and the organic phase was washed with HCl (1M, aq) and concentrated in vacuo. The crude compound was purified by flash chromatography (0%→25% EtOAc in heptane) to give the title compound (10.4 g, 71%).

$^1$H NMR (400 MHz, CDCl$_3$) δ 1.33 (t, 3H), 4.29 (q, 2H), 6.83 (dd, 1H), 7.35-7.45 (m, 2H), 7.67-7.74 (m, 2H).

Intermediate 89: Ethyl (1R,6R and 1S,6S)-6-(4-bromo-2-fluorobenzoyl)cyclohex-3-ene-1-carboxylate

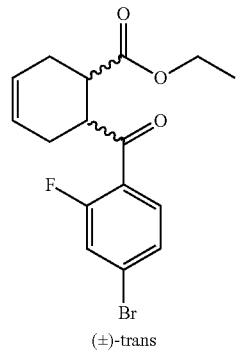 [SMILES: CCOC(=O)C1CC=CCC1C(=O)c1ccc(Br)cc1F]

Buta-1,3-diene (15 mL, 177.5 mmol), condensed at −78° C., was added to a mixture of ethyl (2E)-4-(4-bromo-2-fluorophenyl)-4-oxobut-2-enoate (Intermediate 88, 5.59 g, 18.56 mmol) and hydroquinone (0.035 g, 0.32 mmol) in toluene (15 mL) at −78° C., and the reaction vessel was sealed and stirred at rt for 1 h and then heated at 200° C. for 20 h. The to reaction vessel was cooled to −78° C. and buta-1,3-diene (12 mL, 142 mmol), condensed at −78° C., was added to the reaction mixture. The reaction vessel was sealed and heated at 200° C. over night. The reaction mixture was evaporated in vacuo and the crude product was purified by flash chromatography (0%→25% EtOAc in heptane) to give the title product (5.7 g, 86%).

$^1$H NMR (400 MHz, CDCl$_3$) δ 1.19 (t, 3H), 1.89-2.13 (m, 1H), 2.14-2.26 (m, 1H), 2.37-2.66 (m, 2H), 3.06 (tdd, 1H), 3.68 (td, 1H), 4.08 (q, 2H), 5.73 (s, 2H), 7.3-7.46 (m, 2H), 7.72 (t, 1H).

Intermediate 90: Ethyl (1R,6R and 1S,6S)-6-{2-fluoro-4-[3-methyl-1-(tetrahydro-2H-pyran-2-yl)-1H-pyrazol-5-yl]benzoyl}cyclohex-3-ene-1-carboxylate

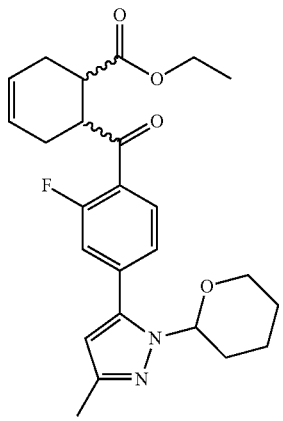 [SMILES: CCOC(=O)C1CC=CCC1C(=O)c1ccc(-c2cc(C)nn2C2CCCCO2)cc1F]

A solution of K$_2$CO$_3$ (0.553 g, 4.00 mmol) in degassed water (8 mL) was added to mixture of ethyl (1R,6R and 1S,6S)-6-(4-bromo-2-fluorobenzoyl)cyclohex-3-ene-1-carboxylate (Intermediate 89, 0.355 g, 1.0 mmol), 3-methyl-1-

(tetrahydro-2H-pyran-2-yl)-5-(4,4,5,5-tetramethyl-1,3,2-dioxaborolan-2-yl)-1H-pyrazole (Intermediate 3, 0.438 g, 1.50 mmol) and Pd(dtbpf)Cl₂ (0.064 g, 0.10 mmol) in degassed dioxane (8 mL). The reaction mixture was heated at 90° C. for 1 h and was then partitioned between EtOAc and NaCl (sat., aq). The aqueous phase was extracted with EtOAc and the combined organic phase was dried over Na₂SO₄, filtered and concentrated in vacuo. The crude product was purified by flash column chromatography (15%→60% EtOAc in heptane) to give the title compound (0.355 g, 81%).

¹H NMR (500 MHz, CDCl₃) δ 1.23 (t, 3H), 1.53-1.63 (m), 1.64-1.67 (m, 2H), 2.02-2.15 (m, 2H), 2.20-2.29 (m, 1H), (d, 1H), 2.34 (s, 3H), 2.44-2.64 (m, 3H), 3.05-3.16 (m, 1H), 3.62 (t, 1H), 3.78 (td, 1H), 4.08-4.19 (m, 3H), 5.09-5.15 (m, 1H), 5.76 (s, 2H), 6.20 (s, 1H), 7.31-7.41 (m, 2H), 7.89-7.96 (m, 1H).

Intermediate 91: 4-({[(1R,6R and 1S,6S)-6-{2-Fluoro-4-[3-methyl-1-(tetrahydro-2H-pyran-2-yl)-1H-pyrazol-5-yl]benzoyl}cyclohex-3-en-1-yl]carbonyl}amino)-1-methyl-1H-pyrazole-5-carboxamide

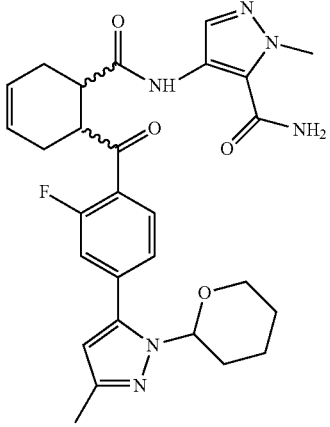 [SMILES: Cc1cc(-c2ccc(C(=O)C3CC=CCC3C(=O)Nc3cnn(C)c3C(N)=O)c(F)c2)n(C2CCCCO2)n1]

Step 1: (1R,6R and 1S,6S)-6-{2-Fluoro-4-[3-methyl-1-(tetrahydro-2H-pyran-2-yl)-1H-pyrazol-5-yl]benzoyl}cyclohex-3-ene-1-carboxylic acid A solution of LiOH (0.041 g, 1.70 mmol) in water (2 mL) was added to a solution of ethyl (1R,6R and 1S,6S)-6-{2-fluoro-4-[3-methyl-1-(tetrahydro-2H-pyran-2-yl)-1H-pyrazol-5-yl]benzoyl}cyclohex-3-ene-1-carboxylate (Intermediate 90, 0.374 g, 0.85 mmol) and the reaction mixture was stirred at rt over night and then at 60° C. for 6 h. Water was added to the reaction mixture and the pH was adjusted to ~4 using KHSO₄ (1M, aq). The aqueous phase was extracted twice with EtOAc and the combined organic phase was dried over Na₂SO₄, filtered and concentrated in vacuo to give the subtitle compound (347 mg, 99%).

MS m/z 411.2 [M−H]⁻

Step 2: 4-({[(1R,6R and 1S,6S)-6-{2-Fluoro-4-[3-methyl-1-(tetrahydro-2H-pyran-2-yl)-1H-pyrazol-5-yl]benzoyl}cyclohex-3-en-1-yl]carbonyl}amino)-1-methyl-1H-pyrazole-5-carboxamide Et₃N (464 μL, 3.35 mmol) and T3P (50% in EtOAc, 598 μL, 1.00 mmol) were added to a suspension of (1R,6R and 1S,6S)-6-{2-fluoro-4-[3-methyl-1-(tetrahydro-2H-pyran-2-yl)-1H-pyrazol-5-yl]benzoyl}cyclohex-3-ene-1-carboxylic acid (Intermediate 91 Step 1, 0.345 g, 0.84 mmol) and 4-amino-1-methyl-1H-pyrazole-5-carboxamide (234 mg, 1.67 mmol) in EtOAc (8 mL) and the reaction mixture was stirred at rt over night. DMF (1 mL) was added and the reaction mixture was stirred at rt for 5.5 h. The reaction mixture was partitioned between EtOAc and NaHCO₃ (sat., aq). The aqueous phase was extracted twice with EtOAc and the combined organic phase was dried over Na₂SO₄, filtered and concentrated in vacuo. The crude compound was purified by flash chromatography (EtOAc) to give the title compound (191 mg, 43%).

MS m/z 535.1 [M+H]⁺

Intermediate 92: 4-[({(1R,2R and 1S,2S)-2-[2-Fluoro-4-(3-methyl-1H-pyrazol-5-yl)benzoyl]cyclohexyl}carbonyl)amino]-1-methyl-1H-pyrazole-5-carboxamide

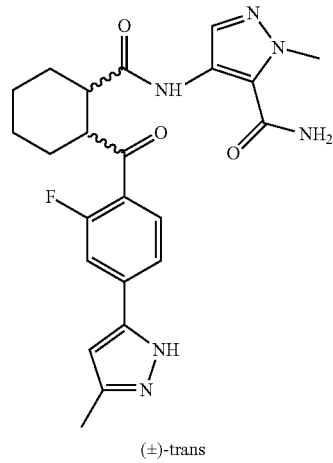 [SMILES: Cc1cc(-c2ccc(C(=O)C3CCCCC3C(=O)Nc3cnn(C)c3C(N)=O)c(F)c2)[nH]n1]

(±)-trans

Step 1: 4-[({(1R,6R and 1S,6S)-6-[2-Fluoro-4-(3-methyl-1H-pyrazol-5-yl)benzoyl]-cyclohex-3-en-1-yl}carbonyl)amino]-1-methyl-1H-pyrazole-5-carboxamide HCl (4M in dioxane, 59 μL, 0.23 mmol) was added to a solution of 4-({[(1R,6R and 1S,6S)-6-{2-fluoro-4-[3-methyl-1-(tetrahydro-2H-pyran-2-yl)-1H-pyrazol-5-yl]benzoyl}cyclohex-3-en-1-yl]carbonyl}amino)-1-methyl-1H-pyrazole-5-carboxamide (Intermediate 91, 157 mg, 0.29 mmol) in dioxane (8 mL) and water (2 mL) and the reaction mixture was stirred at rt for 80 min. NaHCO₃ (sat., aq) and EtOAc were added to the reaction mixture and the phases were separated. The organic phase was washed with NaHCO₃ (sat., aq). The aqueous phase was extracted with EtOAc and the combined organic phase was dried over Na₂SO₄, filtered and concentrated in vacuo to give the subtitle compound (132 mg, 100%).

MS m/z 449.2 [M−H]⁻

Step 2: 4-[({(1R,2R and 1S,2S)-2-[2-Fluoro-4-(3-methyl-1H-pyrazol-5-yl)benzoyl]-cyclohexyl}carbonyl)amino]-1-methyl-1H-pyrazole-5-carboxamide Palladium catalyst (5% Pd/C, 62 mg, 0.03 mmol) was added to a solution 4-[({(1R,6R and 1S,6S)-6-[2-fluoro-4-

(3-methyl-1H-pyrazol-5-yl)benzoyl]cyclohex-3-en-1-yl}carbonyl)amino)-1-methyl-1H-pyrazole-5-carboxamide (Intermediate 92 Step 1, 0.131 g, 0.29 mmol) in MeOH (4 mL) and EtOAc (4 mL) and the reaction mixture was treated to with H₂(g) at 1 atm and at rt over night. The catalyst was filtered off and washed with MeOH. The filtrate was concentrated in vacuo and the crude product was purified by preparative HPLC on a XBridge C18 column (10 μm, 250×19 ID mm) using a gradient of 5-70% MeCN in a H₂O/MeCN/NH₃ (95/5/0.2) buffer system as mobile phase to give the title compound (0.046 g, 35.0%).

¹H NMR (500 MHz, MeOD) δ 1.22 (s, 1H), 1.36-1.68 (m, 3H), 1.88-1.94 (m, 2H), 2.10-2.20 (m, 2H), 2.34 (s, 3H), 2.87 (s, 1H), 3.61 (d, 1H), 4.01 (s, 3H), 6.54 (s, 1H), 7.48 (s, 1H), 7.59 (d, 2H), 7.86 (d, 1H).

Intermediate 93: (1R,2R or 1S,2S)-2-{2-Fluoro-4-[3-methyl-1-(tetrahydro-2H-pyran-2-yl)-1H-pyrazol-5-yl]benzoyl}cyclohexanecarboxylic acid

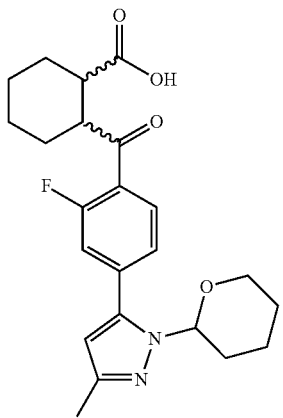 [SMILES: Cc1cc(-c2ccc(C(=O)C3CCCCC3C(=O)O)c(F)c2)n(C2CCCCO2)n1]

3-Methyl-1-(tetrahydro-2H-pyran-2-yl)-5-(4,4,5,5-tetramethyl-1,3,2-dioxaborolan-2-yl)-1H-pyrazole (Intermediate 3, 2.08 g, 7.11 mmol) and a degassed solution of K₂CO₃ (1.96 g, 14.22 mmol) in water (5 mL) were added to a solution of (1R,2R or 1S,2S)-2-(4-bromo-2-fluorobenzoyl)cyclohexanecarboxylic acid (Intermediate 83, 1.17 g, 3.55 mmol) in dioxane (5 mL). Pd(dtbpf)Cl₂ (0.080 g, 0.12 mmol) was added and the reaction mixture was heated in a microwave reactor at 60° C. for 50 min. The reaction mixture was diluted with water and EtOAc. KHSO₄ (1%, aq) was added to the aqueous layer until pH 5 and the aqueous layer was extracted twice with EtOAc. pH of the aqueous layer was adjusted to 3-4 and the aqueous layer was extracted with EtOAc. The combined organic layer was dried using a phase separator and concentrated in vacuo. The crude product was purified by preparative HPLC on a Kromasil C8 column (10 μm, 250×50 ID mm) using a gradient of 10-85% MeCN in a H₂O/MeCN/HCO₂H (95/5/0.2) buffer system as mobile phase to give the title compound (1.2 g, 81%).

MS m/z 413.3 [M−H]⁻

Intermediate 94: 4-({[(1R,2R or 1S,2S)-2-{2-Fluoro-4-[3-methyl-1-(tetrahydro-2H-pyran-2-yl)-1H-pyrazol-5-yl]benzoyl}cyclohexyl]carbonyl}amino)-1H-pyrazole-5-carboxamide

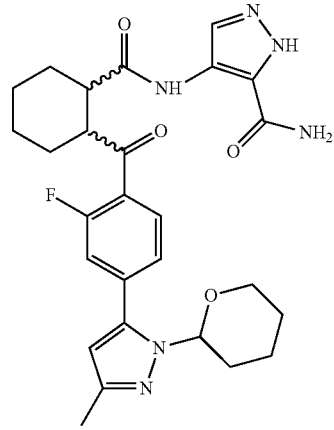 [SMILES: Cc1cc(-c2ccc(C(=O)C3CCCCC3C(=O)Nc3cn[nH]c3C(N)=O)c(F)c2)n(C2CCCCO2)n1]

T3P (50% in EtOAc, 194 μL, 0.33 mmol) was added to a suspension of (1R,2R or 1S,2S)-2-{2-Fluoro-4-[3-methyl-1-(tetrahydro-2H-pyran-2-yl)-1H-pyrazol-5-yl]benzoyl}-cyclohexanecarboxylic acid (Intermediate 93, 90 mg, 0.22 mmol), 4-amino-1H-pyrazole-5-carboxamide hydrochloride (71 mg, 0.43 mmol) and Et₃N (105 μL, 0.76 mmol) in EtOAc (1 mL). DMF (1 mL) was added and the reaction mixture was heated at 80° C. for 3 h. The reaction mixture was diluted with NaHCO₃ (8%, aq) and EtOAc. The organic layer was washed three times with NaHCO₃ (8%, aq), dried using a phase separator and concentrated in vacuo. The crude product was purified by preparative HPLC on a XBridge C18 column (10 μm, 250×19 ID mm) using a gradient of 10-80% MeCN in a H₂O/MeCN/NH₃ (95/5/0.2) buffer system as mobile phase to give the title compound (24 mg, 21%).

MS m/z 521.3 [M−H]⁻

Intermediate 95: (1R,2R or 1S,2S)-2-(4-bromo-2-fluorobenzoyl)-N-(4-oxo-4,5,6,7-tetrahydropyrazolo[1,5-a]pyrazin-3-yl)cyclohexanecarboxamide

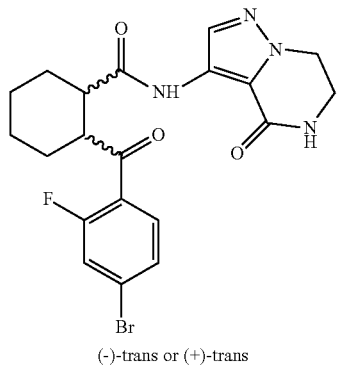 [SMILES: O=C1NCCn2ncc(NC(=O)C3CCCCC3C(=O)c3ccc(Br)cc3F)c21]

(−)-trans or (+)-trans

3-Amino-6,7-dihydropyrazolo[1,5-a]pyrazin-4(5H)-one hydrochloride (Intermediate 12, 300 mg, 1.97 mmol), HATU (1.16 g, 3.05 mmol) and Et₃N (768 mg, 7.59 mmol) was added to a solution of (1R,2R or 1S,2S)-2-(4-bromo-2-fluorobenzoyl)cyclohexanecarboxylic acid (Intermediate 83, 500 mg, 1.52 mmol) in DMF (20 mL) and the reaction mixture was stirred at 38° C. for 12 h. The reaction mixture was concentrated in vacuo and the crude product was purified by silica gel column chromatography (3.8% MeOH in DCM) to give the title compound (300 mg, 43%).

MS m/z 463 [M+H]⁺

Intermediate 96: 4-({[(1R,2R or 1S,2S)-2-(4-bromo-2-fluorobenzoyl)cyclohexyl]-carbonyl}amino)-1,2,5-oxadiazole-3-carboxamide

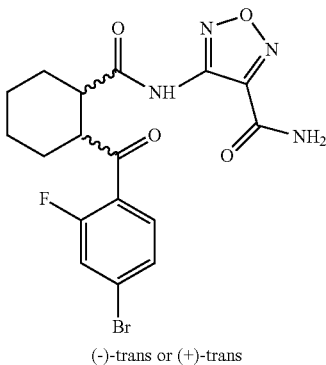 [SMILES: NC(=O)c1nonc1NC(=O)C1CCCCC1C(=O)c1ccc(Br)cc1F]

(−)-trans or (+)-trans

T3P (50% in EtOAc, 0.75 ml, 1.26 mmol) was added to a solution of 4-amino-1,2,5-oxadiazole-3-carboxamide (0.178 g, 1.39 mmol), (1R,2R or 1S,2S)-2-(4-bromo-2-fluorobenzoyl)cyclohexanecarboxylic acid (Intermediate 83, 0.20 g, 0.61 mmol) and DMAP (0.22 g, 1.80 mmol) in THF (2.5 mL) and DCM (0.5 mL) and the reaction mixture was heated in a microwave reactor at 100° C. for 1 h. The reaction mixture was diluted with THF and the crude product was purified by preparative HPLC on a Kromasil C18 column, using MeCN in a H₂O/HOAc (100/0.2) buffer system as mobile phase. The product containing fractions were pooled, concentrated in vacuo and freeze-dried to give the title compound (87 mg, 33%).

MS m/z 439.1 [M−H]⁻

Intermediate 97: (1R,2R or 1S,2S)-2-(4-Bromo-2-fluorobenzoyl)cyclohexanecarbonyl fluoride

(−)-trans or (+)-trans (1R,2R or 1S,2S)-2-(4-Bromo-2-fluorobenzoyl)cyclohexanecarboxylic acid (Intermediate 83, 100 mg, 0.30 mmol) and pyridine (0.052 mL, 0.61 mmol) were dissolved in dry DCM (1 mL) under a nitrogen atmosphere. The reaction mixture was cooled to −10° C., 2,4,6-trifluoro-1,3,5-triazine (0.051 mL, 0.61 mmol) was added and the reaction mixture was stirred at −10° C. for 2 h. The reaction mixture was diluted with DCM and water was added and the reaction mixture was stirred at rt for 30 min. Water and DCM was added and the to phases were separated. The combined organic phase was separated from solids, washed with cold water, dried using a phase separator and evaporated at rt in vacuo to give the title compound (107 mg, 106%).

¹H NMR (500 MHz, CDCl₃) δ 1.19 (qd, 1H), 1.3-1.5 (m, 2H), 1.50-1.63 (m), 1.83-1.97 (m, 2H), 2.14 (d, 1H), 2.23-2.36 (m, 1H), 3.00 (dddd, 1H), 3.43 (td, 1H), 7.33-7.45 (m, 2H), 7.75 (t, 1H).

Intermediate 98: 4-({[(1R,2R and 1S,2S)-2-(4-Bromobenzoyl)cyclohexyl]carbonyl}-amino)-1-ethyl-1H-pyrazole-3-carboxamide

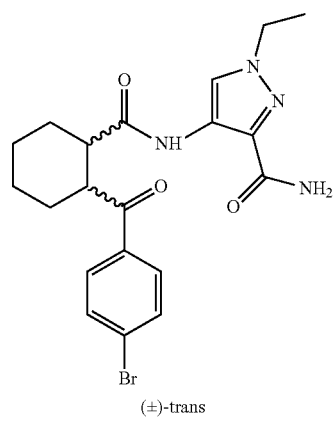 [SMILES: CCn1cc(NC(=O)C2CCCCC2C(=O)c2ccc(Br)cc2)c(C(N)=O)n1]

(±)-trans

Et₃N (178 μL, 1.29 mmol) and T3P (50% in EtOAc, 230 μL, 0.39 mmol) were added to a suspension of (1R,2R and 1S,2S)-2-(4-bromobenzoyl)cyclohexanecarboxylic acid (100 mg, 0.32 mmol) and 4-amino-1-ethyl-1H-pyrazole-3-carboxamide (67 mg, 0.43 mmol) in EtOAc (2 mL) and the reaction mixture was heated at 80° C. for 2 h and then stirred at rt overnight. The reaction mixture was partitioned between EtOAc and NaHCO₃ (sat., aq). The aqueous phase was extracted with EtOAc and the combined organic phase was dried over Na₂SO₄, filtered, and concentrated in vacuo to give the title compound (119 mg, 83%).

MS m/z 449 [M+2]⁺

Intermediate 99: Ethyl 5-({[(1R,2R)-2-(4-bromobenzoyl)cyclohexyl]carbonyl}amino)-1,3,4-oxadiazole-2-carboxylate

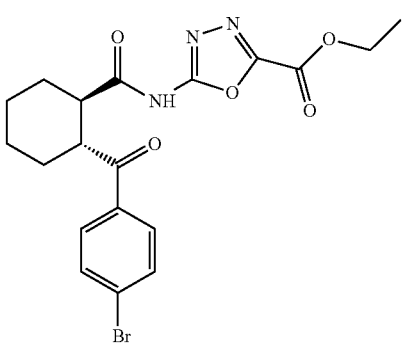 [SMILES: CCOC(=O)c1nnc(NC(=O)[C@@H]2CCCC[C@H]2C(=O)c2ccc(Br)cc2)o1]

Ethyl 5-amino-1,3,4-oxadiazole-2-carboxylate (1.11 g, 7.06 mmol), T₃P (50% in EtOAc, 8.18 g, 25.72 mmol) and Et₃N (2.6 g, 25.69 mmol) were added to a solution of (1R,2R)-2-(4-bromobenzoyl)cyclohexanecarboxylic acid (2 g, 6.43 mmol) in EtOAc (25 mL) and the reaction mixture was heated at 80° C. for 12 h. The reaction mixture was washed twice with water and the combined aqueous phase was extracted with EtOAc. The combined organic layer was dried over Na₂SO₄, filtered and concentrated in vacuo to give the title compound (2.85 g, 98%).

MS m/z 450 [M+H]⁺

Intermediate 100: (1R,2R and 1S,2S)-2-(4-Bromobenzoyl)-N-(3-methyl-1,2-thiazol-5-yl)cyclohexanecarboxamide

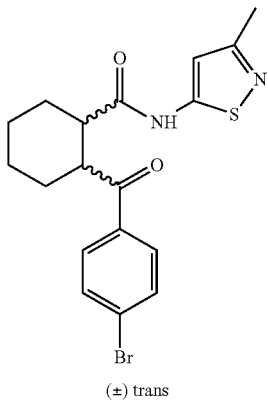 [SMILES: Cc1cc(NC(=O)C2CCCCC2C(=O)c2ccc(Br)cc2)sn1]

(±) trans

T3P (50% in EtOAc, 383 µL, 0.64 mmol) was added to a mixture of (1R,2R and 1S,2S)-2-(4-bromobenzoyl)cyclohexanecarboxylic acid (100 mg, 0.32 mmol), 3-methyl-1,2-thiazol-5-amine hydrochloride (97 mg, 0.64 mmol), and Et₃N (134 µL, 0.96 mmol) in EtOAc (3 mL) and the reaction mixture was heated in a microwave reactor at 150° C. for 30 min. The reaction mixture was diluted with EtOAc and the organic phase was extracted with NaHCO₃ (sat., aq) and brine, dried using a phase separator and concentrated in vacuo. The crude product was purified flash chromatography (25% EtOAc in toluene) to give the title compound (24 mg, 18%).

MS m/z 407.2 [M–H]⁻

Intermediate 101: (1R,2R and 1S,1S)-2-(4-Bromobenzoyl)-N-(4-cyano-3-methyl-1,2-thiazol-5-yl) cyclohexanecarboxamide

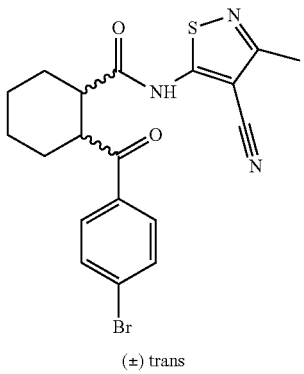 [SMILES: Cc1nsc(NC(=O)C2CCCCC2C(=O)c2ccc(Br)cc2)c1C#N]

(±) trans

T3P (50% in EtOAc, 383 µL, 0.64 mmol) was added to a mixture of (1R,2R and 1S,1S)-2-(4-bromobenzoyl)cyclohexanecarboxylic acid (100 mg, 0.32 mmol), 5-amino-3-methyl-1,2-thiazole-4-carbonitrile (89 mg, 0.64 mmol), and Et₃N (134 µL, 0.96 mmol) in EtOAc (3 mL) and the reaction mixture was heated in a microwave reactor at 150° C. for 30 min. The reaction mixture was diluted with EtOAc and the organic phase was extracted with NaHCO₃ (sat., aq) and brine, dried using a phase separator and concentrated in vacuo. Trituration of the residue from DCM gave the title compound (51 mg, 37%).

MS m/z 432.2 [M–H]⁻

Example 1: 1-Methyl-4-[({(1R,2R or 1S,2S)-2-[4-(1H-pyrazol-3-yl)benzoyl]-cyclohexyl}carbonyl)amino]-1H-pyrazole-3-carboxamide

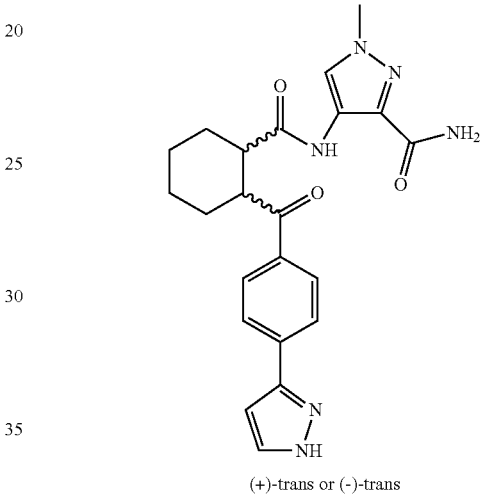

(+)-trans or (−)-trans

Step 1—Methyl 1-methyl-4-[({(1R,2R and 1S,2S)-2-[4-(1H-pyrazol-3-yl)benzoyl]-cyclohexyl}carbonyl)amino]-1H-pyrazole-3-carboxylate A solution of (1R,2R and 1S,2S)-2-(4-(1H-pyrazol-3-yl)benzoyl)cyclohexanecarboxylic acid (Intermediate 1, 200 mg, 0.67 mmol), TBTU (387 mg, 1.21 mmol), methyl 4-amino-1-methyl-1H-pyrazole-3-carboxylate (208 mg, 1.34 mmol) and DIPEA (0.351 mL, 2.01 mmol) in NMP (8 mL) was stirred at 50° C. over night. The reaction was quenched by addition of NaHCO₃ (sat, aq). The mixture was diluted with EtOAc and the phases were separated. The organic layer was washed with brine, NH₄Cl (sat, aq) and finally brine. The organic layer was dried over Na₂SO₄, filtered and evaporated leaving the subtitle compound (292 mg) as a yellow solid.

Step 2—1-Methyl-4-[({(1R,2R and 1S,2S)-2-[4-(1H-pyrazol-3-yl)benzoyl]cyclohexyl}-carbonyl)amino]-1H-pyrazole-3-carboxylic acid A solution of LiOH (1 M aq, 0.80 mL, 0.80 mmol) in water (1.0 mL) was added to a solution of crude product of step 1 (292 mg, 0.67 mmol) in MeOH (2.5 mL) and THF (2.5 mL). The resulting solution was stirred at 50° C. for 1 h. The mixture was diluted with EtOAc and water and the phases were separated and the water phase was washed with EtOAc. The combined water layers were acidified with HCl (6 M) until pH was between 4-5 and the product was extracted into EtOAc. The organic layer was dried over Na₂SO₄, filtered and evaporated to give the subtitle compound (155 mg, 55%) as a slightly brown solid.
MS m/z 420 [M−H]⁻

Step 3—(1R,2R and 1S,2S)-1-Methyl-4-[({2-[4-(1H-pyrazol-3-yl)benzoyl]cyclohexyl}-carbonyl)amino]-1H-pyrazole-3-carboxamide A solution of the product from step 2, (155 mg, 0.37 mmol), TBTU (213 mg, 0.66 mmol), ammonium chloride (39.3 mg, 0.74 mmol) and DIPEA (0.193 mL, 1.10 mmol) in NMP (4 mL) was stirred at 50° C. for 2 h. The reaction was quenched by addition of NaHCO₃ (sat, aq). The mixture was diluted with EtOAc and the phases were separated. The organic layer was washed with brine, NH₄Cl (sat, aq) and finally brine. The organic layer was dried over Na₂SO₄, filtered and evaporated leaving a yellow solid which was purified by preparative reversed phase HPLC on a XBridge C18 column (5 μm OBD 19×150 mm) using a gradient of 5-95% MeCN in H₂O/MeCN/NH₃ (95/5/0.2) buffer system at pH10 as mobile phase to give the title compound (73 mg, 48%).
¹H NMR (600 MHz, DMSO-d₆) δ 1.21 (d, 1H), 1.44 (t, 1H), 1.52 (td, 2H), 1.80 (dd, 2H), 2.01 (dd, 2H), 2.82-2.94 (m, 1H), 3.69-3.78 (m, 1H), 3.80 (s, 3H), 6.86 (t, 1H), 7.48 (s, 1H), 7.66 (s, 1H), 7.85 (d, 1H), 7.98 (d, 2H), 8.03 (d, 2H), 8.07 (s, 1H), 9.77 (s, 1H), 13.09 (s, major rotamer), 13.50 (s, minor rotamer). Mixture of rotamers in ratio major:minor 1:0.25 MS m/z 421.2 [M+H]⁺

Step 4—1-Methyl-4-[({(1R,2R or 1S,2S)-2-[4-(1H-pyrazol-3-yl)benzoyl]cyclohexyl}-carbonyl)amino]-1H-pyrazole-3-carboxamide The enantiomers of (1R,2R and 1S,2S)-1-methyl-4-[({2-[4-(1H-pyrazol-3-yl)benzoyl]cyclohexyl}carbonyl)amino]-1H-pyrazole-3-carboxamide (50 mg, 0.12 mmol) were separated by chiral chromatography on a Chiralpak IA HPLC column (5 μm, 250×20 mm). 50 mg (8 mg/mL in EtOH:DCM, 4:2) was injected and eluted with EtOH:DCM (4:2) at a flow rate of 15 mL/min and detected at 245 nm. The first eluted compound was collected and evaporated to give the title compound (0.019 g, 99.6% ee).
HRMS m/z 841.3857 [2M+H]⁺

Example 2: 1-Methyl-4-[({(1R,2R)-2-[4-(1H-pyrazol-3-yl)benzoyl]cyclohexyl}-carbonyl)amino]-1H-pyrazole-5-carboxamide

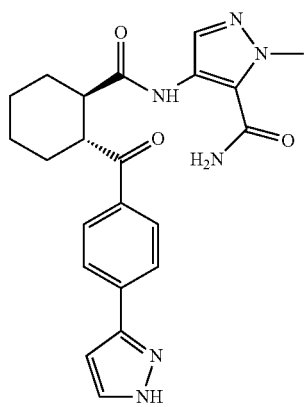 [SMILES: Cn1ncc(NC(=O)[C@@H]2CCCC[C@H]2C(=O)c2ccc(-c3cc[nH]n3)cc2)c1C(N)=O]

4-({[(1R,2R)-2-(4-Bromobenzoyl)cyclohexyl]carbonyl}amino)-1-methyl-1H-pyrazole-5-carboxamide (Intermediate 2, 130 mg, 0.30 mmol), 1H-pyrazol-3-ylboronic acid (70 mg, is 0.63 mmol), K₂CO₃ (170 mg, 1.23 mmol) and Pd(dtbpf)Cl₂ (20 mg, 0.03 mmol) were mixed in dioxane (2.5 mL) and H₂O (1.2 mL) and the reaction mixture was purged with nitrogen. The reaction mixture was heated in a microwave reactor at 80° C. for 45 min. NaHCO₃ (sat, aq) was added and the mixture was extracted with EtOAc. The organic phase was dried using a phase separator and the solvent evaporated. The crude product was purified by preparative HPLC on a XBridge C18 column (10 μm 250×19 ID mm) using a gradient of 20-65% acetonitrile in H₂O/MeCN/NH₃ (95/5/0.2) buffer system as mobile phase. The desired fractions were collected and the solvent evaporated to give the title compound (36 mg, 28%).
¹H NMR (400 MHz, CDCl₃) δ 1.19-1.43 (m, 3H), 1.50 (dd, 1H), 1.73 (dt, 1H), 1.8-1.97 (m, 2H), 2.10 (d, 2H), 2.84-2.96 (m, 1H), 4.02 (s, 3H), 6.66 (dd, 4H), 7.53 (s, 1H), 7.6-7.66 (m, 1H), 7.80 (d, 2H), 7.94 (t, 2H), 8.23 (s, 1H).
MS m/z 421 [M+H]⁺

Example 3: 1-Methyl-4-[({(1R,2R)-2-[4-(3-methyl-1H-pyrazol-5-yl)benzoyl]cyclohexyl}-carbonyl)amino]-1H-pyrazole-5-carboxamide

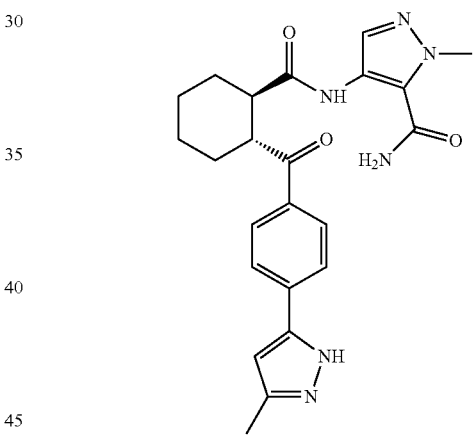

HCl in MeOH (6.0 mL, 7.20 mmol) was added to a solution of 1-methyl-4-({[(1R,2R)-2-{4-[3-methyl-1-(tetrahydro-2H-pyran-2-yl)-1H-pyrazol-5-yl]benzoyl}cyclohexyl]-carbonyl}amino)-1H-pyrazole-5-carboxamide (Intermediate 4, 1.39 g, 2.68 mmol) in MeOH (230 mL). The resulting solution was evaporated in vacuo at 5° C. The residue was dissolved in 230 mL MeOH and evaporated again at 5° C. and the crude product was immediately purified by preparative HPLC on a XBridge C18 column (10 μm 250×19 ID mm) using a gradient of 5-70% MeCN in H₂O/MeCN/NH₃ (95/5/0.2) buffer system as mobile phase. The desired fractions were collected and freeze-dried and repurifed by preparative SFC on a Luna HILIC column (5 μm 250×30 ID mm) using 25% MeOH/DEA (100/0.5) in CO₂(g) (150 bar) as mobile phase. The desired fractions were collected, evaporated and freeze-dried from MeCN/H₂O (1:1) to give the title compound (0.71 g, 67%).
¹H NMR (500 MHz, DMSO) δ 1.17 (dd, 1H), 1.29-1.39 (m, 1H), 1.42-1.57 (m, 2H), 1.72-1.88 (m, 2H), 1.97 (d, 1H), 2.07 (d, 1H), 2.78-2.91 (m, 1H), 3.29 (s, 3H), 3.65-3.74 (m, 1H), 3.89 (s, 3H), 6.56 (s, 1H), 7.89 (d, 2H), 7.99 (d, 2H), 9.49 (s, 1H), 12.74 (s, 1H)

Example 4: 1-Methyl-4-[({(1R,2R)-2-[4-(3-methyl-1H-pyrazol-5-yl)benzoyl]-cyclohexyl}carbonyl)amino]-1H-pyrazole-3-carboxamide

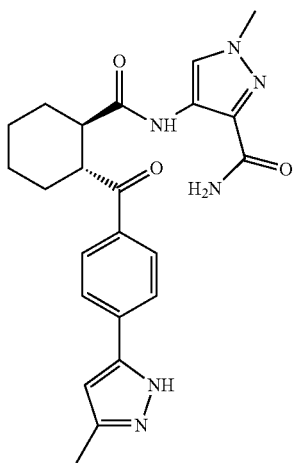 [SMILES: Cc1cc(-c2ccc(C(=O)[C@@H]3CCCC[C@H]3C(=O)Nc3cn(C)nc3C(N)=O)cc2)[nH]n1]

Step 1—1-Methyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-3-carboxamide 3-Methyl-1-(tetrahydro-2H-pyran-2-yl)-5-(4,4,5,5-tetramethyl-1,3,2-dioxaborolan-2-yl)-1H-pyrazole (Intermediate 3, 283 mg, 0.97 mmol) and a degassed solution of K$_2$CO$_3$ (89 mg, 0.65 mmol) in water (1 mL) was added to a solution of 4-({[(1R,2R)-2-(4-bromobenzoyl)cyclohexyl]carbonyl}amino)-1-methyl-1H-pyrazole-3-carboxamide (Intermediate 6, 70 mg, 0.16 mmol) in dioxane (1 mL). Pd(dtbpf)Cl$_2$ (10.40 mg, 0.02 mmol) was added and the resulting mixture was heated in a microwave reactor at 85° C. for 60 min. The reaction mixture was diluted with EtOAc and washed with brine (sat.). The to aqueous phase was extracted twice with EtOAc. The combined organic phase was dried using a phase separator and concentrated. The residue was purified by flash chromatography (100% EtOAc) to give the subtitle compound (118 mg, 141%).
MS m/z 517 [M–H]$^-$ Step 2—1-Methyl-4-[({(1R,2R)-2-[4-(3-methyl-H-pyrazol-5-yl)benzoyl]cyclohexyl}-carbonyl)amino]-1H-pyrazole-3-carboxamide HCl (1.2 M in MeOH) (1 mL, 1.20 mmol) was added to a solution of the product from step 1 (118 mg, 0.23 mmol) in MeOH (10 mL) and the reaction mixture was concentrated at 5° C. The residue was dissolved in 10 mL MeOH and concentrated at 5° C. The compound was immediately purified by preparative HPLC on a XBridge C18 column (10 μm 250×19 ID mm) using a gradient of 5-70% MeCN in H$_2$O/MeCN/NH$_3$ (95/5/0.2) buffer system as mobile phase to give the title compound (46 mg, 46%).
$^1$H NMR (500 MHz, DMSO-d$_6$) δ 1.19 (q, 1H), 1.35-1.56 (m, 3H), 1.75 (d, 2H), 1.81 (d, 1H), 1.95 (d, 1H), 2.01 (d, 1H), 2.28 (s, 3H), 2.8-2.93 (m, 1H), 3.68-3.77 (m, 1H), 3.78 (s, 3H), 6.56 (s, 1H), 7.47 (s, 1H), 7.64 (s, 1H), 7.89 (d, 2H), 8.00 (d, 2H), 8.05 (s, 1H), 9.75 (s, 1H), 12.75 (s, major rotamer), 13.08 (s, minor rotamer). Mixture of rotamers in ratio major:minor 1:0.19.
MS m/z 435.3 [M+H]$^+$ Example 5a: (1S,2S or 1R,2R)—N-(3-Cyano-1-methyl-1H-pyrazol-4-yl)-2-[4-(3-methyl-1H-pyrazol-5-yl)benzoyl]cyclohexanecarboxamide and Example 5b: (1R,2R or 1S,2S)—N-(3-Cyano-1-methyl-1H-pyrazol-4-yl)-2-[4-(3-methyl-1H-pyrazol-5-yl)benzoyl]cyclohexanecarboxamide

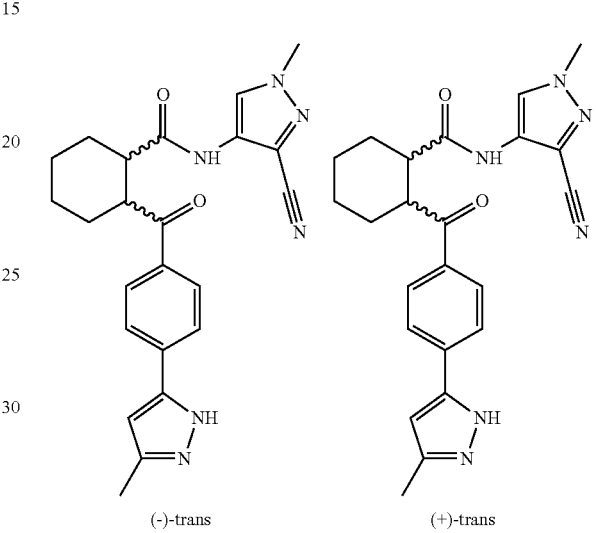

(-)-trans      (+)-trans

Step 1—(1R,2R and 1S,2S)—N-(3-Cyano-1-methyl-1H-pyrazol-4-yl)-2-{4-[3-methyl-1-(tetrahydro-2H-pyran-2-yl)-1H-pyrazol-5-yl]benzoyl}cyclohexanecarboxamide ((1R,2R and 1S,2S)-2-(4-Bromobenzoyl)-N-(3-cyano-1-methyl-1H-pyrazol-4-yl)cyclohexanecarboxamide (Intermediate 7, 150 mg, 0.36 mmol) and 3-methyl-1-(tetrahydro-2H-pyran-2-yl)-5-(4,4,5,5-tetramethyl-1,3,2-dioxaborolan-2-yl)-1H-pyrazole (Intermediate 3, 106 mg, 0.36 mmol) were dissolved in dioxane:DMF (2 mL, 95:5). Pd(dtbpf)Cl$_2$ (7.0 mg, 11 μmol) and a solution of K$_2$CO$_3$ (200 mg, 1.44 mmol) in water (1.5 mL) were added and the reaction mixture was evacuated and purged with nitrogen three times and then heated at 80° C. for 45 min. The reaction mixture was used directly in is Step 2.

Step 2—(1R,2R and 1S,2S)—N-(3-Cyano-1-methyl-1H-pyrazol-4-yl)-2-[4-(3-methyl-1H-pyrazol-5-yl)benzoyl]cyclohexanecarboxamide HCl (2 M in dioxane:water, 1:1, 1 mL) was added to the reaction mixture from Step 1 above and the reaction mixture was stirred at rt for 15 min. The reaction mixture was concentrated and the residue was diluted with EtOAc and washed with NaHCO$_3$ (sat, aq). The aqueous phase was extracted with EtOAc and the combined organic phase was washed with NH$_4$Cl (aq) and brine. The organic layer was dried using a phase separator and the solvent was removed under vacuum. The compound was purified by preparative HPLC on a XBridge C18 column (10 μm 250×19 ID mm) using a gradient of 20-65% MeCN in H$_2$O/MeCN/NH$_3$ (95/5/0.2) buffer system as mobile phase to give the subtitle Step 2 compounds (102 mg, 68%) as a white solid.

¹H NMR (500 MHz, DMSO-d₆) δ 1.1-1.23 (m, 1H), 1.33 (t, 1H), 1.37-1.58 (m, 2H), 1.72-1.80 (m), 1.83 (d, 1H), 1.97 (d, 1H), 2.07 (d, 1H), 2.27 (s, 3H), 2.88-3.01 (m, 1H), 3.74 (t, 1H), 3.81 (s, 3H), 6.56 (s, 1H), 7.88 (d, 2H), 8.00 (d, 2H), 8.10 (s, 1H), 10.41 (s, 1H), 12.75 (s, 1H) MS m/z 417.1 [M+H]⁺

Step 3—(1R,2R or 1S,2S)—N-(3-Cyano-1-methyl-1H-pyrazol-4-yl)-2-[4-(3-methyl-1H-pyrazol-5-yl)benzoyl]cyclohexanecarboxamide and (1S,2S or 1R,2R)—N-(3-cyano-1-methyl-1H-pyrazol-4-yl)-2-[4-(3-methyl-1H-pyrazol-5-yl)benzoyl]-cyclohexanecarboxamide The enantiomers of (1R,2R and 1S,2S)—N-(3-cyano-1-methyl-1H-pyrazol-4-yl)-2-[4-(3-methyl-1H-pyrazol-5-yl)benzoyl]cyclohexanecarboxamide (77 mg, 0.18 mmol) were to separated by chiral chromatography on a Chiralpak AD column (5 μm, 250×20 mm). 52 mg (26 mg/mL in EtOH:DCM, 2:1) was injected and eluted with Heptane:EtOH (30:70) at a flow rate of 18 mL/min and detected at 260 nm. The first eluted compound was collected and evaporated to give Example 5a (31 mg, 40%, 98.2% ee).

¹H NMR (500 MHz, CDCl₃) δ 1.26-1.6 (m, 3H), 1.72 (td, 1H), 1.83-1.98 (m, 2H), 2.11 (td, 2H), 2.39 (s, 3H), 2.92 (ddd, 1H), 3.68-3.79 (m, 1H), 3.83 (s, 3H), 5.31 (s, 1H), 6.44 (s, 1H), 7.80-7.86 (m, 3H), 7.98-8.03 (m, 3H)

Optical rotation: −138.9° (1 g/100 mL in MeCN, 589 nm, 20° C.).

The second eluted compound was collected and evaporated to give Example 5b (30 mg, 39%, 98.6% ee)

Optical rotation: +136.8° (1 g/100 mL in MeCN, 589 nm, 20° C.).

¹H NMR (500 MHz, CDCl₃) δ 1.27-1.56 (m, 3H), 1.65-1.76 (m, 1H), 1.85-1.97 (d, 2H), 2.11 (t, 2H), 2.39 (s, 3H), 2.87-2.95 (m, 1H), 3.69-3.78 (m, 1H), 3.84 (s, 3H), 5.31 (s, 2H), 6.44 (s, 1H), 7.79 (s, 1H), 7.83 (d, 2H), 7.98-8.04 (m, 3H)

Example 6: (1R,2R)-2-[4-(3-Methyl-1H-pyrazol-5-yl)benzoyl]-N-(1H-pyrazol-4-yl)cyclohexanecarboxamide

Step 1—(1R,2R)-2-{4-[3-Methyl-1-(tetrahydro-2H-pyran-2-yl)-1H-pyrazol-5-yl]benzoyl}-N-(1H-pyrazol-4-yl)cyclohexanecarboxamide (1R,2R)-2-{4-[3-Methyl-1-(tetrahydro-2H-pyran-2-yl)-1H-pyrazol-5-yl]benzoyl}-cyclohexanecarboxylic acid (Intermediate 8, 0.167 g, 0.42 mmol) was added to a mixture of 1H-pyrazol-4-amine (0.074 g, 0.89 mmol), T3P (50% in EtOAc, 0.37 mL, 0.63 mmol) and Et₃N (0.23 mL, 1.68 mmol) in EtOAc (8 mL) and the reaction mixture was stirred at rt for 30 min. DMF (1 mL) was added and the reaction mixture was stirred at rt over night. 1H-Pyrazol-4-amine (0.040 g), T3P (50% in EtOAc, 0.150 mL, 0.25 mmol) and DMF (2 mL) was added and the reaction mixture was stirred at rt for 1 h. The reaction mixture was to diluted with EtOAc and the organic phase was washed twice with NaHCO₃ (sat, aq). The organic phase was dried over MgSO₄, filtered and concentrated in vacuo to give the subtitle compound (0.194 g 100%).

MS m/z 460.3 [M−H]⁻

Step 2—(1R,2R)-2-[4-(3-Methyl-1H-pyrazol-5-yl)benzoyl]-N-(1H-pyrazol-4-yl)cyclohexanecarboxamide HCl (2 M HCl in dioxane/water, 1:1, 2 mL) was added to the compound from step 1 (194 mg, 0.42 mmol) and the reaction mixture was stirred at rt for 30 min. The reaction mixture was diluted with EtOAc and the organic phase was washed with NaHCO₃ (sat, aq). The aqueous phase was extracted once with EtOAc and the combined organic phase was dried over MgSO₄, filtered and concentrated in vacuo. The residue was purified by preparative HPLC on a XBridge C18 column (5 μm OBD 19×150 mm) using a gradient of 5-95% MeCN in H₂O/MeCN/NH₃ (95/5/0.2) buffer system at pH10 as mobile phase to give the title compound (52 mg, 33%).

¹H NMR (600 MHz, DMSO-d₆) δ 1.08-1.2 (m, 1H), 1.27-1.37 (m, 1H), 1.40-1.54 (m, 2H), 1.71-1.79 (m, 1H), 1.79-1.86 (m, 1H), 1.92-1.98 (m, 1H), 1.99-2.07 (m, 1H), 2.28 (s, 3H), 2.75-2.83 (m, 1H), 3.68-3.76 (m, 1H), 6.56 (s, 1H), 7.38 (s, 1H), 7.70 (s, 1H), 7.90 (d, 2H), 7.99 (d, 2H), 9.99 (s, 1H), 12.45 (s, 1H), 12.75 (s, major rotamer), 13.10 (s, minor rotamer). Mixtures of rotamers in ratio major:minor 1:0.18.

MS m/z 378.2 [M+H]⁺

Example 7: (1R,2R)-2-[4-(3-Methyl-1H-pyrazol-5-yl)benzoyl]-N-(4-oxo-4,5,6,7-tetrahydropyrazolo[1,5-a]pyrazin-3-yl)cyclohexanecarboxamide

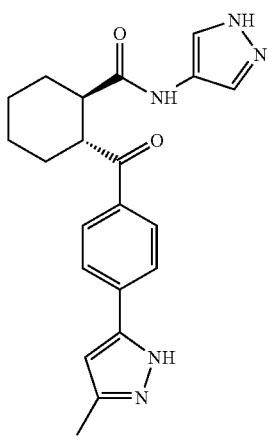 [SMILES: Cc1cc(-c2ccc(C(=O)[C@@H]3CCCC[C@H]3C(=O)Nc3cn[nH]c3)cc2)[nH]n1]

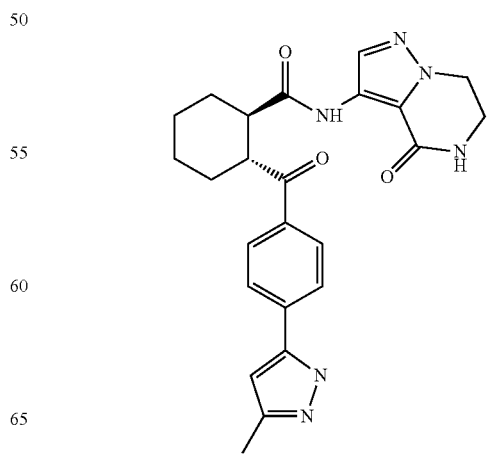

HCl (6 M in water, 20 mL) was added slowly to a solution of (1R,2R)-2-{4-[3-methyl-1-(tetrahydro-2H-pyran-2-yl)-1H-pyrazol-5-yl]benzoyl}-N-(4-oxo-4,5,6,7-tetrahydropyrazolo[1,5-a]pyrazin-3-yl)cyclohexanecarboxamide (Intermediate 14, 3.5 g, 6.60 mmol) in dioxane (40 mL) and water (10 mL) at 4° C. over a period of 2 min. The reaction mixture was stirred at 5 min at 4° C. and was then allowed to reach rt and stirred for 1h. The solvent was removed under vacuum. The residue was diluted with a solution of Na$_2$CO$_3$ (sat, aq) and the aqueous layer was extracted three times with DCM. The solvent was removed under vacuum and the crude product was purified by reversed phase flash chromatography on a C18 column using a gradient of 25-45% MeCN in H$_2$O/HCO$_2$H (99.9/0.1) buffer system as mobile phase. Pure fractions were collected and evaporated to dryness to afford the title compound (1.8 g, 61%) as a light yellow solid.

$^1$H NMR (400 MHz, DMSO-d$_6$) δ 1.10-1.55 (m, 4H), 1.74-1.82 (m, 2H), 1.95-2.08 (m, 2H), 2.28 (s, 3H), 2.99 (t, 1H), 3.70 (s, 2H), 3.82 (t, 1H), 4.21 (t, 2H), 6.58 (s, 1H), 7.82 (s, 1H), 7.90 (d, 2H), 8.01 (d, 2H), 8.33 (s, 1H), 9.15 (s, 1H), 12.76 (s, 1H) MS m/z 469 [M+Na]$^+$

Example 8: (1R,2R)—N-[1-Methyl-5-(methylsulfonyl)-1H-pyrazol-4-yl]-2-[4-(1H-pyrazol-5-yl)benzoyl]cyclohexanecarboxamide

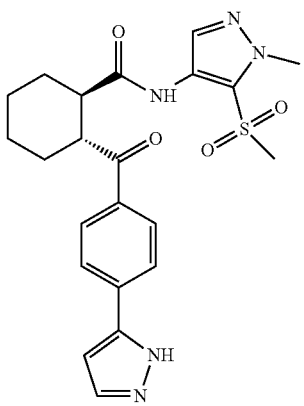 [SMILES: Cn1ncc(NC(=O)[C@@H]2CCCC[C@H]2C(=O)c2ccc(-c3ccn[nH]3)cc2)c1S(C)(=O)=O]

(1H-Pyrazol-3-yl)boronic acid (108 mg, 0.97 mmol), Pd(dppf)Cl$_2$*DCM (105 mg, 0.13 mmol) and a solution of K$_2$CO$_3$ (266 mg, 1.92 mmol) in water (1.5 mL) was added to a solution of (1R,2R)-2-(4-Bromobenzoyl)-N-[1-methyl-5-(methylsulfonyl)-1H-pyrazol-4-yl]cyclohexanecarboxamide (Intermediate 18, 300 mg, 0.66 mmol) in dioxane (10 mL) under an atmosphere of nitrogen. The reaction mixture was stirred at 100° C. for 1.5 h under an atmosphere of nitrogen. A solution of water/EtOAc (1:10) was added to the reaction mixture and the solids were filtered out. The organic layer was washed with water and brine, dried over Na$_2$SO$_4$, filtered and concentrated under vacuum. The residue was purified by preparative TLC (95% DCM in MeOH). The crude product was purified by to preparative HPLC on a Sunfire C18 column (19×150 mm) using a gradient of 5-40% MeCN in H$_2$O/HCO$_2$H (99.9/0.1) buffer system as mobile phase to give the title compound (120 mg, 41%) as a white solid.

$^1$H NMR (400 MHz, DMSO-d$_6$) δ 1.11-1.23 (m, 1H), 1.53-1.32 (m, 3H), 1.73-1.85 (m, 2H), 1.94 (d, 1H), 2.07-2.11 (m, 1H), 2.86-2.93 (t, 1H), 3.41 (s, 3H), 3.71-3.76 (t, 1H), is 3.99 (s, 3H), 6.83 (s, 1H), 7.73 (s, 1H), 7.83-8.13 (m, 5H), 9.19 (s, 1H), 13.07 (s, major rotamer), 13.51 (s, minor rotamer). Mixture of rotamers in ratio major:minor 1:0.23. MS m/z 456 [M+H]$^+$ Example 9: (1R,2R)—N-[3-(Difluoromethoxy)-1-methyl-1H-pyrazol-4-yl]-2-[4-(1H-pyrazol-5-yl)benzoyl]cyclohexanecarboxamide

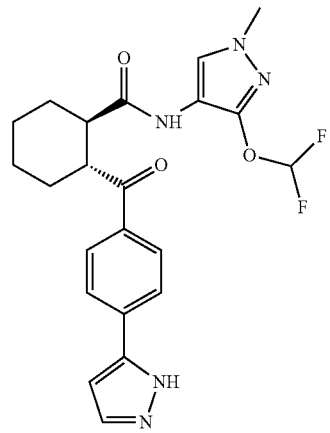 [SMILES: Cn1cc(NC(=O)[C@@H]2CCCC[C@H]2C(=O)c2ccc(-c3ccn[nH]3)cc2)c(OC(F)F)n1]

A solution of K$_2$CO$_3$ (121 mg, 0.88 mmol) in water (2 mL), 1H-pyrazol-3-ylboronic acid (74 mg, 0.66 mmol) and Pd(dppf)Cl$_2$*DCM (72 mg, 0.09 mmol) was added to a solution of (1R,2R)-2-(4-bromobenzoyl)-N-[3-(difluoromethoxy)-1-methyl-1H-pyrazol-4-yl]cyclohexanecarboxamide (Intermediate 21, 200 mg, 0.44 mmol) in dioxane (10 mL) and the reaction mixture was stirred at 80° C. for 1 h. The reaction mixture was concentrated under vacuum and the residue purified by silica gel column chromatography (10%→50% EtOAc in petroleum ether) and then by preparative HPLC on a T3 column, using MeCN in H$_2$O/HCO$_2$H (99.9/0.1) as mobile phase to give the title compound (125 mg, 64%) as a white solid.

$^1$H NMR (400 MHz, CDCl$_3$): δ1.26-2.10 (m, 8H); 2.86 (t, 1H), 3.66 (s, 3H), 3.75 (t, 1H), 6.26 (br, 1H), 6.72 (s, 1H), 6.78 (t, 1H), 7.25 (s, 3H), 7.66 (s, 1H), 7.75 (s, 1H), 7.87 (d, 2H), 8.05 (d, 2H) MS m/z 444 [M+H]$^+$

Example 10: (1R,2R)-2-[4-(3-Methyl-1H-pyrazol-5-yl)benzoyl]-N-(1-methyl-3-sulfamoyl-1H-pyrazol-4-yl)cyclohexanecarboxamide

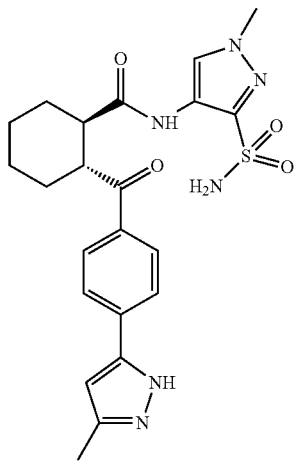 [SMILES: Cc1cc(-c2ccc(C(=O)[C@@H]3CCCC[C@H]3C(=O)Nc3cn(C)nc3S(N)(=O)=O)cc2)[nH]n1]

(5-Methyl-1H-pyrazol-3-yl)boronic acid hydrochloride (Intermediate 31, 209 mg, 1.29 mmol), Pd(dppf)Cl$_2$*DCM (70 mg, 0.09 mmol) and K$_2$CO$_3$ (206 mg, 1.49 mmol) was added to a solution of (1R,2R)-2-(4-bromobenzoyl)-N-(1-methyl-3-sulfamoyl-1H-pyrazol-4-yl)cyclohexanecarboxamide (Intermediate 25, 200 mg, 0.43 mmol) in a mixture of dioxane H$_2$O (15 mL) under an atmosphere of nitrogen and the reaction mixture was stirred at 50° C. for 3 h. The reaction mixture was extracted twice with EtOAc and the combined organic layer was washed three times with water, dried over Na$_2$SO$_4$, filtered and concentrated under vacuum. The crude residue was purified by preparative HPLC on an XBridge C18 OBD column (5 μm 150×19 ID mm) using a gradient of 18-90% MeCN in NH$_4$HCO$_3$ (0.010 M, aq) buffer system as mobile phase to give the title compound (54 mg, 27%) as a white solid.

$^1$H NMR (300 MHz, DMSO-d$_6$) δ 1.10-1.26 (m, 1H), 1.37-1.55 (m, 3H), 1.77-1.87 (m, 2H), 1.96-2.05 (m, 2H), 2.30 (s, 3H), 2.51 (t, 1H), 2.93 (t, 1H), 3.80 (s, 3H), 6.57 (s, 1H), 7.58 (s, 2H), 7.92 (d, 2H), 8.03 (d, 2H), 8.12 (s, 1H), 8.92 (s, 1H), 12.74 (s, major rotamer), 13.1 (s, minor rotamer). Unknown ratio of rotamers.
MS m/z 471 [M+H]$^+$ Example 11: (1R,2R)—N-(2,3-Dihydropyrazolo[5,1-b][1,3]oxazol-7-yl)-2-[4-(3-methyl-1H-pyrazol-5-yl)benzoyl]cyclohexanecarboxamide

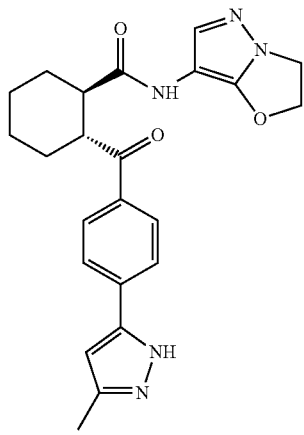 [SMILES: Cc1cc(-c2ccc(C(=O)[C@@H]3CCCC[C@H]3C(=O)Nc3cnn4c3OCC4)cc2)[nH]n1]

K$_2$CO$_3$ (132 mg, 0.96 mmol) and Pd(dppf)Cl$_2$*DCM (78 mg, 0.10 mmol) were added to a solution of (1R,2R)-2-(4-bromobenzoyl)-N-(2,3-dihydropyrazolo[5,1-b][1,3]oxazol-7-yl)cyclohexanecarboxamide (Intermediate 30, 200 mg, 0.48 mmol) and (5-methyl-1H-pyrazol-3-yl)boronic acid (60 mg, 0.48 mmol) in 1,4-dioxane (5 mL) and water (1 mL) at rt and the reaction mixture was heated at 80° C. for 5 h under an atmosphere of nitrogen. The solvent was removed under vacuum and the residue was dissolved in EtOAc. The to organic layer was washed twice with water, dried over Na$_2$SO$_4$, filtered and evaporated.

The residue was purified by preparative TLC (9% MeOH in DCM), then by C18-flash chromatography (0%→50% MeCN in water) to give the title compound (60 mg, 30%) as a white solid.

$^1$H NMR (400 MHz, DMSO-d$_6$) δ 1.20-1.01 (m, 1H). 1.41-1.49 (m, 3H), 1.73-1.82 (m, 2H), 1.90-2.03 (m, 2H), 2.50 (s, 3H), 2.78 (t, 1H), 3.68 (t, 1H), 4.18 (t, 2H), 4.99 (t, 2H), 6.56 (s, 1H), 7.21 (s, 1H), 7.89 (d, 2H), 7.98 (d, 2H), 9.35 (s, 1H), 12.75 (s, major rotamer), 13.1 (s, minor rotamer). Unknown ratio of rotamers.
MS m/z 420 [M+H]$^+$ Example 12: (1R,2R or 1S,2S)—N-(3-Cyano-1-methyl-1H-pyrazol-4-yl)-2-[4-(1H-pyrazol-3-yl)benzoyl]cyclohexanecarboxamide

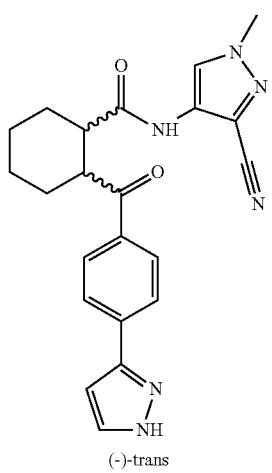 [SMILES: Cn1cc(NC(=O)C2CCCCC2C(=O)c2ccc(-c3cc[nH]n3)cc2)c(C#N)n1]

(-)-trans

Step 1—(1R,2R and 1S,2S)—N-(3-Cyano-1-methyl-1H-pyrazol-4-yl)-2-[4-(1H-pyrazol-3-yl)benzoyl]cyc lohexanecarboxamide (1R,2R and 1S,2S)-2-(4-Bromobenzoyl)-N-(3-cyano-1-methyl-1H-pyrazol-4-yl)cyclohexanecarboxamide (Intermediate 7, 150 mg, 0.36 mmol) was dissolved in dioxane (1.5 mL). 1H-Pyrazol-3-ylboronic acid (73 mg, 0.65 mmol), Pd(dppf)Cl$_2$*DCM (29 mg, 0.04 mmol) and a solution of K$_2$CO$_3$ (0.065 mL, 1.1 mmol) in water (1.5 mL) were added and the reaction mixture was evacuated and purged with nitrogen three times and then heated in a microwave reactor at 60° C. for 30 min and then at 80° C. for 50 min. The reaction mixture was diluted with EtOAc and the organic phase was washed twice to with a solution of brine (sat.). The aqueous phase was extracted twice with EtOAc. The combined organic phase was dried using a phase separator and concentrated and the residue was purified by preparative HPLC on a XBridge C18 column (10 μm 250×19 ID mm) using a gradient of 20-65% MeCN in a H$_2$O/MeCN/NH$_3$ (95/5/0.2) buffer system as mobile phase to give the sub-title compounds (45 mg 31%).

$^1$H NMR (600 MHz, DMSO-d$_6$) δ 1.16 (qd, 1H), 1.27-1.38 (m, 1H), 1.39-1.55 (m, 2H), 1.72-1.79 (m, 1H), 1.82 (d, 1H), 1.95 (d, 1H), 2.02 (d, 1H), 2.28 (s, 3H), 2.74-2.84 (m, 1H), 3.65-3.78 (m, 1H), 6.56 (s, 1H), 7.40 (s, 1H), 7.70 (s, 1H), 7.89 (d, 2H), 7.99 (d, 2H), 9.99 (s, 1H), 12.45 (s, 1H), 12.75 (s, rotamer), 13.09 (s, rotamer) MS m/z 403.1 [M+H]$^+$

Step 2—(1R,2R or 1S,2S)—N-(3-Cyano-1-methyl-1H-pyrazol-4-yl)-2-[4-(1H-pyrazol-3-yl)benzoyl]cyclohexanecarboxamide The enantiomers from step 1 (30 mg, 0.07 mmol) were separated by chiral chromatography on a Chiralpak AD column (5 μm, 250×20 mm). 30 mg (30 mg/mL in EtOH:DCM, 91:9) was injected and eluted with Heptane:EtOH (30:70) at a flow rate of 18 mL/min and detected at 260 nm. The second eluted compound was collected and evaporated to give the title compound (11 mg, 37%, 99.9% ee).

$^1$H NMR (500 MHz, CDCl$_3$) δ 1.25-1.45 (m, 2H), 1.50 (ddd, 1H), 1.69 (qd, 1H), 1.84-1.95 (m, 2H), 2.05-2.17 (m, 2H), 2.96 (ddd, 1H), 3.73-3.83 (m, 4H), 6.70 (d, 1H), 7.67 (d, 1H), 7.87 (d, 2H), 7.99 (s, 1H), 8.04 (d, 2H), 8.22 (s, 1H).

Optical rotation: −153.8° (1 g/100 mL in MeCN, 589 nm, 20° C.).

Example 13: (1R,2R)-2-[4-(3-Methyl-1H-pyrazol-5-yl)benzoyl]-N-(1-methyl-5-sulfamoyl-1H-pyrazol-4-yl)cyclohexanecarboxamide

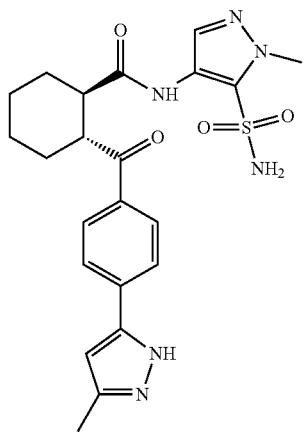 [SMILES: Cc1cc(-c2ccc(C(=O)[C@@H]3CCCC[C@H]3C(=O)Nc3cnn(C)c3S(N)(=O)=O)cc2)[nH]n1]

PdCl$_2$(dppf)-DCM (4.87 g, 5.97 mmol) was added to a mixture of (1R,2R)-2-(4-bromobenzoyl)-N-(1-methyl-5-sulfamoyl-1H-pyrazol-4-yl)cyclohexanecarboxamide (Intermediate 37, 28 g, 59.7 mmol), (5-methyl-1H-pyrazol-3-yl)boronic acid (15.02 g, 119.31 mmol) and sodium carbonate (25.3 g, 238.63 mmol) in dioxane (500 mL) and water (125 mL) under nitrogen atmosphere and the reaction mixture was stirred at 85° C. for 4 h. The reaction mixture was concentrated under vacuum and diluted with EtOAc and the to organic phase was washed with brine (sat., aq), dried over Na$_2$SO$_4$, filtered and evaporated. The crude product was purified by Flash column chromatography on a C18 column (32 μm, 400 g), using a gradient from 0→40% of MeCN in water as mobile phase to give the title compound (12.73 g, 45.3%) as a brown solid.

$^1$H-NMR (300 MHz, DMSO-d$_6$) δ 1.13-1.22 (m, 1H), 1.36-1.52 (m, 3H), 1.74-1.84 (m, 2H), 1.96-2.08 (m, 2H), 2.22 (d, 3H), 2.84-2.90 (m, 1H), 3.35-3.75 (m, 1H), 3.92 (d, 3H), 6.57 (s, 1H), 7.81 (s, 1H), 7.89-7.96 (t, 2H), 8.01-8.16 (m, 4H), 8.82 (s, 1H), 12.78 (s, 1H).

MS m/z 471 [M+H]$^+$

Example 14: (1R,2R and 1S,2S)—N-(5-Methoxy-1-methyl-1H-pyrazol-4-yl)-2-[4-(1H-pyrazol-3-yl)benzoyl]cyclohexanecarboxamide

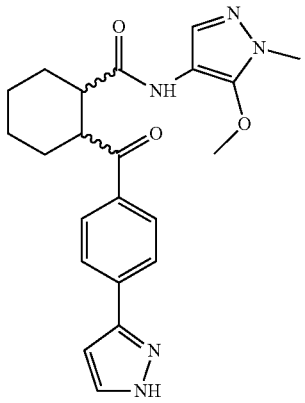

(±)-trans

Step 1—(1R,2R and 1S,2S)-2-(4-bromobenzoyl)-N-(5-methoxy-1-methyl-1H-pyrazol-4-yl)cyclohexanecarboxamide (1R,2R and 1S, 2S)-2-(4-Bromobenzoyl)cyclohexanecarboxylic acid (59 mg, 0.19 mmol), 3-methoxy-1-methyl-1H-pyrazol-4-amine hydrochloride (61.3 mg, 0.37 mmol) and Et$_3$N (105 μl, 0.76 mmol) were suspended in EtOAc (2.1 mL). T3P (50% in EtOAc, 135 μL, 0.23 mmol) was added and the reaction mixture was heated in a microwave reactor at 100° C. for 20 min. The mixture was partitioned between EtOAc and NaHCO$_3$ (sat., aq) and the organic phase was washed with NH$_4$Cl (sat., aq) and brine. The organic phase was dried using a phase separator and concentrated under vacuum to give the subtitle to compound (63 mg, 79%).

MS m/z 420 [M+H]$^+$

Step 2—(1R,2R and 1S,2S)—N-(5-methoxy-1-methyl-1H-pyrazol-4-yl)-2-[4-(1H-pyrazol-3-yl)benzoyl]cyclohexanecarboxamide K$_2$CO$_3$ (83 mg, 0.60 mmol) and Pd(dppf)Cl$_2$*DCM (12 mg, 0.01 mmol) were added to a is solution of the product of step 1 (63 mg, 0.15 mmol) and 1H-pyrazol-3-ylboronic acid (25 mg, 0.22 mmol) in dioxane (0.7 mL) and water (0.7 mL). The mixture was evacuated and purged with nitrogen three times and then heated in a microwave reactor at 100° C. for 30 min. The reaction mixture was diluted with EtOAc and water and the aqueous phase was extracted once with EtOAc. The combined organic layer was washed with brine, NH$_4$Cl (sat., aq), brine, dried using a phase separator and concentrated under vacuum. The crude product was purified by preparative HPLC on a XBridge C18 column (5 μm 150×19 ID mm) using a gradient of 5-95% of MeCN in a H$_2$O/MeCN/NH$_3$ (95/5/0.2) buffer system as mobile phase to give the title compound (11 mg 18%).

$^1$H NMR (600 MHz, DMSO-d$_6$) δ 1.1-1.2 (m, 1H), 1.26-1.35 (m, 1H), 1.36-1.44 (m, 1H), 1.45-1.54 (m, 1H), 1.72-1.83 (m, 2H), 1.91-1.97 (m, 1H), 2-2.06 (m, 1H), 2.91-2.97 (m, 1H), 3.56 (s, 3H), 3.69-3.75 (m, 1H), 3.81 (s, 3H), 6.85 (d, 1H), 7.64 (s, 1H), 7.83 (s, 1H), 7.92-8.07 (m, 4H), 9.44 (s, 1H), 13.08 (s, 1H). MS m/z 408.2 [M+H]$^+$

Example 15: (1R,2R)—N-[5-(Difluoromethyl)-1H-pyrazol-4-yl]-2-[4-(5-methyl-1H-pyrazol-3-yl)benzoyl]cyclohexanecarboxamide

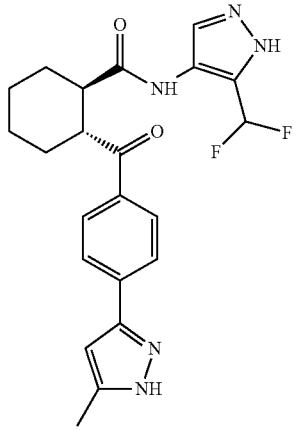 [SMILES: Cc1cc(-c2ccc(C(=O)[C@@H]3CCCC[C@H]3C(=O)Nc3cn[nH]c3C(F)F)cc2)n[nH]1]

Step 1—(1R,2R)—N-[5-(Difluoromethyl)-1-(tetrahydro-2H-pyran-2-yl)-1H-pyrazol-4-yl]-2-[4-(5-methyl-1H-pyrazol-3-yl)benzoyl]cyclohexanecarboxamide (5-Methyl-1H-pyrazol-3-yl)boronic acid (237 mg, 1.88 mmol), $K_2CO_3$ (650 mg, 4.70 mmol), and Pd(dppf)$Cl_2$*DCM (128 mg, 0.16 mmol) were added to a solution of (1R,2R)-2-(4-bromobenzoyl)-N-[5-(difluoromethyl)-1-(tetrahydro-2H-pyran-2-yl)-1H-pyrazol-4-yl]cyclohexanecarboxamide (Intermediate 39, 800 mg, 1.57 mmol) in a mixture of dioxane to and water (4:1, 15 mL) under an atmosphere of nitrogen, and the reaction mixture was stirred at 50° C. for 2 h. The reaction mixture was diluted with EtOAc and the organic phase was washed with water, brine (sat.), dried over $Na_2SO_4$, and concentrated under vacuum. The residue was purified by silica gel column chromatography (33% EtOAc in petroleum ether) to give the subtitle compound (620 mg, 77%) as a yellow solid.

MS m/z 512 [M+H]$^+$

Step 2—(1R,2R)—N-[5-(Difluoromethyl)-1H-pyrazol-4-yl]-2-[4-(5-methyl-1H-pyrazol-3-yl)benzoyl]cyclohexanecarboxamide HCl (3M in MeOH, 5.9 mL) was added to a solution of the product from step 1 (600 mg, 1.17 mmol) in MeOH (30 mL) and the reaction mixture was stirred at rt for 1 h. The pH value of the reaction mixture was adjusted to ~8 using $NaHCO_3$ (aq), and the reaction mixture was extracted with EtOAc. The organic layer was washed with brine (sat.), dried over $Na_2SO_4$ and concentrated under vacuum. The crude product was purified by preparative HPLC on a XBridge Prep C18 OBD column (5 m, 150×19 ID mm) using a gradient of 25-55% of MeCN in water (0.03% $NH_4OH$) as mobile phase to give the title compound (69 mg, 14%) as a white solid.

$^1$H-NMR (300 MHz, DMSO-d$_6$) δ 1.34-1.38 (m, 1H), 1.41-1.53 (m, 3H), 1.73-1.84 (m, 2H), 1.94-2.07 (m, 2H), 2.27 (s, 3H), 2.93-2.96 (m, 1H), 3.69-3.76 (m, 1H), 6.56 (s, 1H), 6.99 (t, J=54.0 Hz, 1H), 7.89-8.07 (m, 5H), 9.67 (s, 1H), 12.74 (s, 1H), 13.04 (s, 1H). MS m/z 428 [M+H]$^+$

Example 16: (1R,2R)—N-(5-Methyl-4-oxo-4,5,6,7-tetrahydroprazolo[1,5-a]pyrazin-3-yl)-2-[4-(5-methyl-1H-pyrazol-3-yl)benzoyl]cyclohexanecarboxamide

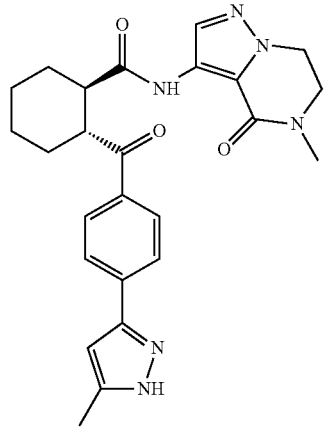 [SMILES: Cc1cc(-c2ccc(C(=O)[C@@H]3CCCC[C@H]3C(=O)Nc3cnn4c3C(=O)N(C)CC4)cc2)n[nH]1]

Pd(dppf)$Cl_2$*DCM (53 mg, 0.07 mmol) was added to (1R,2R)-2-(4-bromobenzoyl)-N-(5-methyl-4-oxo-4,5,6,7-tetrahydropyrazolo[1,5-a]pyrazin-3-yl)cyclohexanecarboxamide (Intermediate 42, 300 mg, 0.65 mmol), (5-methyl-1H-pyrazol-3-yl)boronic acid (164 mg, 1.31 mmol) and $Na_2CO_3$ (138 mg, 1.31 mmol) in 1,4-dioxane (10 mL) and water (1 mL) at 25° C. under an atmosphere of nitrogen and the reaction mixture was stirred at 90° C. for 15 h. Pd(dppf)$Cl_2$*DCM (26 mg, 0.035 mmol), (5-methyl-1H-pyrazole-3-yl)boronic acid (80 mg, 0.65 mmol) and $Na_2CO_3$ (70 mg, 0.65 mmol) were added to the reaction rmixture and it was stirred at 90° C. for 6 h. The reaction mixture was diluted with EtOAc (50 mL), filtered through a pad of celite and concentrated under vacuum. The crude residue was is purified by preparative TLC (5% MeOH in DCM). The crude product was purified by preparative HPLC on a X Bridge C18, column (5 μm 19×150 mm ID) using a gradient of 30-70% of MeCN in a $H_2O/CF_3CO_2H$ (99.95/0.05) buffer system as mobile phase, to give the title compound (130 mg, 43%) as a pale yellow solid.

$^1$H NMR (400 MHz, DMSO-d$_6$) δ 1.10-1.55 (m, 4H), 1.70-1.85 (m, 2H), 1.95-2.10 (m, 2H), 2.30 (s, 3H), 2.98 (t, 1H), 3.02 (s, 3H), 3.70 (t, 1H), 3.78 (t, 2H), 4.30 (t, 2H), 6.52 (s, 1H), 7.82 (s, 1H), 7.90 (d, 2H), 8.00 (d, 2H), 9.20 (s, 1H), 12.78 (s, 1H) MS m/z 461 [M+H]$^+$

Example 17: (1R,2R)—N-(5-Methyl-4-oxo-4,5,6,7-tetrahydropyrazolo[1,5-a]pyrazin-3-yl)-2-[4-(1H-pyrazol-3-yl)benzoyl]cyclohexanecarboxamide

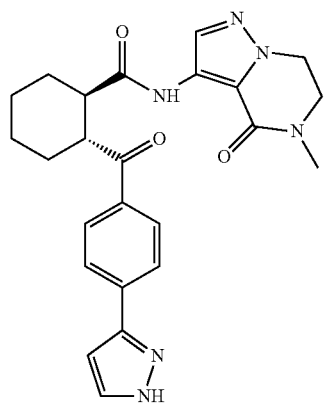 [SMILES: CN1CCn2ncc(NC(=O)[C@@H]3CCCC[C@H]3C(=O)c3ccc(-c4cc[nH]n4)cc3)c2C1=O]

Pd(dppf)Cl$_2$*DCM (53.3 mg, 0.07 mmol) was added to a mixture of (1R,2R)-2-(4-bromobenzoyl)-N-(5-methyl-4-oxo-4,5,6,7-tetrahydropyrazolo[1,5-a]pyrazin-3-yl)cyclohexanecarboxamide (Intermediate 42, 300 mg, 0.65 mmol), 1H-pyrazol-3-ylboronic acid (146 mg, 1.31 mmol) and Na$_2$CO$_3$ (138 mg, 1.31 mmol) in 1,4-dioxane (10 mL) and water (1 mL) at 25° C. under an atmosphere of nitrogen and the reaction mixture was stirred at 90° C. for 15 h. Pd(dppf)Cl$_2$*DCM (27 mg, 0.035 mmol), (1H-pyrazol-3-yl)boronic acid (73 mg, 0.65 mmol) and Na$_2$CO$_3$ (70 mg, 0.65 mmol) were added and the reaction mixture was stirred at 90° C. for 6 h. The reaction mixture was diluted with EtOAc (50 mL), filtered through a pad of celite and concentrated under vacuum. The residue was purified by preparative TLC (5% MeOH in DCM). The crude product was purified by preparative HPLC on a X Bridge C18 column (5 μm, 19×150 mm ID) using a gradient of 30-70% of MeCN in water (0.05% CF$_3$COOH) as mobile phase, to give the title compound (130 mg, 45%) as a white solid.

$^1$H NMR (400 MHz, DMSO-d$_6$) δ 1.10-1.60 (m, 4H), 1.70-1.85 (m, 2H), 1.90-2.10 (m, 2H), 2.99 (t, 1H), 3.01 (s, 3H), 3.74 (t, 1H), 3.79 (t, 2H), 4.20 (t, 2H), 6.88 (s, 1H), 7.85 (s, 2H), 8.01 (d, 2H), 8.08 (d, 2H), 9.20 (s, 1H), 13.10 (s, 1H). MS m/z 447 [M+H]$^+$

Example 18a: (1R,2R or 1S,2S)—N-(5-Cyano-1-methyl-1H-pyrazol-4-yl)-2-[4-(1H-pyrazol-3-yl)benzoyl]cyclohexanecarboxamide and Example 18b: (1S,2S or 1R,2R)—N-(5-Cyano-1-methyl-1H-pyrazol-4-yl)-2-[4-(1H-pyrazol-3-yl)benzoyl]cyclohexanecarboxamide

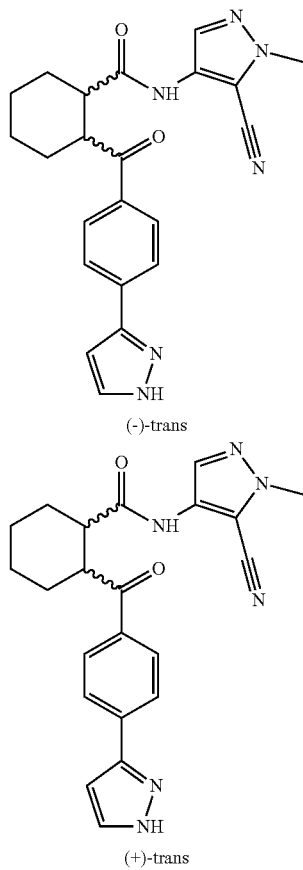

(−)-trans (+)-trans

Step 1—(1R,2R and 1S,2S)—N-(5-Cyano-1-methyl-1H-pyrazol-4-yl)-2-[4-(1H-pyrazol-3-yl)benzoyl]cyclohexanecarboxamide 1H-Pyrazol-3-ylboronic acid (73 mg, 0.65 mmol), Pd(dppf)Cl$_2$*DCM (8.8 mg, 10.8 μmol) and a solution of K$_2$CO$_3$ (149 mg, 1.08 mmol) in water (1.5 mL) were added to a mixture of (1R,2R and 1S,2S)-2-(4-bromobenzoyl)-N-(5-cyano-1-methyl-1H-pyrazol-4-yl)cyclohexanecarboxamide (Intermediate 43, 150 mg, 0.36 mmol) in dioxane (1.5 mL) and the reaction mixture was evacuated and purged with nitrogen and then heated at 80° C. for 3.5 h. The reaction mixture was diluted with EtOAc and the organic phase was washed to twice with brine (sat.). The aqueous phase was extracted twice with EtOAc and the combined organic phase was dried using a phase separator and concentrated in vacuum. The residue was purified by preparative HPLC on a Waters Sunfire C18 OBD column (5 μm, 19×150 mm ID) using a gradient of 5-95% of MeCN in a HCO$_2$H (0.1M, aq) buffer system as a mobile phase. The product containing fractions were concentrated and is dissolved in EtOAc. The organic phase was washed with brine, dried using a phase-separator and concentrated in vacuum to give the title compound (46 mg, 32%).

$^1$H NMR (500 MHz, DMSO-d$_6$) δ 1.1-1.23 (m, 1H), 1.33 (t, 1H), 1.39-1.62 (m, 2H), 1.80 (dd, 2H), 1.94-2.02 (m, 1H), 2.06 (d, 1H), 2.83-2.98 (m, 1H), 3.69-3.79 (m, 1H), 3.89 (s, 3H), 6.84 (d, 1H), 7.70 (s, 1H), 7.9-8.13 (m, 4H), 10.52 (s, 1H), 13.08 (s, 1H) MS m/z 403 [M+H]$^+$

Step 2—(1R,2R or 1S,2S)—N-(5-Cyano-1-methyl-1H-pyrazol-4-yl)-2-[4-(1H-pyrazol-3-yl)benzoyl]cyclohexanecarboxamide (18a) and (1S,2S or 1R,2R)—N-(5-Cyano-1-methyl-1H-pyrazol-4-yl)-2-[4-(1H-pyrazol-3-yl)benzoyl]cyclohexanecarboxamide (18b)

The enantiomers from step 1 (34 mg, 0.08 mmol) were separated by chiral chromatography on a Chiralpak AD column (5 μm, 250×20 mm). 34 mg (17 mg/mL in EtOH) was injected and eluted with Heptane:EtOH (30:70) at a flow rate of 18 mL/min and detected at 260 nm. The first eluted compound was collected and evaporated to give Example 18a (13 mg, 38%, 98% ee).

Optical rotation: −131° (1 g/100 mL in MeCN, 589 nm, 20° C.).

$^1$H NMR (500 MHz, CDCl$_3$) δ 1.23-1.43 (m, 2H), 1.51 (ddd, 1H), 1.76 (qd, 1H), 1.83-1.95 (m, 2H), 2.06-2.16 (m, 2H), 2.92-3.01 (m, 1H), 3.77-3.86 (m, 1H), 3.92 (s, 3H), 6.70 (d, 1H), 7.67 (d, 1H), 7.83-7.91 (m, 3H), 8.04 (d, 2H), 8.37 (s, 1H).

The second eluted compound was collected and evaporated to give Example 18b (13 mg, 38%, 96.0% ee).

Optical rotation: +127° (1 g/100 mL in MeCN, 589 nm, 20° C.).

$^1$H NMR (500 MHz, CDCl$_3$) δ 1.22-1.44 (m, 2H), 1.51 (ddd, 1H), 1.76 (qd, 1H), 1.92 (d, 2H), 2.02-2.22 (m, 2H), 2.96 (td, 1H), 3.73-3.87 (m, 1H), 3.92 (s, 3H), 6.70 (d, 1H), 7.67 (d, 1H), 7.82-7.93 (m, 3H), 8.04 (d, 2H), 8.32 (s, 1H)

Example 19: 1-Ethyl-4-[({(1R,2R)-2-[4-(3-methyl-1H-pyrazol-5-yl)benzoyl]-cyclohexyl}carbonyl)amino]-1H-pyrazole-5-carboxamide

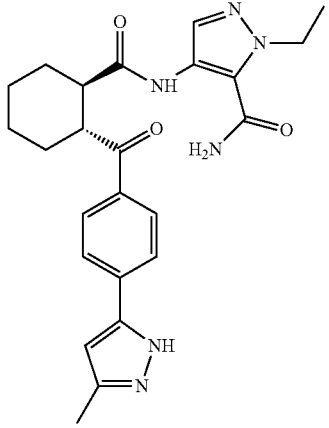 [SMILES: CCn1ncc(NC(=O)[C@@H]2CCCC[C@H]2C(=O)c2ccc(-c3cc(C)n[nH]3)cc2)c1C(N)=O]

HCl in MeOH (1.2M, 0.3 mL, 0.36 mmol) was added to a solution of 1-ethyl-4-({[(1R,2R)-2-{4-[3-methyl-1-(tetrahydro-2H-pyran-2-yl)-1H-pyrazol-5-yl]benzoyl}cyclohexyl]-carbonyl}amino)-1H-pyrazole-5-carboxamide (Intermediate 44, 150 mg, 0.28 mmol) in MeOH (20 mL). The reaction mixture was concentrated in vacuum at 18° C. The residue was dissolved in MeOH (25 mL) and then concentrated at 16° C. The crude product was immediately purified by preparative HPLC on a XBridge C18 column (10 μm 250×19 ID mm) using a gradient of 5-70% MeCN in a H₂O/MeCN/NH₃ (95/5/0.2) buffer system to give the title compound (78 mg, 62%).

¹H NMR (500 MHz, DMSO-d₆) δ 1.12-1.22 (m, 1H), 1.25 (t, 3H), 1.35 (t, 1H), 1.42-1.57 (m, 2H), 1.76 (d, 2H), 1.83 (d, 1H), 1.97 (d, 1H), 2.08 (d, 1H), 2.75-2.96 (m, 1H), 3.69 (t, 1H), 4.28 (q, 2H), 6.56 (s, 1H), 7.38 (s, 2H), 7.89 (d, 2H), 8.00 (d, 2H), 9.48 (s, 1H), 12.74 (s, major rotamer), 13.09 (minor rotamer) Mixture of rotamers in ratio major:minor 1:0.12 MS m/z 449.3 [M+H]⁺

Example 20: N,1-Dimethyl-4-[({(1R,2R and 1S,2S)-2-[4-(1H-pyrazol-3-yl)benzoyl]-cyclohexyl}carbonyl)amino]-1H-pyrazole-3-carboxamide

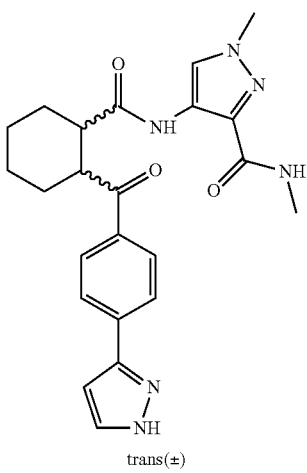 [SMILES: CNC(=O)c1nn(C)cc1NC(=O)C1CCCCC1C(=O)c1ccc(-c2cc[nH]n2)cc1]

trans(±)

Step 1—4-({[(1R,2R)-2-(4-Bromobenzoyl)cyclohexyl]carbonyl}amino)-N,1-dimethyl-1H-pyrazole-3-carboxamide T3P (50% in EtOAc, 268 μL, 0.45 mmol) and Et₃N (0.094 mL, 0.67 mmol) were added to a mixture of (1R,2R)-2-(4-Bromobenzoyl)cyclohexanecarboxylic acid (70 mg, 0.22 mmol) and 4-amino-N, 1-dimethyl-1H-pyrazole-3-carboxamide hydrochloride (86 mg, 0.45 mmol) in EtOAc (2 mL) and the reaction mixture was heated in a microwave reactor at 150° C. for 40 min. T3P (50% in EtOAc, 268 μL, 0.45 mmol) and Et₃N was added and the reaction mixture was heated in a microwave reactor at 150° C. for 20 min. The reaction mixture was diluted with EtOAc and the organic phase was washed with NaHCO₃ (aq) and brine. The organic phase was dried using a phase separator and concentrated to give the subtitle is compound (87 mg, crude).

Step 2—N,1-Dimethyl-4-[({(1R,2R)-2-[4-(1H-pyrazol-3-yl)benzoyl]cyclohexyl}carbonyl)-amino]-1H-pyrazole-3-carboxamide A solution of the product from step 1 (86 mg, 0.19 mmol) in DME (1.5 mL) and ethanol (0.5 mL) was added to Pd(dppf)Cl₂*DCM (16 mg, 0.02 mmol) and 1H-pyrazol-3-ylboronic acid (21.64 mg, 0.19 mmol) under an atmosphere of nitrogen. Potassium phosphate (aq, 12M, 0.047 mL, 0.58 mmol) in water (0.5 mL) was added and the reaction mixture was heated in a microwave reactor at 140° C. for 15 min. 1H-pyrazole-3-carboxamide (16 mg, 0.035 mmol) and Pd(dppf)Cl₂*DCM (10 mg, 0.012 mmol) was added to the reaction mixture and it was heated in a microwave reactor at 140° C. for 10 min. The reaction mixture was diluted with EtOAc and the organic phase was washed with water, dried using a phase separator and concentrated in vacuum. The crude residue was purified by preparative HPLC on a XBridge C18 OBD column (5 μm, 19×150 mm ID) using a gradient of 5-95% of MeCN in a H₂O/MeCN/NH₃ (95/5/0.2) buffer system at pH10 as mobile phase to give the title compound (23 mg, 27%).

¹H NMR (600 MHz, DMSO-d₆) δ 1.20 (q, 1H), 1.43 (t, 1H), 1.52 (q, 2H), 1.72-1.88 (m, 2H), 1.97 (d, 1H), 2.04 (d, 1H), 2.77 (d, 3H), 2.84-2.94 (m, 1H), 3.74 (t, 1H), 3.80 (s, 3H), 6.86 (s, 1H), 7.85 (s, major rotamer), 7.91 (s, minor rotamers), 7.97 (d, major rotamer), 8-8.1 (m, 3H), 8.28 (d, 1H), 9.80 (s, 1H), 13.09 (s, major rotamer), 13.53 (s, minor rotamer). Mixture of rotamers in ratio major:minor 1:0.21 MS m/z 422.2 [M+H]⁺

Example 21: N,1-Dimethyl-4-[({(1R,2R)-2-[4-(5-methyl-1H-pyrazol-3-yl)benzoyl]-cyclohexyl}carbonyl)amino]-1H-pyrazole-5-carboxamide

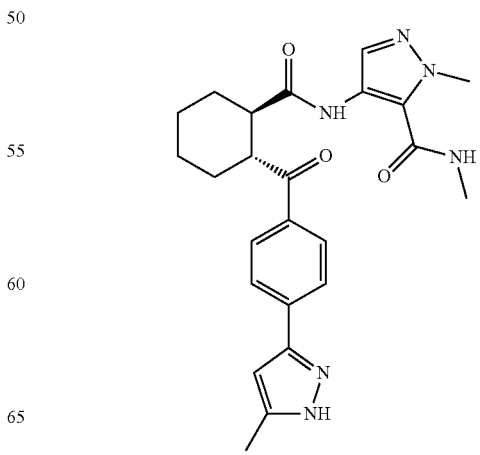

Ice-cooled HCl (2M in dioxane/water, 1:1, 2 mL, 4.00 mmol) was added dropwise to a solution of N,1-dimethyl-4-({[(1R,2R)-2-{4-[3-methyl-1-(tetrahydro-2H-pyran-2-yl)-1H-pyrazol-5-yl]benzoyl}cyclohexyl]carbonyl}amino)-1H-pyrazole-5-carboxamide (Intermediate 47, 0.069 g, 0.13 mmol) in dioxane (3 mL) at 0° C. The reaction mixture was allowed to reach rt and was then stirred at rt for 50 min. The reaction mixture was concentrated in vacuum at 10-15° C. The residue was co-evaporated under vacuum at 10-15° C. with dioxane (3×3 mL). Methylamine (2 M in THF, 1 mL) was added and the reaction mixture was evaporated. The crude product was purified by preparative HPLC on a XBridge C18 column (10 jtm, 250×19 ID mm) using a gradient of 10-60% MeCN in a H₂O/MeCN/NH₃ (95/5/0.2) buffer system to give the title compound (0.044 g, 75.0%).

¹H NMR (500 MHz, CDCl₃) δ 1.26-1.46 (m, 2H), 1.52 (q, 1H), 1.68-1.79 (m, 1H), 1.91 (dd, 2H), 2.12 (t, 2H), 2.36 (s, 3H), 2.72-2.91 (m, 4H), 3.7-3.82 (m, 1H), 4.01 (s, 3H), 6.43 (s, 1H), 7.12 (d, 1H), 7.41 (s, 1H), 7.83 (d, 2H), 7.88 (s, 1H), 7.98 (d, 2H). MS m/z 447.3 [M−H]⁻

Example 22: 5-Methyl-4-[({(1R,2R)-2-[4-(3-methyl-1H-pyrazol-5-yl)benzoyl]-cyclohexyl}carbonyl)amino]-1H-pyrazole-3-carboxamide

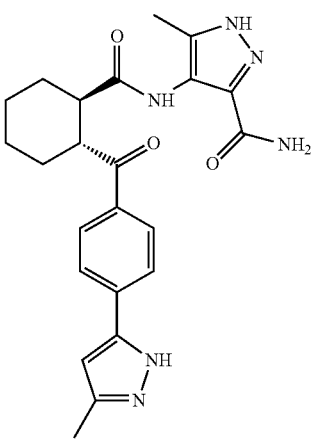 [SMILES: Cc1cc(-c2ccc(C(=O)[C@@H]3CCCC[C@H]3C(=O)Nc3c(C(N)=O)n[nH]c3C)cc2)[nH]n1]

HCl (3.8M in water, 145 μL, 0.55 mmol) was added to a solution of 5-methyl-4-({[(1R,2R)-2-{4-[3-methyl-1-(tetrahydro-2H-pyran-2-yl)-1H-pyrazol-5-yl]benzoyl}cyclohexyl]-carbonyl}amino)-1H-pyrazole-3-carboxamide (Intermediate 48, 190 mg, 0.37 mmol) in a mixture of 1,4-dioxane (3 mL) and water (0.75 mL). The reaction mixture was stirred at rt for 2.5h. The reaction mixture was diluted with EtOAc and water and the organic phase was washed with NaHCO₃ (sat. aq), brine, dried using a phase to separator and concentrated in vacuum. The residue was purified by preparative SFC on a Viridis 2-EP column (5 μm, 30×250 mm ID) using MeOH/DEA (100:0.5) in CO₂(g) as mobile phase, to give the title compound (94 mg, 59.1%)

¹H NMR (600 MHz, DMSO-d₆) δ 1.14-1.24 (m, 1H), 1.29-1.58 (m, 3H), 1.71-2.04 (m, 6H), 2.12-2.33 (m, 4H), 2.78-2.92 (m, 1H), 3.59-3.77 (m, 1H), 6.64 (d, 1H), 7.21 (d, 1H), 7.76-8.11 (m, 4H), 9.30 (d, 1H), 12.66-13.18 (m, 2H)

Example 23: 4-[({(1R,2R)-2-[4-(1H-Pyrazol-5-yl)benzoyl]cyclohexyl}carbonyl)amino]-1H-pyrazole-5-carboxamide

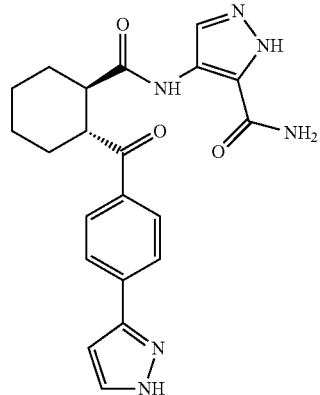 [SMILES: NC(=O)c1[nH]ncc1NC(=O)[C@@H]1CCCC[C@H]1C(=O)c1ccc(-c2cc[nH]n2)cc1]

HCl (1.25 M in MeOH, 0.2 mL, 0.25 mmol) was added to a solution of 4-({[(1R,2R)-2-{4-[1-(tetrahydro-2H-pyran-2-yl)-1H-pyrazol-5-yl]benzoyl}cyclohexyl]carbonyl}amino)-1H-pyrazole-5-carboxamide (Intermediate 49, 90 mg, 0.18 mmol) in MeOH (10 mL). The reaction mixture was concentrated in vacuum at 19° C. The residue was dissolved in MeOH (10 mL) and concentrated in vacuum at 17° C. The residue was immediately purified by preparative HPLC on a XBridge C18 column (10 μm 250×19 ID mm) using a gradient of 5-80% MeCN in a H₂O/MeCN/NH₃ (95/5/0.2) buffer system, to give the title compound (56 mg 75%)

¹H NMR (500 MHz, DMSO) δ 1.11-1.27 (m, 1H), 1.34-1.59 (m, 3H), 1.69-1.84 (m, 2H), 1.99 (dd, 2H), 2.78-2.92 (m, 1H), 3.67-3.78 (m, 1H), 6.84 (d, 1H), 7.39-8.16 (m, 8H), 9.76 (s, 1H), 13.07 (s, 2H), 13.51 (s, OH).

MS m/z 405.3 [M−H]⁻

Example 24: (1R,2R)—N-(4-Oxo-4,5,6,7-tetrahydropyrazolo[1,5-a]pyrazin-3-yl)-2-[4-(1H-pyrazol-5-yl)benzoyl]cyclohexanecarboxamide

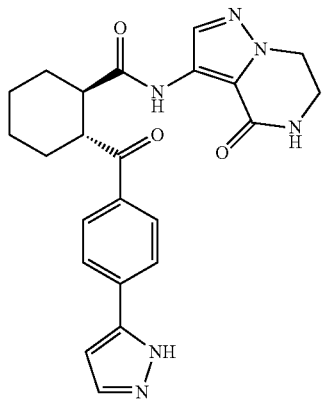 [SMILES: O=C1NCCn2ncc(NC(=O)[C@@H]3CCCC[C@H]3C(=O)c3ccc(-c4ccn[nH]4)cc3)c21]

HCl (3.8M in water, 5 mL, 19 mmol) was added dropwise to a solution of (1R,2R)—N-(4-oxo-4,5,6,7-tetrahydropyrazolo[1,5-a]pyrazin-3-yl)-2-{4-[1-(tetrahydro-2H-pyran-2-yl)-1H-pyrazol-5-yl]benzoyl}cyclohexanecarboxamide (Intermediate 50, 0.46 g, 0.89 mmol) is in dioxane (5 mL) cooled in an ice-bath and the reaction mixture was stirred while cooling for 1h. The reaction mixture was diluted with EtOAc and NaHCO$_3$ (sat., aq) and the aqueous phase was extracted four times with EtOAc. The combined organic phase was washed with NaHCO$_3$ (sat., aq), dried using a phase separator and evaporated in vacuum. The residue was purified by preparative HPLC on a XBridge C18 column (10 μm 250×50 ID mm) using a gradient of 15-55% MeCN in a H$_2$O/MeCN/NH$_3$ (95/5/0.2) buffer system to give the title compound (0.298 g, 77%).

$^1$H NMR (400 MHz, CDCl$_3$) δ 1.14-1.56 (m), 1.6 (m, 2H), 1.88 (m, 2H), 2.12 (t, 2H), 2.95 (m, 1H), 3.69 (m, 3H), 4.30 (t, 2H), 6.70 (d, 1H), 7.65 (d, 1H), 7.86 (d, 2H), 8.05 (d, 2H), 8.15 (s, 1H), 8.82 (s, 1H)

Example 25: (1R,2R)—N-[1-Methyl-5-(methylsulfamoyl)-1H-pyrazol-4-yl]-2-[4-(3-methyl-1H-pyrazol-5-yl)benzoyl]cyclohexanecarboxamide

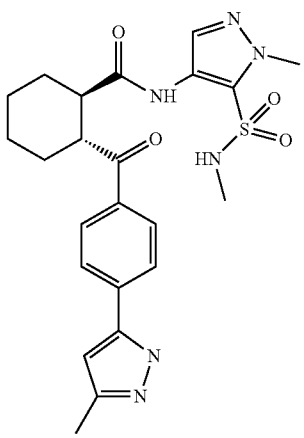 [SMILES: CNS(=O)(=O)c1c(NC(=O)[C@@H]2CCCC[C@H]2C(=O)c2ccc(-c3cc(C)n[nH]3)cc2)cnn1C]

HCl (1.25N in MeOH, 0.76 mL) was added to a solution of (1R,2R)—N-[1-methyl-5-(methylsulfamoyl)-1H-pyrazol-4-yl]-2-{4-[3-methyl-1-(tetrahydro-2H-pyran-2-yl)-1H-pyrazol-5-yl]benzoyl}cyclohexanecarboxamide (Intermediate 56, 180 mg, 0.32 mmol) in MeOH (5 mL) at 0° C. and the reaction mixture was stirred at rt for 30 min. The reaction mixture was concentrated under vacuum. The residue was purified by preparative HPLC on a XBridge Prep C18 OBD column (5 μm, 19×150 mm) using a gradient of 17-55% of MeCN in water (NH$_4$OH, 0.03%) as mobile phase to give the title compound (67 mg, 44%) as a white solid.

$^1$H NMR (300 MHz, DMSO-d$_6$): δ 1.05-1.29 (1H, m), 1.29-1.60 (3H, m), 1.69-1.84 (2H, m), 1.94-2.07 (2H, m), 2.25 (3H, s), 2.87-2.95 (1H, m), 3.67-3.74 (1H, m), 3.93 (3H, s), 6.57 (1H, s), 7.80 (1H, s), 7.87-7.90 (2H, m), 7.98-8.01 (4H, m), 8.08-8.13 (1H, m), 8.84 (1H, s), 12.75 (1H, bs) MS m/z 485 [M+H]$^+$

Example 26: (1R,2R)—N-(1-Methyl-3-sulfamoyl-1H-pyrazol-4-yl)-2-[4-(1H-pyrazol-5-yl)benzoyl]cyclohexanecarboxamide

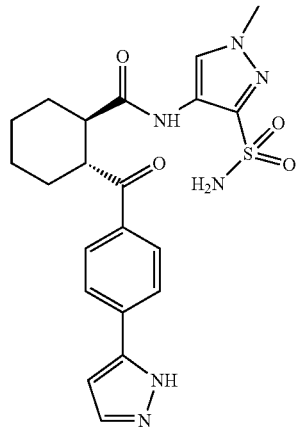 [SMILES: Cn1cc(NC(=O)[C@@H]2CCCC[C@H]2C(=O)c2ccc(-c3ccn[nH]3)cc2)c(S(N)(=O)=O)n1]

1H-Pyrazol-5-ylboronic acid hydrochloride (108 mg, 0.73 mmol), K$_2$CO$_3$ (353 mg, 2.56 mmol) and Pd(dppf)Cl$_2$*DCM (104 mg, 0.13 mmol) was added to a solution of (1R,2R)-2-(4-bromobenzoyl)-N-(1-methyl-3-sulfamoyl-1H-pyrazol-4-yl)cyclohexanecarboxamide (Intermediate 25, 300 mg, 0.64 mmol) in a mixture of dioxane/H$_2$O (1:1, 15 mL) and the reaction mixture was heated at 70° C. for 3 h under an atmosphere of nitrogen. The reaction mixture was extracted with EtOAc and the combined organic layer was washed with water, dried over Na$_2$SO$_4$ and concentrated under vacuum. The residue was purified by preparative HPLC on a XBridge Prep C18 OBD column (5m, 19×150 mm) using a gradient of 19-55% of MeCN in water (NH$_4$OH, 0.03%) as mobile phase to give the title compound (71 mg, 24%) as a white solid.

$^1$H NMR (300 MHz, DMSO-d$_6$): δ1.10-1.26 (m, 1H), 1.37-1.56 (m, 3H), 1.77-1.87 (m, 2H), 1.97-2.09 (m, 2H), 2.89-2.96 (m, 1H), 3.72-3.80 (t, 4H), 6.86 (d, 1H), 7.57 (s, 2H), 7.85-8.12 (m, 6H), 13.07 (s, 1H) MS m/z 457 [M+H]$^+$

Example 27: (1R,2R)—N-[5-(Dimethylsulfamoyl)-1-methyl-1H-pyrazol-4-yl]-2-[4-(1H-pyrazol-5-yl)benzoyl]cyclohexanecarboxamide

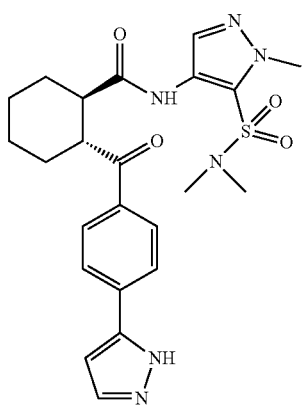 [SMILES: CN(C)S(=O)(=O)c1c(NC(=O)[C@@H]2CCCC[C@H]2C(=O)c2ccc(-c3ccn[nH]3)cc2)cnn1C]

Pd(dppf)Cl$_2$*DCM (43 mg, 0.06 mmol), K$_2$CO$_3$ (108 mg, 0.78 mmol, 3.00 equiv) and water (1 mL) was added to a solution of (1R,2R)-2-(4-bromobenzoyl)-N-[5-(dimethylsulfamoyl)-1-methyl-1H-pyrazol-4-yl]cyclohexanecarboxamide (Intermediate 61, 130 mg, 0.26 mmol) and 1H-pyrazol-5-ylboronic acid (59 mg, 0.53 mmol) in 1,4-dioxane (10 mL) and the reaction mixture was stirred at 85° C. for 15 h. The mixture was diluted with EtOAc and the organic layer was concentrated in vacuum. The residue was purified by preparative TLC (50% MeOH in DCM) followed by C18 column chromatography (20% MeCN in water) to give the title compound (18.7 mg, 15%) as a white solid.

$^1$H NMR (400 MHz, $CD_3OD$) δ 1.72-1.28 (m, 4H), 1.90 (t, 2H), 2.11 (t, 2H), 2.84 (s, 6H), 2.96 (t, 1H), 3.79 (t, 1H), 4.01 (s, 3H), 6.80 (s, 1H), 7.72 (s, 1H), 7.99-7.89 (m, 3H), 8.06 (d, 2H) MS m/z 485 $[M+H]^+$

Example 28: (1R,2R)—N-(2-Methyl-4-oxo-4,5,6,7-tetrahydroprazolo[1,5-a]pyrazin-3-yl)-2-[4-(5-methyl-1H-pyrazol-3-yl)benzoyl]cyclohexanecarboxamide

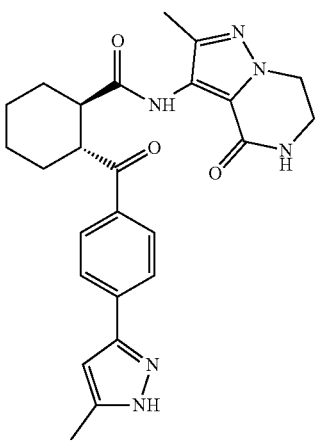 [SMILES: Cc1cc(-c2ccc(C(=O)[C@@H]3CCCC[C@H]3C(=O)Nc3c(C)nn4c3C(=O)NCC4)cc2)n[nH]1]

(1R,2R)-2-(4-Bromobenzoyl)-N-(2-methyl-4-oxo-4,5,6,7-tetrahydropyrazolo[1,5-a]pyrazin-3-yl)cyclohexanecarboxamide (Intermediate 67, 330 mg, 0.72 mmol), Pd(dppf)Cl$_2$*DCM (117 mg, 0.14 mmol), K$_2$CO$_3$ (298 mg, 2.16 mmol) and (5-methyl-1H-pyrazol-3-yl)boronic acid (136 mg, 1.08 mmol) were suspended in a mixture of 1,4-dioxane and water (10:1, 11 mL). The reaction mixture was purged with nitrogen and then heated at 100° C. for 1h under an atmosphere of nitrogen. The reaction mixture was diluted to with EtOAc and water. The solids were filtered off and the organic layer was washed with water and brine, dried over Na$_2$SO$_4$ and concentrated under vacuum. The residue was purified by Flash column chromatography on a C18 column (30 μm, 20 g) using a gradient of 0%→39% of MeCN in a water/NH$_4$HCO$_3$ (99.5/0.5) buffer system as mobile phase, to give the title compound (181 mg, 55%) as a white solid.

$^1$H NMR (300 MHz DMSO-d$_6$) δ 1.19 (m, 1H), 1.48-1.38 (m, 3H), 1.82-1.74 (m, 5H), 1.99-1.93 (m, 1H), 2.28-2.16 (m, 4H), 2.90 (t, 1H), 3.51 (s, 2H), 3.68 (t, 1H), 4.14-4.10 (t, 2H), 6.55 (s, 1H), 7.89-7.87 (d, 2H), 8.04-7.97 (m, 3H), 9.27 (s, 1H), 12.74 (s, 1H) MS m/z 461 $[M+H]^+$

Example 29: (1R,2R)—N-(2-Methyl-4-oxo-4,5,6,7-tetrahydropyrazolo[1,5-a]pyrazin-3-yl)-2-[4-(1H-pyrazol-5-yl)benzoyl]cyclohexanecarboxamide

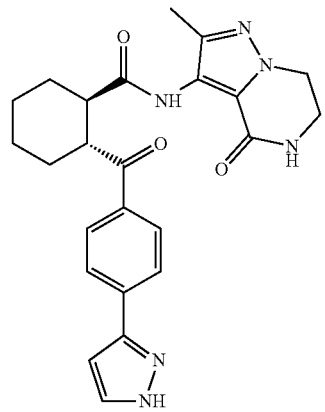 [SMILES: Cc1nn2c(c1NC(=O)[C@@H]1CCCC[C@H]1C(=O)c1ccc(-c3cc[nH]n3)cc1)C(=O)NCC2]

(1R,2R)-2-(4-Bromobenzoyl)-N-(2-methyl-4-oxo-4,5,6,7-tetrahydropyrazolo[1,5-a]pyrazin-3-yl)cyclohexanecarboxamide (Intermediate 67, 300 mg, 0.65 mmol), Pd(dtbpf)Cl$_2$ (107 mg, 0.13 mmol), K$_2$CO$_3$ (271 mg, 1.96 mmol) and (1H-pyrazol-3-yl)boronic acid (110 mg, 0.98 mmol) were suspended in a mixture of dioxane and water (6.7:1, 11.5 mL). The reaction mixture was purged with nitrogen then heated at 100° C. for 1 h. The reaction mixture was diluted with EtOAc and water and the solids were filtered off. The organic layer was washed with water and brine, dried over Na$_2$SO$_4$ and concentrated under vacuum. The residue was purified by Flash column chromatography on a C18 column (30 μm, 20 g) using a gradient of 0%→37% of MeCN in a water/NH$_4$HCO$_3$ (99.5/0.5) buffer system as mobile phase, to give the title compound (1745 mg, 60%) as a white solid.

$^1$H NMR (300 MHz DMSO-d$_6$) δ 1.48-1.10 (m, 4H), 1.80-1.70 (m, 2H), 1.80 (s, 3H), 2.00-1.93 (m, 1H), 2.19-2.16 (m, 1H), 2.90 (t, 1H), 3.51 (s, 2H), 3.70 (t, 1H), 4.14-4.10 (m, 2H), 6.83 (s, 1H), 8.04-7.83 (m, 6H), 9.27 (s, 1H), 13.06 (s, 1H) MS m/z 447 $[M+H]^+$

Example 30: (1R,2R)—N-[5-(Difluoromethyl)-1H-pyrazol-4-yl]-2-[4-(1H-pyrazol-3-yl)benzoyl]cyclohexanecarboxamide

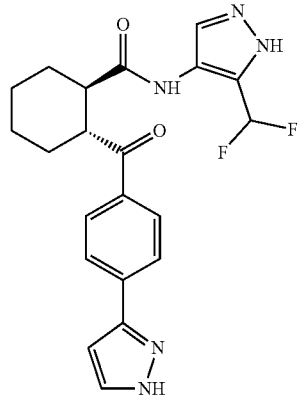 [SMILES: O=C(Nc1cn[nH]c1C(F)F)[C@@H]1CCCC[C@H]1C(=O)c1ccc(-c2cc[nH]n2)cc1]

HCl in MeOH (3 M in MeOH, 5 mL) was added to a solution of (1R,2R)—N-[5-(difluoromethyl)-1-(tetrahydro- 2H-pyran-2-yl)-1H-pyrazol-4-yl]-2-[4-(1H-pyrazol-3-yl)benzoyl]cyclohexanecarboxamide (Intermediate 68, 520 mg, 1.05 mmol) in MeOH (26 mL) and the reaction mixture was stirred at rt for 1 h. The pH value of the solution was adjusted to 8 with NaHCO$_3$ (aq) and the reaction mixture was diluted with EtOAc. The organic phase was washed with water, brine (sat.), dried over Na$_2$SO$_4$ and concentrated in vacuum. The residue was purified by preparative HPLC on a XBridge Prep C18 OBD column (5 μm, 19×150 mm) using a gradient of 37-46% of MeCN in water (0.03% NH$_4$OH) as mobile phase to give the title compound (80.5 mg, 19%) as a white solid.

$^1$H NMR (400 MHz, DMSO-d$_6$) δ 1.32-1.38 (m, 1H), 1.41-1.57 (m, 3H), 1.75-1.85 (m, 2H), 1.96-2.05 (m, 2H), 2.91-3.03 (m, 1H), 3.72-3.78 (m, 1H), 6.85 (s, 1H), 7.02 (t, J=53.6 Hz, 1H)), 7.84-8.04 (m, 6H), 9.71 (s, 1H), 13.09 (s, 1H). MS m/z 414 [M+H]$^+$

Example 31: 4-[({(1R,2R and 1S,2S)-2-[2-Chloro-4-(1H-pyrazol-5-yl)benzoyl]-cyclohexyl}carbonyl)amino]-1-methyl-1H-pyrazole-5-carboxamide

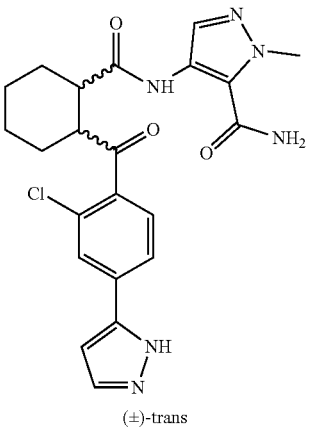 [SMILES: Cn1ncc(NC(=O)C2CCCCC2C(=O)c2ccc(-c3ccn[nH]3)cc2Cl)c1C(N)=O]

(±)-trans

Palladium (10% Pd/C moistured by 50% water, 200 mg, 0.09 mmol) and DMSO (40 mg, 0.51 mmol) was added to a solution of 4-[({(1R,6R and 1S,6S)-6-[2-chloro-4-(1H-pyrazol-5-yl)benzoyl]cyclohex-3-en-1-yl}carbonyl)amino]-1-methyl-1H-pyrazole-5-carboxamide (Intermediate 74, 50 mg, 0.11 mmol) dissolved in EtOH (20 mL) and the reaction mixture was stirred at rt. Triethylsilane (2 g, 17.20 mmol) was added dropwise during 5 min and the reaction mixture was stirred at rt for 10 min. The reaction mixture was filtered through a syringe filter, the filtrate was concentrated under reduced pressure and the crude product is was purified by flash chromatography (0%→33% Aceton in EtOAc). The product containing fractions were collected and concentrated to dryness under reduced pressure. The residue was dissolved in tert-butanol and freeze-dried to give the title compound (28.0 mg, 56%).

$^1$H NMR (600 MHz, MeOD) δ 1.29-1.35 (m), 1.42 (t, 2H), 1.5-1.64 (m, 1H), 1.88 (d, 2H), 2.01 (d, 1H), 2.15 (d, 1H), 2.8-2.88 (m, 1H), 3.51-3.6 (m, 1H), 4.02 (s, 3H), 6.78 (d, 1H), 7.52 (s, 1H), 7.73 (d, 2H), 7.81 (s, 1H), 7.91 (s, 1H). MS m/z 453.2 [M–H]$^-$

Example 32: 4-[({(1R,2R and 1S,2S)-2-[2-Chloro-4-(3-methyl-1H-pyrazol-5-yl)benzoyl]cyclohexyl}carbonyl)amino]-1-methyl-1H-pyrazole-5-carboxamide

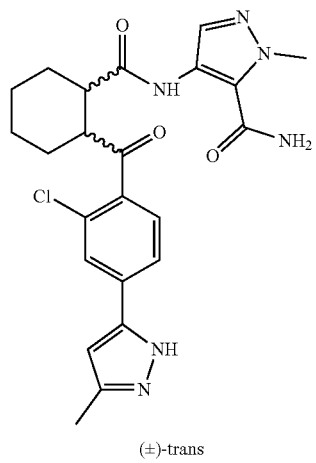 [SMILES: Cc1cc(-c2ccc(C(=O)C3CCCCC3C(=O)Nc3cnn(C)c3C(N)=O)c(Cl)c2)[nH]n1]

(±)-trans

Palladium (10% Pd/C, moistured by 50% water, 200 mg, 0.09 mmol) and DMSO (40 mg, 0.51 mmol) was added to a solution of 4-[({(1R,6R and 1S,6S)-6-[2-chloro-4-(3-methyl-1H-pyrazol-5-yl)benzoyl]cyclohex-3-en-1-yl}carbonyl)amino]-1-methyl-1H-pyrazole-5-carboxamide (Intermediate 75, 40 mg, 0.09 mmol) in EtOH (20 mL). Triethylsilane (2.5 g, 21.5 mmol) was added dropwise at rt during 5 min and the reaction mixture was stirred at rt for 10 min. The reaction mixture was filtered; the filtrate was concentrated in vacuo. The crude product was purified by flash chromatography (0%→33% acetone in EtOAc) and the product was freeze-dried from tert-butanol to give the title compound (20 mg, 50%).

$^1$H NMR (600 MHz, MeOD) δ 1.28-1.34 (m), 1.41 (t, 2H), 1.52-1.62 (m, 1H), 1.88 (d, 2H), 2.00 (d, 1H), 2.14 (d, 1H), 2.79-2.88 (m, 1H), 3.52-3.59 (m, 1H), 4.02 (s, 3H), 6.51 (s, 1H), 7.52 (s, 1H), 7.71 (d, 2H), 7.85 (s, 1H).
MS m/z 467.3 [M–H]$^-$

Example 33: (1R,2R and 1S,2S)—N-(5-Cyclopropyl-1-methyl-1H-1,2,3-triazol-4-yl)-2-[4-(1H-pyrazol-5-yl)benzoyl]cyclohexanecarboxamide

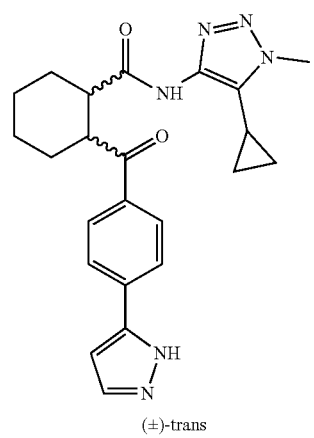 [SMILES: Cn1nnc(NC(=O)C2CCCCC2C(=O)c2ccc(-c3ccn[nH]3)cc2)c1C1CC1]

(±)-trans

Step 1: (1R,2R and 1S,2R)-2-(4-Bromobenzoyl)-N-(5-cyclopropyl-1-methyl-1H-1,2,3-triazol-4-yl)cyclohexanecarboxamide T3P (50% in EtOAc, 383 µL, 0.64 mmol) was added to a mixture of (1R,2R and 1S,2S)-2-(4-bromobenzoyl)cyclohexanecarboxylic acid (100 mg, 0.32 mmol), 5-cyclopropyl-1-methyl-1H-1,2,3-triazol-4-amine (89 mg, 0.64 mmol), and Et₃N (134 µL, 0.96 mmol) and the reaction mixture was heated in a microwave reactor at 150° C. for 30 min. The reaction mixture was diluted with EtOAc and the organic phase was extracted twice with NaHCO₃ (sat., aq) and brine. The organic phase was dried using a phase separator and concentrated in vacuo to give the crude subtitle compound (148 mg).
MS m/z 433.1 [M+2]⁺

Step 2: (1R,2R and 1S,2S)—N-(5-Cyclopropyl-1-methyl-1H-1,2,3-triazol-4-yl)-2-[4-(1H-pyrazol-5-yl)benzoyl]cyclohexanecarboxamide 1H-Pyrazol-5-ylboronic acid (35.8 mg, 0.32 mmol), and Pd(dppf)Cl₂*DCM (25.9 mg, 0.03 mmol) were added to a mixture of (1R,2R and 1S,2R)-2-(4-bromobenzoyl)-N-(5-cyclopropyl-1-methyl-1H-1,2,3-triazol-4-yl)cyclohexanecarboxamide (Example 33 Step 1, 138 mg, 0.32 mmol) in DME (2.4 mL) and water (0.8 mL). A solution of K₃PO₄ (204 mg, 0.96 mmol) in water (0.90 mL) was added to the reaction mixture and it was heated in a microwave reactor at 140° C. for 15 min. The reaction mixture was diluted with EtOAc and the organic phase was extracted with water, dried using a phase separator and concentrated in vacuo. The crude product was purified by preparative HPLC on a Xbridge C18 column (5 µm, 150×19 ID mm) using a gradient of 5-95% MeCN in a H₂O/MeCN/NH₃ (95/5/0.2, pH 10) buffer system as mobile phase to give the title compound (45 mg, 33%).
¹H NMR (600 MHz, DMSO) δ 0.56 (tt, 2H), 0.67-0.79 (m, 2H), 1.13-1.24 (m, 1H), 1.37 (t, 1H), 1.45-1.58 (m, 2H), 1.61 (tt, 1H), 1.78 (d, 1H), 1.87 (d, 1H), 1.96 (d, 1H), 2.17 (d, 1H), 2.88-2.96 (m, 1H), 3.74 (t, 1H), 3.92 (s, 3H), 6.84 (d, 1H), 7.84 (s, 1H), 7.96 (d, major rotamer),7.97-8.97 (m, minor rotamer), 8.03 (d, 2H), 9.70 (s, 1H), 13.08 (s, major rotamer), 13.5 (s, minor rotamer). Mixture of rotamers in ratio major:minor 1:0.19.

Example 34: 4-[({(1R,2R or 1S,2S)-2-[2-Fluoro-4-(1H-pyrazol-5-yl)benzoyl]-cyclohexyl}carbonyl)amino]-1-methyl-1H-pyrazole-5-carboxamide

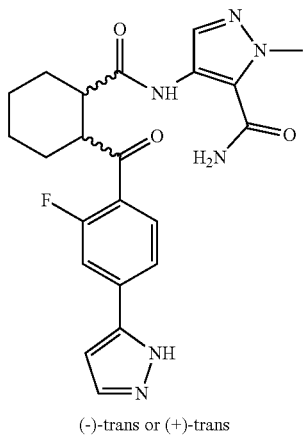 [SMILES: Cn1ncc(NC(=O)C2CCCCC2C(=O)c2ccc(-c3ccn[nH]3)cc2F)c1C(N)=O]

(-)-trans or (+)-trans

Palladium (10% Pd/C, 25 mg, 0.02 mmol) was added to a solution of 4-[({(1R,6R or 1S,6S)-6-[2-fluoro-4-(1H-pyrazol-5-yl)benzoyl]cyclohex-3-en-1-yl}carbonyl)amino]-1-methyl-1H-pyrazole-5-carboxamide (Intermediate 82, 52 mg, 0.12 mmol) in MeOH (5 mL) and the reaction mixture was stirred under an atmosphere of hydrogen (1 atm) at rt for 1 h. The reaction mixture was filtered through a pad of celite and the filtrate was concentrated in vacuo. The crude product was purified by preparative HPLC on a XBridge C18 column (10 µm, 250×19 ID mm) using a gradient of 20-65% MeCN in a H₂O/MeCN/NH₃ (95/5/0.2) buffer system as mobile phase to give the title compound (13 mg, 25%).
¹H NMR (400 MHz, CDCl₃) δ 1.17 (tt, 1H), 1.24-1.39 (m, 1H), 1.39-1.56 (m, 1H), 1.68 (tt, 1H), 1.86 (t, 2H), 2.03-2.19 (m, 2H), 2.81 (t, 1H), 3.56-3.69 (m, 1H), 4.04 (s, 3H), 6.61 (d, 1H), 6.92 (s, 2H), 7.47 (d, 1H), 7.52-7.64 (m, 3H), 7.78 (t, 1H), 8.22 (s, 1H). MS m/z 437.2 [M–H]⁻

Example 35: 4-[({(1R,2R or 1S,2S)-2-[2-Fluoro-4-(1H-pyrazol-5-yl)benzoyl]-cyclohexyl}carbonyl)amino]-1-methyl-1H-pyrazole-3-carboxamide

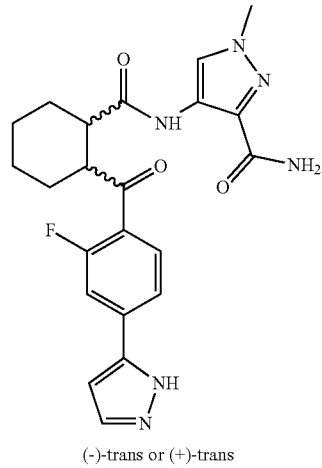 [SMILES: Cn1cc(NC(=O)C2CCCCC2C(=O)c2ccc(-c3ccn[nH]3)cc2F)c(C(N)=O)n1]

(-)-trans or (+)-trans

HCl (1.25 M in MeOH, 0.5 mL, 0.63 mmol) was added to a solution 4-({[(1R,2R or 1 S,2S)-2-{2-fluoro-4-[1-(tetrahydro-2H-pyran-2-yl)-1H-pyrazol-5-yl]benzoyl}cyclohexyl]-carbonyl}amino)-1-methyl-1H-pyrazole-3-carboxamide (Intermediate 85, 270 mg, 0.52 mmol) in MeOH (10 mL) and the reaction mixture was concentrated in vacuo at 16° C. The residue was dissolved in MeOH (10 mL) and concentrated in vacuo at 16° C. The crude product was purified by preparative HPLC on a XBridge C18 column (10 µm, 250×19 ID mm) using a gradient of 5-80% MeCN in a H₂O/ACN/NH₃ (95/5/0.2) buffer system as mobile phase to give the title compound (120 mg, 53%).
¹H NMR (500 MHz, MeOD) δ 1.18-1.33 (m, 1H), 1.37-1.52 (m, 2H), 1.52-1.64 (m, 1H), 1.88 (d, 2H), 2.04-2.17 (m, 2H), 2.8-2.94 (m, 1H), 3.53-3.65 (m, 1H), 3.81 (s, 3H), 6.78 (d, 1H), 7.5-7.79 (m, 3H), 7.84 (t, 1H), 7.98 (s, 1H). MS m/z 437.3 [M–H]⁻

Example 36: 4-[({(1R,2R or 1S,2S)-2-[2-Fluoro-4-(3-methyl-1H-pyrazol-5-yl)benzoyl]-cyclohexyl}carbonyl)amino]-1-methyl-1H-pyrazole-3-carboxamide

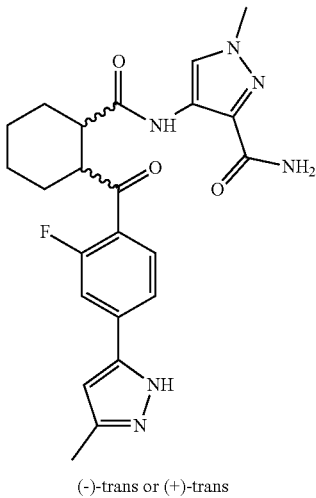 [SMILES: Cc1cc(-c2ccc(C(=O)C3CCCCC3C(=O)Nc3cn(C)nc3C(N)=O)c(F)c2)[nH]n1]

(−)-trans or (+)-trans

HCl (1.25 M in MeOH, 0.5 mL, 0.63 mmol) was added to a solution of 4-({[(1R,2R or 1 S,2S)-2-{2-fluoro-4-[3-methyl-1-(tetrahydro-2H-pyran-2-yl)-1H-pyrazol-5-yl]benzoyl}cyclohexyl]carbonyl}amino)-1-methyl-1H-pyrazole-3-carboxamide (Intermediate 86, 216 mg, 0.40 mmol) in MeOH (10 mL) and the reaction mixture was concentrated in vacuo at 16° C. The residue was dissolved in MeOH (10 mL) and concentrated in vacuo at 16° C. The crude product was purified by preparative HPLC on a XBridge C18 column (10 μm, 250×19 ID mm) using a gradient of 5-80% MeCN in a H₂O/MeCN/NH₃ (95/5/0.2) buffer system as mobile phase to give the title compound (126 mg, 69%).

¹H NMR (500 MHz, MeOD) δ 1.19-1.33 (m, 1H), 1.45 (q, 2H), 1.52-1.62 (m, 1H), 1.88 (d, 2H), 2.05-2.17 (m, 2H), 2.33 (s, 3H), 2.86 (ddd, 1H), 3.54-3.65 (m, 1H), 3.82 (s, 3H), 6.52 (s, 1H), 7.58 (dd, 2H), 7.82 (t, 1H), 7.98 (s, 1H).

Example 37: 4-[({(1R,2R or 1S,2S)-2-[2-Fluoro-4-(3-methyl-1H-pyrazol-5-yl)benzoyl]-cyclohexyl}carbonyl)amino]-1-methyl-1H-pyrazole-5-carboxamide

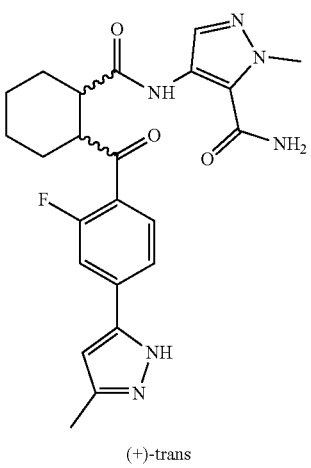 [SMILES: Cc1cc(-c2ccc(C(=O)C3CCCCC3C(=O)Nc3cnn(C)c3C(N)=O)c(F)c2)[nH]n1]

(+)-trans

The enantiomers of the trans-racemate 4-[({(1R,2R and 1S,2S)-2-[2-fluoro-4-(3-methyl-1H-pyrazol-5-yl)benzoyl]cyclohexyl}carbonyl)amino]-1-methyl-1H-pyrazole-5-carboxamide (intermediate 92, 44 mg, 0.10 mmol) were separated by chiral SFC chromatography on a Chiralpak IC HPLC column (5 μm, 250×20 ID mm). 23 mg (16 mg/mL in EtOH) was injected and eluted with 35% EtOH/DEA (100/0.5) in CO₂ (175 bar) at a flow rate of 70 mL/min and detected at 260 nm. The second eluted compound was collected and freeze-dried from a mixture of MeCN/H₂O (1:1). The residue was dissolved in EtOAc and washed with KHSO₄ (0.01M, aq). The aqueous phase was extracted with EtOAc and the combined organic phase was dried using a phase separator and concentrated in vacuo to give the title compound (0.019 g, 99.7% ee).

Optical rotation: +73° (0.5 g/100 mL in MeCN, 589 nm, 20° C.).

¹H NMR (500 MHz, MeOD) δ 1.31-1.68 (m, 4H), 1.91 (s, 2H), 2.15 (s, 2H), 2.34 (s, 3H), 2.89 (d, 1H), 3.60 (t, 1H), 4.01 (s, 3H), 6.54 (s, 1H), 7.41-7.76 (m, 3H), 7.87 (t, 1H). HRMS m/z 453.2079 [M+H]⁺

Example 38: 4-[({(1R,2R or 1S,2S)-2-[2-Fluoro-4-(3-methyl-1H-pyrazol-5-yl)benzoyl]cyclohexyl}carbonyl)amino]-1H-pyrazole-5-carboxamide

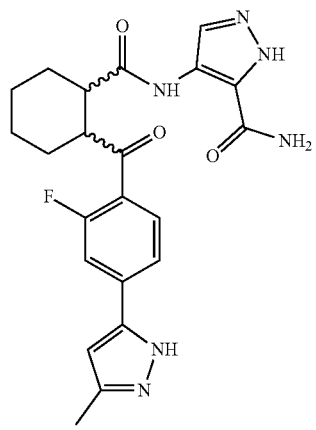

(−)-trans or (+)-trans

HCl (1.2M in MeOH) (0.1 mL, 0.12 mmol) was added to a solution of 4-({[(1R,2R or 1 S,2S)-2-{2-fluoro-4-[3-methyl-1-(tetrahydro-2H-pyran-2-yl)-1H-pyrazol-5-yl]benzoyl}cyclohexyl]carbonyl}amino)-1H-pyrazole-5-carboxamide (Intermediate 94, 24 mg, 0.05 mmol) in MeOH (10 mL) and the reaction mixture was concentrated in vacuo at 17° C. The residue was dissolved in MeOH (10 mL) and concentrated in vacuo at 17° C. The crude product was purified by preparative HPLC on a XBridge C18 column (10 μm, 250×19 ID mm) using a gradient of 5-70% MeCN in a H₂O/MeCN/NH₃ (95/5/0.2) buffer system as mobile phase to give the title compound (10 mg, 46%).

¹H NMR (500 MHz, DMSO) δ 1.17 (q, 1H), 1.41 (dd, 3H), 1.79 (d, 2H), 2.01 (d, 2H), 2.27 (s, 3H), 2.73-2.91 (m, 1H), 3.42-3.55 (m, 1H), 6.62 (s, 1H), 7.48 (s, 1H), 7.57-7.78 (m, 3H), 7.84 (t, 1H), 8.03 (s, 1H), 9.76 (s, 1H), 12.96 (d, 2H).

Example 39: (1R,2R or 1S,2S)-2-[2-Fluoro-4-(3-methyl-1H-pyrazol-5-yl)benzoyl]-N-(4-oxo-4,5,6,7-tetrahydropyrazolo[1,5-a]pyrazin-3-yl)cyclohexanecarboxamide

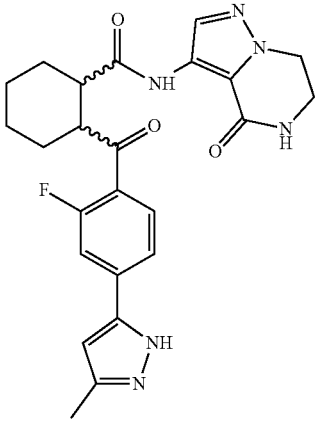

(-)-trans or (+)-trans (3-Methyl-1H-pyrazol-5-yl)boronic acid (164 mg, 1.30 mmol), $K_2CO_3$ (180 mg, 1.29 mmol) and Pd(dppf)Cl$_2$*DCM (106 mg, 0.13 mmol) was added to a solution of (1R,2R or 1S,2S)-2-(4-bromo-2-fluorobenzoyl)-N-(4-oxo-4,5,6,7-tetrahydropyrazolo[1,5-a]pyrazin-3-yl)cyclohexanecarboxamide (Intermediate 95, 300 mg, 0.65 mmol) in a mixture of dioxane and water (10:1, 15 mL) and the reaction mixture was stirred at 100° C. for 2 h. The reaction mixture was filtered and the filtrate was concentrated in vacuo. The residue was to diluted with DCM and the organic layer was washed three times with water. The organic layer was dried over $Na_2SO_4$, filtered and concentrated under reduced pressure. The crude product was purified by preparative HPLC on a XBridge Shield RP 18 OBD Column (5 um, 150×19 ID mm) using a gradient of 45-95% MeOH in a $NH_4HCO_3$/$H_2O$ (10 mM) buffer system as mobile phase to give the title compound (90 mg, 30%).

$^1$H NMR (400 MHz, DMSO-d$_6$): δ 1.27-1.05 (m, 1H), 1.52-1.29 (m, 3H), 1.78 (s, 2H), 2.10-1.98 (t, 2H), 2.28 (s, 3H), 2.95 (t, 1H), 3.50 (t, 1H), 3.60 (s, 2H), 4.32 (t, 2H), 6.62 (s, 1H), 7.32-6.95 (m, 1H), 7.80-7.68 (m, 2H), 7.98-7.81 (m, 2H), 8.32 (s, 1H), 9.16 (s, 1H). MS m/z 465 [M+H]$^+$

Example 40: 4-[({(1R,2R or 1S,2S)-2-[2-Fluoro-4-(3-methyl-1H-pyrazol-5-yl)benzoyl]cyclohexyl}carbonyl)amino]-1,2,5-oxadiazole-3-carboxamide

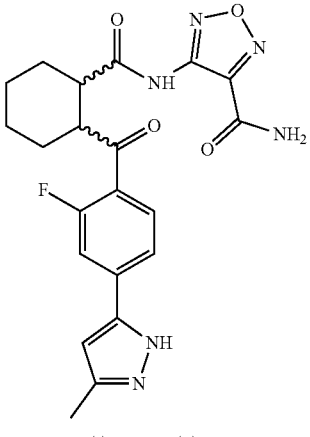

(-)-trans or (+)-trans

Step 1: 4-({[(1R,2R or 1S,2S)-2-{2-Fluoro-4-[3-methyl-1-(tetrahydro-2H-pyran-2-yl)-1H-pyrazol-5-yl]benzoyl}cyclohexyl]carbonyl}amino)-1,2,5-oxadiazole-3-carboxamide A solution of $K_2CO_3$ (110 mg, 0.80 mmol) in water (2 mL) was added to a solution of 3-methyl-1-(tetrahydro-2H-pyran-2-yl)-5-(4,4,5,5-tetramethyl-1,3,2-dioxaborolan-2-yl)-1H-pyrazole (Intermediate 3, 139 mg, 0.48 mmol) and 4-({[(1R,2R or 1S,2S)-2-(4-bromo-2-fluorobenzoyl)cyclohexyl]carbonyl}amino)-1,2,5-oxadiazole-3-carboxamide (Intermediate 96, 87 mg, 0.20 mmol) in 1,4-dioxane (3 mL) and the reaction mixture was purged with $N_2$(g). Pd(dtbpf)Cl$_2$ (15 mg, 0.02 mmol) was added to the reaction mixture and it was heated in a microwave reactor at 90° C. for 1 h. The reaction mixture was to allowed to cool and used directly in the next step.

Step 2: 4-[({(1R,2R or 1S,2S)-2-[2-Fluoro-4-(3-methyl-1H-pyrazol-5-yl)benzoyl]cyclohexyl}carbonyl)amino]-1,2,5-oxadiazole-3-carboxamide HCl (2M, aq, 2 mL) was added to the crude reaction mixture of 4-({[(1R,2R or 1S,2S)-2-{2-fluoro-4-[3-methyl-1-(tetrahydro-2H-pyran-2-yl)-1H-pyrazol-5-yl]benzoyl}-cyclohexyl]carbonyl}amino)-1,2,5-oxadiazole-3-carboxamide (Example 40 Step 1 above) and the reaction mixture was stirred at rt for 1 h. The reaction mixture was concentrated in vacuo and the water phase was extracted with DCM. The organic phase was dried using a phase separator and concentrated in vacuo. The crude compound was purified by preparative HPLC on a Xbridge C18 column (5 m, 150×19 ID mm) using a gradient of 5-95% MeCN in a $H_2O$/MeCN/$NH_3$ (95/5/0.2) buffer system as mobile phase to give the title compound (1.4 mg, 2%).

MS m/z 441.17 [M+H]$^+$

Example 41: 3-[({(1R,2R or 1S,2S)-2-[2-Fluoro-4-(1H-pyrazol-5-yl)benzoyl]-cyclohexyl}carbonyl)amino]-5-methyl-1,2-oxazole-4-carboxamide

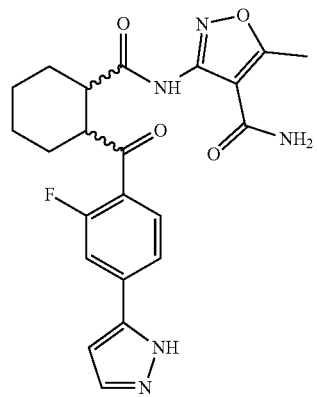

(-)-trans or (+)-trans

Step 1: 3-({[(1R,2R or 1S,2S)-2-(4-Bromo-2-fluorobenzoyl)cyclohexyl]carbonyl}amino)-5-methyl-1,2-oxazole-4-carboxylic acid (1R,2R or 1S,2S)-2-(4-Bromo-2-fluorobenzoyl)cyclohexanecarbonyl fluoride (Intermediate 97, 107 mg, 0.32 mmol) dissolved in DCM (1 mL) was added to a refluxing solution of 3-amino-5-methylisoxazole-4-carboxylic acid (50 mg, 0.36 mmol) and quinoline (0.046 mL, 0.39 mmol) in DCM (1 mL) and the reaction mixture was stirred at reflux for 2 days. The reaction mixture was diluted with tert-butyl methyl ether, and the pH of the reaction mixture was adjusted to 12-14 using NaOH (1M, aq). The organic layer was washed with brine, NH₄Cl (aq) and brine, dried using a phase-separator and concentrated in vacuo. DCM was added to the residue and the mixture was concentrated in vacuo to give the subtitle compound (107 mg).

Step 2: 3-({[(1R,2R or 1S,2S)-2-(4-Bromo-2-fluorobenzoyl)cyclohexyl]carbonyl}amino)-5-methyl-1,2-oxazole-4-carboxamide DIPEA (124 μL, 0.71 mmol) and TBTU (114 mg, 0.35 mmol) were added to a solution of crude 3-({[(1R,2R or 1S,2S)-2-(4-bromo-2-fluorobenzoyl)cyclohexyl] carbonyl}amino)-5-methyl-1,2-oxazole-4-carboxylic acid (Example 41 Step 1, 107 mg) in DMF (3 mL) and the reaction mixture was stirred for 5 min. NH₄Cl (30 mg, 0.57 mmol) was added and the reaction mixture was stirred at rt for 2 h. The reaction mixture was diluted with EtOAc and the organic phase was washed with NaHCO₃ (sat., aq), brine, NH₄Cl (sat., aq), and brine, dried using a phase separator and concentrated in vacuo to give the subtitle compound (96 mg).

Step 3: 3-({[(1R,2R or 1S,2S)-2-{2-Fluoro-4-[1-(tetrahydro-2H-pyran-2-yl)-1H-pyrazol-5-yl] benzoyl}cyclohexyl]carbonyl}amino)-5-methyl-1,2-oxazole-4-carboxamide A solution of K₂CO₃ (117 mg, 0.85 mmol) in degassed water (1 mL) was added to a degassed solution of 3-({[(1R,2R or 1S,2S)-2-(4-bromo-2-fluorobenzoyl)cyclohexyl]carbonyl}amino)-5-methyl-1,2-oxazole-4-carboxamide (Example 41 Step 2, 96 mg) and 1-(tetrahydro-2H-pyran-2-yl)-5-(4,4,5,5-tetramethyl-1,3,2-dioxaborolan-2-yl)-1H-pyrazole (83 mg, 0.30 mmol) in dioxane (1 mL). The solution was evacuated and purged with nitrogen(g). Pd(dtbpf)Cl₂ (3 mg, 4 μmol) was added and the reaction mixture was heated at 60° C. for 2 h. The reaction mixture was cooled to rt and used directly in the next step.

Step 4: 3-[({(1R,2R or 1S,2S)-2-[2-Fluoro-4-(1H-pyrazol-5-yl)benzoyl]cyclohexyl}-carbonyl)amino]-5-methyl-1,2-oxazole-4-carboxamide A solution of HCl (4M in dioxane, 2.5 mL, 10.0 mmol) in water (2.5 mL) was added dropwise to the reaction mixture of 3-({[(1R,2R or 1 S,2S)-2-{2-fluoro-4-[1-(tetrahydro-2H-pyran-2-yl)-1H-pyrazol-5-yl]benzoyl}cyclohexyl] carbonyl}amino)-5-methyl-1,2-oxazole-4-carboxamide (Example 41 Step 3 above) and it was stirred at rt for 10 min. The reaction mixture was diluted with EtOAc and the organic phase was washed twice with NaHCO₃ (sat., aq). The combined aqueous phase was extracted with EtOAc. The combined organic layer was dried using a phase separator and concentrated in vacuo. The crude product was purified by preparative HPLC on a XBridge C18 column (10m, 250×19 ID mm) using a gradient of 5-45% MeCN in a H₂O/MeCN/NH₃ (95/5/0.2) buffer system as mobile phase.

The compound containing fractions were collected, evaporated and partitioned between EtOAc and water. The organic phase was dried using a phase separator and concentrated in to vacuo to give the title compound (1.5 mg, 1%).

MS m/z 440.2 [M+H]⁺

Example 42: 1-Ethyl-4-[({(1R,2R and 1S,2S)-2-[4-(1H-pyrazol-5-yl)benzoyl]-cyclohexyl}carbonyl) amino]-1H-pyrazole-3-carboxamide

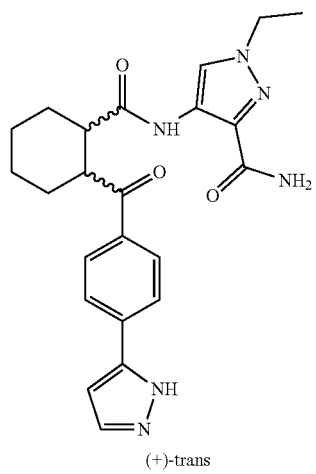 [SMILES: CCn1cc(NC(=O)C2CCCCC2C(=O)c2ccc(-c3ccn[nH]3)cc2)c(C(N)=O)n1]

(+)-trans

A solution of K₂CO₃ (147 mg, 1.06 mmol) in degassed water (1.5 mL) was added to a mixture of 4-({[(1R,2R and 1S, 2S)-2-(4-bromobenzoyl)cyclohexyl]carbonyl}amino)-1-ethyl-1H-pyrazole-3-carboxamide (Intermediate 98, 119 mg, 0.27 mmol), 1H-pyrazol-5-ylboronic acid (45 mg, 0.40 mmol) and Pd(dppf)Cl₂*DCM (22 mg, 0.03 mmol) in degassed dioxane (1.5 mL), and the reaction mixture was heated in a microwave reactor at 100° C. for 1 h. The reaction mixture was partitioned between EtOAc and NaCl (sat., aq) and the aqueous phase was extracted twice with EtOAc. The combined organic phase was dried over Na₂SO₄, filtered and concentrated in vacuo. The crude product was purified by preparative HPLC on a Xbridge Prep C18 column (5 m, 150×19 ID mm) using a gradient of 5-95% MeCN in a H₂O/MeCN/NH₃ (95/5/0.2) buffer system as mobile phase to give the title compound (39 mg, 34%).

¹H NMR (600 MHz, DMSO) δ 1.13-1.25 (m, 1H), 1.31 (t, 3H), 1.43 (t, 1H), 1.51 (t, 2H), 1.79 (dd, 2H), 2.00 (dd, 2H), 2.82-2.91 (m, 1H), 3.73 (t, 1H), 4.08 (q, 2H), 6.85 (d, 1H), 7.48 (s, 1H), 7.63 (s, 1H), 7.79-8.11 (m, 6H), 9.77 (s, 1H), 13.09 (s, 1H). MS m/z 433.2 [M–H]⁻

Example 43: (1R,2R)-2-[4-(3-Methyl-1H-pyrazol-5-yl)benzoyl]-N-(1,3,4-oxadiazol-2-yl)cyclohexanecarboxamide

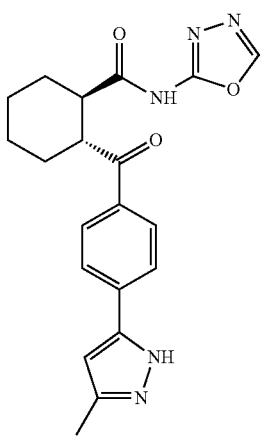 [SMILES: Cc1cc(-c2ccc(C(=O)[C@@H]3CCCC[C@H]3C(=O)Nc3nnco3)cc2)[nH]n1]

Step 1: (1R,2R)-2-(4-Bromobenzoyl)-N-(1,3,4-oxadiazol-2-yl)cyclohexanecarboxamide LiOH (213 mg, 8.89 mmol) was added to a solution of ethyl 5-({[(1R,2R)-2-(4-bromobenzoyl)cyclohexyl]carbonyl}amino)-1,3,4-oxadiazole-2-carboxylate (Intermediate 99, 1 g, 2.22 mmol) in MeOH (15 mL) and water (15 mL) and the reaction mixture was stirred at rt for 1 h. The reaction mixture was concentrated in vacuo. The residue was dissolved in water (50 mL) and the pH of the solution was adjusted to 1-2 using HCl (1M, aq). The aqueous phase was extracted three times with DCM. The combined organic phase is was dried over Na$_2$SO$_4$, filtered and concentrated in vacuo to give the subtitle compound (1 g).
MS m/z 378 [M+H]$^+$

Step 2: (1R,2R)-2-[4-(3-Methyl-1H-pyrazol-5-yl)benzoyl]-N-(1,3,4-oxadiazol-2-yl)cyclohexanecarboxamide (3-Methyl-1H-pyrazol-5-yl)boronic acid (666 mg, 5.29 mmol), K$_2$CO$_3$ (730 mg, 5.28 mmol), Pd(dppf)Cl$_2$*DCM (432 mg, 0.53 mmol) and water (1 mL) were added to a solution of (1R,2R)-2-(4-bromobenzoyl)-N-(1,3,4-oxadiazol-2-yl)cyclohexanecarboxamide (Example 43 Step 1, 1 g, 2.64 mmol) in dioxane (10 mL) and the reaction mixture was heated at 80° C. for 4 h under an atmosphere of nitrogen. The reaction mixture was diluted with EtOAc and washed twice with water and the combined aqueous phase was extracted with EtOAc. The combined organic layer was dried over Na$_2$SO$_4$, filtered and concentrated in vacuo. The crude product was purified by preparative HPLC on a XBridge Shield C18 OBD Column (5 um, 150×19 ID mm) using a gradient of 5-85% of MeCN in a H$_2$O/HCO$_2$H (100/0.1) buffer system as mobile phase to give the title compound (84 mg, 8%) as a light yellow solid.
$^1$H NMR (300 MHz, DMSO): δ 1.03-1.57 (m, 4H), 1.69-1.87 (m, 2H), 1.90-2.13 (m, 2H), 2.28 (s, 3H), 2.96 (s, 1H), 3.72 (t, 1H), 6.57 (s, 1H), 7.90 (d, 2H), 8.02 (d, 2H), 8.92 (s, 1H), 11.79 (s, 1H), 12.76 (s, 1H).
MS m/z 380 [M+H]$^+$

Example 44: (1R,2R and 1S,2S)—N-(3-Methyl-1,2-oxazol-5-yl)-2-[4-(1H-pyrazol-5-yl)benzoyl]cyclohexanecarboxamide

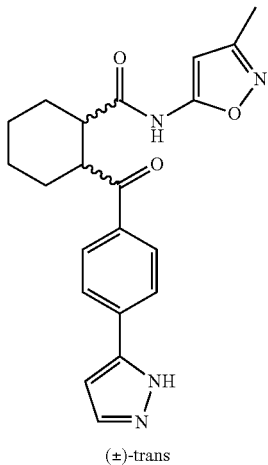 [SMILES: Cc1cc(NC(=O)C2CCCCC2C(=O)c2ccc(-c3ccn[nH]3)cc2)on1]

(±)-trans

Step 1: (1R,2R and 1S, 2S)-2-(4-Bromobenzoyl)-N-(3-methyl-1,2-oxazol-5-yl)cyclohexanecarboxamide T3P (50% in EtOAc, 383 µL, 0.64 mmol) was added to a mixture of (1R,2R and 1S,2S)-2-(4-bromobenzoyl)cyclohexanecarboxylic acid (100 mg, 0.32 mmol), 3-methyl-1,2-oxazol-5-amine (63.1 mg, 0.64 mmol), and Et$_3$N (134 µL, 0.96 mmol) in EtOAc (3 mL) and the reaction mixture was heated in a microwave reactor at 150° C. for 30 min. The reaction mixture was diluted with EtOAc and the organic phase was washed twice with NaHCO$_3$ (sat., aq) and brine, dried using a phase separator and concentrated in vacuo to give the subtitle compound (95 mg, 76%).
MS m/z 391.2 [M–H]$^-$

Step 2: (1R,2R and 1S,2S)—N-(3-Methyl-1,2-oxazol-5-yl)-2-[4-(1H-pyrazol-5-yl)benzoyl]cyclohexanecarboxamide A solution of K$_3$PO$_4$ (155 mg, 0.73 mmol) in water (0.6 mL) was added to a mixture of (1R,2R and 1S,2S)-2-(4-bromobenzoyl)-N-(3-methyl-1,2-oxazol-5-yl)cyclohexanecarboxamide (Example 44 Step 1, 95 mg, 0.24 mmol), 1H-pyrazol-5-ylboronic acid (27 mg, 0.24 mmol) and Pd(dppf)Cl$_2$*DCM (20 mg, 0.02 mmol) in a mixture of DME (1.8 mL) and EtOH (0.6 mL) and the reaction mixture was heated at 140° C. for 15 min. 1H-Pyrazol-5-ylboronic acid (27 mg, 0.24 mmol) and Pd(dppf)Cl$_2$*DCM (20 mg, 0.02 mmol) were added and the reaction mixture was heated at 140° C. for 15 min. The reaction mixture was diluted with EtOAc and the organic layer was washed with water, dried using a phase separator and concentrated in vacuo. The crude product was purified by preparative HPLC on a XBridge C18 OBD column (5 m, 150×19 ID mm) using a gradient of 10-60% MeCN in a H$_2$O/NH$_3$ (100/0.2, pH10) buffer system as mobile phase and then by preparative HPLC on a Sunfire Prep C18 column (5 m, 150×19 ID mm) using a gradient of 5-95% MeCN in a HCO$_2$H/H$_2$O (0.1M) buffer system as mobile phase to give the title compound (10 mg, 11%).
$^1$H NMR (600 MHz, DMSO) δ 1.11-1.21 (m, 1H), 1.32 (d, 1H), 1.39-1.5 (m, 1H), 1.55 (d, 1H), 1.77 (d, 1H), 1.85 (d, 1H), 2.01 (d, 1H), 2.11 (s, 4H), 2.82-2.97 (m, 1H), 3.66-3.85 (m, 1H), 5.97 (s, 1H), 6.86 (d, 1H), 8.04 (d, 5H), 11.64 (s, 1H), 13.10 (s, 1H). MS m/z 379.2 [M+H]$^+$

Example 45: (1R,2R and 1S,2S)—N-(4-Methyl-1,3-oxazol-2-yl)-2-[4-(1H-pyrazol-5-yl)benzoyl]cyclohexanecarboxamide

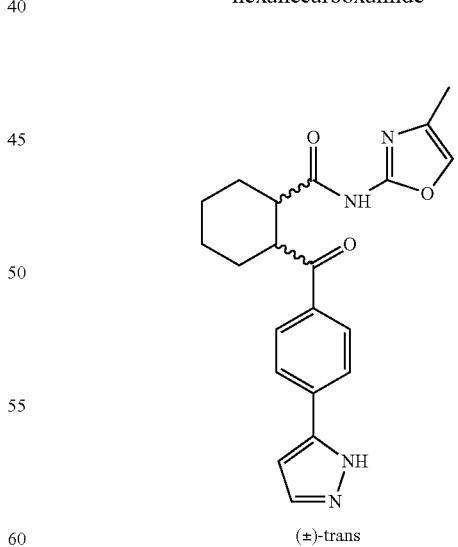

(±)-trans

Step 1: (1R,2R and 1S,2S)-2-(4-Bromobenzoyl)-N-(4-methyl-1,3-oxazol-2-yl)cyclohexanecarboxamide DIPEA (336 µL, 1.93 mmol), and TBTU (371 mg, 1.16 mmol) was added to a stirred solution of (1R,2R and 1S,2S)-2-(4-bromobenzoyl)cyclohexanecarboxylic acid (300 mg, 0.96 mmol) and 4-methyl-1,3-oxazol-2-amine (113 mg, 1.16 mmol) in DCM (5 mL) and the reaction mixture was stirred at rt for 3 days. The reaction mixture was washed with $Na_2CO_3$ (1M, aq) and the phases were separated. The organic layer was dried using a phase separator and concentrated in vacuo. The crude product was purified by flash chromatography (40% EtOAc in heptane) to give the subtitle compound (85 mg, 23%).

Step 2: (1R,2R and 1S,2S)—N-(4-Methyl-1,3-oxazol-2-yl)-2-[4-(1H-pyrazol-5-yl)benzoyl]cyclohexanecarboxamide $K_2CO_3$ (113 mg, 0.82 mmol) dissolved in water (1 mL) was added to a mixture of (1R,2R and 1S,2S)-2-(4-bromobenzoyl)-N-(4-methyl-1,3-oxazol-2-yl)cyclohexanecarboxamide (Example 45 Step 1, 80 mg, 0.20 mmol), 1H-pyrazol-5-ylboronic acid (46 mg, 0.41 mmol) and Pd(dppf)$Cl_2$*DCM (13.2 mg, 0.02 mmol) in dioxane (2 mL). The reaction mixture was evacuated and purged with nitrogen (g), and then heated at 80° C. for 2.5 h.

The reaction mixture was partitioned between EtOAc and $NaHCO_3$ (sat., aq). The organic phase was filtered using a phase separator, concentrated in vacuo, and the crude product to was purified by flash chromatography (80% EtOAc in heptane). The product containing fractions were collected, evaporated and triturated with $Et_2O$. The crude product was purified by flash chromatography (80% EtOAc in heptane) and the product containing fractions were combined and evaporated to dryness and finally triturated with $Et_2O$ to give the title compound (21 mg, 28%).

$^1$H NMR (500 MHz, $CDCl_3$, 28° C.) δ 1.15-1.38 (m, 2H), 1.38-1.57 (m, 1H), 1.77-1.94 (m, 3H), 2.07 (d, 5H), 2.92 (d, 1H), 3.69-3.87 (m, 1H), 6.69 (d, 1H), 7.09 (s, 1H), 7.65 (d, 1H), 7.86 (d, 2H), 8.02 (d, 2H).

MS m/z 377.2 [M−H]$^-$

Example 46: (1R,2R and 1S,2S)—N-(5-Cyano-1-methyl-1H-pyrazol-4-yl)-2-[4-(3-methyl-1H-pyrazol-5-yl)benzoyl]cyclohexanecarboxamide

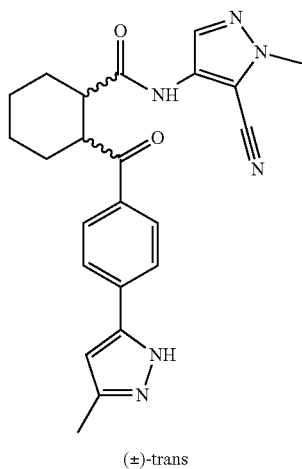 [SMILES: Cc1cc(-c2ccc(C(=O)C3CCCCC3C(=O)Nc3cnn(C)c3C#N)cc2)[nH]n1]

(±)-trans

Step 1: (1R,2R and 1S,2S)—N-(5-Cyano-1-methyl-1H-pyrazol-4-yl)-2-{4-[3-methyl-1-(tetrahydro-2H-pyran-2-yl)-1H-pyrazol-5-yl]benzoyl}cyclohexanecarboxamide Pd(dtbpf)$Cl_2$ (6.97 mg, 10.84 μmol) and a solution of $K_2CO_3$ (150 mg, 1.08 mmol) in water (1.5 mL) were added to a mixture of (1R,2R and 1S,2S)-2-(4-bromobenzoyl)-N-(5-cyano-1-methyl-1H-pyrazol-4-yl)cyclohexanecarboxamide (Intermediate 43, 150 mg, 0.36 mmol) and 3-methyl-1-(tetrahydro-2H-pyran-2-yl)-5-(4,4,5,5-tetramethyl-1,3,2-dioxaborolan-2-yl)-1H-pyrazole (Intermediate 3, 106 mg, 0.36 mmol) in dioxane (2 mL) and the reaction mixture was evacuated and purged with nitrogen (g) three times, and then heated at 80° C. for 1 h. The reaction mixture was diluted with EtOAc and the organic phase was washed twice with NaCl (sat., aq). The combined aqueous phase was extracted twice with EtOAc. The combined organic layer was dried using a phase separator and concentrated in vacuo to give the subtitle compound (180 mg).

MS m/z 499.3 [M−H]$^-$

Step 2: (1R,2R and 1S,2S)—N-(5-Cyano-1-methyl-1H-pyrazol-4-yl)-2-[4-(3-methyl-1H-pyrazol-5-yl)benzoyl]cyclohexanecarboxamide A solution of HCl (4M in dioxane, 0.5 mL) in water (0.5 mL) was added to a solution of (1R,2R and 1S,2S)—N-(5-cyano-1-methyl-1H-pyrazol-4-yl)-2-{4-[3-methyl-1-(tetrahydro-2H-pyran-2-yl)-1H-pyrazol-5-yl]benzoyl}cyclohexanecarboxamide (Example 45 Step 1, 180 mg) in dioxane (2 mL) and the reaction mixture was stirred at rt for 15 min. The reaction mixture was concentrated and the crude product was purified by preparative HPLC on a Waters Sunfire C18 OBD column (5 μm, 150×19 ID mm) using a gradient of 5-95% MeCN in a $HCO_2H/H_2O$ (0.1M, pH3) buffer system and then by preparative HPLC on a XBridge C18 column (10 μm, 250×19 ID mm) using a gradient of 20-60% MeCN in a $H_2O/MeCN/NH_3$ (95/5/0.2) buffer system as mobile phase to give the title compound (28 mg, 19%).

$^1$H NMR (500 MHz, DMSO) δ 1.09-1.23 (m, 1H), 1.33 (t, 1H), 1.4-1.57 (m, 2H), 1.76 (d, 1H), 1.84 (d, 1H), 1.98 (d, 1H), 2.05 (d, 1H), 2.27 (s, 3H), 2.86-2.94 (m, 1H), 3.69-3.78 (m, 1H), 3.89 (s, 3H), 6.56 (s, 1H), 7.70 (s, 1H), 7.88 (d, 2H), 8.00 (d, 2H), 10.51 (s, 1H), 12.7 (s, 1H).

MS m/z 417.1 [M+H]$^+$

Example 47: (1R,2R and 1S,2S)—N-(3-Cyclopropyl-1,2,4-thiadiazol-5-yl)-2-[4-(1H-pyrazol-5-yl)benzoyl]cyclohexanecarboxamide

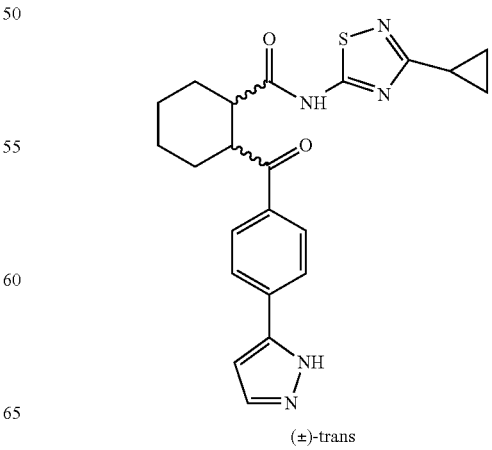

(±)-trans

Step 1: (1R,2R and 1S,2S)-2-(4-Bromobenzoyl)-N-(3-cyclopropyl-1,2,4-thiadiazol-5-yl)cyclohexanecarboxamide T3P (50% in EtOAc, 383 µL, 0.64 mmol) was added to a mixture of (1R,2R and 1S,2S)-2-(4-bromobenzoyl)cyclohexanecarboxylic acid (100 mg, 0.32 mmol), 3-cyclopropyl-1,2,4-thiadiazol-5-amine (91 mg, 0.64 mmol), and Et$_3$N (134 µL, 0.96 mmol) in EtOAc (3 mL) and the reaction mixture was heated in a microwave reactor at 150° C. for 30 min. The reaction mixture was diluted with EtOAc and the organic phase was extracted with NaHCO$_3$ (sat., aq) and brine, dried using a phase separator and concentrated in vacuo to give the subtitle compound (151 mg).
MS m/z 434.2 [M+H]$^+$

Step 2: (1R,2R and 1S,2S)—N-(3-Cyclopropyl-1,2,4-thiadiazol-5-yl)-2-[4-(1H-pyrazol-5-yl)benzoyl]cyclohexanecarboxamide A solution of K$_3$PO$_4$ (204 mg, 0.96 mmol) in water (0.9 mL) was added to a mixture (1R,2R and 1S,2S)-2-(4-bromobenzoyl)-N-(3-cyclopropyl-1,2,4-thiadiazol-5-yl)cyclohexanecarboxamide (Example 47 Step 1, 139 mg, 0.32 mmol), 1H-pyrazol-5-ylboronic acid (36 mg, 0.32 mmol), and Pd(dppf)Cl$_2$*DCM (26 mg, 0.03 mmol) in a mixture of DME (2.4 mL) and EtOH (0.8 mL) and the reaction mixture was heated at 140° C. for 15 min. The reaction mixture was diluted with EtOAc and the organic phase was washed with water, dried using a phase separator and concentrated in vacuo. The crude product was purified by preparative HPLC on a Xbridge Prep OBD C18 column (5 m, 150×19 ID mm) using a gradient of 5-95% MeCN in a H$_2$O/NH$_3$ (100/0.2, pH10) buffer system as mobile phase to give the title compound (35 mg, 26%).
$^1$H NMR (600 MHz, DMSO) δ 0.85-1.05 (m, 4H), 1.09-1.24 (m, 1H), 1.32 (d, 1H), 1.39-1.51 (m, 1H), 1.81 (dd, 2H), 1.96-2.21 (m, 3H), 2.95-3.09 (m, 1H), 3.72-3.87 (m, 1H), 6.86 (d, 1H), 7.85 (s, 1H), 7.89-8.14 (m, 4H), 13.10 (s, 2H). MS m/z 422.2 [M+H]$^+$

Example 48: (1R,2R and 1S,2S)—N-(3-Methyl-1,2-thiazol-5-yl)-2-[4-(1H-pyrazol-5-yl)benzoyl]cyclohexanecarboxamide

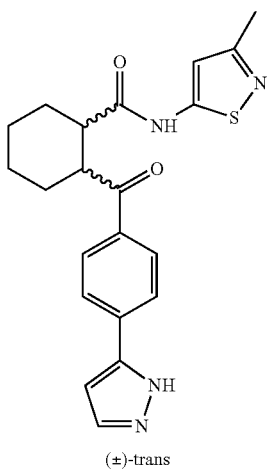 [SMILES: Cc1cc(NC(=O)C2CCCCC2C(=O)c2ccc(-c3ccn[nH]3)cc2)sn1]

(±)-trans

A solution of K$_3$PO$_4$ (38 mg, 0.18 mmol) in water (0.2 mL) was added to a mixture of (1R,2R and 1S,2S)-2-(4-bromobenzoyl)-N-(3-methyl-1,2-thiazol-5-yl)cyclohexanecarboxamide (Intermediate 100, 24 mg, 0.06 mmol), 1H-pyrazol-5-ylboronic acid (7 mg, 0.06 mmol), and Pd(dppf)Cl$_2$ (5 mg, 5.89 µmol) in a mixture of DME (0.6 mL) and EtOH (0.2 mL) and the reaction mixture was heated at 140° C. for 15 min. The reaction mixture was diluted with EtOAc and the organic phase was extracted with water, dried using a phase separator and concentrated in vacuo. The crude product was purified by preparative HPLC on a Xbridge Prep C18 OBD column (5 µm, 150×19 ID mm) using a gradient of 5-95% MeCN in a H$_2$O/NH$_3$ (100/0.2, pH10) buffer system as mobile phase to give the titel compound (8 mg, 35%).
$^1$H NMR (600 MHz, DMSO) δ 1.1-1.3 (m, 1H), 1.3-1.44 (m, 1H), 1.44-1.64 (m, 2H), 1.78 (d, 1H), 1.86 (d, 1H), 1.97-2.12 (m, 2H), 2.29 (s, 3H), 2.84-3.04 (m, 1H), 3.81 (s, 1H), 6.69 (s, 1H), 6.86 (d, 1H), 7.73-8.15 (m, 5H), 11.96 (s, 1H), 13.10 (s, 1H). MS m/z 395.2 [M+H]$^+$

Example 49: (1R,2R and 1S,1S)—N-(4-Cyano-3-methyl-1,2-thiazol-5-yl)-2-[4-(1H-pyrazol-5-yl)benzoyl]cyclohexanecarboxamide

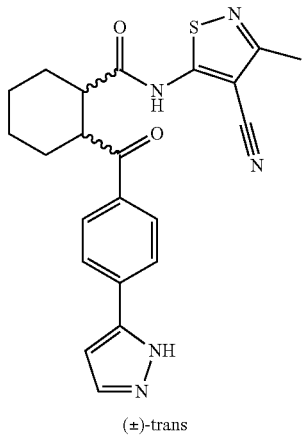 [SMILES: Cc1nsc(NC(=O)C2CCCCC2C(=O)c2ccc(-c3ccn[nH]3)cc2)c1C#N]

(±)-trans

A solution of K$_3$PO$_4$ (74 mg, 0.35 mmol) in water (0.3 mL) was added to a mixture of (1R,2R and 1S,1S)-2-(4-bromobenzoyl)-N-(4-cyano-3-methyl-1,2-thiazol-5-yl)cyclohexanecarboxamide (Intermediate 101, 51 mg, 0.12 mmol), 1H-pyrazol-5-ylboronic acid (13 mg, 0.12 mmol), and Pd(dppf)Cl$_2$*DCM (10 mg, 0.01 mmol) in a mixture of DME (1 mL) and EtOH (0.3 mL) and the reaction mixture was heated at 140° C. for 15 min. The reaction mixture was diluted with EtOAc and the organic phase was washed with water, dried using a phase separator and concentrated in vacuo. The crude product was purified by preparative HPLC on a Xbridge Prep C18 OBD column (5 µm, 150×19 ID mm) using a gradient of 5-95% MeCN in a H$_2$O/NH$_3$ (100/0.2, pH10) buffer system as mobile phase to give the title compound (14 mg, 29%).
$^1$H NMR (600 MHz, DMSO) δ 1.15-1.24 (m, 1H), 1.28-1.39 (m, 1H), 1.46 (d, 1H), 1.59 (d, 1H), 1.78 (s, 1H), 1.87 (d, 1H), 2.05 (s, 1H), 2.12 (d, 1H), 2.41 (s, 3H), 3.21 (s, 1H), 3.84 (s, 1H), 6.86 (d, 1H), 7.76-8.2 (m, 5H), 12.83 (s, 1H), 13.10 (s, 1H). MS m/z 420.1 [M+]$^+$

The invention claimed is:
1. A compound according to Formula (I):

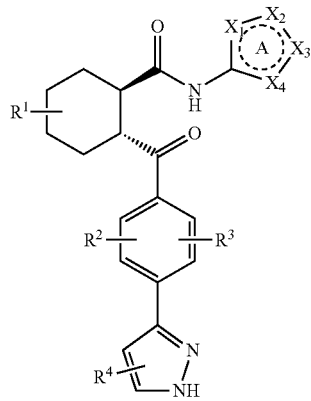

or a pharmaceutically acceptable salt thereof, wherein:
$R^1$ is H, $C_1$-$C_3$ alkyl, halo, $C_1$-$C_3$ alkoxy, $C_1$-$C_3$ haloalkyl or $C_1$-$C_3$ haloalkoxy;
each of $R^2$ and $R^3$ is independently H, $C_1$-$C_3$ alkyl, $C_1$-$C_3$ alkoxy, —CN or halo;
$R^4$ is H, —$CH_3$, —$CH_2F$, —$CHF_2$, —$CF_3$ or halo;
Ring A contains 2 double bonds;
each $X_1$, $X_2$, $X_3$ and $X_4$ of Ring A is independently $CR^5$, CH, O, S, $NR^6$ or N; wherein at least one of $X_1$, $X_2$, $X_3$ and $X_4$ in Ring A is $NR^6$;
each $R^5$ is optionally and independently $C_1$-$C_6$ alkyl, $C_1$-$C_6$ alkoxy, $C_1$-$C_3$ haloalkyl, $C_1$-$C_3$ haloalkoxy, —$S(O)_pR^7$, —CN, —CONR'R", or $C_3$-$C_6$ cycloalkyl;
each p is independently 0, 1 or 2;
$R^6$ is H, —$CH_3$ or $CH_2CH_3$;
or wherein when $X_4$ is $CR^5$ and $X_3$ is $NR^6$, then the $R^5$ and $R^6$ may be taken together to form a 5 to 6-membered heterocyclyl ring fused to Ring A, which heterocyclyl may optionally contain an additional heteroatom selected from N, O and S; said fused heterocyclyl may additionally contain a carbonyl or a $S(O)_2$ directly adjacent to a heteroatom therein; and may be further substituted with one or two substituents selected from the group consisting of —$CH_3$ and halo;
$R^7$ is —$CH_3$ or —NR'R"; and
each R' and R" is independently —H or —$CH_3$;
provided that the total number of substituents on Ring A is 0, 1 or 2; and further provided that when $R^5$ and $R^6$ are not combined to form a heterocyclyl ring fused to Ring A, that the total number of $R^5$ and $R^6$ substituents which is alkyl and/or haloalkyl is 0 or 1.

2. The compound of claim 1, wherein $R^4$ is —H or —$CH_3$.
3. The compound of claim 1, wherein $R^2$ and $R^3$ are each independently —F or —H.
4. The compound of claim 1, wherein $R^1$ is —H.
5. The compound of claim 1, according to formula (II):

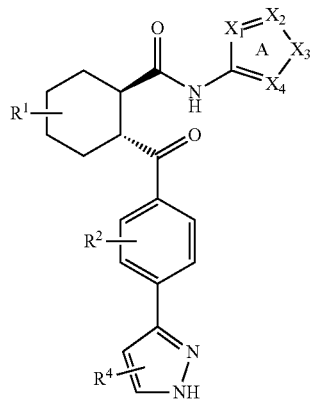

or a pharmaceutically acceptable salt thereof, wherein
each $X_1$, $X_2$ and $X_4$ of Ring A is independently $CR^5$, CH, or N; wherein at least one of $X_1$, $X_2$ and $X_4$ in Ring A is N; and $X_3$ is O, S or $NR^6$;
or wherein when $X_4$ is $CR^5$ and $X_3$ is $NR^6$, then the $R^5$ and $R^6$ may be taken together to form a 5 to 6-membered heterocyclyl ring fused to Ring A, which heterocyclyl may optionally contain an additional heteroatom selected from N, O and S; said fused heterocyclyl may additionally contain a carbonyl or a —$S(O)_2$ directly adjacent to a heteroatom therein; and may be further substituted with one or two substituents selected from the group consisting of —$CH_3$ and halo;
and $R^1$, $R^2$, $R^4$, $R^5$ and $R^6$ are as defined in claim 1.

6. The compound of claim 1, wherein $X^1$ is CH or $CR^5$, wherein $R^5$ is as defined in claim 1.
7. The compound of claim 1, wherein $X^4$ is $CR^5$ wherein $R^5$ is as defined in claim 1.
8. The compound of claim 1, wherein Ring A is an optionally and independently substituted pyrazole, triazole, oxazole, thiazole, oxadiazole or thiadiazole.
9. The compound of claim 1, according to formula (III):

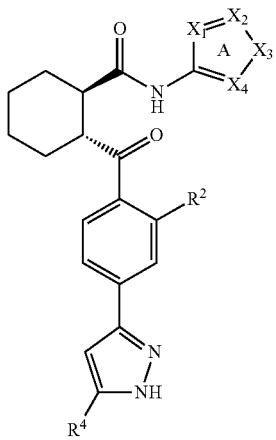

or a pharmaceutically acceptable salt thereof; wherein:
$X^1$ is CH or $CR^5$;
$X^2$ is N;
$X^3$ is O, S, or $NR^6$;
$X^4$ is CH or $CR^5$;
$R^2$ is —H or —F;
$R^5$ is —$S(O)_2NR'R"$, —$SO_2CH_3$; —C(O)NR'R", —CN, $C_1$-$C_2$ alkoxy, $C_1$-$C_2$ haloalkoxy or $C_1$-$C_2$ haloalkyl;
$R^6$ is H, —$CH_3$ or —$CH_2CH_3$;
each R' and R" is independently —H or —$CH_3$;
or wherein when $X_4$ is $CR^5$ and $X_3$ is $NR^6$, then the $R^5$ and $R^6$ may be taken together to form a 5 to 6-membered heterocyclyl ring fused to Ring A, which heterocyclyl may optionally contain an additional heteroatom selected from N, O and S; said fused heterocyclyl may additionally contain a carbonyl or a —$S(O)_2$ directly adjacent to a heteroatom therein; and may be further substituted with one or two substituents selected from the group consisting of —$CH_3$ and halo;
and
$R^4$ is as defined in claim 1.

10. The compound of claim 9, wherein one of $X^1$ is CH, $X^2$ is N and $X^3$ is $NR^6$ and $R^6$ is as defined in claim 9.

11. The compound of claim 9, wherein $X^4$ is $CR^5$ and $X^3$ is $NR^6$ and together the $R^5$ and $R^6$ substituents form a 5-6 membered heterocyclyl ring fused to Ring A, to form a bicyclic ring together with ring A selected from:

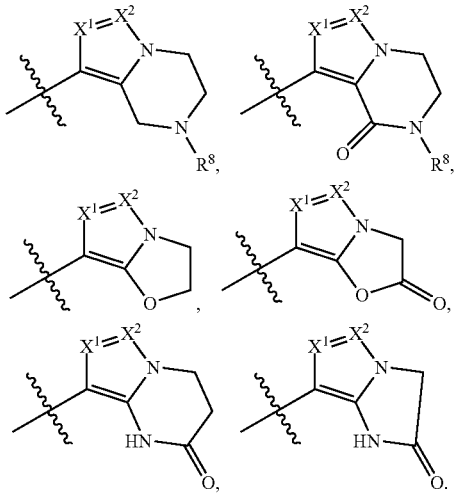

12. The compound of claim 1, according to formula (IV):

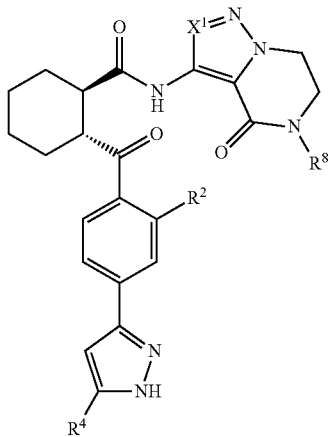

or a pharmaceutically acceptable salt thereof, wherein:
$X^1$ is CH or $CR^5$;
$R^5$, if present, is —$CH_3$;
$R^2$ is —H or —F;
$R^4$ is —H or —$CH_3$; and
$R^8$ is —H or $CH_3$.

13. A compound of claim 1, according to the formula (V):

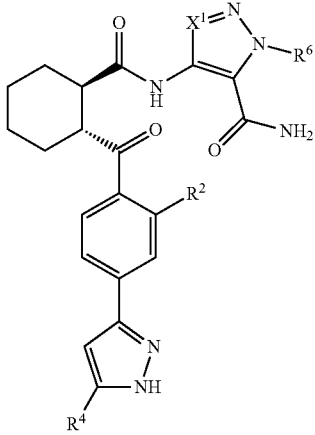

or a pharmaceutically acceptable salt thereof, wherein:
$X^1$ is CH or $CR^5$;
$R^2$ is —H or —F;
$R^4$ is —H or —$CH_3$;
$R^5$, if present, is —$CH_3$; and
$R^6$ is —H or —$CH_3$;
provided that $R^5$ and $R^6$ are not both —$CH_3$ at the same time.

14. The compound of claim 1, according to formula (VI):

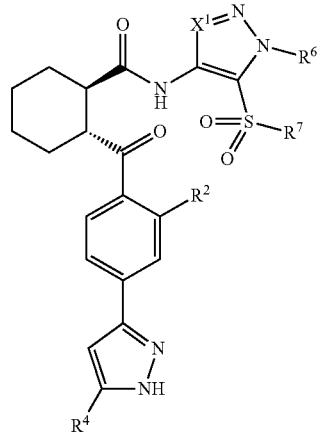

or a pharmaceutically acceptable salt, wherein:
$X^1$ is CH or $CR^5$;
$R^2$ is —H or —F;
$R^4$ is —H or —$CH_3$;
$R^5$, if present, is —$CH_3$; and
$R^6$ is —H or —$CH_3$;
provided that $R^5$ and $R^6$ are not both —$CH_3$ at the same time.

15. The compound of claim 1, according to formula (VII):

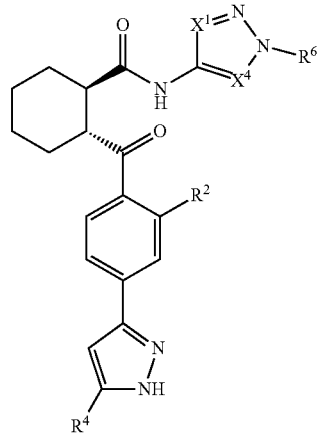

or a pharmaceutically acceptable salt, wherein:
one of $X^1$ and $X^4$ is CH, and the other is $CR^5$;
$R^2$ is —H or —F;
$R^4$ is —H or —$CH_3$;
$R^5$ is —$CH_3$ or $C_1$-haloalkyl; and
$R^6$ is —H or —$CH_3$;
provided that the total number of $R^5$ and $R^6$ substituents in the A ring which is alkyl is 0 or 1.

16. A compound selected from the group consisting of:
Trans(+) or Trans(−) 1-Methyl-4-[({(1R,2R or 1S,2S)-2-[4-(1H-pyrazol-3-yl)benzoyl]-cyclohexyl}carbonyl)amino]-1H-pyrazole-3-carboxamide;

1-Methyl-4-[({(1R,2R)-2-[4-(1H-pyrazol-3-yl)benzoyl]cyclohexyl}carbonyl)amino]-1H-pyrazole-5-carboxamide;

1-Methyl-4-[({(1R,2R)-2-[4-(3-methyl-1H-pyrazol-5-yl)benzoyl]cyclohexyl}carbonyl)amino]-1H-pyrazole-5-carboxamide;

1-Methyl-4-[({1R,2R)-2-[4-(3-methyl-1H-pyrazol-5-yl)benzoyl]cyclohexyl}carbonyl)amino]-1H-pyrazole-3-carboxamide;

Trans(−) (1S,2S or 1R, 2R)—N-(3-Cyano-1-methyl-1H-pyrazol-4-yl)-2-[4-(3-methyl-1H-pyrazol-5-yl)benzoyl]cyclohexanecarboxamide;

Trans(+) (1R,2R or 1S,2S)—N-(3-Cyano-1-methyl-1H-pyrazol-4-yl)-2-[4-(3-methyl-1H-pyrazol-5-yl)benzoyl]cyclohexanecarboxamide;

(1R,2R)-2-[4-(3-Methyl-1H-pyrazol-5-yl)benzoyl]-N-(1H-pyrazol-4-yl)cyclohexanecarboxamide;

(1R,2R)-2-[4-(3-Methyl-1H-pyrazol-5-yl)benzoyl]-N-(4-oxo-4,5,6,7-tetrahydropyrazolo[1,5-a]pyrazin-3-yl)cyclohexanecarboxamide;

((1R,2R)—N-[1-Methyl-5-(methylsulfonyl)-1H-pyrazol-4-yl]-2-[4-(1H-pyrazol-5-yl)benzoyl]cyclohexanecarboxamide;

(1R,2R)—N-[3-(Difluoromethoxy)-1-methyl-1H-pyrazol-4-yl]-2-(4-(1H-pyrazol-5-yl)benzoyl)-cyclohexanecarboxamide;

(1R,2R)-2-[4-(3-Methyl-1H-pyrazol-5-yl)benzoyl]-N-(1-methyl-3-sulfamoyl-1H-pyrazol-4-yl)cyclohexanecarboxamide;

(1R,2R)—N-(2,3-Dihydropyrazolo[5,1-b][1,3]oxazol-7-yl)-2-[4-(3-methyl-1H-pyrazol-5-yl)benzoyl]cyclohexanecarboxamide;

Trans(−) (1R,2R or 1S,2S)—N-(3-Cyano-1-methyl-1H-pyrazol-4-yl)-2-[4-(1H-pyrazol-3-yl)benzoyl]cyclohexanecarboxamide;

(1R,2R)-2-[4-(3-Methyl-1H-pyrazol-5-yl)benzoyl]-N-(1-methyl-5-sulfamoyl-1H-pyrazol-4-yl)cyclohexanecarboxamide;

Trans (+/−) (1R,2R and 1S,2S)—N-(5-Methoxy-1-methyl-1H-pyrazol-4-yl)-2-[4-(1H-pyrazol-3-yl)benzoyl]cyclohexanecarboxamide;

(1R,2R)—N-[5-(Difluoromethyl)-1H-pyrazol-4-yl]-2-[4-(5-methyl-1H-pyrazol-3-yl)benzoyl]cyclohexanecarboxamide;

(1R,2R)—N-(5-Methyl-4-oxo-4,5,6,7-tetrahydropyrazolo[1,5-c]pyrazin-3-yl)-2-[4-(5-methyl-1H-pyrazol-3-yl)benzoyl]cyclohexanecarboxamide;

(1R,2R)—N-(5-Methyl-4-oxo-4,5,6,7-tetrahydropyrazolo[1,5-a]pyrazin-3-yl)-2-[4-(1H-pyrazol-3-yl)benzoyl]cyclohexanecarboxamide;

Trans(−) (1R,2R or 1S, 2S)—N-(5-Cyano-1-methyl-1H-pyrazol-4-yl)-2-[4-(1H-pyrazol-3-yl)benzoyl]cyclohexanecarboxamide;

Trans(+) (1S,2S or 1R, 2R)—N-(5-Cyano-1-methyl-1H-pyrazol-4-yl)-2-[4-(1H-pyrazol-3-yl)benzoyl]cyclohexanecarboxamide;

1-Ethyl-4-[({(1R,2R)-2-[4-(3-methyl-1H-pyrazol-5-yl)benzoyl]cyclohexyl}-carbonyl)amino]-1H-pyrazole-5-carboxamide;

Trans(±)-N,1-Dimethyl-4-[({(1R,2R and 1S,2S)-2-[4-(1H-pyrazol-3-yl)benzoyl]cyclohexyl}-carbonyl)amino]-1H-pyrazole-3-carboxamide;

N,1-Dimethyl-4-[({(1R,2R)-2-[4-(5-methyl-1H-pyrazol-3-yl)benzoyl]-cyclohexyl}carbonyl)amino]-1H-pyrazole-5-carboxamide;

5-Methyl-4-[({(1R,2R)-2-[4-(3-methyl-1H-pyrazol-5-yl)benzoyl]-cyclohexyl}carbonyl)amino]-1H-pyrazole-3-carboxamide;

4-[({(1R,2R)-2-[4-(1H-Pyrazol-5-yl)benzoyl]cyclohexyl}carbonyl)amino]-1H-pyrazole-5-carboxamide;

(1R,2R)—N-(4-Oxo-4,5,6,7-tetrahydropyrazolo[1,5-c]pyrazin-3-yl)-2-[4-(1H-pyrazol-5-yl)benzoyl]cyclohexanecarboxamide;

(1R,2R)—N-[1-Methyl-5-(methylsulfamoyl)-1H-pyrazol-4-yl]-2-[4-(3-methyl-1H-pyrazol-5-yl)benzoyl]cyclohexanecarboxamide;

(1R,2R)—N-(1-Methyl-3-sulfamoyl-1H-pyrazol-4-yl)-2-[4-(1H-pyrazol-5-yl)benzoyl]cyclohexanecarboxamide;

(1R,2R)—N-[5-(Dimethylsulfamoyl)-1-methyl-1H-pyrazol-4-yl]-2-[4-(1H-pyrazol-5-yl)benzoyl]cyclohexanecarboxamide;

(1R,2R)—N-(2-Methyl-4-oxo-4,5,6,7-tetrahydropyrazolo[1,5-c]pyrazin-3-yl)-2-[4-(5-methyl-1H-pyrazol-3-yl)benzoyl]cyclohexanecarboxamide;

(1R,2R)—N-(2-Methyl-4-oxo-4,5,6,7-tetrahydropyrazolo[1,5-a]pyrazin-3-yl)-2-[4-(1H-pyrazol-5-yl)benzoyl]cyclohexanecarboxamide; and (1R,2R)—N-[5-(Difluoromethyl)-1H-pyrazol-4-yl]-2-[4-(1H-pyrazol-3-yl)benzoyl]cyclohexanecarboxamide;

Trans(±)-4-[({(1R,2R and 1S,2S)-2-[2-Chloro-4-(1H-pyrazol-5-yl)benzoyl]cyclohexyl}-carbonyl)amino]-1-methyl-1H-pyrazole-5-carboxamide;

Trans(±)-4-[({(1R,2R and 1S,2S)-2-[2-Chloro-4-(3-methyl-1H-pyrazol-5-yl)benzoyl]-cyclohexyl}carbonyl)amino]-1-methyl-1H-pyrazole-5-carboxamide;

Trans(±)-(1R,2R and 1S,2S)—N-(5-Cyclopropyl-1-methyl-1H-1,2,3-triazol-4-yl)-2-[4-(1H-pyrazol-5-yl)benzoyl]cyclohexanecarboxamide;

4-[({(1R,2R or 1S,2S)-2-[2-Fluoro-4-(1H-pyrazol-5-yl)benzoyl]cyclohexyl}-carbonyl)amino]-1-methyl-1H-pyrazole-5-carboxamide;

4-[({(1R,2R or 1S,2S)-2-[2-Fluoro-4-(1H-pyrazol-5-yl)benzoyl]cyclohexyl}-carbonyl)amino]-1-methyl-1H-pyrazole-3-carboxamide;

4-[({(1R,2R or 1S,2S)-2-[2-Fluoro-4-(3-methyl-1H-pyrazol-5-yl)benzoyl]-cyclohexyl}carbonyl)amino]-1-methyl-1H-pyrazole-3-carboxamide;

4-[({(1R,2R or 1S,2S)-2-[2-Fluoro-4-(3-methyl-1H-pyrazol-5-yl)benzoyl]cyclohexyl}-carbonyl)amino]-1-methyl-1H-pyrazole-5-carboxamide;

4-[({(1R,2R or 1S,2S)-2-[2-Fluoro-4-(3-methyl-1H-pyrazol-5-yl)benzoyl]cyclohexyl}-carbonyl)amino]-1H-pyrazole-5-carboxamide;

(1R,2R or 1S,2S)-2-[2-Fluoro-4-(3-methyl-1H-pyrazol-5-yl)benzoyl]-N-(4-oxo-4,5,6,7-tetrahydropyrazolo[1,5-a]pyrazin-3-yl)cyclohexanecarboxamide;

4-[({(1R,2R or 1S,2S)-2-[2-Fluoro-4-(3-methyl-1H-pyrazol-5-yl)benzoyl]cyclohexyl}-carbonyl)amino]-1,2,5-oxadiazole-3-carboxamide;

3-[({(1R,2R or 1S,2S)-2-[2-Fluoro-4-(1H-pyrazol-5-yl)benzoyl]cyclohexyl}carbonyl)-amino]-5-methyl-1,2-oxazole-4-carboxamide;

Trans(±)-1-Ethyl-4-[({(1R,2R and 1S,2S)-2-[4-(1H-pyrazol-5-yl)benzoyl]cyclohexyl}-carbonyl)amino]-1H-pyrazole-3-carboxamide;

(1R,2R)-2-[4-(3-Methyl-1H-pyrazol-5-yl)benzoyl]-N-(1,3,4-oxadiazol-2-yl)cyclohexanecarboxamide;

Trans(±)-(1R,2R and 1S,2S)—N-(3-Methyl-1,2-oxazol-5-yl)-2-[4-(1H-pyrazol-5-yl)benzoyl]cyclohexanecarboxamide;

Trans(±)-(1R,2R and 1S,2S)—N-(4-Methyl-1,3-oxazol-2-yl)-2-[4-(1H-pyrazol-5-yl)benzoyl]cyclohexanecarboxamide;

Trans(±)-(1R,2R and 1S,2S)—N-(5-Cyano-1-methyl-1H-pyrazol-4-yl)-2-[4-(3-methyl-1H-pyrazol-5-yl)benzoyl]cyclohexanecarboxamide;

Trans(±)-(1R,2R and 1S,2S)—N-(3-Cyclopropyl-1,2,4-thiadiazol-5-yl)-2-[4-(1H-pyrazol-5-yl)benzoyl]cyclohexanecarboxamide;

Trans(±)-(1R,2R and 1S,2S)—N-(3-Methyl-1,2-thiazol-5-yl)-2-[4-(1H-pyrazol-5-yl)benzoyl]cyclohexanecarboxamide; and Trans(±)-(1R,2R and 1S,1S)—N-(4-Cyano-3-methyl-1,2-thiazol-5-yl)-2-[4-(1H-pyrazol-5-yl)benzoyl]cyclohexanecarboxamide;

or a pharmaceutically acceptable salt thereof.

17. A compound according to claim 16, which is (1R, 2R)-2-[4-(3-Methyl-1H-pyrazol-5-yl)benzoyl]-N-(1-methyl-5-sulfamoyl-1H-pyrazol-4-yl)cyclohexanecarboxamide; or a pharmaceutically acceptable salt thereof.

18. A pharmaceutical composition comprising a compound of Formula (I), or a pharmaceutically acceptable salt thereof, as claimed in claim 1, and at least one pharmaceutically acceptable carrier, diluent, or excipient.

* * * * *

UNITED STATES PATENT AND TRADEMARK OFFICE
CERTIFICATE OF CORRECTION

PATENT NO.      : 10,508,119 B2
APPLICATION NO. : 16/196217
DATED           : December 17, 2019
INVENTOR(S)     : Johan Olof Broddefalk et al.

Page 1 of 1

It is certified that error appears in the above-identified patent and that said Letters Patent is hereby corrected as shown below:

On the Title Page

Item (54) and In the Specification, Column 1, Line 1-3, please replace:
"PYRAZOLE DERIVATIVES USEFUL AS 5-LIPDXYGENASE ACTIVATING PROTEIN (FLAP) INHIBITORS"
With:
--PYRAZOLE DERIVATIVES USEFUL AS 5-LIPOXYGENASE ACTIVATING PROTEIN (FLAP) INHIBITORS--.

Signed and Sealed this
Nineteenth Day of January, 2021

Andrei Iancu
*Director of the United States Patent and Trademark Office*